US008198449B2

(12) United States Patent
Pracitto et al.

(10) Patent No.: US 8,198,449 B2
(45) Date of Patent: *Jun. 12, 2012

(54) COMPOUNDS FOR THE TREATMENT OF HEPATITIS C

(75) Inventors: Richard Pracitto, Wallingford, CT (US); John F. Kadow, Wallingford, CT (US); John A. Bender, Middletown, CT (US); Brett R. Beno, Cromwell, CT (US); Katharine A. Grant-Young, Madison, CT (US); Ying Han, Cheshire, CT (US); Piyasena Hewawasam, Middletown, CT (US); Andrew Nickel, San Marino, CA (US); Kyle E. Parcella, Wallingford, CT (US); Kap-Sun Yeung, Madison, CT (US); Louis S. Chupak, Old Saybrook, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 259 days.

This patent is subject to a terminal disclaimer.

(21) Appl. No.: 12/549,983

(22) Filed: Aug. 28, 2009

(65) Prior Publication Data

US 2010/0063068 A1 Mar. 11, 2010

Related U.S. Application Data

(60) Provisional application No. 61/096,004, filed on Sep. 11, 2008.

(51) Int. Cl.
*A61K 31/437* (2006.01)
*C07D 471/04* (2006.01)
(52) U.S. Cl. ........................................ 546/121; 514/300
(58) Field of Classification Search .................. 546/121; 514/300
See application file for complete search history.

(56) References Cited

U.S. PATENT DOCUMENTS

| | | | |
|---|---|---|---|
| 7,265,152 B2 | 9/2007 | Saha et al. | |
| 2004/0110763 A1* | 6/2004 | Akahane et al. | 514/252.04 |
| 2006/0189606 A1 | 8/2006 | Karp et al. | |
| 2009/0281336 A1 | 11/2009 | Saha et al. | |

FOREIGN PATENT DOCUMENTS

| | | |
|---|---|---|
| EP | 0 595 150 | 5/1994 |
| EP | 1 961 745 | 8/2008 |
| JP | 57-123181 | 7/1982 |
| JP | 2008-247878 | 10/2008 |
| WO | WO 02/16359 | 2/2002 |
| WO | WO 02/078701 | 10/2002 |
| WO | WO 03/097062 | 11/2003 |
| WO | WO 2004/041201 | 5/2004 |
| WO | WO 2008/125874 | 10/2008 |
| WO | WO 2009/101022 | 8/2009 |
| WO | WO 2009/137493 | 11/2009 |
| WO | WO 2009/137500 | 11/2009 |

OTHER PUBLICATIONS

Trappani et. al. "Synthesis and Binding Affinity of 2-Phenylimidazo[1,2-a]pyridine Derivatives for both Central and Peripheral Benzodiazepine Receptors. A New Series of High-Affinity and Selective Ligands for the Peripheral Type" J. Med. Chem. 1997, 40, 3109-3118.*
Database Caplus [Online], Chemical Abstracts Service, Columbus, OH, US, Grinev, A.N. et al, "Aminomethyl and aminomethyl derivatives of 5-methoxybenzofuran", Zhurnal Obshchei Khimii, 33(5):1436-1442, Coden: ZOKHA4; ISSN: 0044-460X (1963), retrieved from STN Database, Accession No. 1963:469003, RN 94004-97-4, 94623-08-2, 95220-34-1, Abstract.
Database Caplus [Online], Chemical Abstracts Service, Columbus, OH, US, JP 57 123181 A (Mitsubishi Paper Mills Ltd.), "Manufacture of pyrazole[1,5-a]pyridine derivatives" (Jul. 31, 1982), retrieved from STN Database, Accession No, 1982:618041, Compound with RN 87358-96-7, Abstract.
Abignente, E. et al., "Research on Heterocyclic Compounds. XXIII. Phenyl Derivatives of Fused Imidazole Systems", J. Heterocyclic Chem., vol. 26, pp. 1875-1880 (1989).
Di Chiacchio, A. et al., "Research on Heterocyclic Compounds, Part 40. 2-Phenylimidazo[1,2-*a*]pyridine-3-carboxylic Acid Derivatives: Synthesis and Antiinflammatory Activity", Arch. Pharm. Pharm. Med. Chem., pp. 273-278 (1998).
Katagiri, N. et al., "Studies on Ketene and its Derivatives. Part 119[1]. Reactions of Haloketenes with 2-Arylideneaminopyridines", J. Heterocyclic Chem., vol. 21, pp. 407-412 (1984).
Trapani, G. et al., "Synthesis and Binding Affinity of 2-Phenylimidazo[1,2-*a*]pyridine Derivatives for Both Central and Peripheral Benzodiazepine Receptors. A New Series of High-Affinity and Selective Ligands for the Peripheral Type", Journal of Medicinal Chemistry, vol. 40, No. 19, pp. 3109-3118 (1997).
Cheung, M., "The identification of pyrazolo[1,5-*a*]pyridines as potent p38 kinase inhibitors", Bioorganic & Medicinal Chemistry Letters, vol. 18, pp. 5428-5430 (2008).
Elsner, J. et al., "Bicyclic melatonin receptor agonists containing a ring-junction nitrogen: Synthesis, biological evaluation, and molecular modeling of the putative bioactive conformation", Bioorganic & Medicinal Chemistry, vol. 14, pp. 1949-1958 (2006).
Flint, M. et al., "Selection and Characterization of Hepatitis C Virus Replicons Dually Resistant to the Polymerase and Protease Inhibitors HCV-796 and Boceprevir (SCH 503034)", Antimicrobial Agents and Chemotherapy, vol. 53, No. 2, pp. 401-411 (2009).
Hang, J.Q. et al., "Slow Binding Inhibition and Mechanism of Resistance of Non-nucleoside Polymerase Inhibitors of Hepatitis C Virus", The Journal of Biological Chemistry, vol. 284, No. 23, pp. 15517-15529 (2009).
Kakehi, A. et al., "Preparation of New Nitrogen-Bridged Heterocycles. XIV. Further Investigation of the Desulfurization and the Rearrangement of Pyrido[1,2-*d*]-1,3,4-thiacliazine Intermediates", Chem. Pharm. Bull., vol. 35, No. 1, pp. 156-169 (1987).
Miki, Y. et al., "Acid-Catalyzed Reactions of 3-(Hydroxymethyl)- and 3-(1-Hydroxyethyl)pyrazolo[1,5-*a*]pyridines", J. Heterocyclic Chem., vol. 26, pp. 1739-1745 (1989).

* cited by examiner

Primary Examiner — David K O'Dell
(74) Attorney, Agent, or Firm — James Epperson

(57) ABSTRACT

The disclosure provides compounds of formula I, II, III, IV, and V, including their salts, as well as compositions and methods of using the compounds. The compounds have activity against hepatitis C virus (HCV) and may be useful in treating those infected with HCV.

10 Claims, No Drawings

COMPOUNDS FOR THE TREATMENT OF HEPATITIS C

CROSS-REFERENCE TO RELATED APPLICATIONS

This application claims the benefit of U.S. provisional application Ser. No. 61/096,004 filed Sep. 11, 2008.

BACKGROUND OF THE INVENTION

The disclosure generally relates to the novel compounds of formula I, II, III, IV, and V, including their salts, which have activity against hepatitis C virus (HCV) and are useful in treating those infected with HCV. The disclosure also relates to compositions and methods of using these compounds.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. N. *Engl. J. Med.* 2001, 395, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein, appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV-796, an HCV NS5B inhibitor, showed an ability to reduce HCV RNA levels in patients. The viral RNA levels decreased transiently and then rebounded during dosing when treatment was with the compound as a single agent but levels dropped more robustly when combined with the standard of care which is a form of interferon and ribavirin. The development of this compound was suspended due to hepatic toxicity observed during extended dosing of the combination regimens. U.S. Pat. No. 7,265,152 and the corresponding PCT patent application WO2004/041201 A2 describe compounds of the HCV-796 class.

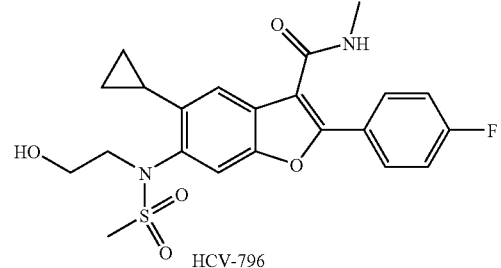

HCV-796

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I, II, III, IV, or V

I

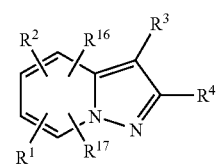

II

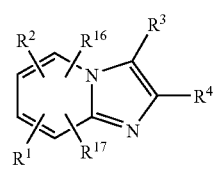

III

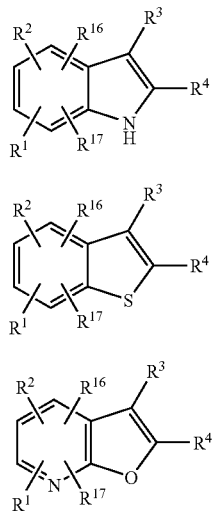

where:

R¹ is halo, alkyl, cycloalkyl, alkoxy, oxazolidinonyl, dioxothiazinyl, R⁵R⁶N,

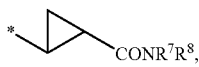

piperidinonyl substituted with 1

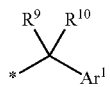

substituent, pyrrolyl substituted with 1

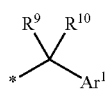

substituent, or phenyl where said phenyl is substituted with 1-2 substituents selected from the group consisting of alkyl, alkoxy, hydroxyalkyl, alkoxyalkyl, carboxy, and CONR⁷R⁸, and where said phenyl is also substituted with 0-2 halo, alkyl, alkoxy, pyridinyl, phenyl or halophenyl substituents;

R² is hydrogen, halo, alkyl, cycloalkyl, alkoxy, or R⁵R⁶N;

R³ is cyano, alkoxycarbonyl, (cycloalkyl)oxycarbonyl, (alkylsulfonyl)aminocarbonyl, CONR¹¹R¹², (R¹³)(R¹⁴)NCONH, triazolyl, thiazolyl, or tetrazolyl;

R⁴ is phenyl substituted with 0-2 halo;

R⁵ is hydrogen, alkyl, cycloalkyl, (cycloalkyl)alkyl, benzyl, alkylcarbonyl, haloalkyl carbonyl, phenyl carbonyl, (alkoxyphenyl)carbonyl, alkylsulfonyl, phenylsulfonyl, (alkoxyphenyl)sulfonyl or (haloalkoxyphenyl)sulfonyl;

R⁶ is hydrogen, alkyl, hydroxyalkyl, or alkoxyalkyl;

or R⁵ and R⁶ taken together with the nitrogen to which they are attached is oxazolidinonyl or dioxothiazinyl;

R⁷ is hydrogen, alkyl,

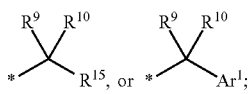

R⁸ is hydrogen or alkyl;
R⁹ is hydrogen or alkyl;
R¹⁰ is hydrogen or alkyl;
or R⁹ and R¹⁰ taken together is ethylene, propylene, butylene, or pentylene;
R¹¹ is hydrogen or alkyl;
R¹² is hydrogen or alkyl;
or R¹¹ and R¹² taken together with the nitrogen to which they are attached is azetidinyl, pyrrolidinyl, piperidinyl, piperazinyl, or morpholinyl;
R¹³ is hydrogen or alkyl;
R¹⁴ is hydrogen or alkyl;
or R¹³ and R¹⁴ taken together with the nitrogen to which they are attached is azetidinyl, pyrrolidinyl, piperidinyl, piperazinyl, or morpholinyl;
R¹⁵ is alkyl or cycloalkyl;
R¹⁶ is hydrogen, halo, alkyl, or alkoxy;
R¹⁷ is hydrogen, halo, alkyl, or alkoxy; and
Ar¹ is isoxazolyl, oxadiazolyl, pyridinyl, pyrimidinyl, or phenyl, and is substituted with 0-1 halo, alkyl, or phenyl substituents;

or a pharmaceutically acceptable salt thereof.

Another aspect of the invention is a compound of formula I, II, III, IV, or V where
R¹ is halo, alkoxy, oxazolidinonyl, dioxothiazinyl, R⁵R⁶N, or phenyl where said phenyl is substituted with 1-2 substituents selected from the group consisting of alkyl, alkoxy, hydroxyalkyl, alkoxyalkyl, and CONR⁷R⁸, and where said phenyl is substituted with 0-1 alkyl substituents;
R² is hydrogen, halo, alkoxy, or R⁵R⁶N;
R³ is cyano, alkoxycarbonyl, (cycloalkyl)oxycarbonyl, (alkylsulfonyl)aminocarbonyl, CONR¹¹R¹², (R¹³)(R¹⁴)NCONH, triazolyl, thiazolyl, or tetrazolyl;
R⁴ is phenyl substituted with 0-2 halo;
R⁵ is alkylsulfonyl;
R⁶ is hydrogen, alkyl, hydroxyalkyl, or alkoxyalkyl;
R⁷ is hydrogen, alkyl, or

R⁸ is hydrogen or alkyl;
R⁹ is hydrogen or alkyl;
R¹⁰ is hydrogen or alkyl;
or R⁹ and R¹⁰ taken together is ethylene, propylene, butylene, or pentylene;
R¹¹ is hydrogen or alkyl;
R¹² is hydrogen or alkyl;
R¹³ is hydrogen or alkyl;
R¹⁴ is hydrogen or alkyl;
or R¹³ and R¹⁴ taken together with the nitrogen to which they are attached is azetidinyl, pyrrolidinyl, piperidinyl, piperazinyl, or morpholinyl;
R¹⁶ is hydrogen;
R¹⁷ is hydrogen; and
Ar¹ is phenyl or pyridinyl;
or a pharmaceutically acceptable salt thereof.

Another aspect of the invention is a compound of formula I, II, III, IV, or V where
R¹ is alkoxy or phenyl where said phenyl is substituted with 1-2 substituents selected from the group consisting of alkyl, alkoxy, hydroxyalkyl, and CONR⁷R⁸, and where said phenyl is also substituted with 0-2 alkyl substituents;
R² is hydrogen, halo or R⁵R⁶N;
R³ is CONR¹³R¹⁴;
R⁴ is phenyl substituted with 0-2 halo;
R⁵ is alkylsulfonyl;
R⁶ is hydrogen or hydroxyalkyl;
R⁷ is hydrogen, alkyl, or

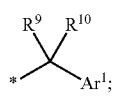

R⁸ is hydrogen;
R⁹ is alkyl;
R¹⁰ is alkyl;
or R⁹ and R¹⁰ taken together is ethylene or propylene;
R¹¹ is hydrogen or alkyl;
R¹² is hydrogen or alkyl;
R¹³ is hydrogen or alkyl;
R¹⁴ is hydrogen or alkyl;
or R¹³ and R¹⁴ taken together with the nitrogen to which they are attached is azetidinyl, pyrrolidinyl, piperidinyl, piperazinyl, or morpholinyl;
R¹⁶ is hydrogen;
R¹⁷ is hydrogen; and
Ar¹ is pyridinyl or phenyl, and is substituted with 0-1 alkyl or phenyl substituents;
or a pharmaceutically acceptable salt thereof.

Another aspect of the invention is a compound of formula I, II, III, IV, or V where
R¹ is cycloalkyl, alkoxy,

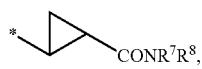

piperidinonyl substituted with 1

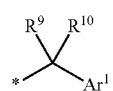

substituent, pyrrolyl substituted with 1

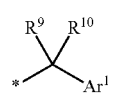

substituent, or phenyl where said phenyl is substituted with 1-2 substituents selected from the group consisting of alkyl, alkoxy, hydroxyalkyl, carboxy, and CONR⁷R⁸, and where said phenyl is also substituted with 0-2 halo, alkyl, alkoxy, pyridinyl, phenyl or halophenyl substituents;
R² is hydrogen, halo, cycloalkyl, or R⁵R⁶N;
R³ is CONR¹¹R¹²;
R⁴ is phenyl substituted with 0-2 halo;

R⁵ is hydrogen, (cycloalkyl)alkyl, benzyl, haloalkylcarbonyl, (alkoxyphenyl)carbonyl, alkylsulfonyl, (alkoxyphenyl)sulfonyl or (haloalkoxyphenyl)sulfonyl;
R⁶ is hydrogen or hydroxyalkyl;
R⁷ is hydrogen, alkyl,

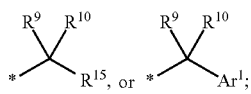

R⁸ is hydrogen;
R⁹ is alkyl;
R¹⁰ is alkyl;
or R⁹ and R¹⁶ taken together is ethylene or propylene;
R¹¹ is alkyl;
R¹² is hydrogen;
R¹⁵ is alkyl or cycloalkyl;
R¹⁶ is hydrogen;
R¹⁷ is hydrogen; and
Ar¹ is isoxazolyl, oxadiazolyl, pyridinyl, pyrimidinyl, or phenyl, and is substituted with 0-1 alkyl or phenyl substituents;
or a pharmaceutically acceptable salt thereof.

Another aspect of the invention is a compound of formula Ia, IIa, IIIa, IVa, or Va where

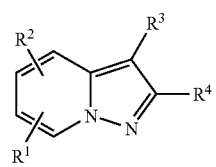

Ia

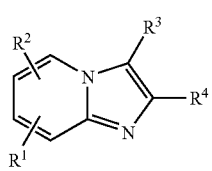

IIa

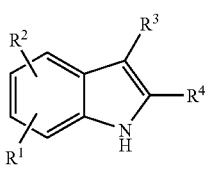

IIIa

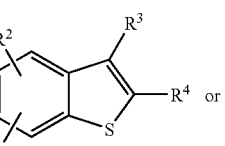

IVa

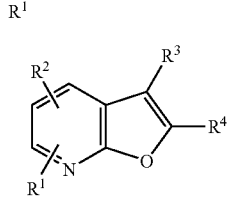

Va where:
R¹ is halo, alkoxy, oxazolidinonyl, dioxothiazinyl, R⁵R⁶N, or phenyl where phenyl is substituted with 1-2 substituents selected from the group consisting of alkyl, alkoxy, hydroxyalkyl, alkoxyalkyl, and CONR⁷R⁸, and where phenyl is substituted with 0-1 alkyl substituent;
R² is hydrogen, halo, alkoxy, or R⁵R⁶N;
R³ is cyano, alkoxycarbonyl, (cycloalkyl)oxycarbonyl, (alkylsulfonyl)aminocarbonyl, CONR¹¹R¹², (R¹³)(R¹⁴)NCONH, triazolyl, thiazolyl, or tetrazolyl;
R⁴ is phenyl substituted with 0-2 halo;
R⁵ is alkylsulfonyl;
R⁶ is hydrogen, alkyl, hydroxyalkyl, or alkoxyalkyl;
R⁷ is hydrogen, alkyl, or

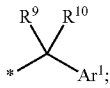

R⁸ is hydrogen or alkyl;
R⁹ is hydrogen or alkyl;
R¹⁰ is hydrogen or alkyl;
or R⁹ and R¹⁰ taken together is ethylene, propylene, butylene, or pentylene;
R¹¹ is hydrogen or alkyl;
R¹² is hydrogen or alkyl;
or R¹¹ and R¹² taken together with the nitrogen to which they are attached is azetidinyl, pyrrolidinyl, piperidinyl, piperazinyl, or morpholinyl; and
R¹³ is hydrogen or alkyl;
R¹⁴ is hydrogen or alkyl;
or R¹³ and R¹⁴ taken together with the nitrogen to which they are attached is azetidinyl, pyrrolidinyl, piperidinyl, piperazinyl, or morpholinyl; and
Ar¹ is phenyl or pyridinyl;
or a pharmaceutically acceptable salt thereof.

Another aspect of the invention is a compound of formula Ia where R¹⁶ and R¹⁷ are hydrogen.

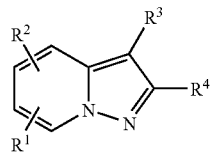

Another aspect of the invention is a compound of formula IIa where R¹⁶ and R¹⁷ are hydrogen.

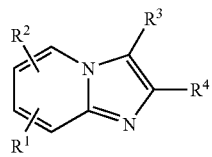

Another aspect of the invention is a compound of formula IIIa where R¹⁶ and R¹⁷ are hydrogen.

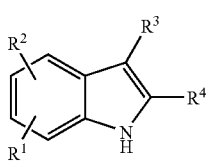

Another aspect of the invention is a compound of formula IVa where R¹⁶ and R¹⁷ are hydrogen.

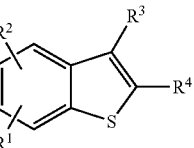

Another aspect of the invention is a compound of formula Va where R¹⁶ and R¹⁷ are hydrogen.

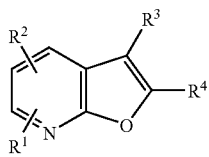

Another aspect of the invention is a compound of formula I, II, III, IV, or V where R¹ is phenyl substituted with 1 CONR⁷R⁸ substituent and 0-2 halo, alkyl, or alkoxy substituents; R² is hydrogen, halo, alkyl, or R⁵R⁶N; R³ is CONR¹¹R¹²; R⁴ is monofluorophenyl; R⁵ is alkylsulfonyl; R⁶ is alkyl; R⁷ is

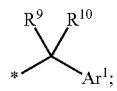

R⁸ is hydrogen; R⁹ is methyl; R¹⁰ is methyl; or R⁹ and R¹⁰ taken together is ethylene; R¹¹ is alkyl; R¹² is hydrogen or alkyl; R¹⁶ is hydrogen; R¹⁷ is hydrogen; and Ar¹ is oxadiazolyl, pyridinyl, pyrimidinyl, or phenyl, and is substituted with 0-1 halo or alkyl substituents; or a pharmaceutically acceptable salt thereof.

Another aspect of the invention is a compound of formula I, II, III, IV, or V where R¹ is phenyl substituted with 1-2 substituents selected from the group consisting of alkyl, alkoxy, hydroxyalkyl, alkoxyalkyl, carboxy, and CONR⁷R⁸, and where said phenyl is also substituted with 0-2 halo, alkyl, alkoxy, pyridinyl, phenyl or halophenyl substituents.

Another aspect of the invention is a compound of formula I, II, III, IV, or V where R¹ is phenyl substituted with 1-2 substituents selected from the group consisting of alkyl, alkoxy, hydroxyalkyl, alkoxyalkyl, and CONR⁷R⁸, and where said phenyl is substituted with 0-1 halo, alkyl, or alkoxy substituents;

Another aspect of the invention is a compound of formula I, II, III, IV, or V where R² is R⁵R⁶N;

Another aspect of the invention is a compound of formula I, II, III, IV, or V where R³ is CONR¹¹R¹².

Another aspect of the invention is a compound of formula I, II, III, IV, or V where $R^4$ is phenyl or monofluorophenyl.

Another aspect of the invention is a compound of formula I, II, III, IV, or V where $Ar^1$ is phenyl.

Any scope of any variable, including $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, or $Ar^1$ can be used independently with the scope of any other instance of a variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R. Substituents which are illustrated by chemical drawing to bond at variable positions on a multiple ring system (for example a bicyclic ring system) are intended to bond to the ring where they are drawn to append. For example, substituents $R^1$ and $R^2$ of formula IV are intended to bond to the benzene ring of formula IV and not to the thiophene ring.

Ethylene means ethanediyl or —$CH_2CH_2$—; propylene means propanediyl or —$CH_2CH_2CH_2$—; butylene means butanediyl or —$CH_2CH_2CH_2CH_2$—; pentylene means pentanediyl or —$CH_2CH_2CH_2CH_2CH_2$—.

Dioxothiazinyl means

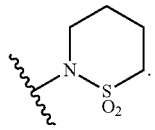

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "$Et_2O$" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2$—; and "TMOF" for trimethylorthoformate.

As shown in Scheme 1, some compounds of the invention may be prepared by coupling an aryl triflate or halide to a substituted phenyl boronic acid that in some examples contains a carboxylic acid or carboxylic acid ester. Other coupling partner, techniques and conditions are known in the art as are other carbon-carbon bond forming reactions. Acids and esters may be converted to amides by methods known in the art.

Scheme 1.
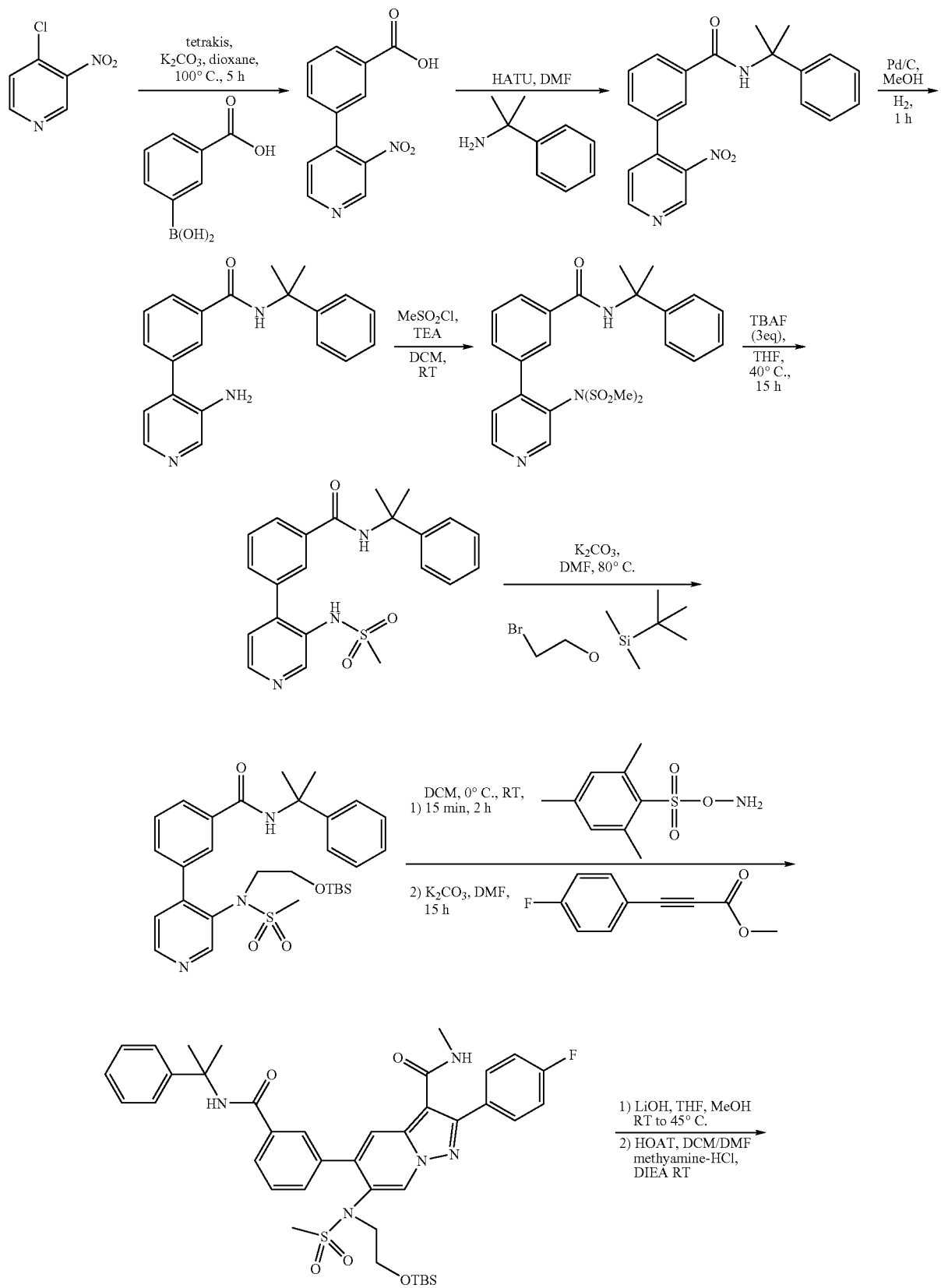

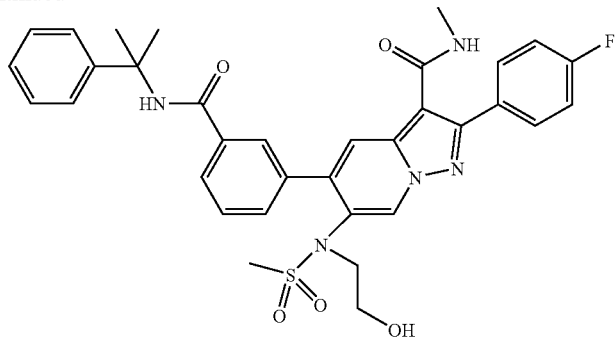
15
Bis-sulfonamides may be selectively hydrolyzed to a monosulfonamide. The monosulfonamide may be alkylated again with either a simple or functionalized alkyl.
Scheme 2.
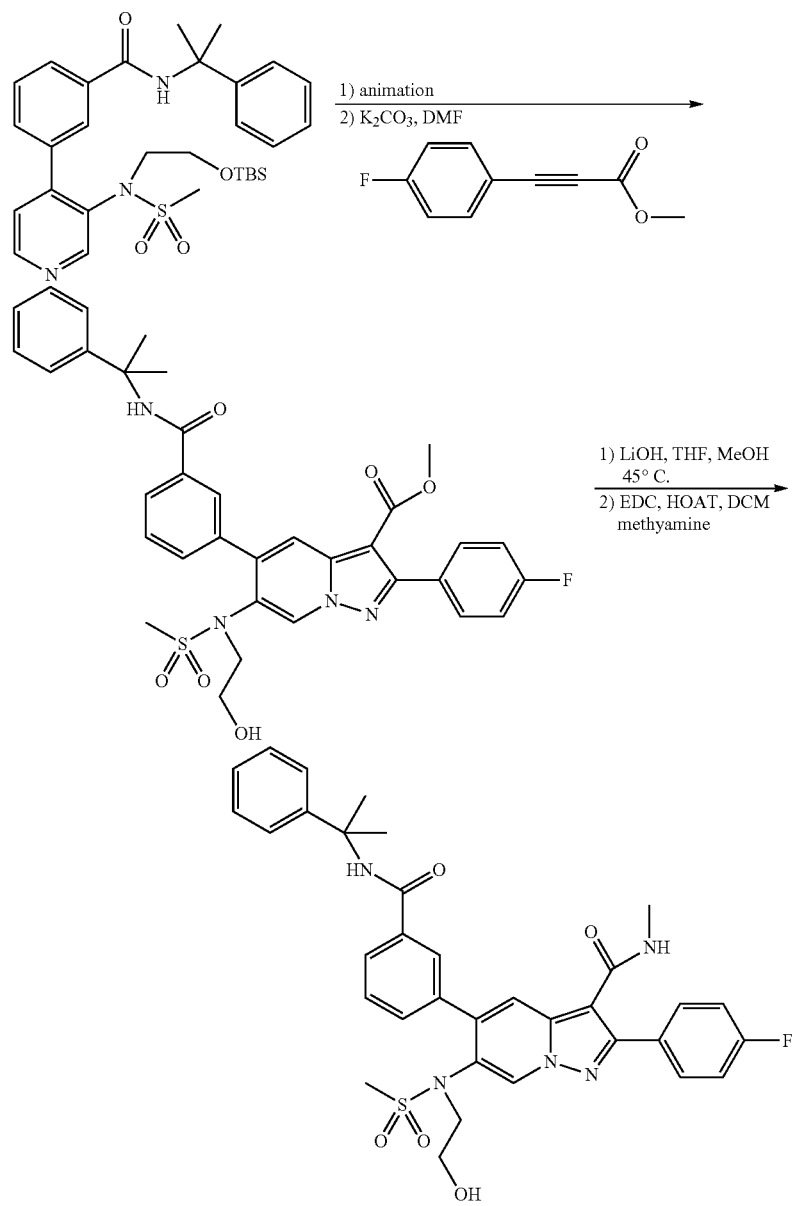

-continued
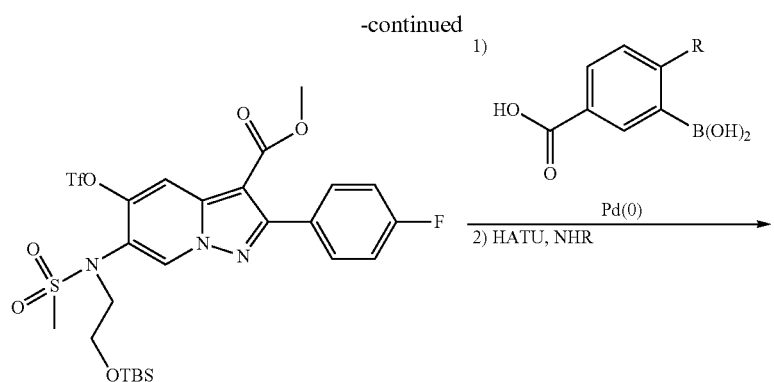
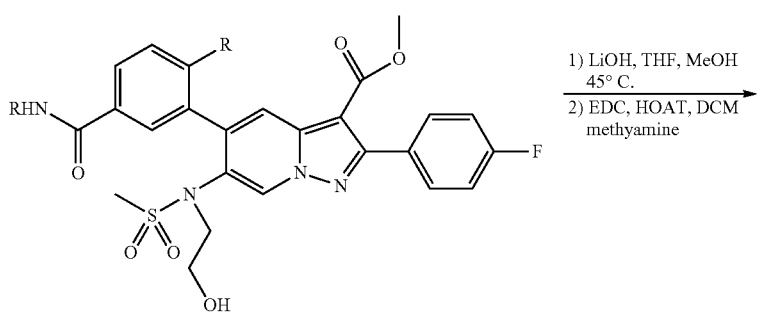
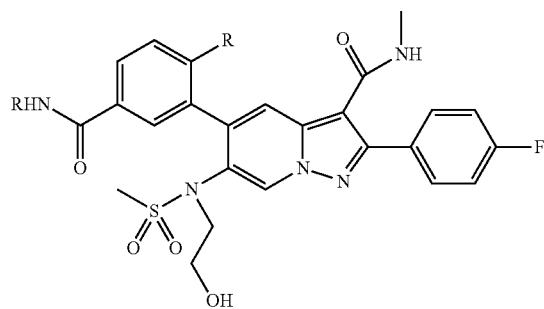
Scheme 3.
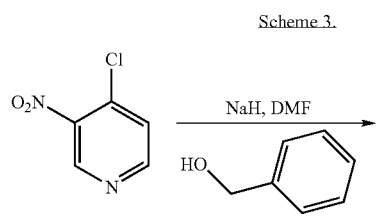
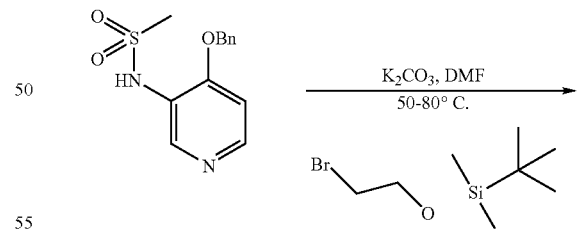
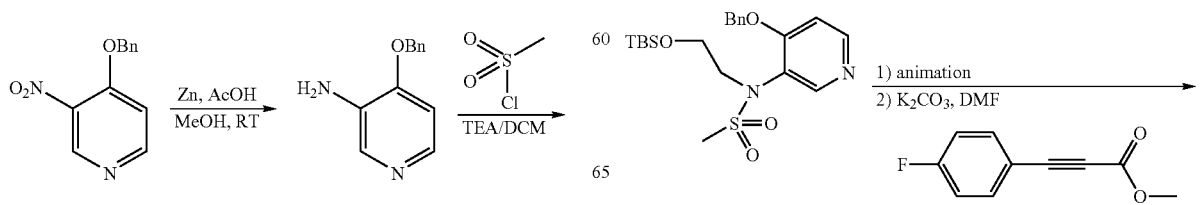

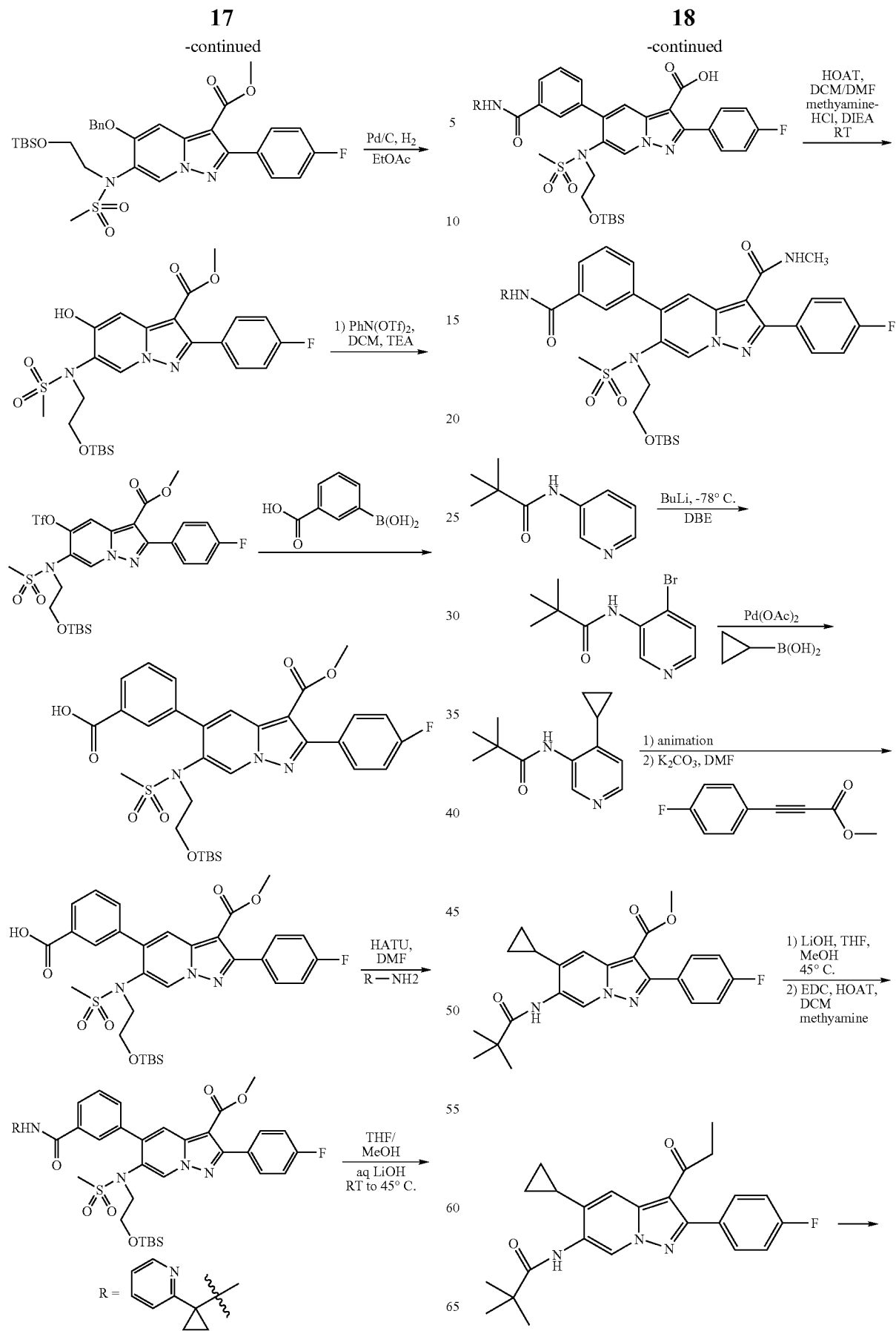

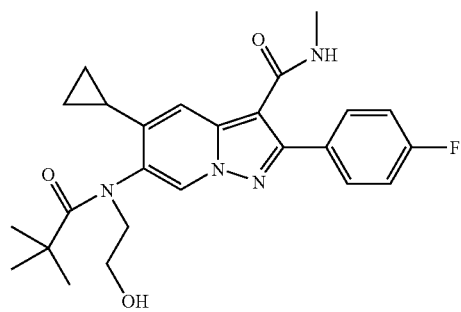
Scheme 4.
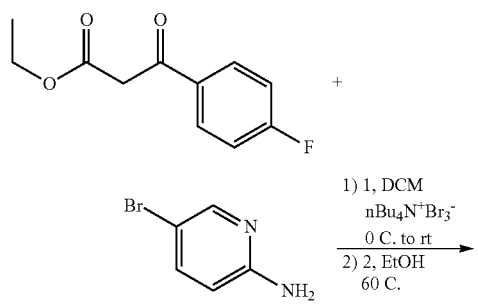
Scheme 5.
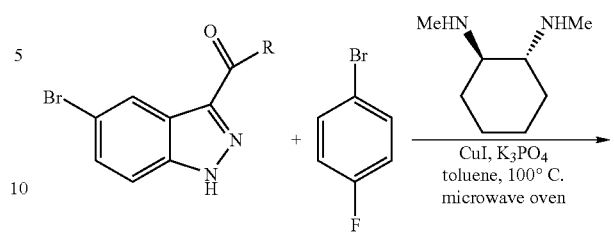
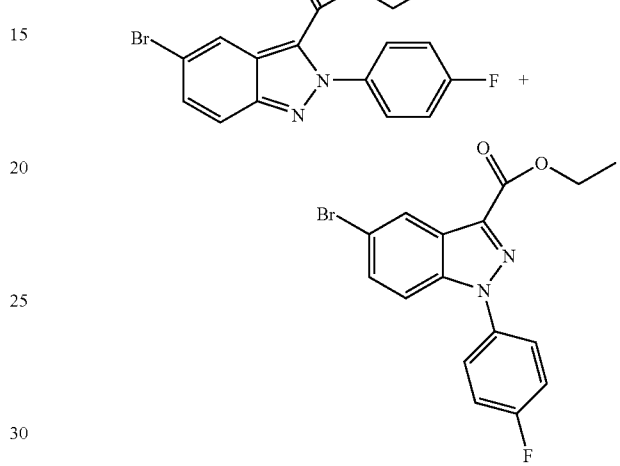
Scheme 6.
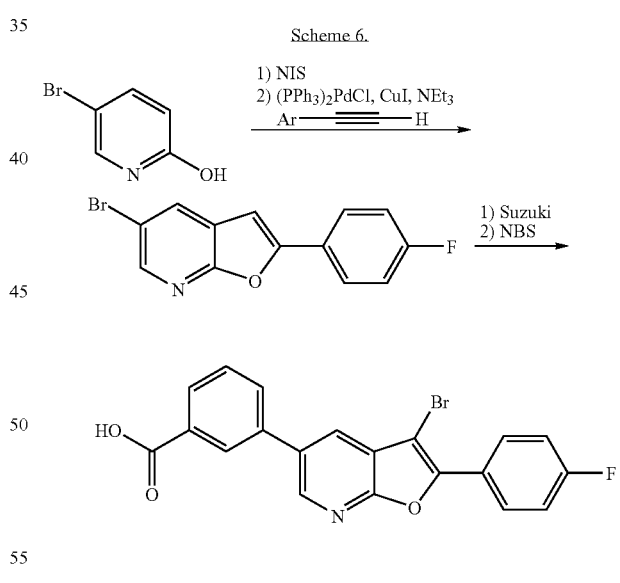
Scheme 7.
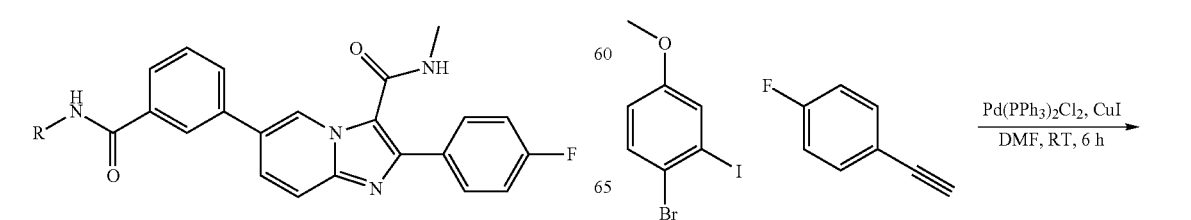

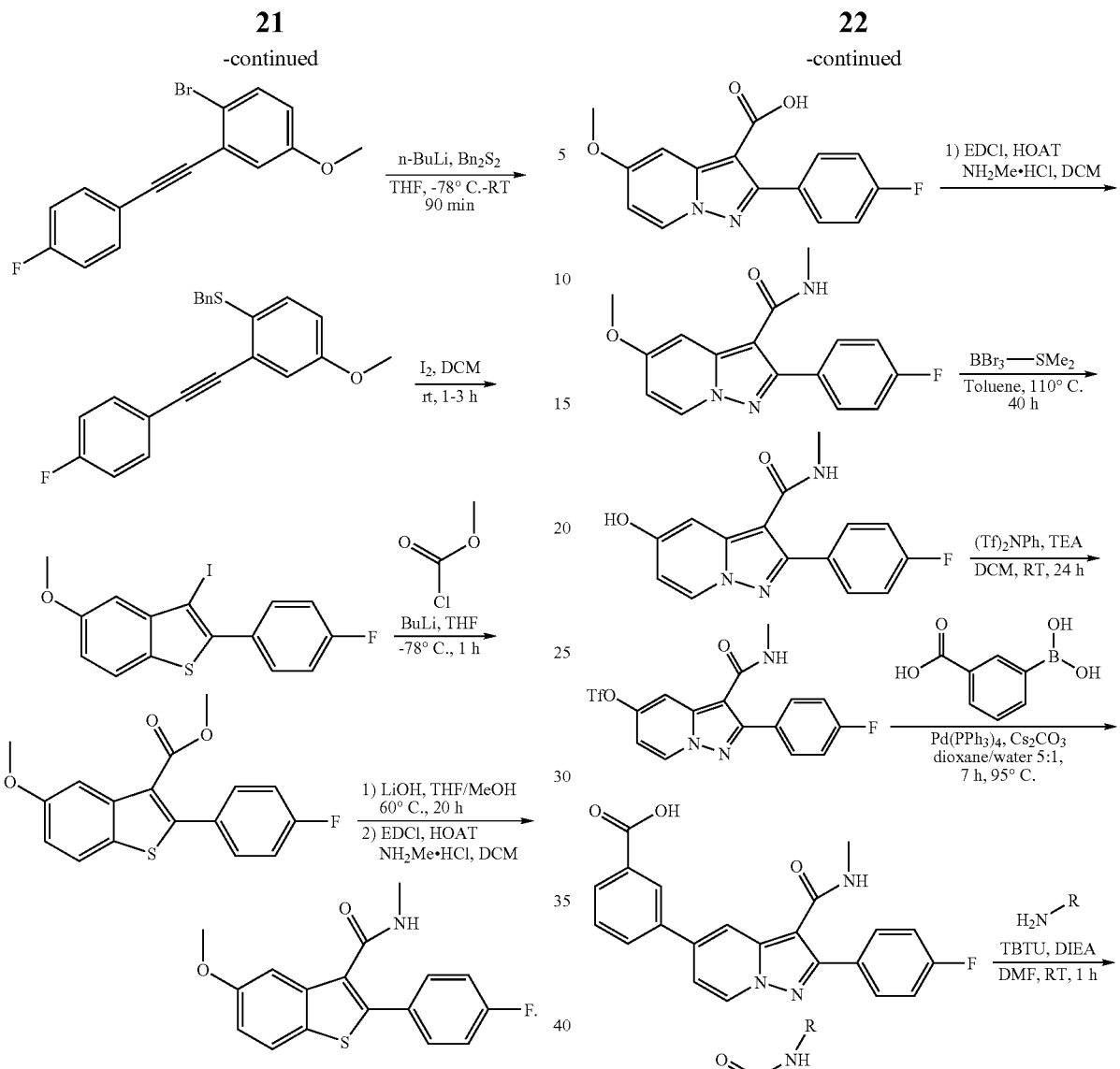
Scheme 8.
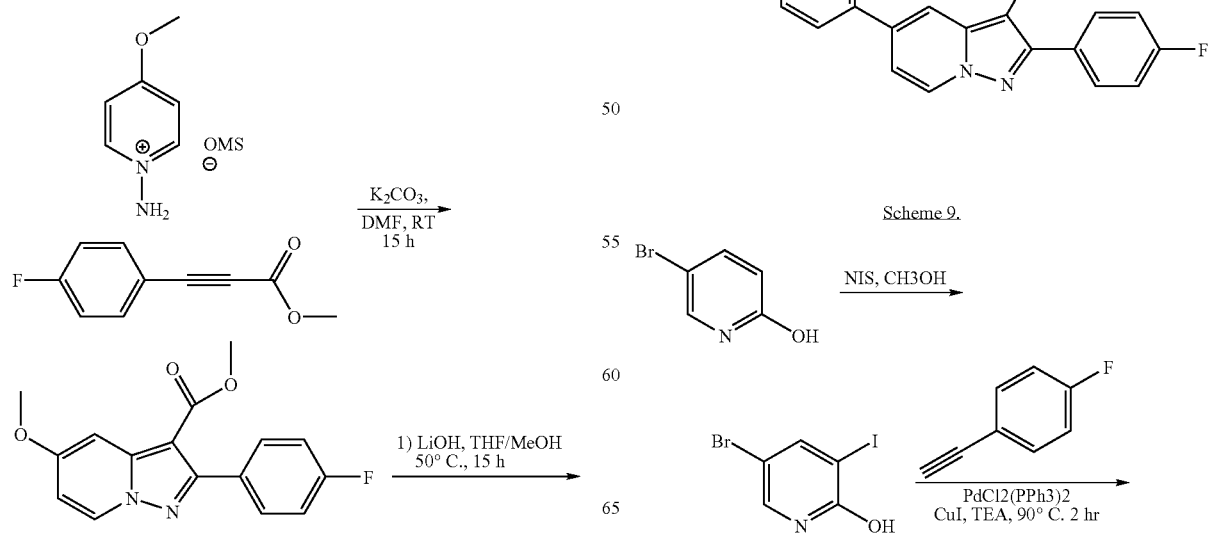
Scheme 9.

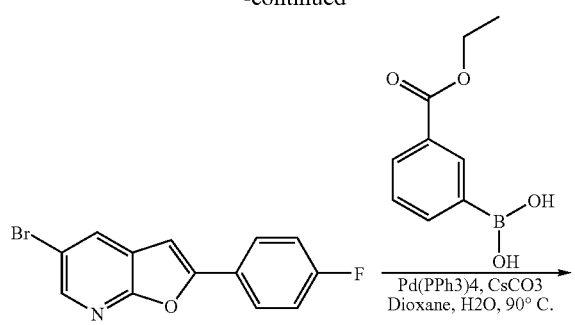
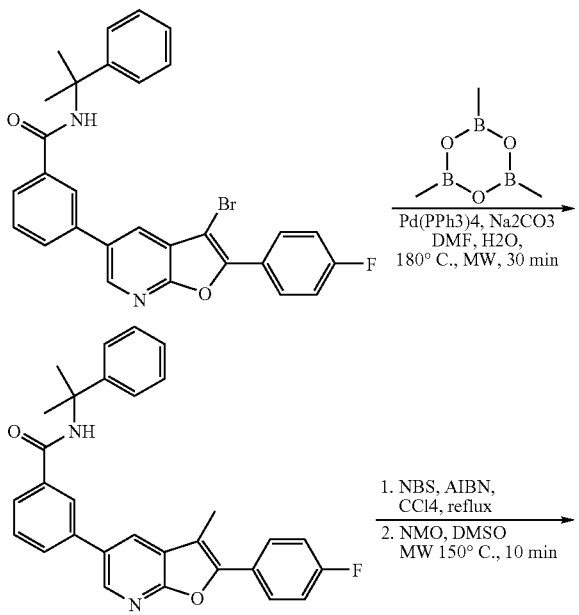
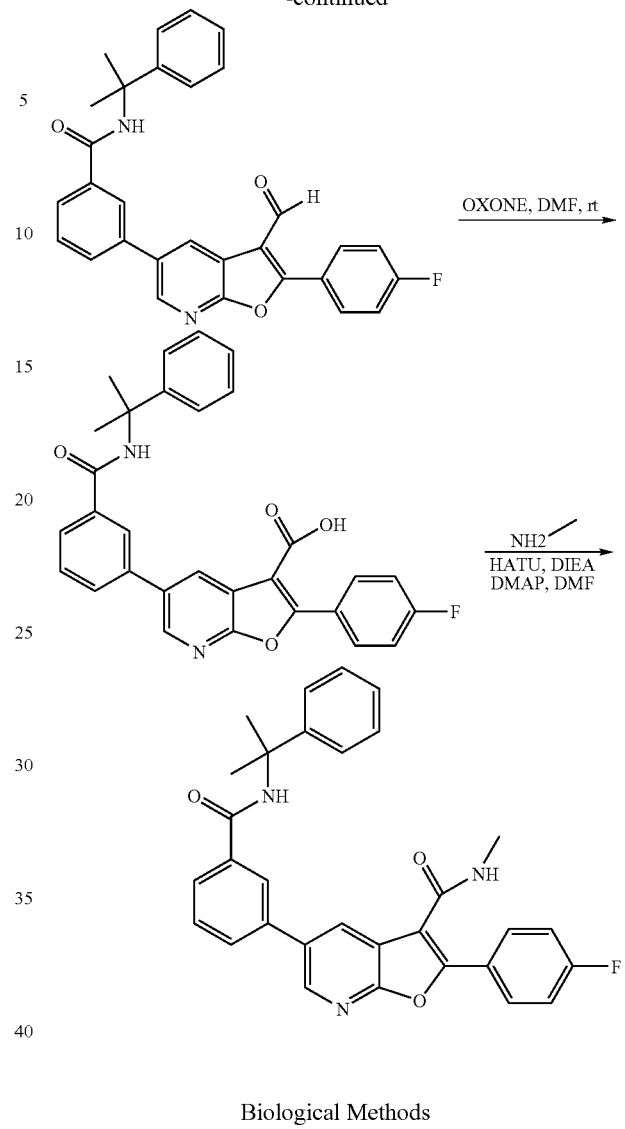

Biological Methods

The compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 μg/ml and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 μm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 μl in 96 well plates (Costar 3912). The assay buffer is composed of 20 mM Hepes, pH 7.5, 2.5 mM KCl, 2.5 mM MgCl2, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 μCi (0.29 μM total UTP). Reactions were initiated by the addition of enzyme, incubated at 30° C. for 60 min, and stopped by adding 25 μl of 50 mM EDTA containing SPA beads (4 μg/μl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 μg/μl beads. Order of addition in the assay: enzyme (14 nM) was added to diluted compound followed by the addition of a mixture of template (0.2 nM), 3H-UTP (0.6 μCi, 0.29 μM), and primer-bound beads, to initiate the reaction; concentrations given are final. Reactions were allowed to proceed for 4 hours at 30° C.

$IC_{50}$ values for compounds were determined using seven different [I]. $IC_{50}$ values were calculated from the inhibition using the formula $y=A+((B-A)/(1+((C/x)^D)))$.

FRET Assay Preparation. To perform the HCV FRET screening assay, 96-well cell culture plates were used. The FRET peptide (Anaspec, Inc.) (Taliani et al., Anal. Biochem. 1996, 290, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with dH2O, NaCl added to 150 mM final, the FRET peptide diluted to 20 μM final from a 2 mM stock.

To prepare plates, HCV replicon cells, with or without a Renilla luciferase reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a $CO_2$ incubator at 37° C.

Assays. Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naïve Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values for a protease inhibitor titration were calculated as the concentration which caused a 50% reduction in FRET or luciferase activity. The two numbers generated for the compound plate, percent cytoxicity and percent activity were used to determine compounds of interest for further analysis.

HCV Replicon Luciferase Reporter Assay

The HCV replicon luciferase assay was developed to monitor the inhibitory effects of compounds described in the disclosure on HCV viral replication. Utilization of a replicon luciferase reporter assay was first described by Krieger et al (Krieger N, Lohmann V, and Bartenschlager R, J. Virol. 75(10):4614-4624 (2001)). HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/ml G418 (Gibco-BRL). Compounds were serially diluted 3 folds in DMSO for a twenty-point titration and subsequently transferred to sterile 384-well tissue-culture treated plates (Corning cat #3571). The plates were then seeded with 50 μl of cells at a density of $3.0 \times 10^3$ cells/well in DMEM containing 4% FCS (final DMSO concentration at 0.5%). After 3 days incubation at 37° C., cells were analyzed for Renilla Luciferase activity using the EnduRen as substrate (Promega cat

E6485). The EnduRen substrate was diluted in DMEM and then added to the plates to a final concentration of 7.5 μM. The plates were incubated for 2 hrs at 37° C. and then read immediately for 30 seconds with Viewlux Imager (PerkinElmer) using a luminescence program. To assess cytotoxicity of compounds, $CC_{50}$ values were generated by multiplexing the EnduRen-containing plates with Cell Titer-Blue (Promega, cat #G8082). 3 μl of Cell-Titer Blue was added to each well and incubated for 8 hrs at 37° C. The fluorescence signal from each well was read, with an excitation wavelength at 525/10 nm and an emission wavelength of 598/10 nm, using the Viewlux Imager.

Representative data for compounds are reported in Tables 1 and 2.

TABLE 1

| Structure | $IC_{50}$ | $EC_{50}$ |
|---|---|---|
| 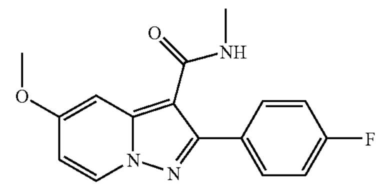 | E | E |
| 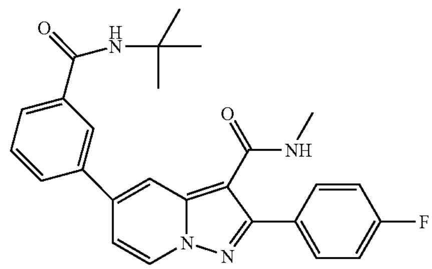 | B | A |
| | A | A |
| | A | A |
| | A | A |

TABLE 1-continued

| Structure | IC$_{50}$ | EC$_{50}$ |
|---|---|---|
| | E | E |
| | E | E |
| | E | E |
| | E | E |
| | E | E |

TABLE 1-continued

| Structure | IC$_{50}$ | EC$_{50}$ |
|---|---|---|
| (structure) | C | C |
| (structure) | E | E |
| (structure) | E | E |
| (structure) | C | C |
| (structure) | E | E |

TABLE 1-continued

| Structure | IC$_{50}$ | EC$_{50}$ |
| --- | --- | --- |
| | E | E |
| | E | E |
| | E | E |
| | E | E |
| | E | E |
| | E | E |
| | E | E |

TABLE 1-continued

| Structure | IC$_{50}$ | EC$_{50}$ |
|---|---|---|
| | E | E |
| | E | E |
| | E | E |
| | A | A |
| | A | A |

TABLE 1-continued

| Structure | IC$_{50}$ | EC$_{50}$ |
|---|---|---|
| | E | E |
| | E | E |
| | E | E |
| | E | E |
| | E | E |
| | E | E |
| | E | E |

TABLE 1-continued

| Structure | IC$_{50}$ | EC$_{50}$ |
|---|---|---|
| | E | E |
| | E | E |
| 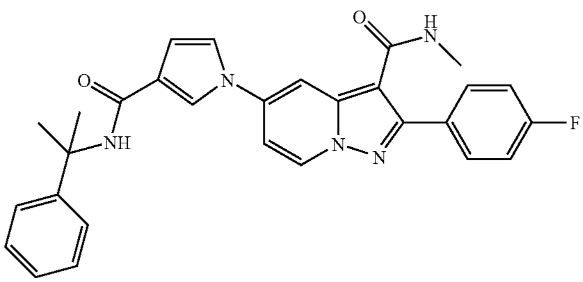 | C | E |
| | A | |
| | A | |
| | E | E |

TABLE 1-continued

| Structure | IC$_{50}$ | EC$_{50}$ |
|---|---|---|
| | B | B |
| | A | A |
| | A | A |
| | B | B |
| 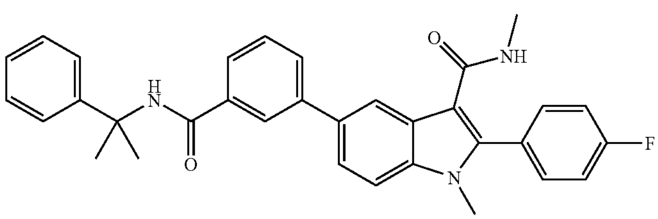 | E | E |
| | A | A |

TABLE 1-continued

| Structure | IC$_{50}$ | EC$_{50}$ |
|---|---|---|
| | A | B |
| 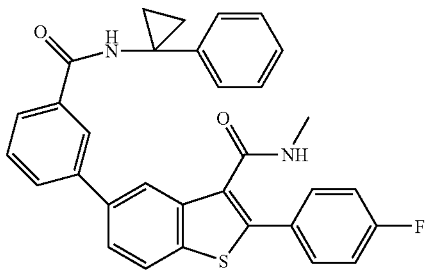 | B | C |
| 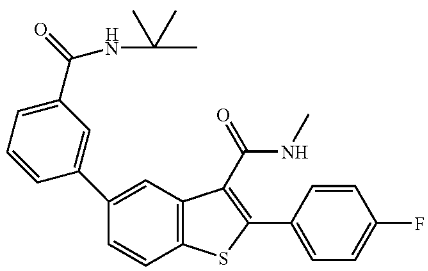 | L | C |
| | A | C |
| | A | A |
| | A | A |

TABLE 1-continued

| Structure | IC$_{50}$ | EC$_{50}$ |
|---|---|---|
| | A | B |
| | A | C |
| | A | A |
| | A | A |
| | A | B |
| | A | A |

TABLE 1-continued

| Structure | IC$_{50}$ | EC$_{50}$ |
|---|---|---|
| (structure) | A | A |
| (structure) | A | A |
| (structure) | A | A |
| (structure) | A | A |
| (structure) | A | A |

TABLE 1-continued

| Structure | IC$_{50}$ | EC$_{50}$ |
|---|---|---|
| *structure* | A | C |
| *structure* | A | A |
| *structure* | A | B |
| *structure* | A | A |
| *structure* | C | C |
| *structure* | A | B |
| *structure* | C | C |

TABLE 1-continued
| Structure | IC$_{50}$ | EC$_{50}$ |
|---|---|---|
| 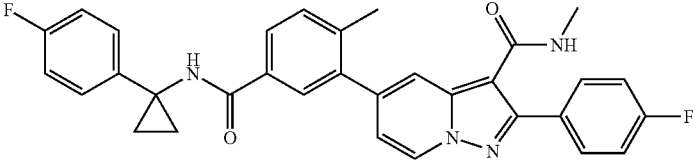 | A | A |
| 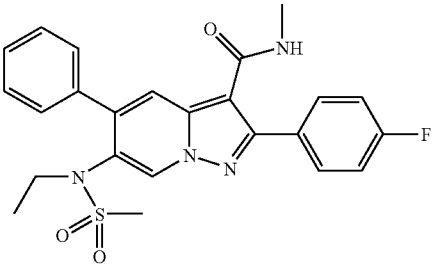 | A | B |
| 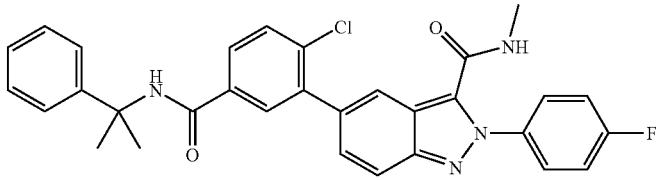 | A | A |
| 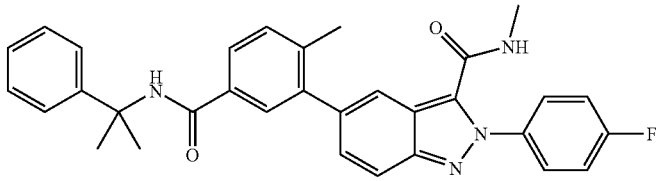 | A | A |
| 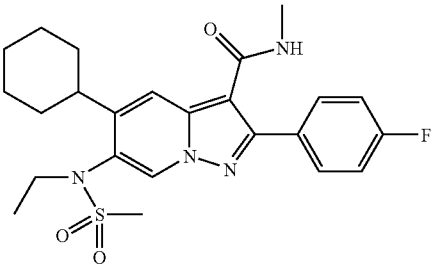 | C | C |
| 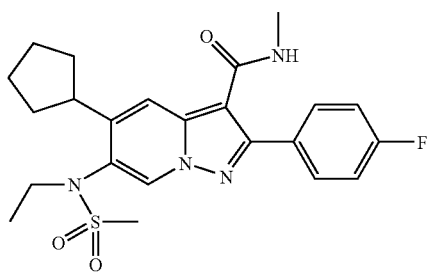 | B | C |
| 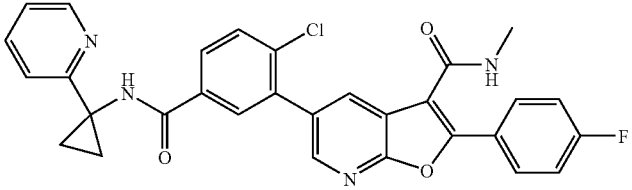 | A | A |

TABLE 1-continued

| Structure | IC$_{50}$ | EC$_{50}$ |
|---|---|---|
| (structure) | A | A |
| (structure) | A | A |
| (structure) | A | A |
| (structure) |  | B |
| (structure) | A | A |
| (structure) | A | A |

TABLE 1-continued

| Structure | IC$_{50}$ M | EC$_{50}$ B |
|---|---|---|
| 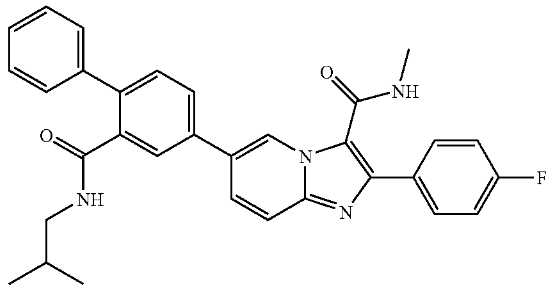 | M | B |
| | | A |
| | A | A |
| | A | A |
| | | B |
| | A | A |

TABLE 1-continued
| Structure | IC$_{50}$ | EC$_{50}$ |
|---|---|---|
| 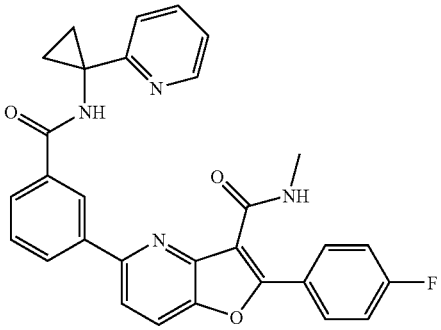 | C | B |
| 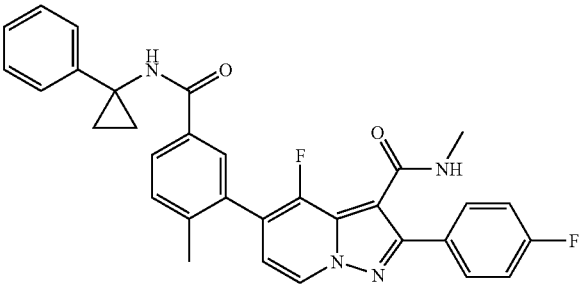 | A | A |
| 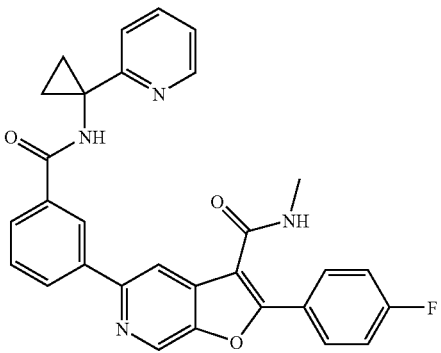 | A | C |
| 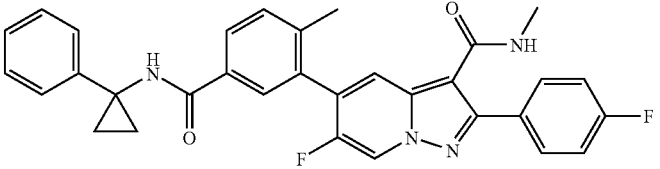 | A | A |
| 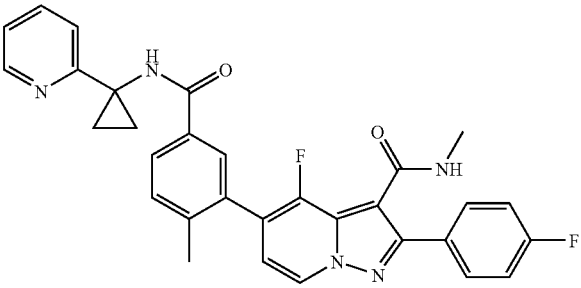 | A | A |

TABLE 1-continued

| Structure | IC$_{50}$ | EC$_{50}$ |
|---|---|---|
| 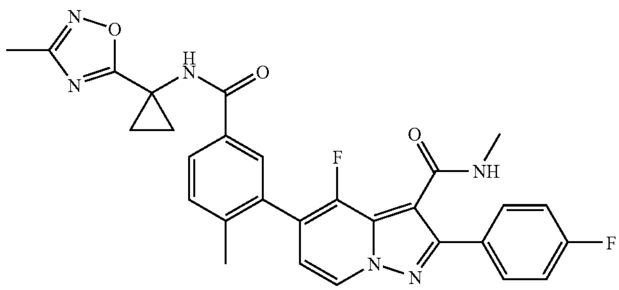 | C | E |
| | A | A |
| | A | A |
| | A | A |
| | A | A |

TABLE 1-continued

| Structure | IC$_{50}$ | EC$_{50}$ |
|---|---|---|
| | | E |
| | | C |
| | | A |
| | | A |
| | | A |

TABLE 1-continued
| Structure | IC$_{50}$ | EC$_{50}$ |
|---|---|---|
| 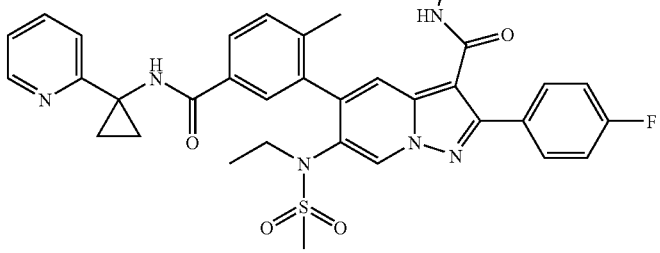 | A | A |
| 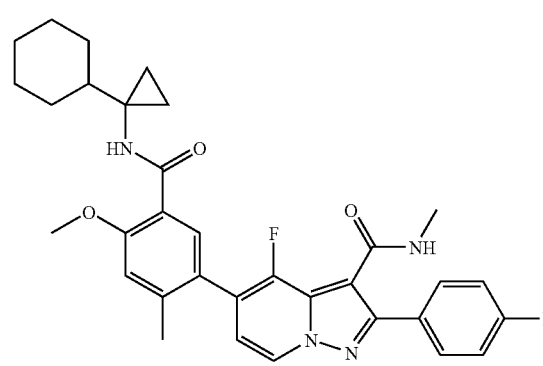 | A | A |
| 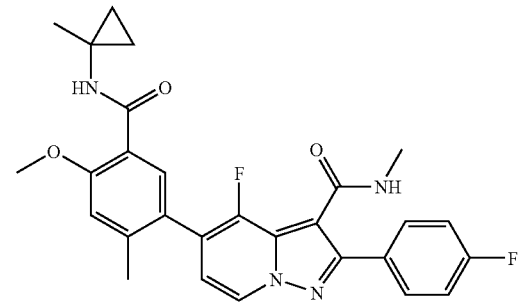 | A | A |
| 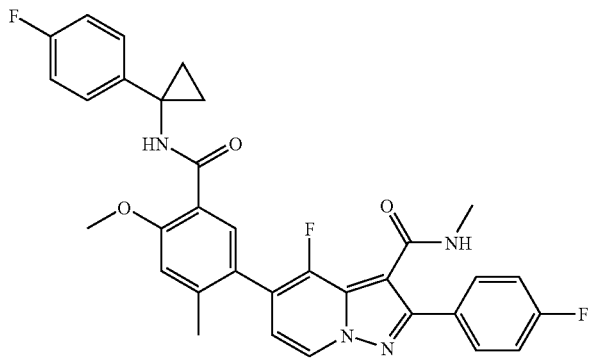 | A | A |

TABLE 1-continued

| Structure | IC$_{50}$ | EC$_{50}$ |
|---|---|---|
| | A | A |
| | A | A |
| | A | A |
| | A | B |

TABLE 1-continued
| Structure | IC$_{50}$ | EC$_{50}$ |
|---|---|---|
| 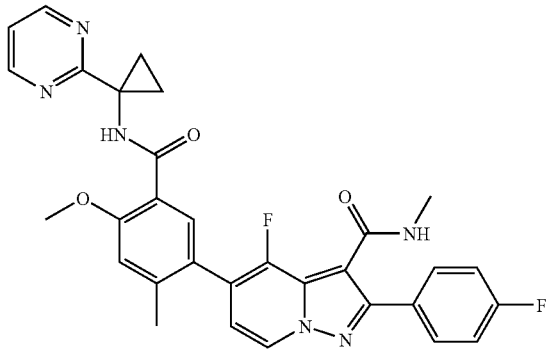 | A | A |
| 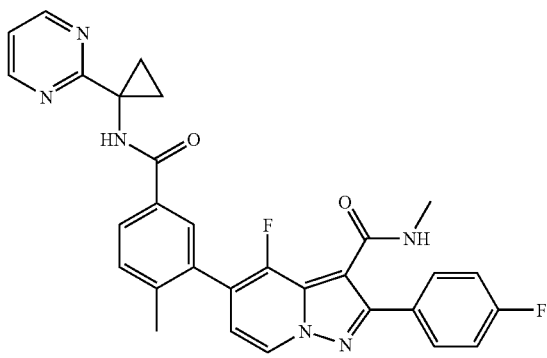 | A | A |
| 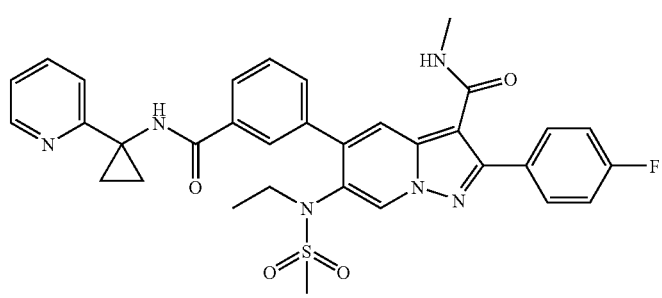 | A | A |
| 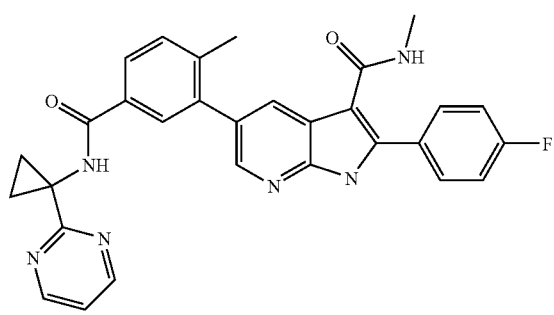 | A | A |

TABLE 1-continued
| Structure | IC$_{50}$ | EC$_{50}$ |
|---|---|---|
| 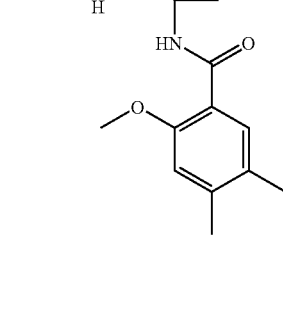 | A | |
| 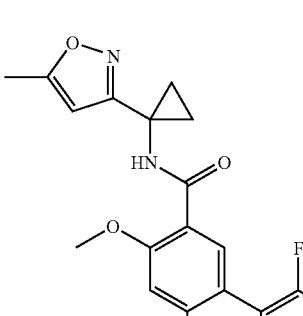 | A | A |
| 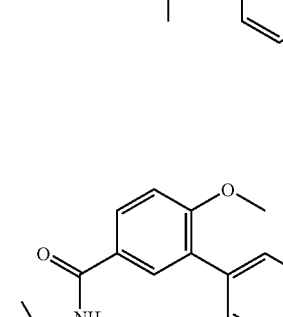 | A | A |
| 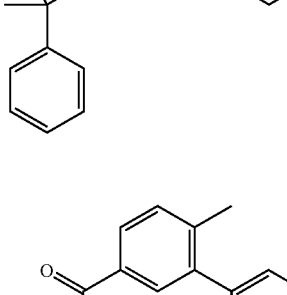 | A | A |

TABLE 1-continued

| Structure | IC$_{50}$ | EC$_{50}$ |
|---|---|---|
| | A | A |
| | A | A |
| 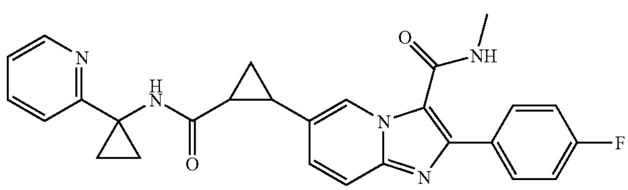 | E | E |
| | | E |
| | | B |
| | | M |

TABLE 1-continued

| Structure | IC$_{50}$ | EC$_{50}$ |
|---|---|---|

A 0.002 or less to 0.25 μM;
B >0.25 μM – <1.0 μM;
C 1.0 μM-10.0 μM;
D >0.67 μM but an exact value was not determined;
E >10.0 μM;
F >0.4 μM; but an exact value was not determined;
G >1.39 μM but an exact value was not determined;
H >0.62 μM but an exact value was not determined;
I >4 μM but an exact value was not determined;
J >3.7 μM but an exact value was not determined;
K >1.23 μM but an exact value was not determined;
L >4.17 μM but an exact value was not determined;
M >0.5 μM but an exact value was not determined.

TABLE 2

| Structure | IC$_{50}$ (μM) | EC$_{50}$ (μM) |
|---|---|---|
| 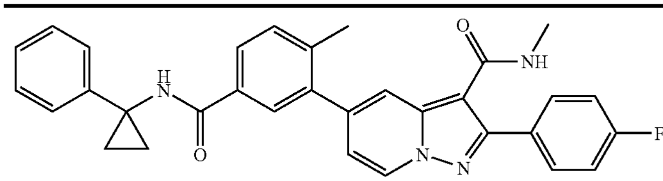 | 4.75E−03 | 2.37E−03 |
| 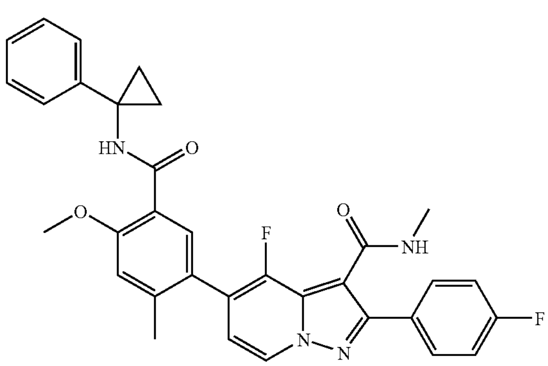 | 0.01 | 3.92E−03 |

TABLE 2-continued

| Structure | IC$_{50}$ (μM) | EC$_{50}$ (μM) |
|---|---|---|
| 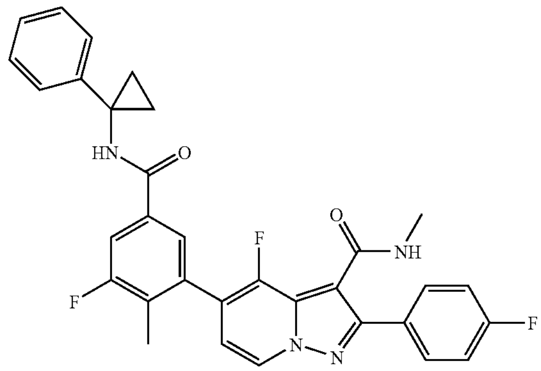 | 0.03 | 4.32E−03 |
| 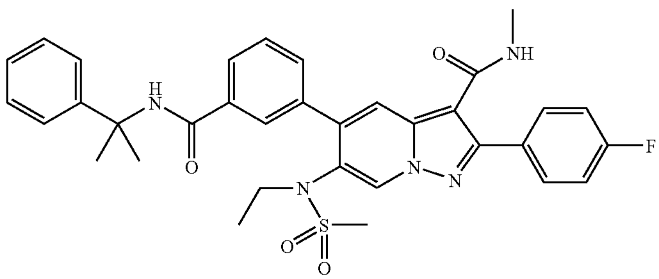 | 9.60E−03 | 5.98E−03 |
| 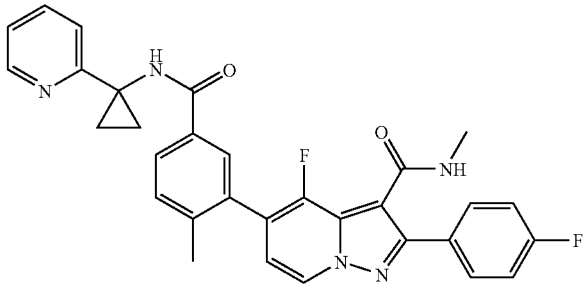 | 5.00E−03 | 7.15E−03 |
| 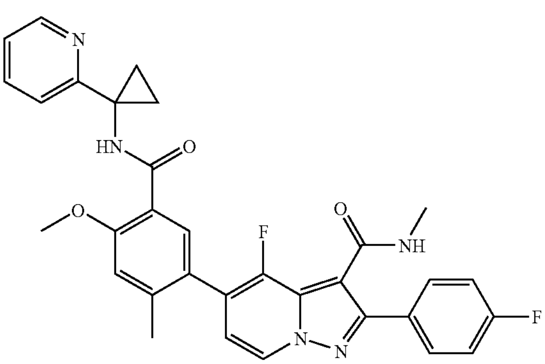 | 0.02 | 8.39E−03 |
| 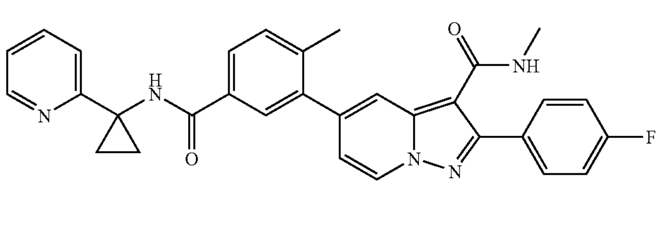 | 5.15E−03 | 0.01 |

TABLE 2-continued
| Structure | IC$_{50}$ (μM) | EC$_{50}$ (μM) |
|---|---|---|
| 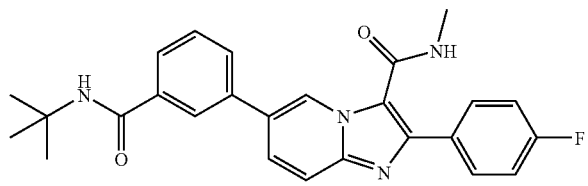 | 0.64 | 0.40 |
| 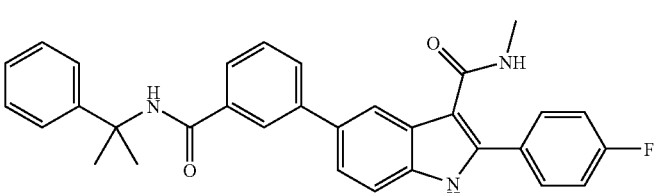 | 0.72 | 0.46 |
| 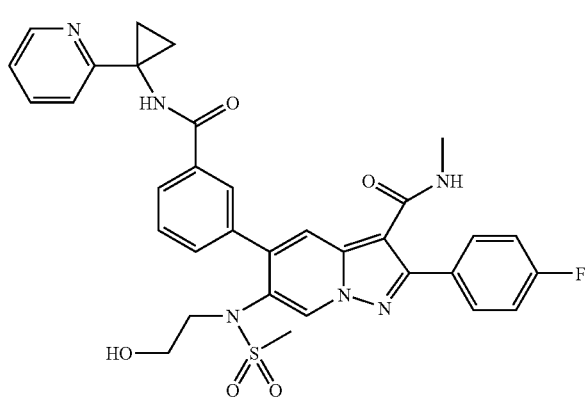 | 0.06 | 1.56 |
| 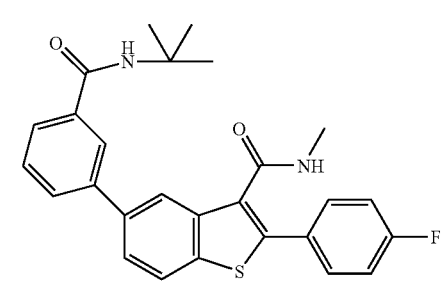 | >4.17 | 1.86 |
| 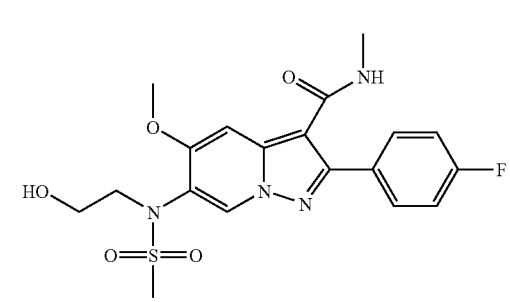 | 2.92 | 3.99 |

TABLE 2-continued

| Structure | IC$_{50}$ (μM) | EC$_{50}$ (μM) |
|---|---|---|
| | | 8.50E–04* |
| 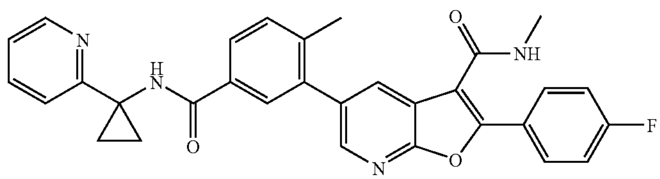 | 4.65E–03 | 2.04E–03* |
| 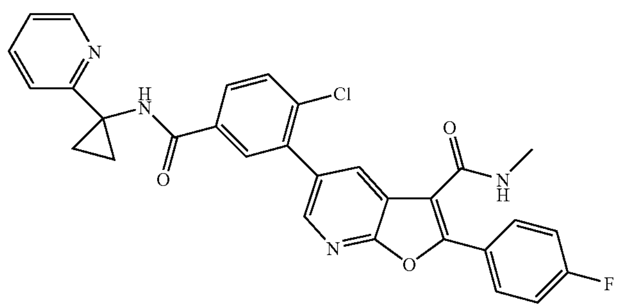 | 5..4E–03 | 1.5E–03* |

*EC$_{50}$ determined using the 384 well plate protocol

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
|---|---|---|
| Omega IFN | IFN-ω | Intarcia Therapeutics |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon - α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |

TABLE 2-continued

| Brand Name | Type of Inhibitor or Target | Source Company |
|---|---|---|
| Intron A and Zadaxin | IFN-α2b/α1-thymosin | RegeneRx Biopharmiceuticals Inc., Bethesda, MD/ SciClone Pharmaceuticals Inc, San Mateo, CA |
| Levovirin | IMPDH inhibitor | Ribapharm Inc., Costa Mesa, CA |
| Viramidine | Ribavirin Prodrug | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | Immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| Batabulin (T67) | β-tubulin inhibitor | Tularik Inc., South San Francisco, CA |
| Merimepodib (VX-497) | IMPDH inhibitor | Vertex Pharmaceuticals Inc., Cambridge, MA |
| Telaprevir (VX-950, LY-570310) | NS3 serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-6865 (XTL-002) | monoclonal antibody | XTL Biopharmaceuticals Ltd., Rehovot, Isreal |
| HCV-796 | NS5B Replicase Inhibitor | Wyeth/Viropharma |
| NM-283 | NS5B Replicase Inhibitor | Idenix/Novartis |
| GL-59728 | NS5B Replicase Inhibitor | Gene Labs/Novartis |
| GL-60667 | NS5B Replicase Inhibitor | Gene Labs/Novartis |
| 2'C MeA | NS5B Replicase Inhibitor | Gilead |
| PSI 6130 | NS5B Replicase Inhibitor | Roche |
| R1626 | NS5B Replicase Inhibitor | Roche |
| SCH 503034 | serine protease inhibitor | Schering Plough |
| NIM811 | Cyclophilin Inhibitor | Novartis |
| Suvus | Methylene blue | Bioenvision |
| Multiferon | Long lasting IFN | Viragen/Valentis |
| Actilon (CPG10101) | TLR9 agonist | Coley |
| Interferon-β | Interferon-β-1a | Serono |
| Zadaxin | Immunomodulator | Sciclone |
| Pyrazolopyrimidine compounds and salts From WO-2005047288 26 May 2005 | HCV Inhibitors | Arrow Therapeutics Ltd. |
| 2'C Methyl adenosine | NS5B Replicase Inhibitor | Merck |
| GS-9132 (ACH-806) | HCV Inhibitor | Achillion/Gilead |

Description of Specific Embodiments

Abbreviations used in the schemes generally follow conventions used in the art. Chemical abbreviations used in the specification and Examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL," for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

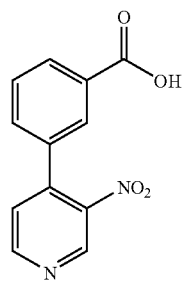

3-(3-nitropyridin-4-yl)benzoic acid. To a degassed mixture containing 4-chloro-3-nitropyridine (3.0 g, 18.9 mmol), 3-boronobenzoic acid (3.7 g, 22.7 mmol), potassium carbonate (5.2 g, 37.8 mmol) and dioxane (189 mL) was added tetrakis(tiphenylphosphine)palladium(0) (0.30 g, 0.28 mmol) in one portion under a nitrogen atmosphere. The mixture was heated with fast stirring at 100° C. for 15 h, cooled to room temperature, filtered and concentrated to afford 3-(3-nitropyridin-4-yl)benzoic acid as a tan residue which was used without further purification. LCMS: retention time: 1.375 min. LC data was recorded on a Shimadzu LC-10AS liquid chromatograph equipped with a Waters-Sunfire, 5u, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% CH$_3$CN/90% H$_2$O/10 mM TFA and solvent B was 10% H$_2$O/90% CH$_3$CN/10 mM TFA. MS data was determined using a Micromass Platform for LC in electrospray mode. m/z 245 (MH$^+$).

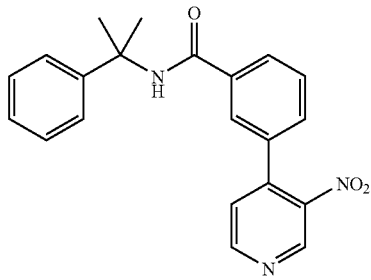

3-(3-nitropyridin-4-yl)-N-(2-phenylpropan-2-yl)benzamide. To a solution containing 2-phenylpropan-2-amine (5.5 g, 40.4 mmol), diisopropylethylamine (18.8 mL, 108 mmol), 3-(3-nitropyridin-4-yl)benzoic acid (8.8 g, 27.0 mmol) and DMF (180 mL) was added HATU (15.4 g, 40.4 mmol) in one portion. The solution was maintained at room temperature for 1 h then concentrated. Purification on silica gel (50-100% ethyl acetate/hexanes, 60 min. gradient) afforded 3-(3-nitropyridin-4-yl)-N-(2-phenylpropan-2-yl)benzamide as a dark yellow, fluffy solid. 1H NMR (400 MHz, DMSO-D6) δ ppm 9.21 (s, 1H), 8.93 (d, J=5.02 Hz, 1H), 8.51 (s, 1H), 7.97 (dt, J=7.03, 1.76 Hz, 1H), 7.92 (s, 1H), 7.73 (d, J=5.02 Hz, 1H), 7.52-7.61 (m, 2H), 7.34-7.41 (m, 2H), 7.27 (t, J=7.65 Hz, 2H), 7.16 (t, J=7.28 Hz, 1H), 1.64-1.72 (m, 6H). LCMS: retention time: 2.060 min. LC data was recorded on a Shimadzu LC-10AS liquid chromatograph equipped with a Phenomenex-Luna, 10u, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 mM where solvent A was 10% methanol/90% H$_2$O/10 mM TFA and solvent B was 10% H$_2$O/90% methanol/10 in M TFA. MS data was determined using a Micromass Platform for LC in electrospray mode. m/z 362 (MH$^+$).

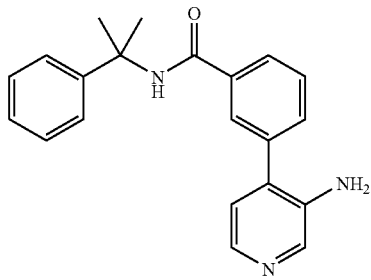

3-(3-aminopyridin-4-yl)-N-(2-phenylpropan-2-yl)benzamide. To a solution containing 3-(3-nitropyridin-4-yl)-N-(2-phenylpropan-2-yl)benzamide (2.0 g, 5.5 mmol) and methanol (18.5 mL) was added 10% Pd/C (1.6 g, 0.76 mmol, wet, 50% water) in one portion under a nitrogen atmosphere. The reaction mixture was stirred for 2 h under an atmosphere of hydrogen gas (balloon), filtered and concentrated to afford 3-(3-aminopyridin-4-yl)-N-(2-phenylpropan-2-yl)benzamide as a pale yellow oil which was used without further purification. 1H NMR (400 MHz, DMSO-D6) δ ppm 8.47 (s, 1H), 8.11 (s, 1H), 7.93 (s, 1H), 7.85 (d, J=4.77 Hz, 1H), 7.81 (ddd, J=7.65, 1.63, 1.51 Hz, 1H), 7.52-7.61 (m, 2H), 7.36-7.41 (m, 2H), 7.24-7.30 (m, 2H), 7.15 (t, J=7.28 Hz, 1H), 7.04 (d, J=5.02 Hz, 1H), 5.15 (s, 2H), 1.64-1.70 (m, 6H). LCMS: retention time: 1.240 min. LC data was recorded on a Shimadzu LC-10AS liquid chromatograph equipped with a Waters-Sunfire, 5u, C18, 4.6×50 mm column using a SPD-10AV UV-Vis detector at a detector wave length of 220 nM. The elution conditions employed a flow rate of 4 ml/min, a gradient of 100% solvent A/0% solvent B to 0% solvent A/100% solvent B, a gradient time of 3 min, a hold time of 1 min, and an analysis time of 4 min where solvent A was 10% CH$_3$CN/90% H$_2$O/10 mM TFA and solvent B was 10% H$_2$O/90% CH$_3$CN/10 mM TFA. MS data was determined using a Micromass Platform for LC in electrospray mode. m/z 332 (MH$^+$).

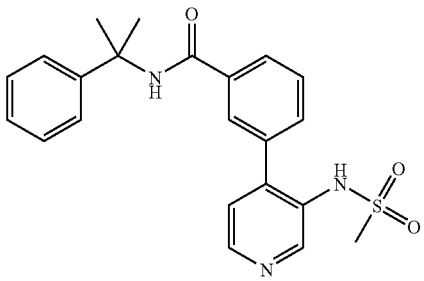

3-(3-(methylsulfonamido)pyridin-4-yl)-N-(2-phenylpropan-2-yl)benzamide. To a solution containing 3-(3-aminopyridin-4-yl)-N-(2-phenylpropan-2-yl)benzamide (1.7 g, 5.1 mmol), triethylamine (5.2 g, 51.3 mmol), and dichloromethane (85 mL) was added methanesulfonylchloride (0.90 mL, 11.3 mmol) in dichloromethane (75 mL) dropwise over 3 min. The solution was maintained at room temperature for 1 h and concentrated to remove all solvent. The residue thus obtained was dissolved in THF (51 mL) and tetrabutylammoniumfluoride (24 mL, 1.0 M in THF) was added in a steady stream via syringe. The solution was maintained at 60° C. for 18 h, concentrated and dissolved in ethyl acetate (75 mL). The solution was washed with water (5×50 mL), washed with brine (50 mL), dried over MgSO4, filtered and concentrated. Purification on silica gel (0-8% methanol/dichloromethane, 60 min gradient) afforded 3-(3-(methylsulfonamido)pyridin-4-yl)-N-(2-phenylpropan-2-yl)benzamide as a pale yellow foam. 1H NMR (500 MHz, DMSO-D6) δ ppm 9.42 (s, 1H), 8.64 (s, 1H), 8.56 (d, J=4.88 Hz, 1H), 8.45 (s, 1H), 8.03 (s, 1H), 7.90 (d, J=7.63 Hz, 1H), 7.71 (d, J=7.63-7.63 Hz, 1H), 7.58 (t, J=7.78 Hz, 1H), 7.49 (d, J=4.88 Hz, 1H), 7.40 (d, J=7.93 Hz, 2H), 7.29 (t, J=7.63 Hz, 2H), 7.17 (t, J=7.17 Hz, 1H), 2.85 (s, 3H), 1.69 (s, 6H). LCMS: retention time: 1.277 min. LC data was recorded on a Shimadzu LC-10AS liquid chromatograph equipped with a Waters-Sunfire, 5u, C18, 4.6×50 mm column using a SPD-10AV LTV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 mM where solvent A was 10% CH₃CN/ 90% H₂O/10 mM TFA and solvent B was 10% H₂O/90% CH₃CN/10 mM TFA. MS data was determined using a Micromass Platform for LC in electrospray mode. m/z 410 (MH⁺).

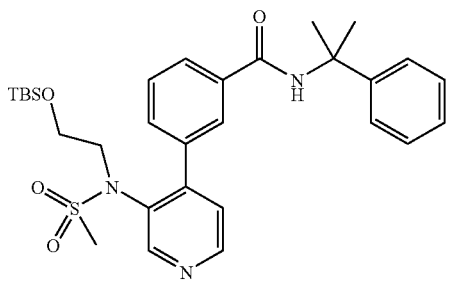

3-(3-(N-(2-(tert-butyldimethylsilyloxy)ethyl)methylsulfonamido)pyridin-4-yl)-N-(2-phenylpropan-2-yl)benzamide. To a mixture containing 3-(3-(methylsulfonamido)pyridin-4-yl)-N-(2-phenylpropan-2-yl)benzamide (0.20 g, 0.50 mmol), potassium carbonate (0.30 g, 2.0 mmol) and DMF (1.6 mL) was added (2-bromoethoxy)(tert-butyl)dimethylsilane (0.10 mL, 0.50 mmol) in a steady stream via syringe. The mixture was stirred at 80° C. for 4 h, cooled to room temperature, filtered, concentrated and purified on silica gel (0-10% methanol/dichloromethane, 60 min gradient) to afford 3-(3-(N-(2-(tert-butyldimethylsilyloxy)ethyl)methylsulfonamido) pyridin-4-yl)-N-(2-phenylpropan-2-yl)benzamide as a brown oil. 1H NMR (500 MHz, DMSO-D6) δ ppm 8.75 (s, 1H), 8.64 (d, J=4.88 Hz, 1H), 8.35 (s, 1H), 7.96 (s, 1H), 7.91 (d, J=7.94 Hz, 1H), 7.77 (d, J=7.93 Hz, 1H), 7.52-7.60 (m, 2H), 7.40 (d, J=7.32 Hz, 2H), 7.28 (t, J=7.63 Hz, 2H), 7.17 (t, J=7.32 Hz, 1H), 3.42-3.50 (m, 1H), 3.25 (s, 3H), 3.03 (s, 1H), 1.64-1.71 (m, 6H), 0.71-0.78 (m, 9H), −0.12-−0.06 (m, 6H). LCMS: retention time: 2.497 min. LC data was recorded on a Shimadzu LC-10AS liquid chromatograph equipped with a Waters-Sunfire, 5u, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% CH₃CN/90% H₂O/10 mM TFA and solvent B was 10% H₂O/ 90% CH₃CN/10 mM TFA. MS data was determined using a Micromass Platform for LC in electrospray mode. m/z 568 (MH⁺).

Methyl 2-(4-fluorophenyl)-6-(N-(2-hydroxyethyl)methylsulfonamido)-5-(3-(2-phenylpropan-2-ylcarbamoyl)phenyl)pyrazolo[1,5-a]pyridine-3-carboxylate. To a cooled solution (0° C., ice bath) containing 3-(3-(N-(2-(tert-butyldimethylsilyloxy)ethyl)methylsulfonamido)pyridin-4-yl)-N-(2-phenylpropan-2-yl)benzamide (0.090 g, 0.12 mmol) and dichloromethane (2 mL) was added 0-(mesitylsulfonyl) hydroxylamine (0.080 g, 0.37 mmol) in dichloromethane (2 mL) quickly, dropwise. The solution was maintained at 0° C. for 15 min, removed from the cooling bath and maintained at ambient temperature for 2 h. The solution was concentrated, dissolved in methanol (5 mL) and re-concentrated to afford 1-amino-3-(N-(2-hydroxyethyl)methylsulfonamido)-4-(3-(2-phenylpropan-2-ylcarbamoyl)phenyl)pyridinium 2,4,6-trimethylbenzenesulfonate as a light yellow foam (470, MH⁺). The product thus obtained was dissolved in DMF (2.4 mL) and added slowly dropwise over 20 mM to a cooled mixture (0° C., ice bath) containing potassium carbonate (0.070 g, 0.50 mmol), methyl 3-(4-fluorophenyl)propiolate (0.030 g, 0.19 mmol) and DMF (2.0 mL). The mixture was kept in the cooling bath with stirring and allowed to proceed for 15 h at ambient temperature. The mixture was filtered and concentrated. Purification on silica gel (0-100% ethyl acetate/ hexanes, 60 min gradient) afforded methyl 2-(4-fluorophenyl)-6-(N-(2-hydroxyethyl)methylsulfonamido)-5-(3-(2-phenylpropan-2-ylcarbamoyl)phenyl)pyrazolo[1,5-a] pyridine-3-carboxylate as a yellow residue. 1H NMR (500 MHz, CHLOROFORM-D) δ ppm 8.72 (s, 1H), 8.24 (s, 1H), 8.16 (s, 1H), 7.97-8.00 (m, 1H), 7.89 (t, J=7.93 Hz, 1H), 7.77-7.84 (m, 2H), 7.50-7.59 (m, 2H), 7.40-7.49 (m, 3H), 7.23-7.33 (m, 3H), 7.12-7.19 (m, 3H), 3.83 (s, 3H), 3.62-3.71 (m, 1H), 3.39-3.46 (m, 1H), 3.30-3.39 (m, 1H), 3.18-323 (m, 3H), 2.63-2.72 (m, 1H), 1.78 (t, J=12.21 Hz, 6H). LCMS: retention time: 2.403 min. LC data was recorded on a Shimadzu LC-10AS liquid chromatograph equipped with a Waters-Sunfire, 5u, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 mM where solvent A was 10% CH₃CN/90% H₂O/10 mM TFA and solvent B was 10% H₂O/ 90% CH₃CN/10 mM TFA. MS data was determined using a Micromass Platform for LC in electrospray mode. m/z 645 (MH⁺).

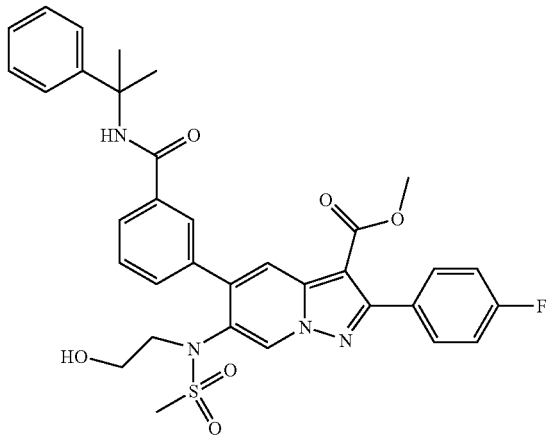

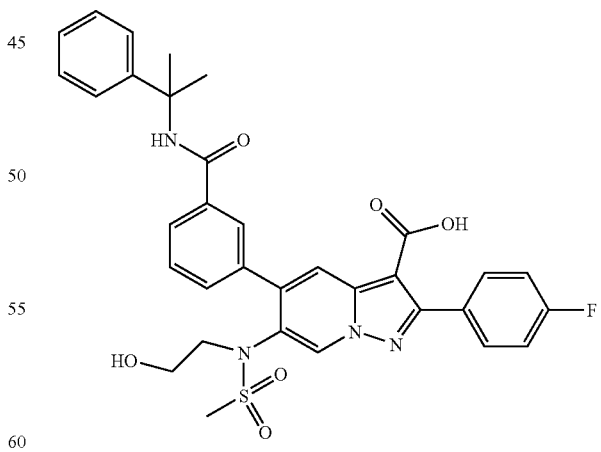

2-(4-fluorophenyl)-6-(N-(2-hydroxyethyl)methylsulfonamido)-5-(3-(2-phenylpropan-2-ylcarbamoyl)phenyl)pyrazolo[1,5-a]pyridine-3-carboxylic acid. To a solution containing methyl 2-(4-fluorophenyl)-6-(N-(2-hydroxyethyl) methylsulfonamido)-5-(3-(2-phenylpropan-2-ylcarbamoyl) phenyl)pyrazolo[1,5-a]pyridine-3-carboxylate (0.021 g, 0.33 mmol), THF (0.20 mL) and methanol (0.13 mL) was added aqueous lithium hydroxide (0.081 mL, 2.0 M). The solution was maintained at room temperature for 20 h, then at 45° C. for 8 h. The solution was adjusted to below pH 4 with aqueous HCl (0.21 mL, 1.0 N) and extracted with ethyl acetate (2×0.50 mL). The combined organic portions were washed with brine (0.50 mL) and concentrated to afford 2-(4-fluorophenyl)-6-(N-(2-hydroxyethyl)methylsulfonamido)-5-(3-(2-phenylpropan-2-ylcarbamoyl)phenyl)pyrazolo[1,5-a]pyridine-3-carboxylic acid as a light yellow residue which was used without further purification. LCMS: retention time: 1.778 min. LC data was recorded on a Shimadzu LC-10AS liquid chromatograph equipped with a Phenomenex-Luna, 10u, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 2 min, a hold time of 1 min, and an analysis time of 3 min where solvent A was 10% methanol/90% H$_2$O/10 mM TFA and solvent B was 10% H$_2$O/90% methanol/10 mM TFA. MS data was determined using a Micromass Platform for LC in electrospray mode. m/z 631 (MH$^+$).

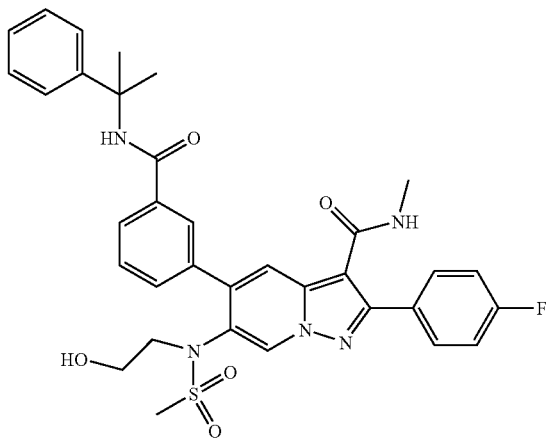

2-(4-fluorophenyl)-6-(N-(2-hydroxyethyl)methylsulfonamido)-N-methyl-5-(3-(2-phenylpropan-2-ylcarbamoyl)phenyl)pyrazolo[1,5-a]pyridine-3-carboxamide. To a solution containing 2-(4-fluorophenyl)-6-(N-(2-hydroxyethyl)methylsulfonamido)-5-(3-(2-phenylpropan-2-ylcarbamoyl)phenyl)pyrazolo[1,5-a]pyridine-3-carboxylic acid (0.021 g, 0.033 mmol), HOAT (0.0050 g, 0.036 mmol), diisopropylethylamine (0.070 mL, 0.40 mmol), methylamine hydrochloride (0.0090 g, 0.13 mmol), dichloromethane (0.70 mL) and DMF (0.14 mL) was added EDCI (0.020 g, 0.10 mmol). The solution was maintained at room temperature for 15 h and concentrated. Purification by preparative HPLC (Waters-Xbridge, 50×100 mm, 5 micron, C18 column; 0.1M ammonium acetate, 0-100% B (B=5% H$_2$O/CH$_3$CN)/A (A=95% H$_2$O/CH$_3$CN), 12 min. gradient) afforded 2-(4-fluorophenyl)-6-(N-(2-hydroxyethyl)methylsulfonamido)-N-methyl-5-(3-(2-phenylpropan-2-ylcarbamoyl)phenyl)pyrazolo[1,5-a]pyridine-3-carboxamide as a white solid. Preparative HPLC retention time 7.4 min. 1H NMR (400 MHz, DMSO-D6) δ ppm 9.13 (s, 1H), 8.28 (s, 1H), 8.05 (s, 1H), 8.00 (q, J=4.27 Hz, 1H), 7.86-7.94 (m, 3H), 7.78 (d, J=8.03 Hz, 1. H), 7.75 (s, 1H), 7.56 (t, J=7.78 Hz, 1H), 7.37-7.42 (m, 2H), 7.25-7.35 (m, 4H), 7.16 (t, J=7.28 Hz, 1H), 4.95 (t, J=4.89 Hz, 1H), 3.58 (dd, J=14.18, 5.65 Hz, 1H), 3.38 (s, 2H), 3.21-3.26 (m, 3H), 2.86-2.96 (m, 1H), 2.75 (d, J=4.52 Hz, 3H), 1.67 (s, 6H). LCMS: retention time: 2.825 min. LC data was recorded on a Shimadzu LC-10AS liquid chromatograph equipped with a Phenomenex-Luna, 10u, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 10% methanol/90% H$_2$O/10 mM TFA and solvent B was 10% H$_2$O/90% methanol/10 mM TFA. MS data was determined using a Micromass Platform for LC in electrospray mode. m/z 644 (MH$^+$).

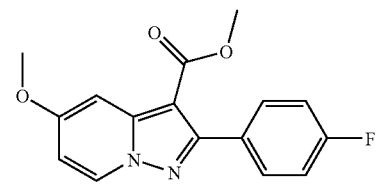

Methyl 2-(4-fluorophenyl)-5-methoxypyrazolo[1,5-a]pyridine-3-carboxylate. Methyl 2-(4-fluorophenyl)-5-methoxypyrazolo[1,5-a]pyridine-3-carboxylate was prepared from 4-methoxypyridine (0.55 g, 3.1 mmol). 1H NMR (500 MHz, CHLOROFORM-D) δ ppm 8.38 (d, J=7.63 Hz, 1H), 7.73-7.77 (m, 1H), 7.73 (d, J=5.49 Hz, 1H), 7.49 (d, J=2.75 Hz, 1H), 7.13 (t, J=8.70 Hz, 2H), 6.66 (dd, J=7.63, 2.75 Hz, 1H), 3.94 (s, 3H), 3.81 (s, 3H). LCMS: retention time: 2.706 min. LC data was recorded on a Shimadzu LC-10AS liquid chromatograph equipped with a Phenomenex-Luna, 10u, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% CH$_3$CN/95% H$_2$O/10 mM ammonium acetate and solvent B was 5% H$_2$O/95% CH$_3$CN/10 mM ammonium acetate. MS data was determined using a Micromass Platform for LC in electrospray mode. m/z 301 (MH$^+$).

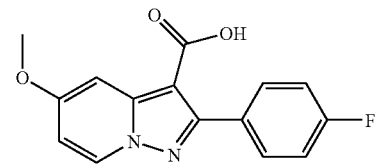

2-(4-fluorophenyl)-5-methoxypyrazolo[1,5-a]pyridine-3-carboxylic acid. 7,2-(4-fluorophenyl)-5-methoxypyrazolo[1,5-a]pyridine-3-carboxylic acid was prepared from methyl 2-(4-fluorophenyl)-5-methoxypyrazolo[1,5-a]pyridine-3-carboxylate (0.99 g, 3.3 mmol). 1H NMR (500 MHz, DMSO-D6) δ ppm 12.30 (s, 1H), 8.70 (d, J=7.32 Hz, 1H), 7.79 (dd, J=8.85, 5.80 Hz, 2H), 7.43 (d, J=2.75 Hz, 1H), 7.27 (t, J=9.00 Hz, 2H), 6.83 (dd, J=7.63, 2.75 Hz, 1H), 3.92 (s, 3H). LCMS: retention time: 1.420 min. LC data was recorded on a Shimadzu LC-10AS liquid chromatograph equipped with a Phenomenex-Luna, 10u, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% CH₃CN/95% H₂O/10 mM ammonium acetate and solvent B was 5% H₂O/95% CH₃CN/10 mM ammonium acetate. MS data was determined using a Micromass Platform for LC in electrospray mode. m/z 287 (MH⁺).

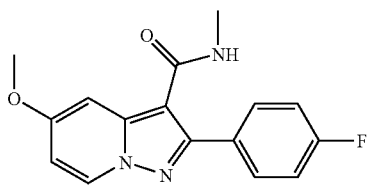

2-(4-fluorophenyl)-5-methoxy-N-methylpyrazolo[1,5-a]pyridine-3-carboxamide. 2-(4-fluorophenyl)-5-methoxy-N-methylpyrazolo[1,5-a]pyridine-3-carboxamide was prepared from 2-(4-fluorophenyl)-5-methoxypyrazolo[1,5-a]pyridine-3-carboxylic acid. (0.88 g, 2.6 mmol). 1H NMR (500 MHz, MeOD) δ ppm 8.42 (d, J=7.63 Hz, 1H), 7.71-7.78 (m, 2H), 7.30 (d, J=2.75 Hz, 1H), 7.25 (t, J=8.85 Hz, 2H), 6.73 (dd, J=7.63, 2.75 Hz, 1H), 3.96 (s, 3H), 2.86 (s, 3H). LCMS: retention time: 1.935 min. LC data was recorded on a Shimadzu LC-10AS liquid chromatograph equipped with a Phenomenex-Luna, 10u, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 mM, and an analysis time of 5 min where solvent A was 5% CH₃CN/95% H₂O/10 mM ammonium acetate and solvent B was 5% H₂O/95% CH₃CN/10 mM ammonium acetate. MS data was determined using a Micromass Platform for LC in electrospray mode. m/z 300 (MH⁺).

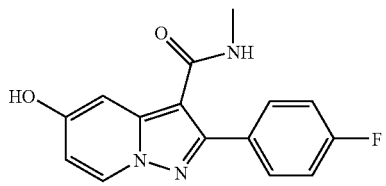

2-(4-fluorophenyl)-5-hydroxy-N-methylpyrazolo[1,5-a]pyridine-3-carboxamide. To a suspension containing 2-(4-fluorophenyl)-5-methoxy-N-methylpyrazolo[1,5-a]pyridine-3-carboxamide (0.30 g, 1.0 mmol) and toluene (10 mL), was added boron tribromide-methylsulfide complex (1.3 g, 4.0 mmol) in one portion. The mixture was stirred in a closed vessel at 105° C. for 40 h under a nitrogen atmosphere, cooled to room temperature and extracted with aqueous sodium hydroxide (3×20 mL, 2.0 M). The combined aqueous extracts were neutralized with aqueous HCl (2.0 M, approx. 60 mL) and extracted with ethyl acetate (3×50 mL). The combined organic portions were dried over MgSO4, filtered and concentrated to afford 2-(4-fluorophenyl)-5-hydroxy-N-methylpyrazolo[1,5-a]pyridine-3-carboxamide as a tan solid which was used without further purification. 1H NMR (500 MHz, DMSO-D6) δ ppm 10.69 (s, 1H), 8.55 (d, J=7.32 Hz, 1H), 7.75-7.82 (m, 2H), 7.50 (d, J=4.58 Hz, 1H), 7.28 (t, J=9.00 Hz, 2H), 7.05 (d, J=2.44 Hz, 1H), 6.65 (dd, J=7.48, 2.59 Hz, 1H), 2.72 (d, J=4.58 Hz, 3H). LCMS: retention time: 1.102 min. LC data was recorded on a Shimadzu LC-10AS liquid chromatograph equipped with a Phenomenex-Luna, 10u, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 10% CH₃CN/90% H₂O/10 mM TFA and solvent B was 10% H₂O/90% CH₃CN/10 mM TFA. MS data was determined using a Micromass Platform for LC in electrospray mode. m/z 285 (MH⁺).

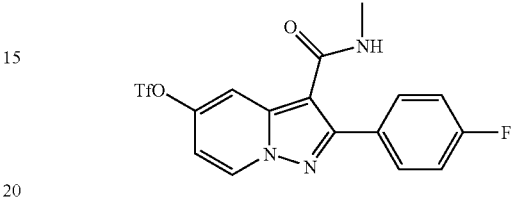

2-(4-fluorophenyl)-3-(methylcarbamoyl)pyrazolo[1,5-a]pyridin-5-yl trifluoromethanesulfonate. A solution containing 2-(4-fluorophenyl)-5-hydroxy-N-methylpyrazolo[1,5-a]pyridine-3-carboxamide (0.25 g, 0.66 mmol), N-Phenylbis(trifluoromethane)sulfonamide (0.35 g, 0.99 mmol), triethylamine (0.46 mL, 3.3 mmol) and dichloromethane (6.5 mL) was maintained at room temperature for 18 h. The solution was further diluted with dichloromethane (10 mL), washed with saturated, aqueous sodium bicarbonate (10 mL), washed with water (5 mL), dried over MgSO4, filtered and concentrated. Purification on silica gel (0-100% ethyl acetate/hexanes, 45 min gradient) afforded 2-(4-fluorophenyl)-3-(methylcarbamoyl)pyrazolo[1,5-a]pyridin-5-yl trifluoromethanesulfonate as a white solid. 1H NMR (500 MHz, DMSO-D6) δ ppm 9.00 (d, J=7.63 Hz, 1H), 7.98 (d, J=2.44 Hz, 1H), 7.94 (d, J=4.58 Hz, 1H), 7.83-7.89 (m, 2H), 7.41 (s, 1H), 7.32-7.38 (m, 2H), 7.25 (dd, J=7.48, 2.90 Hz, 1H), 2.77 (d, J=4.58 Hz, 3H). LCMS: retention time: 2.623 min. LC data was recorded on a Shimadzu LC-10AS liquid chromatograph equipped with a Phenomenex-Luna, 10u, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% CH₃CN/95% H₂O/10 in M ammonium acetate and solvent B was 5% H₂O/95% CH₃CN/10 mM ammonium acetate. MS data was determined using a Micromass Platform for LC in electrospray mode. m/z 418 (MH⁺).

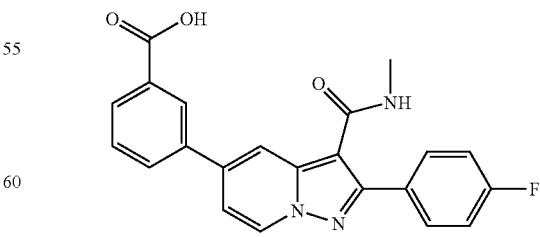

3-(2-(4-fluorophenyl)-3-(methylcarbamoyl)pyrazolo[1,5-a]pyridin-5-yl)benzoic acid. To a degassed solution containing 2-(4-fluorophenyl)-3-(methylcarbamoyl)pyrazolo[1,5-a]pyridin-5-yl trifluoromethanesulfonate (0.19 g, 0.44 mmol), 3-boronobenzoic acid (0.11 g, 0.67 mmol), cesium carbonate (0.22 g, 0.67 mmol), dioxane (3.7 mL) and water (0.74 mL) was added tetrakis(tiphenylphosphine)palladium(0) (0.0090 g, 0.010 mmol). The solution was maintained at 95° C. for 7 h. The solution was cooled to room temperature, concentrated and dissolved in a solution containing water and methanol (1.8/1, 14 mL). The solution was filtered to remove fine particulates and washed with dichloromethane (3×5 mL). The aqueous portion was concentrated to dryness to afford 3-(2-(4-fluorophenyl)-3-(methylcarbamoyl)pyrazolo[1,5-a]pyridin-5-yl)benzoic acid as a pale grey solid which was used without further purification. LCMS: retention time: 1.830 min. LC data was recorded on a Shimadzu LC-10AS liquid chromatograph equipped with a Phenomenex-Luna, 10u, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 10% $CH_3CN$/90% $H_2O$/10 mM TFA and solvent B was 10% $H_2O$/90% $CH_3CN$/10 mM TFA. MS data was determined using a Micromass Platform for LC in electrospray mode. m/z 390 (MH+).

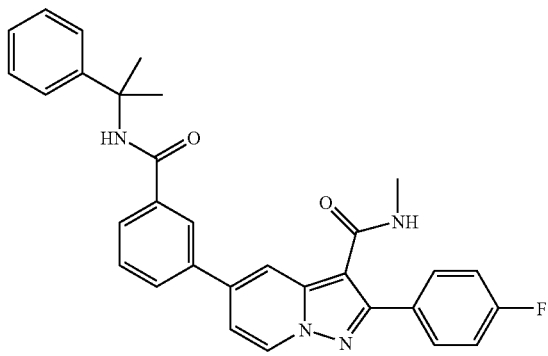

2-(4-fluorophenyl)-N-methyl-5-(3-(2-phenylpropan-2-yl-carbamoyl)phenyl)pyrazolo[1,5-a]pyridine-3-carboxamide.
To a solution containing 2-phenylpropan-2-amine (0.040 g, 0.29 mmol), diisopropylethylamine (0.10 mL, 0.58 mmol), 3-(2-(4-fluorophenyl)-3-(methylcarbamoyl)pyrazolo[1,5-a]pyridin-5-yl)benzoic acid (0.10 g, 0.20 mmol) and DMF (1.3 mL) was added HATU (0.10 g, 0.25 mmol) in one portion. The solution was maintained at room temperature for 1 h and concentrated. The resultant residue was purified using preparative HPLC (Waters-Xbridge, 50×100 mm, 5 micron, C18 column; 0.1M ammonium acetate, 0-100% B (B=5% $H_2O$/$CH_3CN$)/A (A=95% $H_2O$/$CH_3CN$), 12 min. gradient) afforded 2-(4-fluorophenyl)-N-methyl-5-(3-(2-phenylpropan-2-ylcarbamoyl)phenyl)pyrazolo[1,5-a]pyridine-3-carboxamide as a white solid. Preparative HPLC: retention time: 8.0 mM. 1H NMR (500 MHz, DMSO-D6) δ ppm 8.90 (d, J=7.32 Hz, 1H), 8.65 (s, 1H), 8.26 (s, 1H), 8.10 (s, 1H), 8.00 (d, J=6.10 Hz, 2H), 7.88-7.94 (m, 3H), 7.61-7.66 (m, 1H), 7.49 (dd, J=7.17, 1.68 Hz, 1H), 7.42 (d, J=7.63 Hz, 2H), 7.28-7.35 (m, 4H), 7.19 (s, 1H), 2.81 (d, J=4.58 Hz, 3H), 1.72 (s, 6H). LCMS: retention time: 3.325 min. LC data was recorded on a Shimadzu LC-10AS liquid chromatograph equipped with a Phenomenex-Luna, 10u, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 mM, a hold time of 1 min, and an analysis time of 4 min where solvent A was 10% $CH_3OH$/90% $H_2O$/10 mM TFA and solvent B was 10% $H_2O$/90% $CH_3OH$/10 mM TFA. MS data was determined using a Micromass Platform for LC in electrospray mode. m/z 507 (MH+).

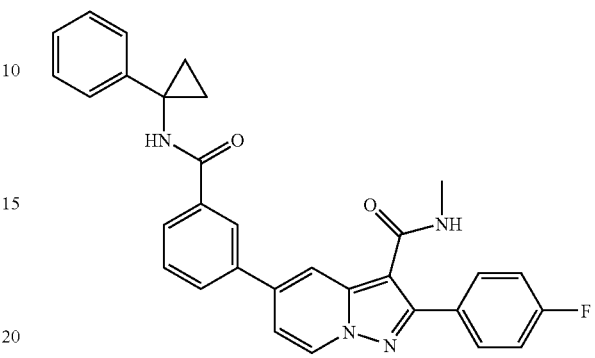

2-(4-fluorophenyl)-N-methyl-5-(3-(1-phenylcyclopropyl-carbamoyl)phenyl)pyrazolo[1,5-a]pyridine-3-carboxamide.
2-(4-fluorophenyl)-N-methyl-5-(3-(1-phenylcyclopropyl-carbamoyl)phenyl)pyrazolo[1,5-a]pyridine-3-carboxamide was prepared from 3-(2-(4-fluorophenyl)-3-(methylcarbamoyl)pyrazolo[1,5-a]pyridin-5-yl)benzoic acid (0.070 g, 0.14 mmol) and 1-phenylcyclopropanamine hydrochloride (0.040 g, 0.20 mmol). 1H NMR (500 MHz, DMSO-D6) δ ppm 9.40 (s, 1H), 8.90 (d, J=7.32 Hz, 1H), 8.35 (s, 1H), 8.11 (d, J=1.22 Hz, 1H), 8.03 (d, J=7.93 Hz, 1H), 7.98 (d, J=7.63 Hz, 2H), 7.90 (dd, J=8.70, 5.65 Hz, 2H), 7.65 (t, J=7.78 Hz, 1H), 7.49 (dd, J=7.32, 1.83 Hz, 1H), 7.28-7.35 (m, 4H), 7.23-7.26 (m, 2H), 7.15-7.20 (m, 1H), 2.81 (d, J=4.58 Hz, 3H), 1.32 (d, J=9.16 Hz, 4H). LCMS: retention time: 3.053 min. LC data was recorded on a Shimadzu LC-10AS liquid chromatograph equipped with a Phenomenex-Luna, 10u, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% $CH_3OH$/90% $H_2O$/10 mM TFA and solvent B was 10% $H_2O$/90% $CH_3OH$/10 mM TFA. MS data was determined using a Micromass Platform for LC in electrospray mode. m/z 505 (MH+).

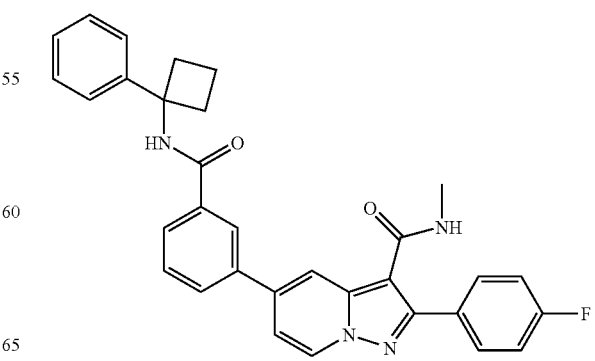

2-(4-fluorophenyl)-N-methyl-5-(3-(1-phenylcyclobutyl-carbamoyl)phenyl)pyrazolo[1,5-a]pyridine-3-carboxamide. 2-(4-fluorophenyl)-N-methyl-5-(3-(1-phenylcyclobutylcar-bamoyl)phenyl)pyrazolo[1,5-a]pyridine-3-carboxamide was prepared from 3-(2-(4-fluorophenyl)-3-(methylcarbamoyl) pyrazolo[1,5-a]pyridin-5-yl)benzoic acid (0.070 g, 0.14 mmol) and 1-phenylcyclobutanamine hydrochloride (0.040 g, 0.20 mmol). 1H NMR (500 MHz, DMSO-D6) δ ppm 9.21 (s, 1H), 8.90 (d, J=7.02 Hz, 1H), 8.30 (s, 1H), 8.09 (s, 1H), 7.96-8.03 (m, 2H), 7.88-7.96 (m, 3H), 7.63 (t, J=7.63 Hz, 1H), 7.53 (d, J=7.63 Hz, 2H), 7.48 (dd, J=7.32, 1.83 Hz, 1H), 7.30-7.37 (m, 4H), 7.21 (t, J=7.32 Hz, 1H), 2.82 (d, J=4.58 Hz, 3H), 2.63-2.71 (m, 2H), 2.58 (ddd, J=12.13, 8.62, 6.10 Hz, 2H), 2.03-2.11 (m, 1H), 1.84-1.93 (m, 1H). LCMS: retention time: 3.225 min. LC data was recorded on a Shimadzu LC-10AS liquid chromatograph equipped with a Phenomenex-Luna, 10u, C18, 4.6×30 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% $CH_3OH$/90% $H_2O$/10 mM TFA and solvent B was 10% $H_2O$/90% $CH_3OH$/10 mM TFA. MS data was determined using a Micromass Platform for LC in electrospray mode. m/z 519 ($MH^+$).

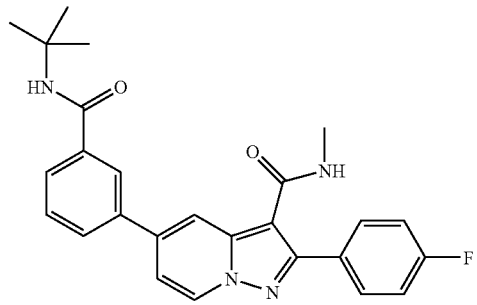

5-(3-(tert-butylcarbamoyl)phenyl)-2-(4-fluorophenyl)-N-methylpyrazolo[1,5-a]pyridine-3-carboxamide. 5-(3-(tert-butylcarbamoyl)phenyl)-2-(4-fluorophenyl)-N-methylpyrazolo[1,5-a]pyridine-3-carboxamide was prepared from 3-(2-(4-fluorophenyl)-3-(methylcarbamoyl)pyrazolo[1,5-a] pyridin-5-yl)benzoic acid (0.10 g, 0.20 mmol) and 2-methylpropan-2-amine (0.020 g, 0.30 mmol). 1H NMR (500 MHz, DMSO-D6) δ ppm 8.88 (d, J=7.02 Hz, 1H), 8.19 (s, 1H), 8.09 (d, J=1.22 Hz, 1H), 7.95-8.02 (m, 3H), 7.87-7.93 (m, 3H), 7.58-7.64 (m, 1H), 7.47 (dd, J=7.32, 1.83 Hz, 1H), 7.33 (t, J=9.00 Hz, 2H), 2.82 (d, J=4.58 Hz, 3H), 1.43 (s, 9H). LCMS: retention time: 2.940 min. LC data was recorded on a Shimadzu LC-10AS liquid chromatograph equipped with a Phenomenex-Luna, 10u, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% $CH_3OH$/90% $H_2O$/10 mM TFA and solvent B was 10% $H_2O$/90% $CH_3OH$/10 mM TFA. MS data was determined using a Micromass Platform for LC in electrospray mode. m/z 445 ($MH^+$).

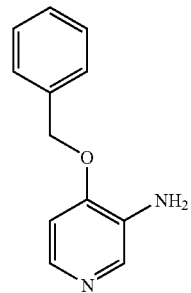

4-(benzyloxy)pyridin-3-amine. To a mixture containing 4-(benzyloxy)-3-nitropyridine (7.2 g, 31.3 mmol) and zinc powder (6.1 g, 91.0 mmol) was added acetic acid (7.2 mL, 7.5 mmol). The mixture was stirred for 6 h at room temperature, filtered and concentrated. The resultant residue was dissolved in ethyl acetate (300 mL), washed with aqueous, saturated ammonium chloride (3×100 mL), washed with brine (100 mL), dried over $MgSO_4$, filtered and concentrated to afford 4-(benzyloxy)pyridin-3-amine as an orange oil which was used without further purification. 1H NMR (500 MHz, DMSO-D6) δ ppm 7.91 (s, 1H), 7.72 (d, J=5.49 Hz, 1H), 7.50 (d, J=7.63 Hz, 2H), 7.41 (t, J=7.32 Hz, 2H), 7.34 (s, 1H), 7.03 (d, J=5.49 Hz, 1H), 5.24 (s, 2H), 5.13 (s, 2H). LCMS: retention time: 1.372 min. LC data was recorded on a Shimadzu LC-10AS liquid chromatograph equipped with a Phenomenex-Luna, 10 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 mM, and an analysis time of 5 min where solvent A was 5% $CH_3CN$/95% $H_2O$/10 mM ammonium acetate and solvent B was 5% $H_2O$/95% $CH_3CN$/10 mM ammonium acetate. MS data was determined using a Micromass Platform for LC in electrospray mode. m/z 201 ($MH^+$).

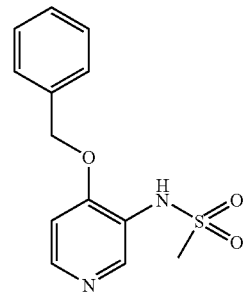

N-(4-(benzyloxy)pyridin-3-yl)methanesulfonamide. To a solution containing 4-(benzyloxy)pyridin-3-amine (6.2 g, 15.8 mmol), triethylamine (11 mL, 79 mmol), and dichloromethane (163 mL) was added methanesulfonylchloride (1.2 mL, 15.8 mmol) in dichloromethane (100 mL) drop wise over 90 min. The solution was maintained at room temperature for 6 h and concentrated to afford N-(4-(benzyloxy) pyridin-3-yl)methanesulfonamide which was used without further purification. LCMS: retention time: 1.305 min. LC data was recorded on a Shimadzu LC-10AS liquid chromatograph equipped with a Waters-Xterra, 5 micron, C18, 4.6×30 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 mM where solvent A was 5% CH₃CN/95% H₂O/10 mM ammonium acetate and solvent B was 5% H₂O/95% CH₃CN/10 mM ammonium acetate. MS data was determined using a Micromass Platform for LC in electrospray mode. m/z 279 (MH⁺).

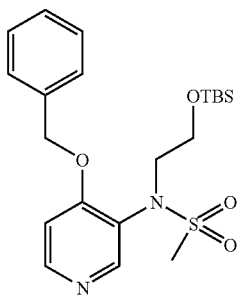

N-(4-(benzyloxy)pyridin-3-yl)-N-(2-(tert-butyldimethylsilyloxy)ethyl)methanesulfonamide. N-(4-(benzyloxy)pyridin-3-yl)-N-(2-(tert-butyldimethylsilyloxy)ethyl)methanesulfonamide was prepared from N-(4-(benzyloxy)pyridin-3-yl)methanesulfonamide (4.6 g, 10.6 mmol). 1H NMR (400 MHz, DMSO-D6) δ ppm 8.40 (d, J=5.77 Hz, 1H), 8.30 (s, 1H), 7.45-7.51 (m, 2H), 7.33-7.43 (m, 3H), 7.26 (d, J=5.77 Hz, 1H), 5.27 (s, 2H), 3.59 (s, 4H), 2.94 (s, 3H), 0.78 (s, 9H), −0.07 (s, 6H). LCMS: retention time: 3.221 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% CH₃CN/95% H₂O/10 mM ammonium acetate and solvent B was 5% H₂O/95% CH₃CN/10 mM ammonium acetate. MS data was determined using a Micromass Platform for LC in electrospray mode. m/z 437 (MH⁺).

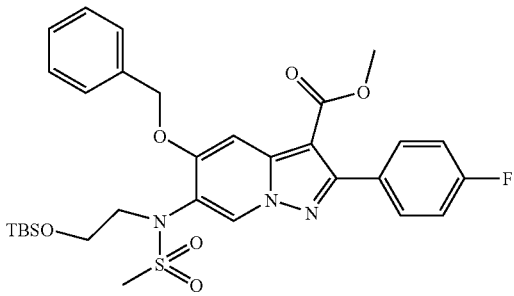

Methyl 6-(N-(2-(tert-butyldimethylsilyloxy)ethyl)methylsulfonamido)-2-(4-fluorophenyl)-5-hydroxypyrazolo[1,5-a]pyridine-3-carboxylate. Methyl 6-(N-(2-(tert-butyldimethylsilyloxy)ethyl)methylsulfonamido)-2-(4-fluorophenyl)-5-hydroxypyrazolo[1,5-a]pyridine-3-carboxylate was prepared from N-(4-(benzyloxy)pyridin-3-yl)-N-(2-(tert-butyldimethylsilyloxy)ethyl)methanesulfonamide (2.4 g, 5.5 mmol). 1H NMR (500 MHz, CHLOROFORM-D) δ ppm 8.50 (s, 1H), 7.69-7.75 (m, 2H), 7.66 (s, 1H), 7.39-7.47 (m, 5H), 7.13 (t, J=8.70 Hz, 2H), 5.24 (s, 2H), 3.81 (s, 4H), 3.74 (s, 3H), 2.87 (s, 3H), 0.80 (s, 9H), −0.01 (s, 6H). LCMS: retention time: 3.190 min. LC data was recorded on a Shimadzu LC-10AS liquid chromatograph equipped with a Waters-Sunfire, 5 micron, C18, 4.6×50 mm column using a SPD-10AV UV-Vis detector at a detector wave length of 254 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% CH₃CN/90% H₂O/10 mM TFA and solvent B was 10% H₂O/90% CH₃CN/10 mM TFA. MS data was determined using a Micromass Platform for LC in electrospray mode. m/z 628 (MH⁺).

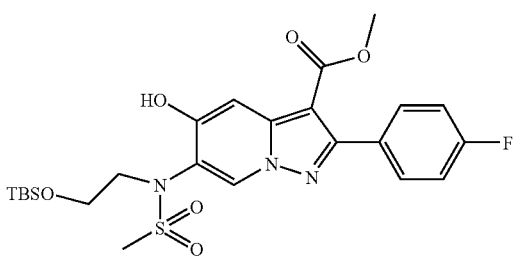

Methyl 2-(4-fluorophenyl)-5-hydroxy-6-(N-(2-hydroxyethyl)methylsulfonamido) pyrazolo[1,5-a]pyridine-3-carboxylate. To a solution containing Methyl 6-(N-(2-(tert-butyldimethylsilyloxy)ethyl)methylsulfonamido)-2-(4-fluorophenyl)-5-hydroxypyrazolo[1,5-a]pyridine-3-carboxylate (0.17 g, 0.27 mmol) and ethyl acetate (5.4 mL) was added 10% Pd/C (0.04 g, 0.04 mmol Pd) in one portion under a nitrogen atmosphere. The reaction mixture was stirred for 2 h under an atmosphere of hydrogen gas (balloon), filtered and concentrated to afford Methyl 2-(4-fluorophenyl)-5-hydroxy-6-(N-(2-hydroxyethyl)methylsulfonamido) pyrazolo[1,5-a]pyridine-3-carboxylate as a light yellow oil. ¹H NMR (400 MHz, DMSO-D6) δ ppm 11.71 (s, 1H), 8.68 (s, 1H), 7.73 (ddd, J=11.98, 5.33, 2.76 Hz, 2H), 7.46 (s, 1H), 7.25-7.31 (m, 2H), 3.70 (s, 7H), 3.11-3.14 (m, 3H), 0.74 (s, 9H), −0.06-−0.04 (m, 6H). LCMS: retention time: 2.750 min. LC data was recorded on a Shimadzu LC-10AS liquid chromatograph equipped with a Waters-Sunfire, 5 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% CH₃CN/90% H₂O/10 mM TFA and solvent B was 10% H₂O/90% CH₃CN/10 mM TFA. MS data was determined using a Micromass Platform for LC in electrospray mode. m/z 538 (MH⁺).

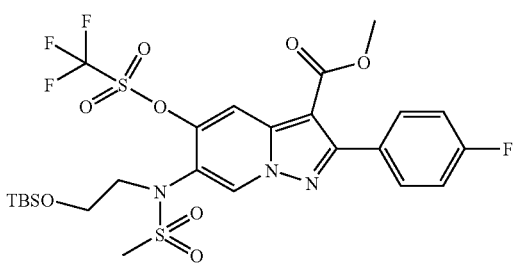

Methyl 6-(N-(2-(tert-butyldimethylsilyloxy)ethyl)methylsulfonamido)-2-(4-fluorophenyl)-5-(trifluoromethylsulfonyloxy)pyrazolo[1,5-a]pyridine-3-carboxylate. Methyl 6-(N-(2-(tert-butyldimethylsilyloxy)ethyl)methylsulfonamido)-2-(4-fluorophenyl)-5-(trifluoromethylsulfonyloxy) pyrazolo[1,5-a]pyridine-3-carboxylate was prepared from Methyl 2-(4-fluorophenyl)-5-hydroxy-6-(N-(2-hydroxyethyl)methylsulfonamido) pyrazolo[1,5-a]pyridine-3-carboxylate (0.15 g, 0.29 mmol). LCMS: retention time: 3.200 min. LC data was recorded on a Shimadzu LC-10AS liquid chromatograph equipped with a Waters-Sunfire, 5 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% $CH_3CN$/90% $H_2O$/10 mM TFA and solvent B was 10% $H_2O$/90% $CH_3CN$/10 mM TFA. MS data was determined using a Micromass Platform for LC in electrospray mode. m/z 670 ($MH^+$).

Methyl 2-(4-fluorophenyl)-6-(N-(2-hydroxyethyl)methylsulfonamido)-5-(3-(1-(pyridin-2-yl)cyclopropylcarbamoyl)phenyl)pyrazolo[1,5-a]pyridine-3-carboxylate. Methyl 2-(4-fluorophenyl)-6-(N-(2-hydroxyethyl)methylsulfonamido)-5-(3-(1-(pyridin-2-yl)cyclopropylcarbamoyl)phenyl) pyrazolo[1,5-a]pyridine-3-carboxylate was prepared from 3-(2-(4-fluorophenyl)-6-(N-(2-hydroxyethyl)methylsulfonamido)-3-(methoxycarbonyl)pyrazolo[1,5-a]pyridin-5-yl)benzoic acid (0.05 g, 0.10 mmol) and 1-(pyridin-2-yl)cyclopropanamine dihydrochloride (0.03 g, 0.15 mmol). LCMS: retention time: 1.473 mM. LC data was recorded on a Shimadzu LC-10AS liquid chromatograph equipped with a Waters-Sunfire, 5 micron, C18, 4.6×50 mm column using a SPD-10AV UV-Vis detector at a detector wave length of 254 nM. The elution conditions employed a flow rate of 4 mL/min, a gradient of 100% solvent A/0% solvent B to 0% solvent A/100% solvent B, a gradient time of 3 min, a hold time of 1 mM, and an analysis time of 4 min where solvent A was 10% $CH_3CN$/90% $H_2O$/10 mM TFA and solvent B was 10% $H_2O$/90% $CH_3CN$/10 mM TFA. MS data was determined using a Micromass Platform for LC in electrospray mode. m/z 644 ($MH^+$).

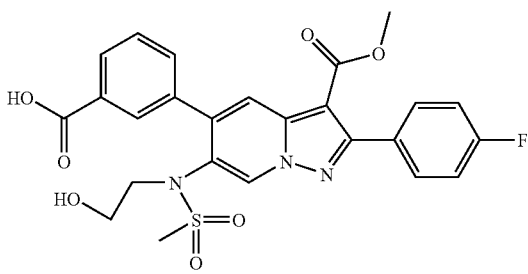

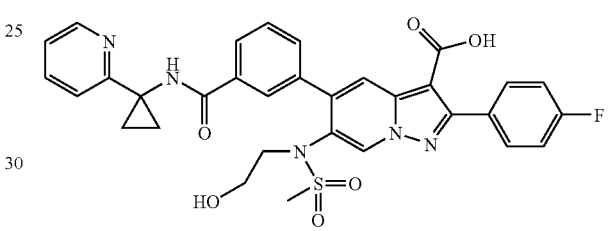

3-(2-(4-fluorophenyl)-6-(N-(2-hydroxyethyl)methylsulfonamido)-3-(methoxycarbonyl)pyrazolo[1,5-a]pyridin-5-yl)benzoic acid. 3-(2-(4-fluorophenyl)-6-(N-(2-hydroxyethyl)methylsulfonamido)-3-(methoxycarbonyl)pyrazolo[1,5-a]pyridin-5-yl)benzoic acid was prepared from Methyl 6-(N-(2-(tert-butyldimethylsilyloxy)ethyl)methylsulfonamido)-2-(4-fluorophenyl)-5-(trifluoromethyl-sulfonyloxy)pyrazolo[1,5-a]pyridine-3-carboxylate (0.07 g, 0.10 mmol). LCMS: retention time: 1.845 min. LC data was recorded on a Shimadzu LC-10AS liquid chromatograph equipped with a Waters-Sunfire, 5 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% $CH_3CN$/90% $H_2O$/10 mM TFA and solvent B was 10% $H_2O$/90% $CH_3CN$/10 mM TFA. MS data was determined using a Micromass Platform for LC in electrospray mode. m/z 528 ($MH^+$).

2-(4-fluorophenyl)-6-(N-(2-hydroxyethyl)methylsulfonamido)-5-(3-(1-(pyridin-2-yl)cyclopropylcarbamoyl)phenyl)pyrazolo[1,5-a]pyridine-3-carboxylic acid. 2-(4-fluorophenyl)-6-(N-(2-hydroxyethyl)methylsulfonamido)-5-(3-(1-(pyridin-2-yl)cyclopropylcarbamoyl)phenyl)pyrazolo[1,5-a]pyridine-3-carboxylic acid was prepared from methyl 2-(4-fluorophenyl)-6-(N-(2-hydroxyethyl)methylsulfonamido)-5-(3-(1-(pyridin-2-yl)cyclopropylcarbamoyl)phenyl)pyrazolo[1,5-a]pyridine-3-carboxylate (0.06 g, 0.10 mmol). LCMS: retention time: 1.220 min. LC data was recorded on a Shimadzu LC-10AS liquid chromatograph equipped with a Waters-Sunfire, 5 micron, C18, 4.6×50 mm column using a SPD-10AV UV-Vis detector at a detector wave length of 220 nM, The elution conditions employed a flow rate of 4 mL/min, a gradient of 100% solvent A/0% solvent B to 0% solvent A/100% solvent B, a gradient time of 3 min, a hold time of 1 min, and an analysis time of 4 mM where solvent A was 10% $CH_3CN$/90% $H_2O$/10 mM TFA and solvent B was 10% $H_2O$/90% $CH_3CN$/10 mM TFA. MS data was determined using a Micromass Platform for LC in electrospray mode. m/z 630 ($MH^+$).

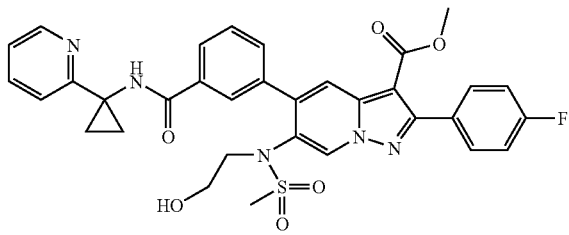

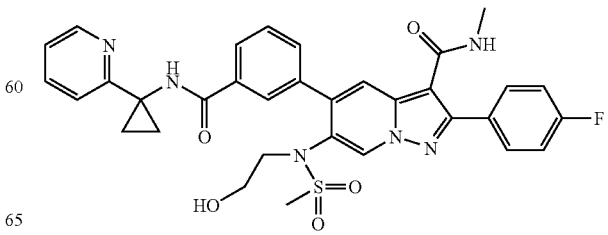

2-(4-fluorophenyl)-6-(N-(2-hydroxyethyl)methylsulfonamido)-N-methyl-5-(3-(1-(pyridin-2-yl)cyclopropylcarbamoyl)phenyl)pyrazolo[1,5-a]pyridine-3-carboxamide. 2-(4-fluorophenyl)-6-(N-(2-hydroxyethyl)methylsulfonamido)-N-methyl-5-(3-(1-(pyridin-2-yl)cyclopropyl carbamoyl) phenyl)pyrazolo[1,5-a]pyridine-3-carboxamide was prepared from 2-(4-fluorophenyl)-6-(N-(2-hydroxyethyl) methylsulfonamido)-5-(3-(1-(pyridin-2-yl)cyclopropylcarbamoyl)phenyl)pyrazolo[1,5-a]pyridine-3-carboxylic acid (0.04 g, 0.06 mmol). 1H NMR (500 MHz, DMSO-D6) δ ppm 9.26 (s, 1H), 9.16 (s, 1H), 8.45 (d, J=3.05 Hz, 1H), 8.11 (s, 1H), 8.05 (q, 14.27 Hz, 1H), 7.95-8.01 (m, 1H), 7.88-7.93 (m, 2H), 7.87 (d, J=8.24 Hz, 1H), 7.78 (s, 1H), 7.65-7.70 (m, 1H), 7.59-7.64 (m, 1H), 7.31-7.40 (m, 3H), 7.16 (dd, J=7.02, 5.19 Hz, 1H), 5.01 (s, 1H), 3.58-3.65 (m, 1H), 3.42 (s, 1H), 3.25 (s, 4H), 2.94 (dt, J=14.65, 4.43 Hz, 1H), 2.74-2.78 (m, 3H), 1.53-1.59 (m, 2H), 1.24-1.31 (m, 2H). LCMS: retention time: 1.517 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% methanol/90% H$_2$O/10 mM TFA and solvent B was 10% H$_2$O/90% methanol/10 mM TFA. MS data was determined using a Micromass Platform for LC in electrospray mode. m/z 643 (MH$^+$).

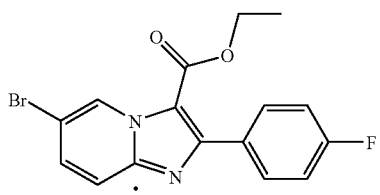

Ethyl 6-bromo-2-(4-fluorophenyl)imidazo[1,2-a]pyridine-3-carboxylate. Ethyl 3-(4-fluorophenyl)-3-oxopropanoate (2.6 g, 12 mmol) was dissolved into DCM (32 mL), cooled to 0° C. and treated with tetra-n-butylammonium tribromide (6.75 g, 14.0 mmol). The reaction mixture was stirred at 0° C. for 1 h, rt for 1 h and then washed with sat NaHCO$_3$ (aq) (2×50 mL), dried (MgSO$_4$), filtered and concentrated. The crude material was dissolved into EtOH (60 mL) and then 5-bromopyridin-2-amine (6.22 g, 36.0 mmol) was added and the reaction was stirred at 70° C. under nitrogen overnight (complete by LCMS). The reaction mixture was diluted with DCM (~120 mL), washed with sat. NaHCO$_3$ (aq) (2×100 mL) and the organic layer was dried (MgSO4), filtered and concentrated. The resulting solid was dissolved into DCM (~30 mL), diluted with hexanes (~70 mL) and stirred. The solids were filtered away (contained some desired product) and the mother liquor was concentrated, dissolved into DCM and purified by Biotage Horizon (40M, 10% EtOAc/hex, SiO$_2$) (the compound crashed out in the instrument resulting in an unknown quantity being shunted to waste). The collected fractions had solid material precipitating out which was collected by filtration to yield ethyl 6-bromo-2-(4-fluorophenyl)imidazo[1,2-a]pyridine-3-carboxylate (594 mg, 1.636 mmol, 13% yield) as a white fluffy solid. $^1$H NMR (500 MHz, CDCl$_3$) δ ppm 9.60 (s, 1H), 7.75 (d, J=8.4 Hz, 1H), 7.74 (d, J=8.4 Hz, 1H), 7.62 (d, J=9.2 Hz, 1H), 7.52 (dd, J=9.2, 1.5 Hz, 1H), 7.13 (d, J=8.5 Hz, 1H), 7.12 (d, J=8.5 Hz, 1H), 4.33 (q, J=7.1 Hz, 2H), 1.25 (t, J=7.1 Hz, 3H). LCMS: m/e=743 (M+H)$^+$, retention time=2.24 min, (Column=(2)phenomenex 4.6×50 mm C18 10 um, Solvent A=10% MeOH-90% H$_2$O-0.1% TFA, Solvent B=90% MeOH-10% H2O-0.1% TFA Start % B=0, Final % B=100, Gradient Time=2 min, Hold time=1 min, Flow Rate=5 mL/min). LC-MS retention time 104 min; m/z 362, 364 (MH+). LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 5 mL/min, a gradient of 100% solvent A/0% solvent B to 0% solvent A/100% solvent B, a gradient time of 3 min, a hold time of 1 min, and an analysis time of 4 min where solvent. A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

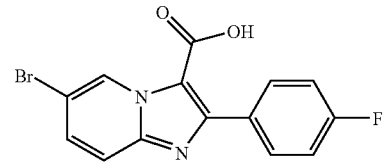

6-Bromo-2-(4-fluorophenyl)imidazo[1,2-a]pyridine-3-carboxylic acid. Ethyl 6-bromo-2-(4-fluorophenyl)imidazo[1,2-a]pyridine-3-carboxylate (394 mg, 1.09 mmol) was dissolved into MeOH (10 mL) and THF (10 mL) and then 1M aqueous NaOH (7.5 mL, 7.50 mmol) was added and the reaction was heated at 70° C. for 1 h. The reaction was treated with aqueous 1M HCl (8 mL) (white prec. formed), cooled to rt, diluted with water (30 ml) and filtered to collect the precipitate (rinsed with water). The solid was dried overnight under vacuum to yield 6-bromo-2-(4-fluorophenyl)imidazo[1,2-a]pyridine-3-carboxylic acid (290 mg, 0.87 mmol, 80% yield) as a white solid. $^1$H NMR (500 MHz, DMSO-d$_6$) δ ppm 13.40 (br s, 1H), 9.53 (s, 1H), 7.86 (d, J=8.6 Hz, 1H), 7.84 (d, J=8.6 Hz, 1H), 7.78 (d, J=9.5 Hz, 1H), 7.73 (dd, J=9.5, 1.5 Hz, 1H), 7.30 (d, J=8.9 Hz, 1H), 7.28 (d, J=8.9 Hz, 1H). LC-MS retention time 0.94 min; m/z 334, 336 (MH+). LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 5 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% TFA and solvent B was 10% H2O/90% acetonitrile/0.1% TFA. MS data was determined using a Micromass Platform for LC in electrospray mode.

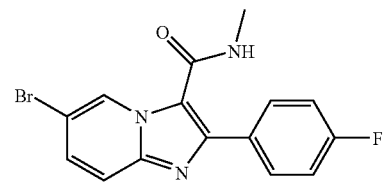

6-Bromo-2-(4-fluorophenyl)-N-methylimidazo[1,2-a]pyridine-3-carboxamide. 6-Bromo-2-(4-fluorophenyl)imidazo

[1,2-a]pyridine-3-carboxylic acid (250 mg, 0.746 mmol) was slurried into DCE (8 mL) and then oxalyl chloride (0.30 mL, 3.4 mmol) was added and the slurry was stirred for 5 min. Then DMF (50 μL, 0.65 mmol) was added (foaming) and the slurry was stirred 1 h before methanamine (5 mL, 10 mmol) 2M in THF (exothermic) and TEA (~3 mL) (exothermic) were added. The reaction was stirred at rt overnight. The reaction was partitioned between water (~30 mL) and DCM/MeOH (9/1, 3×30 mL). The combined organics were concentrated to dryness and the residue was slurried in MeOH/EtOAc (1:1~40 mL) and filtered to collect 6-bromo-2-(4-fluorophenyl)-N-methylimidazo[1,2-a]pyridine-3-carboxamide (172 mg, 0.494 mmol, 66% yield) as a white solid. $^1$H NMR (500 MHz, DMSO-d$_6$) δ ppm 8.92 (s, 1H), 8.25 (s, 1H), 7.85 (d, J=7.9 Hz, 1H), 7.83 (d, J=7.9 Hz, 1H), 7.69 (d, J=9.5 Hz, 1H), 7.56 (d, J=9.5 Hz, 1H), 7.33 (d, J=8.5 Hz, 1H), 7.31 (d, J=8.5 Hz, 1H), 2.79 (d, J=4.0 Hz, 3H). LC-MS retention time 1.73 min; ink 348, 350 (MH+). LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 5 mL/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

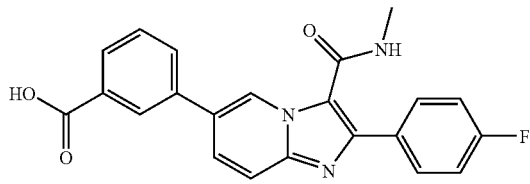

3-(2-(4-Fluorophenyl)-3-(methylcarbamoyl)imidazo[1,2-a]pyridin-6-yl)benzoic acid. 6-Bromo-2-(4-fluorophenyl)-N-methylimidazo[1,2-a]pyridine-3-carboxamide (150 mg, 0.431 mmol) and 3-boronobenzoic acid (107 mg, 0.646 mmol) were slurried into dioxane (5 mL) and water (1 mL). To the reaction mixture was added Cs$_2$CO$_3$ (211 mg, 0.646 mmol) followed by Pd(PPh$_3$)$_4$ (50 mg, 0.043 mmol). The reaction was sealed and heated at 100° C. overnight. The reaction solution was cooled to rt, filter to remove solids, diluted with water (~10 mL) and acidified with 1N HCl (aq) (1.5 mL, 1.5 mmol). The white precipitate that formed was collected by filtration, washed with water and dried to yield 3-(2-(4-fluorophenyl)-3-(methylcarbamoyl)imidazo[1,2-a]pyridin-6-yl)benzoic acid (174 mg, 0.335 mmol, 78% yield) as a white solid. $^1$H NMR (500 MHz, DMSO-d$_6$) δ ppm 13.15 (br s, 1H), 9.01 (s, 1H), 8.25-8.17 (m, 2H), 8.00 (t, J=7.5 Hz, 2H), 7.87 (d, J=8.7 Hz, 1H), 7.86 (d, J=8.6 Hz, 1H), 7.67 (t, J=7.8 Hz, 1H), 7.65-7.59 (m, 1H), 7.59-7.53 (m, 1H), 7.32 (d, J=8.9 Hz, 2H), 2.82 (d, J=4.0 Hz, 3H). LC-MS retention time 1.18 min: m/z 388 (MH−). LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 4 min, a hold time of 1 min, and an analysis time of 5 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

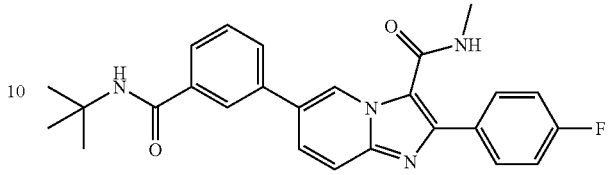

6-(3-(tert-Butylcarbamoyl)phenyl)-2-(4-fluorophenyl)-N-methylimidazo[1,2-a]pyridine-3-carboxamide. 3-(2-(4-Fluorophenyl)-3-(methylcarbamoyl)imidazo[1,2-a]pyridin-6-yl)benzoic acid (40 mg, 0.10 mmol) was slurried into DMF (0.7 mL) and TEA (0.1 mL). To this slurry was added 2-methylpropan-2-amine (11.27 mg, 0.154 mmol) and then HATU (59 mg, 0.15 mmol) (solution became yellow). The reaction was stirred at rt overnight (complete by LCMS). The reaction was diluted with MeOH (0.7 mL), filtered and purified by prep HPLC (acetonitrile/water, with 10 mM ammonium acetate buffer) to yield 6-(3-(tert-butylcarbamoyl)phenyl)-2-(4-fluorophenyl)-N-methylimidazo[1,2-a]pyridine-3-carboxamide (19.6 mg, 0.042 mmol, 41% yield) as a white solid. $^1$H NMR (500 MHz, CD$_3$OD) δ ppm 9.25 (br s, 1H), 8.08 (t, J=1.8 Hz, 1H), 7.90 (dd, J=9.2, 1.8 Hz, 1H), 7.88-7.85 (m, 1H), 7.84-7.82 (m, 1H), 7.81-7.78 (m, 2H), 7.77 (br d, J=9.2 Hz, 1H), 7.61 (t, J=7.8 Hz, 1H), 7.29 (t, J=8.9 Hz, 2H), 2.69 (s, 3H), 1.52 (s, 9H). LC-MS retention time 1.39 min; m/z 443 (MH−). LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 mM where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

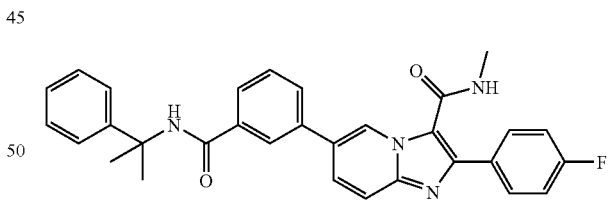

2-(4-Fluorophenyl)-N-methyl-6-(3-(2-phenylpropan-2-ylcarbamoyl)phenyl)imidazo[1,2-a]pyridine-3-carboxamide. 3-(2-(4-Fluorophenyl)-3-(methylcarbamoyl)imidazo[1,2-a]pyridin-6-yl)benzoic acid (40 mg, 0.10 mmol) and 2-phenylpropan-2-amine (21 mg, 0.15 mmol) were dissolved into DMF (0.7 mL) and TEA (0.1 mL). HATU (59 mg, 0.15 mmol) was added to this solution (solution became yellow). The reaction was stirred at rt for 2 hrs (complete by LCMS). The reaction was diluted with MeOH (0.7 mL), filtered and purified by prep HPLC (acetonitrile/water, with 10 mM ammonium acetate buffer) to yield 2-(4-fluorophenyl)-N-methyl-6-(3-(2-phenylpropan-2-ylcarbamoyl)phenyl)imidazo-[1,2-a]pyridine-3-carboxamide (24.1 mg, 0.045 mmol, 44% yield) as a white solid. $^1$H NMR (500 MHz, CD$_3$OD) δ ppm 9.25 (br s, 1H), 8.14 (br s, 1H), 7.92-7.86 (m 3H), 7.81-7.79 (m, 3H), 7.63 (t, J=7.8 Hz, 1H), 7.49 (d, J=7.6 Hz, 2H), 7.35 (d, J=7.3 Hz, 1H), 7.33 (d, J=8.2 Hz, 1H), 7.29 (d, J=8.9 Hz, 1H), 7.27 (d, J=8.6 Hz, 1H), 7.22 (t, J=7.2 Hz, 1H), 2.90 (s, 3H), 1.81 (s, 6H). LC-MS retention time 1.74 min; m/z 507 (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 4 min, a hold time of 1 mM, and an analysis time of 5 min where solvent A was 10% acetonitrile/90% H2O/0.1% TFA and solvent B was 10% H2O/90% acetonitrile/0.1% TFA. MS data was determined using a Micromass Platform for LC in electrospray mode.

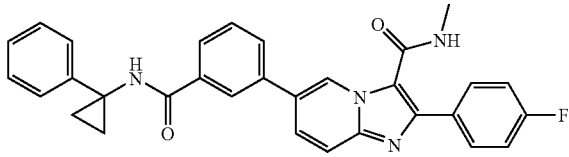

2-(4-Fluorophenyl)-N-methyl-6-(3-(1-phenylcyclopropylcarbamoyl)phenyl)imidazo[1,2-a]pyridine-3-carboxamide. 3-(2-(4-Fluorophenyl)-3-(methylcarbamoyl)imidazo[1,2-a]pyridin-6-yl)benzoic acid (40 mg, 0.10 mmol) and 1-phenylcyclopropanamine, HCl (26 mg, 0.15 mmol) were slurried into DMF (0.7 mL) and TEA (0.1 mL). HATU (59 mg, 0.15 mmol) was added to this slurry (solution became yellow). The reaction was stirred at rt for 2 hrs (complete by LCMS). The reaction was diluted with MeOH (0.7 mL), filtered and purified by prep HPLC (acetonitrile/water, with 10 mM ammonium acetate buffer) to yield 2-(4-fluorophenyl)-N-methyl-6-(3-(1-phenylcyclopropylcarbamoyl)phenyl)imidazo[1,2-a]pyridine-3-carboxamide (15.2 mg, 0.028 mmol, 28% yield) as a white solid. $^1$H NMR (500 MHz, CD$_3$OD) δ ppm 9.27 (br s, 1H), 8.31 (br s, 1H), 7.97-7.88 (m 3H), 7.82-7.76 (m, 3H), 7.66 (t, J=7.8 Hz, 1H), 7.35-7.26 (m, 6H), 7.22-7.17 (m, 1H), 2.90 (s, 3H), 1.45-1.36 (m, 4H). LC-MS retention time 1.63 min; m/z 505 (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 4 min, a hold time of 1 min, and an analysis time of 5 min where solvent A was 10% acetonitrile/90% H2O/0.1% TFA and solvent B was 10% H2O/90% acetonitrile/0.1% TFA. MS data was determined using a Micromass Platform for LC in electrospray mode.

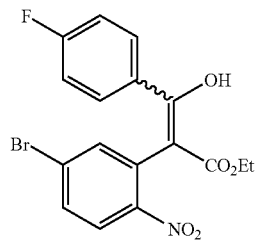

Ethyl 2-(5-bromo-2-nitrophenyl)-3-(4-fluorophenyl)-3-hydroxyacrylate. Potassium carbonate (3.3 g, 24 mmol) was added to a stirred solution of 4-bromo-2-fluoro-1-nitrobenzene (2.45 g, 11 mmol) and ethyl 3-(4-fluorophenyl)-3-oxopropanoate (2.7 g, 13 mmol) in DMSO (11 mL). The yellow solution turned purple and the reaction was stirred at r.t. After 8 h, the reaction was neutralized with 25 mL of 1 N HCl and extracted with EtOAc. The organic phase was washed with water (×3) and brine, dried over Na$_2$SO$_4$, filtered, and concentrated. The residue was purified by silica gel chromatography on a Biotage 40+M column (gradient elution 5% to 25% EtOAc/hexanes over 10 column volumes, fraction collection at λ=254 nm) to afford the title compound as a viscous amber oil, 4.8 g (105% yield, contains ~10 weight % EtOAc by $^1$H NMR). $^1$H NMR (~0.6:1 ratio of keto:enol tautomers, 500 MHz, CDCl$_3$) δ ppm 13.47 (s, 1H) 7.94-8.05 (m, 2H) 7.86 (d, J=8.55 Hz, 1H) 7.62-7.72 (m, 1.2H) 7.51 (dd, J=8.55, 2.14 Hz, 1H) 7.29-7.35 (m, 2H) 7.15-7.21 (m, 1.2H) 7.12 (d, J=2.14 Hz, 1H) 6.94 (t, J=8.55 Hz, 2H) 6.35 (s, 0.6H) 4.20-4.34 (m, 2H) 4.04-4.11 (m, 1.2H) 1.23-1.27 (m, 2H) 1.18 (t, J=7.17 Hz, 3 H). LC/MS was performed on a Shimadzu-VP instrument with UV detection at 220 nm and Waters Micromass. LC/MS method: solvent A=5% CH$_3$CN/95% H$_2$O/10 mM NH$_4$OAc, solvent B=95% CH$_3$CN/5% H$_2$O/10 mM NH$_4$OAc, start % B=0, final % B=100, gradient time=2 min, stop time=3 min, flow rate=5 ml/min, column: XBridge C18 5 μm 4.6×50 mm; 2 peaks elute with HPLC R$_t$=1.69 and 1.83 mM (~1:2 ratio), (ES−) m/z (M$^-$) for both=408, 410 (1:1 ratio).

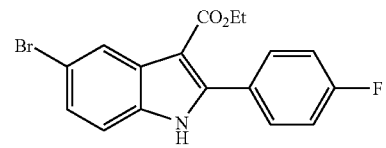

Ethyl 5-bromo-2-(4-fluorophenyl)-1H-indole-3-carboxylate. Iron powder (710 mg, 13 mmol) was added to a stirred solution of ethyl 2-(5-bromo-2-nitrophenyl)-3-(4-fluorophenyl)-3-hydroxyacrylate (1.0 g, 2.4 mmol) in EtOH (20 mL)/AcOH (16 mL) in a 250 mL round bottomed flask. The flask was immediate placed in a preheated (100° C.) oil bath under an air condenser and the slurry was stirred vigorously. After 1.5 h, the reaction was cooled to r.t., diluted with EtOAc (200 mL), and the solids were removed by filtration. The filtrate was washed with water repeatedly until the organic phase was no longer red. The organic phase was then washed with sat'd NaHCO$_3$ and brine, dried over Na$_2$SO$_4$, filtered, and concentrated (PhMe azeotrope to remove residual AcOH) to give an off-white solid. The crude product was triturated with 1:1 CH$_2$Cl$_2$/hexanes and the filtrate purified by silica gel chromatography with a Biotage 40+M cartridge (gradient elution 10% to 40% EtOAc/hexanes over 10 column volumes, fraction collection at λ=254 nm). The off-white ppt. from above was further triturated with CH$_2$Cl$_2$ to give a white solid, and the filtrate was concentrated to give an off-white solid. Both ppt. and filtrate were chromatographed separately with the same method as above, but with fraction collection at λ=320 nm. Each of the three columns afforded two major peaks. The combined first peaks elute were concentrated to give the title compound (335 mg, 38% yield). $^1$H NMR (300 MHz, CDCl$_3$) δ ppm 8.67 (br. s., 1H) 8.36 (br. s., 1H) 7.54-7.70 (m, 2H) 7.36 (d, J=7.68 Hz, 1H) 7.25 (t, J=7.68 Hz, 1H) 7.11 (t, J=8.23 Hz, 2H) 4.31 (q, J=6.83 Hz, 2H) 1.33 (t, J=7.14 Hz, 3H). LC/MS was performed on a Shimadzu-VP instrument with UV detection at 220 nm and Waters Micromass. LC/MS method: solvent A=5% $CH_3CN$/95% $H_2O$/10 mM $NH_4OAc$, solvent B=95% $CH_3CN$/5% $H_2O$/10 mM $NH_4OAc$, start % B=0, final % B=100, gradient time=2 min, stop time=3 min, flow rate=5 ml/min, column: XBridge C18 5 µm 4.6×50 mm; HPLC $R_t$=1.73, (ES+) ink ($MH^+$)=362, 364 (1:1 ratio).

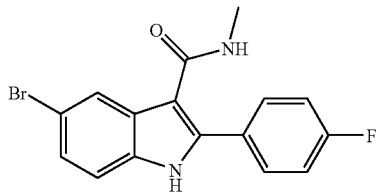

5-bromo-2-(4-fluorophenyl)-N-methyl-1H-indole-3-carboxamide. A suspension of ethyl 5-bromo-2-(4-fluorophenyl)-1H-indole-3-carboxylate (90 mg, 0.25 mmol) in 1,2-dichloroethane (3 mL) was cooled in an ice bath under an atmosphere of $N_2$. A solution of boron tribromide in $CH_2Cl_2$ (1 M, 0.75 mL, 0.75 mmol) was added the reaction was allowed warm to r.t. under N2 over 4 h. Then the reaction was then quenched by the addition of a solution of methylamine in THF (2 M, 5 mL, 10 mmol). The reaction was partitioned between EtOAc and water, the organic phase was washed with water and brine, dried over $Na_2SO_4$, filtered, and concentrated to give a colorless oil. $Et_2O$/hexanes was added and a white precipitate formed. The powder was collected by filtration, washed with $Et_2O$, and air dried to give the title compound (60 mg, 70% yield). $^1$H NMR (500 MHz, DMSO-$d_6$) δ ppm 11.93 (s, 1H) 7.82 (d, J=1.83 Hz, 1H) 7.71-7.78 (m, 3H) 7.32-7.41 (m, 3H) 7.29 (dd, J=8.55, 1.83 Hz, 1H) 2.75 (d, J=4.58 Hz, 3H). LC/MS was performed on a Shimadzu-VP instrument with UV detection at 220 nm and Waters Micromass. LC/MS method: solvent A=5% $CH_3CN$/95% $H_2O$/10 mM $NH_4OAc$, solvent B=95% $CH_3CN$/5% $H_2O$/10 nM $NH_4OAc$, start % B=0, final % B=100, gradient time=2 min, stop time=3 mM, flow rate=5 ml/min, column: XBridge C18 5 µm 4.6×50 mm; HPLC $R_t$=1.26, (ES+) m/z ($MH^+$)=347, 349 (1:1 ratio).

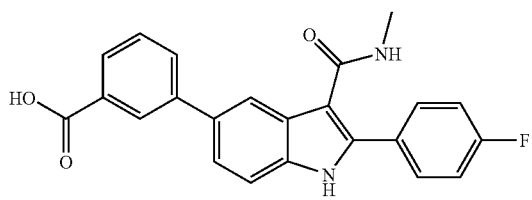

3-(2-(4-fluorophenyl)-3-(methylcarbamoyl)-1H-indol-5-yl)benzoic acid. In a 7 mL scintillation vial were combined 5-bromo-2-(4-fluorophenyl)-N-methyl-1H-indole-3-carboxamide (59 mg, 0.17 mmol), 3-boronobenzoic acid (47 mg, 0.28 mmol), $Cs_2CO_3$ (100 mg, 0.31 mmol), and $Pd(PPh_3)_4$ (17 mg, 0.015 mmol). 1,4-Dioxane (1.25 mL) and water (0.25 mL) were added, the vial was capped, and the reaction was heated in an oil bath to 90° C. After 7 h, the reaction was cooled to r.t. and diluted with water. 1 mL of 1 N HCl was added and a ppt. formed. The suspension was extracted with EtOAc (+MeOH to aid dissolution), and the organic phase was washed with brine, dried over $Na_2SO_4$, filtered, and concentrated to give a tan solid. This was purified by prep HPLC, and concentrated to give a white solid, (12 mg, 18% yield). $^1$H NMR (500 MHz, MeOD) δ ppm 8.34 (s, 1H) 8.06 (s, 1H) 7.97 (d, J=7.63 Hz, 1H) 7.92 (d, J=7.93 Hz, 1H) 7.65-7.74 (m, 2H) 7.54 (t, J=7.78 Hz, 1H) 7.51 (s, 2H) 7.23 (t, J=8.85 Hz, 2H) 2.89 (s, 3H). LC/MS was performed on a Shimadzu-VP instrument with UV detection at 220 nm and Waters Micromass. LC/MS method: solvent A=5% $CH_3CN$/95% $H_2O$/10 mM $NH_4OAc$, solvent B=95% $CH_3CN$/5% $H_2O$/10 mM $NH_4OAc$, start % B=0, final % B=100, gradient time=2 min, stop time=3 min, flow rate=5 ml/min, column: XBridge C18 5 µm 4.6×50 mm; HPLC $R_t$=0.88, (ES+) m/z ($MH^+$)=389.

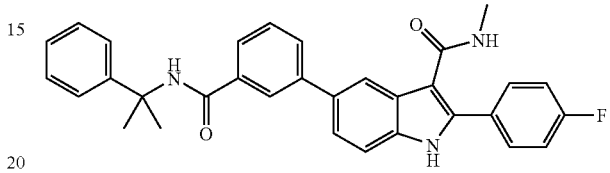

2-(4-fluorophenyl)-N-methyl-5-(3-(2-phenylpropan-2-ylcarbamoyl)phenyl)-1H-indole-3-carboxamide. To a solution of 3-(2-(4-fluorophenyl)-3-(methylcarbamoyl)-1H-indol-5-yl)benzoic acid (12 mg, 0.031 mmol) and DIPEA (20 µL, 0.115 mmol) in 1,2-dichloroethane (0.5 mL)/DMF (0.1 mL) was added cumylamine (15 µL, 0.10 mmol) and HATU (15 mg, 0.039 mmol). The reaction was stirred at r.t. for 30 min, then the volatiles were evaporated and the residue was purified directly by prep HPLC. Concentration afforded the title compound as a white powder (11 mg, 68% yield). $^1$H NMR (500 MHz, MeOD) δ ppm 8.52 (s, 1H) 8.09 (d, J=7.93 Hz, 2H) 7.85 (d, J=7.63 Hz, 1H) 7.66-7.77 (m, 3H) 7.49-7.57 (m, 3H) 7.47 (d, J=8.24 Hz, 2H) 7.31 (t, J=7.78 Hz, 2H) 7.23 (t, J=8.85 Hz, 2H) 7.19 (t, J=7.32 Hz, 1H) 2.89 (s, 3H) 1.78 (s, 6H). LC/MS was performed on a Shimadzu-VP instrument with UV detection at 220 nm and Waters Micromass. LC/MS method: solvent A=10% $CH_3CN$/90% $H_2O$/0.1% TFA, solvent B=90% $CH_3CN$/10% $H_2O$/0.1% TFA, start % B=0, final % B=100, gradient time=3 min, stop time=4 min, flow rate=4 ml/min, column: Sunfire C18 5 µm 4.6×50 mm; HPLC $R_t$=1.49 min, (ES+) m/z ($MH^+$)=506. Analytical HPLC method: solvent A=5% $CH_3CN$/95% $H_2O$/0.1% TFA, solvent B=95% $CH_3CN$/5% $H_2O$/0.1% TFA, start % B=10, final % B=100, gradient time=15 min, stop time=18 min, flow rate=1 ml/min. Column: Waters Sunfire C-18, 3.5 µm 4.6×150 mm, $R_t$=15.29 min, purity=97%; column: Waters Xbridge Phenyl 3.5 µm 4.6×150 mm, $R_t$=11.59 min, purity=98%.

For the experimental procedures that follow until noted the LCMS conditions employed were: Luna 4.6×50 mm S10, Wavelegnth=220 nm, flow rate=4 mL/min, gradient=5 to 95% acetonitrile in 10 mM aqueous ammonium acetate.

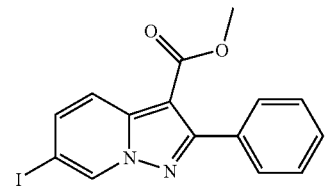

Methyl 6-iodo-2-phenylpyrazolo[1,5-a]pyridine-3-carboxylate. Dichloromethane (10 mL) and 3-Iodopyridine (928 mg, 4.53 mmol) were charged to a 100 mL, round-bottomed flask equipped with a magnetic stir bar. This colorless solution was cooled on an ice bath and O-(mesitylsulfonyl)hydroxylamine (975 mg, 4.53 mmol) in dichloromethane (10 mL) was added dropwise over 5 minutes. After to stirring at room temperature for 30 minutes, the solvent was removed by rotary evaporation to give a white solid. Methyl phenylpropiolate (1000 mg, 6.24 mmol) was added in dimethylformamide (9 mL). Potassium carbonate (2504 mg, 18.12 mmol) was added. Reaction slowly turned dark green. After stirring at room temp for 2 hours, the reaction was poured into diethyl ether (300 mL and extracted 8×25 mL water. The solvent was removed from the organic portion by rotary evaporation. The crude product was dissolved in a minimum amount of dichloromethane and charged to a 90 g "Single Sep" silica gel cartridge and eluted with 0 to 40% ethyl acetate in hexanes over 1000 mL. The title compound (200 mg, 12%) was isolated as an orange solid. 1H NMR (500 MHz, CHLOROFORM-D) δ ppm 3.83 (s, 3H) 7.46 (m, 3H) 7.59 (dd, J=9.16, 1.53 Hz, 1H) 7.7.5 (m, 2H) 8.00 (dd, J=9.31, 0.76 Hz, 1H) 8.82 (s, 1H). LCMS: 2.4 minutes, M+1=379.

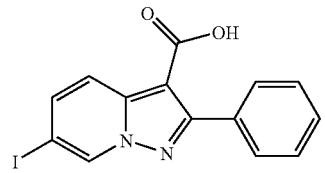

6-Iodo-2-phenylpyrazolo[1,5-a]pyridine-3-carboxylic acid. Methyl-6-iodo-2-phenylpyrazolo[1,5-a]pyridine-3-carboxylate (250 mg, 0.661 mmol) was dissolve in aqueous LiOH (2N, 1 mL), methanol (2 mL) and tetrahydrofuran (7 mL). This solution was stirred overnight at 45° C. After 24 hours, 2 mL 2M LiOH and 2 mL methanol were added. Heated at 55° C. overnight. The reaction was cooled on an ice water bath and aqueous hydrochloric acid (10 mL, 1N) was added dropwise until acidic by pH paper. Ethylacetate (200 mL) and water (40 mL) were added. The organic portion was extracted with brine (20 mL) and was dried over magnesium sulfate. The solvent was removed by rotary evaporation. The residue was place under vacuum overnight to give of a white solid (204 mg, 85%). 1H NMR (500 MHz, DMSO-D6) δ ppm 7.47 (m, 3H) 7.77 (m, 2H) 7.97 (d, J=9.46 Hz, 1H) 9.27 (s, 1H).

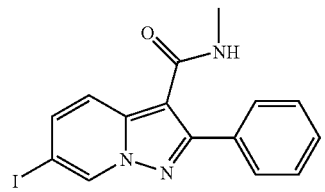

6-Iodo-N-methyl-2-phenylpyrazolo[1,5-a]pyridine-3-carboxamide. To a 250 mL round-bottomed flask equipped with a magnetic stir bar was charged 6-iodo-2-phenylpyrazolo[1,5-a]pyridine-3-carboxylic acid (200 mg, 0.549 mmol), 1-Hydroxy-7-azabenzotriazole (74.8 mg, 0.549 mmol), methylamine hydrochloride (55.6 mg, 0.824 mmol), diisopropylethylamine (671 µL, 3.84 mmol), dichloromethane (5000 µL) and dimethylfomamide (500 µL). To this yellow solution 1-(3-Dimethylaminopropyl)-3-ethylcarbodiimide hydrochloride (147 mg, 0.769 mmol) was added. The reaction was stirred at room temperature for six hours and diluted with ethylacetate (200 mL). The organic portion was washed 5× with 0.5N hydrochloric acid, 1× saturated sodium bicarbonate and 2× brine. The organic portion was dried over magnesium sulfate. The solvent was removed by rotary evaporation. The residue was place under vacuum overnight to give a white solid (130 mg, 90%). 1H NMR (500 MHz, MeOD) δ ppm 2.87 (m, 3H) 7.51 (m, 3H) 7.63 (dd, J=9.31, 1.37 Hz, 1H) 7.76 (m, 3H) 8.94 (s, 1H). LCMS: 1.8 minutes, M+1=378.

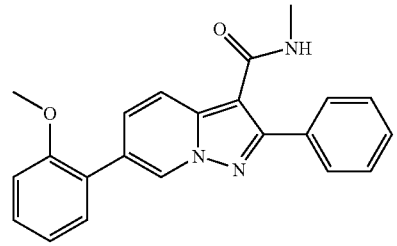

6-(2-Methoxyphenyl)-N-methyl-2-phenylpyrazolo[1,5-a]pyridine-3-carboxamide. To a microwave vial equipped with a magnetic stir bar was charged 2-methoxyphenylboronic acid (12.09 mg, 0.080 mmol), 6-iodo-N-methyl-2-phenylpyrazolo[1,5-a]pyridine-3-carboxamide (15 mg, 0.040 mmol), sodium carbonate (7.38 mg, 0.070 mmol), palladium (II) acetate (0.893 mg, 3.98 µmol) and dimethylfomamide (1.0 mL). This mixture was placed under an argon atmosphere and heated at 150° C. for 10 minutes. The title compound (5.7 mg, 36%) was isolated by reverse phase HPLC: Start % B=30 to Final % B=80, Gradient time=10 minutes, Flow Rate=35 mL/minute, Wavelength=220 nm, Solvent A=10% methanol, 90% water with 0.1% TFA; Solvent B=90% methanol, 10% water with 0.1% TFA, Column=Phenomenex-Luna 30×50 mm S10, Product peak at 7.6 minutes. 1H NMR (500 MHz, CHLOROFORM-D) δ ppm 2.85 (d, J=4.88 Hz, 3H) 3.86 (s, 3H) 7.03 (d, J=7.93 Hz, 1H) 7.08 (t, J=7.02 Hz, 1H) 7.39 (m, 2H) 7.54 (m, 3H) 7.63 (dd, J=9.16, 1.53 Hz, 1H) 7.69 (m, 1H) 8.36 (dd, J=9.16, 0.61 Hz, 1H) 8.76 (m, 1H). LCMS: 2.0 minutes, M+1=358.

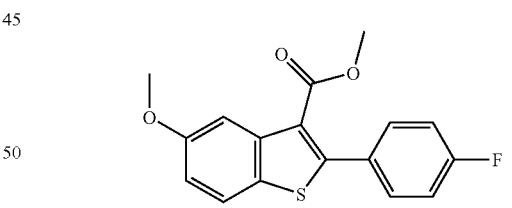

Methyl 2-(4-fluorophenyl)-5-methoxybenzo[b]thiophene-3-carboxylate. To a cooled solution (−78° C., dry ice, acetone) containing 2-(4-fluorophenyl)-3-iodo-5-methoxybenzo[b]thiophene (1.0 g, 2.6 mmol,) and THF (26 mL) was added n-butyllithium (2.0 mL, 1.0 M THF) over 5 min. The solution was maintained at −78° C. for 1 h. Methylchloroformate (0.80 mL, 10.4 mmol) was then added quickly in a steady stream via syringe. The solution was removed from cooling and allowed to stand at ambient temperature for 1.5 h. The solution was concentrated and purified on silica gel (0-10% ethyl acetate/hexanes, 40 min. gradient) to afford methyl 2-(4-fluorophenyl)-5-methoxybenzo[b]thiophene-3-carboxylate as a yellow residue. 1H NMR (500 MHz, CHLOROFORM-D) δ ppm 7.88 (d, J=2.44 Hz, 1H), 7.66 (d, J=8.85

Hz, 1H), 7.47 (dd, J=8.85, 5.19 Hz, 2H), 7.12 (t, J=8.70 Hz, 2H), 7.05 (dd, J=8.70, 2.59 Hz, 1H), 3.91 (s, 3H), 3.74 (s, 3H). LCMS: retention time: 3.355 min. LC data was recorded on a Shimadzu LC-10AS liquid chromatograph equipped with a Phenomenex-Luna, 10 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% $CH_3CN$/95% $H_2O$/10 mM ammonium acetate and solvent B was 5% $H_2O$/95% $CH_3CN$/10 mM ammonium acetate. MS data was determined using a Micromass Platform for LC in electrospray mode. m/z 317 (MH+).

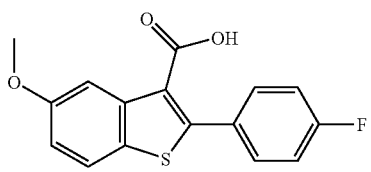

2-(4-fluorophenyl)-5-methoxybenzo[b]thiophene-3-carboxylic acid. To a solution containing methyl 2-(4-fluorophenyl)-5-methoxybenzo[b]thiophene-3-carboxylate (0.59 g, 1.9 mmol), THF (13.5 mL) and methanol (8.5 mL) was added aqueous lithium hydroxide (9.3 mL, 2.0 M). The solution was maintained at 50° C. for 15 h. The solution was cooled to room temperature, adjusted to below pH 4 with aqueous HCl (22 mL, 1.0 N) and extracted with ethyl acetate (3×15 mL). The combined organic portions were washed with brine (15 mL), dried over $MgSO_4$, filtered and concentrated to afford 2-(4-fluorophenyl)-5-methoxybenzo[b]thiophene-3-carboxylic acid as white solid which was used without further purification. 1H NMR (500 MHz, DMSO-D6) δ ppm 12.99 (s, 1H), 7.93 (d, J=8.55 Hz, 1H), 7.80 (d, J=2.44 Hz, 1H), 7.59 (dd, J=8.55, 5.49 Hz, 2H), 7.32 (t, J=8.70 Hz, 2H), 7.11 (dd, J=8.85, 2.44 Hz, 1H), 3.82-3.87 (m, 3H). LCMS: retention time: 1.532 min. LC data was recorded on a Shimadzu LC-10AS liquid chromatograph equipped with a Phenomenex-Luna, 10 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% $CH_3CN$/95% $H_2O$/10 mM ammonium acetate and solvent B was 5% $H_2O$/95% $CH_3CN$/10 mM ammonium acetate. MS data was determined using a Micromass Platform for LC in electrospray mode. m/z 303 (MH+).

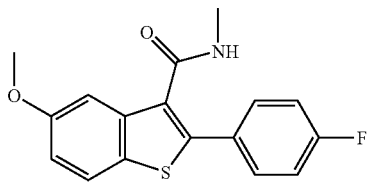

2-(4-fluorophenyl)-5-methoxy-N-methylbenzo[b]thiophene-3-carboxamide. To a solution containing 2-(4-fluorophenyl)-5-methoxybenzo[b]thiophene-3-carboxylic acid (0.57 g, 1.9 mmol), HOAT (0.28 g, 2.1 mmol), diisopropylethylamine (2.3 mL, 13.2 mmol), methylamine hydrochloride (0.20 g, 2.8 mmol) and dichloromethane (20 mL) was added EDCI (0.51 g, 13.2 mmol). The solution was maintained at room temperature for 6 h, diluted with additional DCM (20 mL), washed with water (20 mL), washed with aqueous HCl (2×20 mL, 0.1 N), dried over $MgSO_4$, filtered and concentrated to afford 2-(4-fluorophenyl)-5-methoxy-N-methylbenzo[b]thiophene-3-carboxamide which was used without further purification. 1H NMR (500 MHz, DMSO-D6) δ ppm 8.30 (d, J=4.27 Hz, 1H), 7.90 (d, J=8.85 Hz, 1H), 7.60 (dd, J=8.70, 5.34 Hz, 2H), 7.34 (t, J=8.85 Hz, 2H), 7.16 (d, J=2.14 Hz, 1H), 7.07 (dd, J=8.85, 2.44 Hz, 1H), 3.81 (s, 3H), 2.74 (d, J=4.58 Hz, 3H). LCMS: retention time: 2.513 min. LC data was recorded on a Shimadzu LC-10AS liquid chromatograph equipped with a Phenomenex-Luna, 10 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% $CH_3CN$/95% $H_2O$/10 mM ammonium acetate and solvent B was 5% $H_2O$/95% $CH_3CN$/10 mM ammonium acetate. MS data was determined using a Micromass Platform for LC in electrospray mode. m/z 316 (MH+).

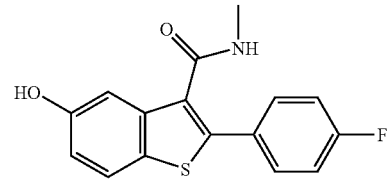

2-(4-fluorophenyl)-5-hydroxy-N-methylbenzo[b]thiophene-3-carboxamide. To a suspension containing 2-(4-fluorophenyl)-5-methoxy-N-methylbenzo[b]thiophene-3-carboxamide (0.58 g, 1.8 mmol) and DCE (18 mL), was added boron tribromide-methylsulfide complex (2.3 g, 7.4 mmol) in one portion. The mixture was stirred in a closed vessel at 83° C. for 9 h under a nitrogen atmosphere, cooled to room temperature and quenched with aqueous HCl (20 mL, 1.0 N). The mixture was concentrated to remove all solvent and water was added (50 mL). The aqueous mixture was extracted with ethyl acetate (3×20 mL), dried over MgSO4, filtered and concentrated to afford 2-(4-fluorophenyl)-5-hydroxy-N-methylbenzo[b]thiophene-3-carboxamide as a tan solid which was used without further purification. 1H NMR (500 MHz, DMSO-D6) δ ppm 9.56 (s, 1H), 8.31 (d, J=4.58 Hz, 1H), 7.78 (d, J=8.55 Hz, 1H), 7.55-7.63 (m, 2H), 7.29-7.37 (m, 2H), 7.08 (d, J=2.14 Hz, 1H), 6.91 (dd, J=8.85, 2.44 Hz, 1H), 2.73 (d, J=4.58 Hz, 3H). LCMS: retention time: 2.137 mM. LC data was recorded on a Shimadzu LC-10AS liquid chromatograph equipped with a Phenomenex-Luna, 10 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 mM where solvent A was 5% $CH_3CN$/95% $H_2O$/10 mM ammonium acetate and solvent B was 5% $H_2O$/95% $CH_3CN$/10 mM ammonium acetate. MS data was determined using a Micromass Platform for LC in electrospray mode. m/z 302 (MH+).

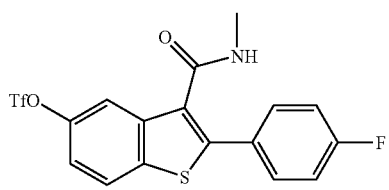

2-(4-fluorophenyl)-3-(methylcarbamoyl)benzo[b]thiophen-5-yl trifluoromethanesulfonate. A solution containing 2-(4-fluorophenyl)-5-hydroxy-N-methylbenzo[b]thiophene-3-carboxamide (0.47 g, 0.93 mmol), N-Phenylbis(trifluoromethane)sulfonamide (0.50 g, 1.4 mmol), triethylamine (0.64 mL, 4.6 mmol) and dichloromethane (9.2 mL) was maintained at room temperature for 16 h. The solution was further diluted with dichloromethane (30 mL), washed with saturated, aqueous sodium bicarbonate (20 mL), washed with water (10 mL), dried over MgSO4, filtered and concentrated. Purification on silica gel (0-100% ethyl acetate/hexanes, 45 min gradient) afforded 2-(4-fluorophenyl)-3-(methylcarbamoyl)benzo[b]thiophen-5-yl trifluoromethanesulfonate as a white solid. 1H NMR (500 MHz, CHLOROFORM-D) δ ppm 8.07 (d, J=2.44 Hz, 1H), 7.85 (d, J=8.54 Hz, 1H), 7.55-7.59 (m, 2H), 7.30 (dd, J=8.85, 2.44 Hz, 1H), 7.18 (t, J=8.55 Hz, 2H), 2.88 (s, 3H). LCMS: retention time: 2.981 min. LC data was recorded on a Shimadzu LC-10AS liquid chromatograph equipped with a Phenomenex-Luna, 10 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 5% CH$_3$CN/95% H$_2$O/10 mM ammonium acetate and solvent B was 5% H$_2$O/95% CH$_3$CN/10 mM ammonium acetate. MS data was determined using a Micromass Platform for LC in electrospray mode. m/z 434 (MH$^+$).

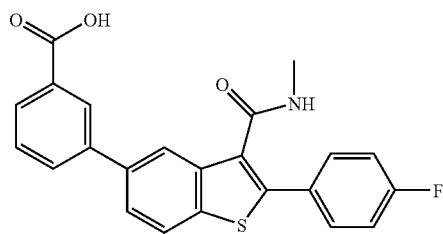

3-(2-(4-fluorophenyl)-3-(methylcarbamoyl)benzo[b]thiophen-5-yl)benzoic acid. To a degassed solution containing 2-(4-fluorophenyl)-3-(methylcarbamoyl)benzo[b]thiophen-5-yl trifluoromethanesulfonate (0.32 g, 0.74 mmol), 3-boronobenzoic acid (0.18 g, 1.1 mmol), cesium carbonate (0.36 g, 1.1 mmol), dioxane (6.2 mL) and water (1.2 mL) was added tetrakis(tiphenylphosphine)palladium(0) (0.02 g, 0.016 mmol). The solution was maintained at 95° C. for 90 min. The solution was cooled to room temperature, concentrated and suspended in ethyl acetate (20 mL) with stirring for 1 h. The mixture was filtered, washed with water (3×20 mL) and air dried to afford 3-(2-(4-fluorophenyl)-3-(methylcarbamoyl)benzo[b]thiophen-5-yl)benzoic acid as a grey solid which was used without further purification. LCMS: retention time: 2.132 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 4 min, a hold time of 1 min, and an analysis time of 5 min where solvent A was 10% CH$_3$CN/90% H$_2$O/10 mM TFA and solvent B was 10% H$_2$O/90% CH$_3$CN/10 mM TFA. MS data was determined using a Micromass Platform for LC in electrospray mode. m/z 406 (MH$^+$).

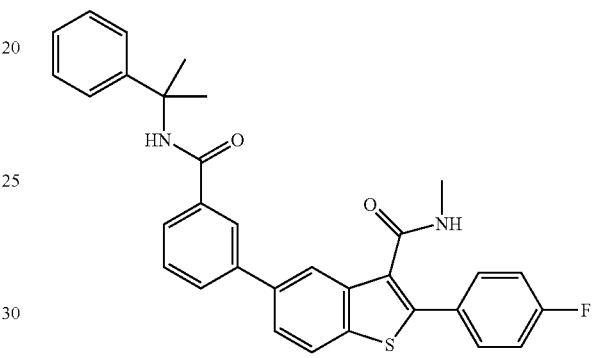

2-(4-fluorophenyl)-N-methyl-5-(3-(2-phenylpropan-2-ylcarbamoyl)phenyl)benzo[b]thiophene-3-carboxamide. To a solution containing 2-phenylpropan-2-amine (0.030 g, 0.23 mmol), diisopropylethylamine (0.13 mL, 0.75 mmol), 3-(2-(4-fluorophenyl)-3-(methylcarbamoyl)benzo[b]thiophen-5-yl)benzoic acid (0.075 g, 0.15 mmol) and DMF (1.0 mL) was added HATU (0.74 g, 0.20 mmol) in one portion. The solution was maintained at room temperature for 15 h and concentrated. The resultant residue was purified using preparative HPLC (Waters-Xbridge, 50×100 mm, 5 micron, C18 column; 0.1M ammonium acetate, 0-100% B (B=5% H$_2$O/CH$_3$CN)/A (A=95% H$_2$O/CH$_3$CN), 10 min. gradient) afforded 2-(4-fluorophenyl)-N-methyl-5-(3-(2-phenylpropan-2-ylcarbamoyl)phenyl)benzo[b]thiophene-3-carboxamide as a white solid. Preparative HPLC: retention time: 8.5 min. 1H NMR (500 MHz, DMSO-D6) δ ppm 8.62 (s, 1H), 8.42 (d, J=4.88 Hz, 1H), 8.17 (d, J=8.55 Hz, 1H), 8.13 (s, 1H), 7.99 (s, 1H), 7.84-7.89 (m, 2H), 7.82 (dd, J=8.55, 1.53 Hz, 1H), 7.66 (dd, J=8.70, 5.34 Hz, 2H), 7.59 (t, J=7.78 Hz, 1H), 7.42 (d, J=7.32 Hz, 2H), 7.37 (t, J=8.70 Hz, 2H), 7.30 (t, J=7.63 Hz, 2H), 7.18 (t, J=7.32 Hz, 1H), 2.77 (d, J=4.58 Hz, 3H), 1.71 (s, 6H). LCMS: retention time: 3.305 min. LC data was recorded on a Shimadzu LC-10AS liquid chromatograph equipped with a Phenomenex-Luna, 10 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 mM where solvent A was 10% CH$_3$OH/90% H$_2$O/10 mM TFA and solvent B was 10% H$_2$O/90% CH$_3$OH/10 mM TFA. MS data was determined using a Micromass Platform for LC in electrospray mode. m/z 523 (MH$^+$).

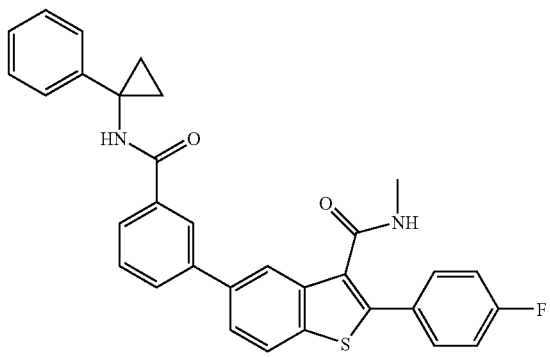

2-(4-fluorophenyl)-N-methyl-5-(3-(1-phenylcyclopropyl-carbamoyl)phenyl)benzo[b]thiophene-3-carboxamide. 2-(4-fluorophenyl)-N-methyl-5-(3-(1-phenylcyclopropylcarbamoyl)phenyl)benzo[b]thiophene-3-carboxamide was prepared from 3-(2-(4-fluorophenyl)-3-(methylcarbamoyl)benzo[b]thiophen-5-yl)benzoic acid (0.075 g, 0.154 mmol) and 1-phenylcyclopropanamine hydrochloride (0.038 g, 0.22 mmol). 1H NMR (500 MHz, DMSO-D6) δ ppm 9.36 (s, 1H), 8.41 (d, J=4.58 Hz, 1H), 8.22 (s, 1H), 8.17 (d, J=8.24 Hz, 1H), 7.98 (d, J=1.53 Hz, 1H), 7.93 (d, J=7.63 Hz, 1H), 7.89 (d, J=7.94 Hz, 1H), 7.83 (dd, J=8.39, 1.68 Hz, 1H), 7.66-7.68 (m, 1H), 7.65 (d, J=5.19 Hz, 1H), 7.61 (t, J=7.78 Hz, 1H), 7.37 (t, J=8.70 Hz, 2H), 7.29 (t, J=7.63 Hz, 2H), 7.22-7.26 (m, 2H), 7.15-7.19 (m, 1H), 2.77 (d, J=4.58 Hz, 3H), 1.31 (d, J=11.90 Hz, 4H). LCMS: retention time: 3.250 min. LC data was recorded on a Shimadzu LC-10AS liquid chromatograph equipped with a Phenomenex-Luna, 10 micron, C18, 4.6×30 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 mM, a hold time of 1 min, and an analysis time of 4 min where solvent A was 10% CH$_3$OH/90% H$_2$O/10 mM TFA and solvent B was 10% H$_2$O/90% CH$_3$OH/10 mM TFA. MS data was determined using a Micromass Platform for LC in electrospray mode. m/z 521 (MH$^+$).

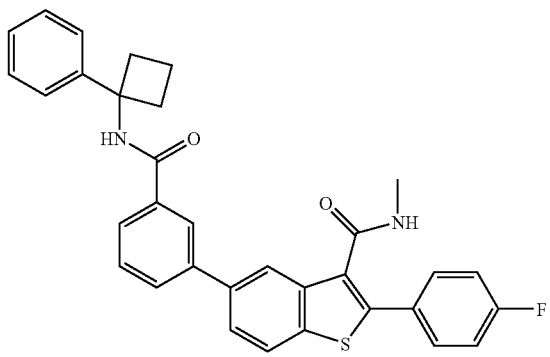

2-(4-fluorophenyl)-N-methyl-5-(3-(1-phenylcyclobutyl-carbamoyl)phenyl)benzo[b]thiophene-3-carboxamide. 2-(4-fluorophenyl)-N-methyl-5-(3-(1-phenylcyclobutylcarbamoyl)phenyl)benzo[b]thiophene-3-carboxamide was prepared from 3-(2-(4-fluorophenyl)-3-(methylcarbamoyl)benzo[b]thiophen-5-yl)benzoic acid (0.075 g, 0.15 mmol) and 1-phenylcyclobutanamine hydrochloride (0.041 g, 0.22 mmol). 1H NMR (500 MHz, DMSO-D6) δ ppm 9.18 (s, 1H), 8.42 (d, J=4.58 Hz, 1H), 8.14-8.22 (m, 2H), 7.97 (s, 1H), 7.88 (dd, J=16.02, 7.48 Hz, 2H), 7.82 (d, J=8.54 Hz, 1H), 7.66 (dd, J=8.24, 5.80 Hz, 2H), 7.59 (t, J=7.63 Hz, 1H), 7.52 (d, J=7.63 Hz, 2H), 7.31-7.40 (m, 4H), 7.21 (t, J=7.32 Hz, 1H), 2.77 (d, J=4.58 Hz, 3H), 2.62-2.71 (m, 2H), 2.53-2.60 (m, 2H), 2.02-2.11 (m, 1H), 1.83-1.92 (m, 1H). LCMS: retention time: 3.370 mM. LC data was recorded on a Shimadzu LC-10AS liquid chromatograph equipped with a Phenomenex-Luna, 10 micron, C18, 4.6×30 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% CH$_3$OH/90% H$_2$O/10 mM TFA and solvent B was 10% H$_2$O/90% CH$_3$OH/10 mM TFA. MS data was determined using a Micromass Platform for LC in electrospray mode. m/z 535 (MH$^+$).

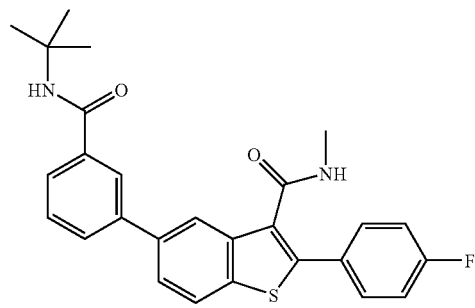

5-(3-(tert-butylcarbamoyl)phenyl)-2-(4-fluorophenyl)-N-methylbenzo[b]thiophene-3-carboxamide. 5-(3-(tert-butylcarbamoyl)phenyl)-2-(4-fluorophenyl)-N-methylbenzo[b]thiophene-3-carboxamide was prepared from 3-(2-(4-fluorophenyl)-3-(methylcarbamoyl)benzo[b]thiophen-5-yl)benzoic acid (0.075 g, 0.15 mmol) and 2-methylpropan-2-amine (0.016 g, 0.22 mmol). 1H NMR (500 MHz, DMSO-D6) δ ppm 8.42 (s, 1H), 8.16 (s, 1H), 8.07 (s, 1H), 7.96 (s, 2H), 7.82 (s, 3H), 7.66 (s, 2H), 7.57 (s, 1H), 7.37 (s, 2H), 2.78 (s, 3H), 1.42 (s, 9H). LCMS: retention time: 3.218 min. LC data was recorded on a Shimadzu LC-10AS liquid chromatograph equipped with a Phenomenex-Luna, 10 micron, C18, 4.6×30 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% CH$_3$OH/90% H$_2$O/10 mM TFA and solvent B was 10% H$_2$O/90% CH$_3$OH/10 mM TFA. MS data was determined using a Micromass Platform for LC in electrospray mode. m/z 461 (MH$^+$).

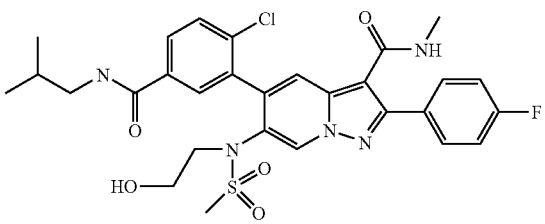

5-(2-chloro-5-(isobutylcarbamoyl)phenyl)-2-(4-fluorophenyl)-6-(N-(2-hydroxyethyl)methylsulfonamido)-N-methylpyrazolo[1,5-a]pyridine-3-carboxamide. 5-(2-chloro-5-(isobutylcarbamoyl)phenyl)-2-(4-fluorophenyl)-6-(N-(2-hydroxyethyl)methylsulfonamido)-N-methylpyrazolo[1,5-a]pyridine-3-carboxamide was prepared from 5-(2-chloro-5-(isobutylcarbamoyl)phenyl)-2-(4-fluorophenyl)-6-(N-(2-hydroxyethyl)methylsulfonamido)pyrazolo[1,5-a]pyridine-3-carboxylic acid (0.027 g, 0.045 mmol) and methylamine hydrochloride (0.013 g, 0.18 mmol). The resultant residue was purified using preparative HPLC (Waters-Xbridge, 50×100 mm, 5 micron, C18 column; 0.1M ammonium acetate, 0-100% B (B=5% $H_2O$/$CH_3CN$)/A (A=95% $H_2O$/$CH_3CN$), 10 min. gradient) to afford 5-(2-chloro-5-(isobutylcarbamoyl)phenyl)-2-(4-fluorophenyl)-6-(N-(2-hydroxyethyl)methylsulfonamido)-N-methylpyrazolo[1,5-a]pyridine-3-carboxamide as a white solid. Preparative HPLC retention time: 6 min. 1H NMR (500 MHz, MeOD) δ ppm 9.01 (s, 1H), 8.11 (s, 2H), 7.92 (s, 1H), 7.84-7.91 (m, 3H), 7.71 (d, J=8.55 Hz, 1H), 7.24-7.30 (m, 2H), 3.65 (s, 1H), 3.56 (s, 1H), 3.30 (d, J=1.22 Hz, 2H), 3.18-3.27 (m, 3H), 2.82-2.91 (m, 4H), 1.92 (dq, J=13.47, 6.80 Hz, 1H), 0.99 (d, J=6.71 Hz, 6H). LCMS retention time: 1.800 min. LC data was recorded on a Shimadzu LC-10AS liquid chromatograph equipped with a Sunfire C18, 5 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% $CH_3CN$/90% $H_2O$/10 mM TFA and solvent B was 10% $H_2O$/90% $CH_3CN$/10 mM TFA. MS data was determined using a Micromass Platform for LC in electrospray mode. m/z 638 (MNa$^+$).

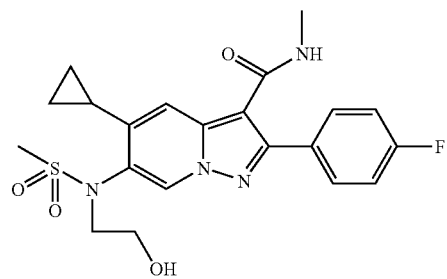

5-cyclopropyl-2-(4-fluorophenyl)-6-(N-(2-hydroxyethyl)methylsulfonamido)-N-methylpyrazolo[1,5-a]pyridine-3-carboxamide. 5-cyclopropyl-2-(4-fluorophenyl)-6-(N-(2-hydroxyethyl)methylsulfonamido)-N-methylpyrazolo[1,5-a]pyridine-3-carboxamide was prepared from 5-cyclopropyl-2-(4-fluorophenyl)-6-(N-(2-hydroxyethyl)methylsulfonamido)pyrazolo[1,5-a]pyridine-3-carboxylic acid (0.013 g, 0.030 mmol) and methylamine hydrochloride (0.008 g, 0.12 mmol). The resultant residue was purified using preparative HPLC (Waters-Xbridge, 50×100 mm, 5 micron, C18 column; 0.1M TFA, 0-100% B (B=5% $H_2O$/$CH_3CN$)/A (A=95% $H_2O$/$CH_3CN$), 10 min. gradient) to afford 5-cyclopropyl-2-(4-fluorophenyl)-6-(N-(2-hydroxyethyl)methylsulfonamido)-N-methylpyrazolo[1,5-a]pyridine-3-carboxamide as a white solid. Preparative HPLC retention time: 5.5 min. 1H NMR (500 MHz, MeOD) δ ppm 8.79 (s, 1H), 7.77-7.82 (m, 2H), 7.42 (s, 1H), 7.23-7.28 (m, 2H), 4.06-4.14 (m, 1H), 3.72-3.79 (m, 1H), 3.63-3.70 (m, 2H), 3.26 (s, 3H), 2.87 (s, 3H), 2.30-2.37 (m, 1H), 1.15-1.24 (m, 2H), 1.02-1.10 (m, 1H), 0.80 (dd, J=8.85, 3.36 Hz, 1H). LCMS retention time: 1.397 min. LC data was recorded on a Shimadzu LC-10AS liquid chromatograph equipped with a Sunfire C18, 5 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% $CH_3CN$/90% $H_2O$/10 mM TFA and solvent B was 10% $H_2O$/90% $CH_3CN$/10 mM TFA. MS data was determined using a Micromass Platform for LC in electrospray mode. m/z 468.8 (MNa$^+$).

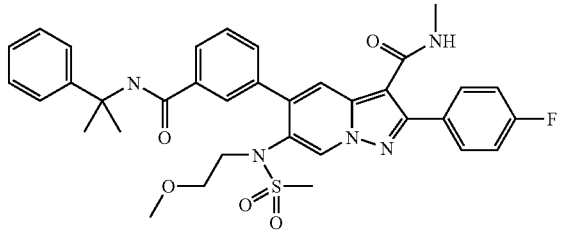

2-(4-fluorophenyl)-6-(N-(2-methoxyethyl)methylsulfonamido)-N-methyl-5-(3-(2-phenylpropan-2-ylcarbamoyl)phenyl)pyrazolo[1,5-a]pyridine-3-carboxamide. 2-(4-fluorophenyl)-6-(N-(2-methoxyethyl)methylsulfonamido)-N-methyl-5-(3-(2-phenylpropan-2-ylcarbamoyl)phenyl)pyrazolo[1,5-a]pyridine-3-carboxamide was prepared from 2-(4-fluorophenyl)-6-(N-(2-methoxyethyl)methylsulfonamido)-5-(3-(2-phenylpropan-2-ylcarbamoyl)phenyl)pyrazolo[1,5-a]pyridine-3-carboxylic acid (0.032 g, 0.049 mmol) and methylamine hydrochloride (0.014 g, 0.19 mmol). The resultant residue was purified using preparative HPLC (Waters-Xbridge, 50×100 mm, 5 micron, C18 column; 0.1M ammonium acetate, 0-100% B (B=5% $H_2O$/$CH_3CN$)/A (A=95% $H_2O$/$CH_3CN$), 10 min. gradient) to afford 2-(4-fluorophenyl)-6-(N-(2-methoxyethyl)methylsulfonamido)-N-methyl-5-(3-(2-phenylpropan-2-ylcarbamoyl)phenyl)pyrazolo[1,5-a]pyridine-3-carboxamide as a white solid. Preparative HPLC retention time: 8 min. 1H NMR (400 MHz, CHLOROFORM-d) δ ppm 8.58 (s, 1H), 8.38 (s, 1H), 8.25 (s, 1H), 7.92-7.98 (m, 1H), 7.73 (ddd, J=11.80, 5.14, 2.89 Hz, 2H), 7.61-7.66 (m, 1H), 7.52-7.58 (m, 1H), 7.47 (dd, J=8.41, 1.13 Hz, 2H), 7.24-7.34 (m, 10H), 7.18-7.23 (m, 1H), 5.61 (d, J=4.52 Hz, 1H), 3.76-3.87 (m, 1H), 3.26-3.34 (m, 7H), 3.18-3.26 (m, 3H), 2.88 (d, J=5.02 Hz, 3H), 2.61 (d, J=15.56 Hz, 1H), 1.82 (s, 6H). LCMS retention time: 2.232 mM. LC data was recorded on a Shimadzu LC-10AS liquid chromatograph equipped with a Sunfire C18, 5u, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% $CH_3CN$/90% $H_2O$/10 mM TFA and solvent B was 10% $H_2O$/90% $CH_3CN$/10 mM TFA. MS data was determined using a Micromass Platform for LC in electrospray mode. m/z 657.7 (MNa$^+$).

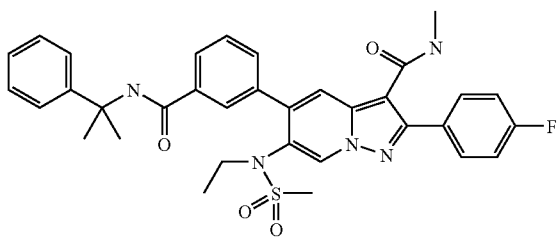

6-(N-ethylmethylsulfonamido)-2-(4-fluorophenyl)-N-methyl-5-(3-(2-phenylpropan-2-ylcarbamoyl)phenyl)pyrazolo[1,5-a]pyridine-3-carboxamide. 6-(N-ethylmethylsulfonamido)-2-(4-fluorophenyl)-N-methyl-5-(3-(2-phenylpropan-2-ylcarbamoyl)phenyl)pyrazolo[1,5-a]pyridine-3-carboxamide was prepared from 6-(N-ethylmethylsulfonamido)-2-(4-fluorophenyl)-5-(3-(2-phenylpropan-2-ylcarbamoyl)phenyl)pyrazolo[1,5-a]pyridine-3-carboxylic acid (0.030 g, 0.049 mmol) and methylamine hydrochloride (0.014 g, 0.19 mmol). The resultant residue was purified using preparative HPLC (Waters-Xbridge, 50×100 mm, 5 micron, C18 column; 0.1M ammonium acetate, 0-100% B (B=5% H$_2$O/CH$_3$CN)/A (A=95% H$_2$O/CH$_3$CN), 10 min. gradient) to afford 6-(N-ethylmethylsulfonamido)-2-(4-fluorophenyl)-N-methyl-5-(3-(2-phenylpropan-2-ylcarbamoyl)phenyl)pyrazolo[1,5-a]pyridine-3-carboxamide as a white solid. Preparative HPLC: retention time: 8.5 min. 1H NMR (500 MHz, DMSO-d$_6$) δ ppm 9.25 (s, 1H), 8.36 (s, 1H), 8.05 (q, J=4.37 Hz, 1H), 8.02 (s, 1H), 7.89-7.95 (m, 3H), 7.78 (s, 1H), 7.75 (d, J=7.63 Hz, 1H), 7.58 (t, J=7.78 Hz, 1H), 7.40 (d, J=7.32 Hz, 2H), 7.35 (t, J=8.85 Hz, 2H), 7.29 (t, J=7.78 Hz, 2H), 7.18 (t, J=7.32 Hz, 1H), 3.52 (s, 1H), 3.21 (s, 3H), 3.12 (s, 1H), 2.77 (d, J=4.58 Hz, 3H), 1.69 (s, 6H), 0.95 (t, J=7.17 Hz, 3H). LCMS retention time: 2.213 min. LC data was recorded on a Shimadzu LC-10AS liquid chromatograph equipped with a Sunfire C18, 5 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% CH$_3$CN/90% H$_2$O/10 mM TFA and solvent B was 10% H$_2$O/90% CH$_3$CN/10 mM TFA. MS data was determined using a Micromass Platform for LC in electrospray mode. m/z 628 (MH$^+$).

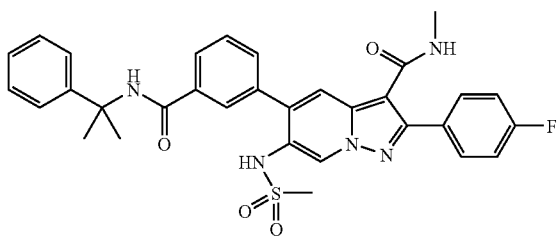

2-(4-fluorophenyl)-N-methyl-6-(methylsulfonamido)-5-(3-(2-phenylpropan-2-ylcarbamoyl)phenyl)pyrazolo[1,5-a]pyridine-3-carboxamide. 2-(4-fluorophenyl)-N-methyl-6-(methylsulfonamido)-5-(3-(2-phenylpropan-2-ylcarbamoyl)phenyl)pyrazolo[1,5-a]pyridine-3-carboxamide was prepared from 2-(4-fluorophenyl)-6-(methylsulfonamido)-5-(3-(2-phenylpropan-2-ylcarbamoyl)phenyl)pyrazolo[1,5-a]pyridine-3-carboxylic acid (0.088 g, 0.090 mmol) and methy-lamine hydrochloride (0.024 g, 0.36 mmol). The resultant residue was purified using preparative HPLC (Waters-Xbridge, 50×100 mm, 5 micron, C18 column; 0.1M ammonium acetate, 10-80% B (B=5% H$_2$O/CH$_3$CN)/A (A=95% H$_2$O/CH$_3$CN), 20 min. gradient) to afford 2-(4-fluorophenyl)-N-methyl-6-(methylsulfonamido)-5-(3-(2-phenylpropan-2-ylcarbamoyl)phenyl)pyrazolo[1,5-a]pyridine-3-carboxamide as a white solid. Preparative HPLC retention time: 14 min. 1H NMR (500 MHz, DMSO-d$_6$) δ ppm 9.43 (br. s., 1H), 8.82-8.92 (m, 3H), 8.46 (s, 3H), 8.04 (s, 4H), 7.88-7.98 (m, 13H), 7.69-7.78 (m, 7H), 7.54-7.62 (m, 4H), 7.41 (d, J=7.93 Hz, 7H), 7.26-7.36 (m, 14H), 7.18 (t, J=7.17 Hz, 3H), 2.84 (s, 10H), 2.71-2.80 (m, 11H), 1.65-1.75 (m, 21H). LCMS retention time: 2.002 min. LC data was recorded on a Shimadzu LC-10AS liquid chromatograph equipped with a Sunfire C18, 5 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% CH$_3$CN/90% H$_2$O/10 mM TFA and solvent B was 10% H$_2$O/90% CH$_3$CN/10 mM TFA. MS data was determined using a Micromass Platform for LC in electrospray mode. m/z 600 (MH$^+$).

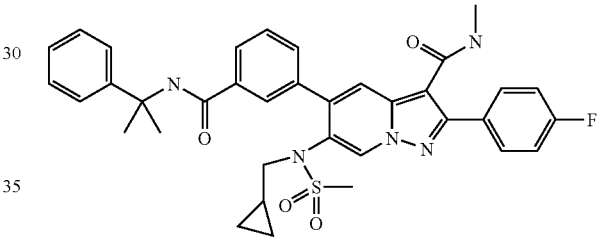

6-(N-(cyclopropylmethyl)methylsulfonamido)-2-(4-fluorophenyl)-N-methyl-5-(3-(2-phenylpropan-2-ylcarbamoyl)phenyl)pyrazolo[1,5-a]pyridine-3-carboxamide. A mixture containing 2-(4-fluorophenyl)-N-methyl-6-(methylsulfonamido)-5-(3-(2-phenylpropan-2-ylcarbamoyl)phenyl)pyrazolo[1,5-a]pyridine-3-carboxamide (0.030 g, 0.050 mmol), bromomethyl)cyclopropane (0.010 g, 0.075 mmol), potassium carbonate (0.028 g, 0.20 mmol) and DMF (0.5 mL) was stirred at 60° C. for 15 h. The solution was filtered and concentrated to afford a residue containing 6-(N-(cyclopropylmethyl)methylsulfonamido)-2-(4-fluorophenyl)-N-methyl-5-(3-(2-phenylpropan-2-ylcarbamoyl)phenyl)pyrazolo[1,5-a]pyridine-3-carboxamide which was isolated as a white solid using preparative HPLC (Waters-Xbridge, 50×100 mm, 5 micron, C18 column; 0.1M ammonium acetate, 10-80% B (B=5% H$_2$O/CH$_3$CN)/A (A=95% H$_2$O/CH$_3$CN), 20 min. gradient). Preparative HPLC retention time: 17 min. 1H NMR (500 MHz, DMSO-d$_6$) δ ppm 9.27 (s, 1H), 8.35 (s, 1H), 8.06 (br. s., 2H), 7.92 (dd, J=8.70, 5.65 Hz, 3H), 7.76-7.86 (m, 2H), 7.55-7.65 (m, 1H), 7.33-7.42 (m, 4H), 7.29 (t, J=7.63 Hz, 2H), 7.15-7.25 (m, 1H), 3.41 (dd, J=14.04, 6.71 Hz, 1H), 3.21 (s, 3H), 2.96 (dd, J=14.19, 717 Hz, 1H), 2.77 (d, J=4.27 Hz, 3H), 1.68 (s, 6H), 0.73-0.83 (m, 1H), 0.34-0.44 (m, 1H), 0.29 (ddd, J=8.16, 4.43, 4.20 Hz, 1H), 0.01-0.11 (m, 1H), −0.04 (dt, J=9.38, 4.62 Hz, 1H). LCMS retention time: 2.352 min. LC data was recorded on a Shimadzu LC-10AS liquid chromatograph equipped with a Sunfire C18, 5 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 mM, and an analysis time of 4 min where solvent A was 10% CH$_3$CN/90% H$_2$O/10 mM TFA and solvent B was 10% H$_2$O/90% CH$_3$CN/10 mM TFA. MS data was determined using a Micromass Platform for LC in electrospray mode. m/z 654 (M$^+$).

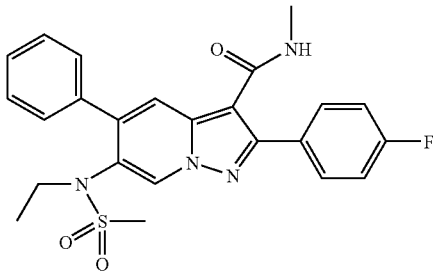

6-(N-ethylmethylsulfonamido)-2-(4-fluorophenyl)-N-methyl-5-phenylpyrazolo[1,5-a]pyridine-3-carboxamide. 6-(N-ethylmethylsulfonamido)-2-(4-fluorophenyl)-N-methyl-5-phenylpyrazolo[1,5-a]pyridine-3-carboxamide was prepared from 6-(N-ethylmethylsulfonamido)-2-(4-fluorophenyl)-5-phenylpyrazolo[1,5-a]pyridine-3-carboxylic acid (0.019 g, 0.042 mmol) and methylamine hydrochloride (0.011 g, 0.16 mmol). The resultant residue was purified using preparative HPLC (Waters-Xbridge, 50×100 mm, 5 micron, C18 column; 0.1M TFA, 10-100% B (B=5% H$_2$O/CH$_3$CN)/A (A=95% H$_2$O/CH$_3$CN), 10 min. gradient) to afford 6-(N-ethylmethylsulfonamido)-2-(4-fluorophenyl)-N-methyl-5-phenylpyrazolo[1,5-a]pyridine-3-carboxamide as a white solid. Preparative HPLC retention time: 7 min. 1H NMR (400 1H NMR (400 MHz, CHLOROFORM-d) δ ppm 8.56 (s, 1H), 8.32 (s, 1H), 7.67-7.77 (m, 2H), 7.54 (d, J=2.01 Hz, 1H), 7.52 (d, J=1.51 Hz, 1H), 7.40-7.50 (m, 3H), 7.20-7.30 (m, 4H), 5.54 (d, J=4.02 Hz, 1H), 2.81-2.93 (m, 3H), 2.70-2.81 (m, 3H), 1.16 (t, J=7.15 Hz, 3H). LCMS retention time: 1.443 min. LC data was recorded on a Shimadzu LC-10AS liquid chromatograph equipped with a Xterra, 7 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of min, and an analysis time of 4 min where solvent A was 10% methanol/90% H$_2$O/10 mM TFA and solvent B was 10% H$_2$O/90% methanol/10 mM TFA. MS data was determined using a Micromass Platform for LC in electrospray mode. m/z 466.9 (MH$^+$).

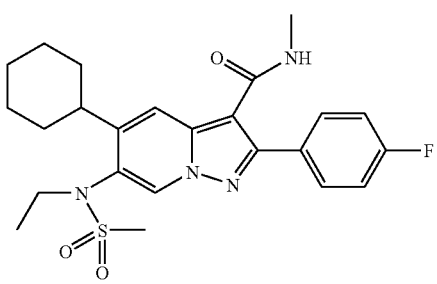

5-cyclohexyl-6-(N-ethylmethylsulfonamido)-2-(4-fluorophenyl)-N-methylpyrazolo[1,5-a]pyridine-3-carboxamide. 5-cyclohexyl-6-(N-ethylmethylsulfonamido)-2-(4-fluorophenyl)-N-methylpyrazolo[1,5-a]pyridine-3-carboxamide was prepared from 5-cyclohexyl-6-(N-ethylmethylsulfonamido)-2-(4-fluorophenyl)pyrazolo[1,5-a]pyridine-3-carboxylic acid (0.018 g, 0.039 mmol) and methylamine hydrochloride (0.011 g, 0.16 mmol). The resultant residue was purified using preparative HPLC (Waters-Xbridge, 50×100 mm, 5 micron, C18 column; 0.1M TFA, 10-100% B (B=5% H$_2$O/CH$_3$CN)/A (A=95% H$_2$O/CH$_3$CN), 15 min. gradient) to afford 5-cyclohexyl-6-(N-ethylmethylsulfonamido)-2-(4-fluorophenyl)-N-methylpyrazolo[1,5-a]pyridine-3-carboxamide. Preparative HPLC retention time: 10 min. 1H NMR (400 MHz, CHLOROFORM-d) δ ppm 8.47 (s, 1H), 8.31 (s, 1H), 7.63-7.75 (m, 2H), 7.22-7.28 (m, 5H), 3.84 (dq, J=14.05, 7.03 Hz, 1H), 3.57 (dq, J=14.02, 7.12 Hz, 1H), 3.03-3.07 (m, 3H), 2.90-2.99 (m, J=11.86, 11.86, 3.39, 3.26 Hz, 1H), 2.88 (d, J=4.77 Hz, 3H), 2.00 (d, J=13.05 Hz, 1H), 1.89 (d, J=11.29 Hz, 2H), 1.73-1.85 (m, 2H), 1.54-1.64 (m, 2H), 1.35-1.48 (m, 3H), 1.20-1.27 (m, 3H). LCMS retention time: 1.577 min. LC data was recorded on a Shimadzu LC-10AS liquid chromatograph equipped with a Xterra, 7 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 2 min, a hold time of 1 mM, and an analysis time of 3 mM where solvent A was 10% methanol/90% H$_2$O/10 mM TFA and solvent B was 10% H$_2$O/90% methanol/10 mM TFA. MS data was determined using a Micromass Platform for LC in electrospray mode. m/z 473 (MH$^+$).

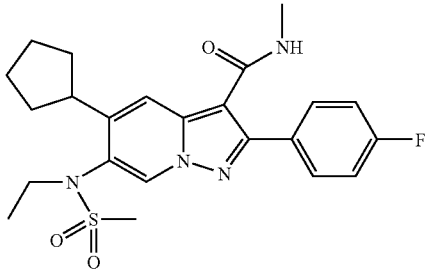

5-cyclopentyl-6-(N-ethylmethylsulfonamido)-2-(4-fluorophenyl)-N-methylpyrazolo[1,5-a]pyridine-3-carboxamide. 5-cyclopentyl-6-(N-ethyl methylsulfonamido)-2-(4-fluorophenyl)-N-methylpyrazolo[1,5-a]pyridine-3-carboxamide was prepared from 5-cyclohexyl-6-(N-ethylmethylsulfonamido)-2-(4-fluorophenyl)pyrazolo[1,5-a]pyridine-3-carboxylic acid (0.015 g, 0.034 mmol) and methylamine hydrochloride (0.009 g, 0.13 mmol). The resultant residue was purified using preparative HPLC (Waters-Xbridge, 50×100 mm, 5 micron, C18 column; 0.1M TFA, 10-100% B (B=5% H$_2$O/CH$_3$CN)/A (A=95% H$_2$O/CH$_3$CN), 15 min. gradient) to afford 5-cyclopentyl-6-(N-ethylmethylsulfonamido)-2-(4-fluorophenyl)-N-methylpyrazolo[1,5-a] pyridine-3-carboxamide as a white solid. Preparative HPLC retention time: 9 min. 1H NMR (400 MHz, CHLOROFORM-d) δ ppm 8.42-8.50 (m, 1H), 8.30-8.42 (m, 1H), 7.64-7.73 (m, 2H), 7.21-7.33 (m, 2H), 5.51 (br. s., 1H), 3.83 (dd, J=13.80, 7.03 Hz, 1H), 3.56-3.69 (m, 1H), 3.41 (d, J=8.53 Hz, 1H), 3.00-3.12 (m, 3H), 2.87 (d, J=4.77 Hz, 3H), 2.25 (br. s., 1H), 2.11 (br. s., 1H), 1.95 (br. s., 2H), 1.75 (br. s., 6H), 1.19-1.31 (m, 3H). LCMS retention time: 1.500 min. LC data was recorded on a Shimadzu LC-10AS liquid chromatograph equipped with a Xterra, 7 micron, C18, 3.0×50 mm column using a SPD-10AV UV-Vis detector at a detector wave length of 220 nM. The elution conditions employed a flow rate of 4 ml/min, a gradient of 100% solvent A/0% solvent B to 0% solvent A/100% solvent B, a gradient time of 2 mM, a hold time of 1 min, and an analysis time of 3 min where solvent A was 10% methanol/90% H$_2$O/10 mM TFA and solvent B was 10% H$_2$O/90% methanol/10 mM TFA. MS data was determined using a Micromass Platform for LC in electrospray mode. m/z 459 (MH$^+$).

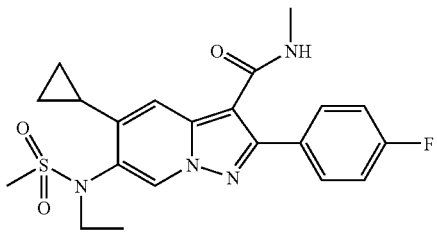

5-cyclopropyl-6-(N-ethylmethylsulfonamido)-2-(4-fluorophenyl)-N-methylpyrazolo[1,5-a]pyridine-3-carboxamide. To a degassed solution containing 6-(N-ethylmethylsulfonamido)-2-(4-fluorophenyl)-3-(methylcarbamoyl)pyrazolo[1,5-a]pyridin-5-yl trifluoromethanesulfonate (0.050 g, 0.093 mmol), cyclopropylboronic acid (0.012 g, 0.14 mmol), Potassium phosphate tribasic monohydrate (0.69 g, 0.33 mmol), tricyclohexylphosphine (0.260 mg, 0.93 μmol), toluene (0.9 mL) and water (0.08 mL) was added palladium acetate (1.0 mg, 4.64 μmol). The solution was maintained at 95° C. for 2 h. The solution was filtered to remove solids and concentrated to afford a residue containing 5-cyclopropyl-6-(N-ethylmethylsulfonamido)-2-(4-fluorophenyl)-N-methylpyrazolo[1,5-a]pyridine-3-carboxamide. The compound was isolated as a white solid using preparative HPLC (Waters-Xbridge, 50×100 mm, 5 micron, C18 column; 0.1M TFA, 10-100% B (B=5% H$_2$O/CH$_3$CN)/A (A=95% H$_2$O/CH$_3$CN), 15 min. gradient). Preparative HPLC retention time: 8.5 mM. 1H NMR (400 MHz, CHLOROFORM-d) δ ppm 8.50 (s, 1H), 7.84 (s, 1H), 7.62-7.74 (m, 2H), 7.17-7.29 (m, 2H), 5.52 (br. s., 1H), 3.90 (br. s., 1H), 3.70 (d, J=7.78 Hz, 1H), 3.08 (s, 3H), 2.86 (d, J=4.77 Hz, 3H), 2.23 (tt, J=8.31, 5.24 Hz, 2H), 1.27 (t, J=7.15 Hz, 3H), 1.19 (ddd, J=8.22, 3.07, 1.51 Hz, 2H), 1.13 (d, J=14.31 Hz, 1H). LCMS retention time: 1.322 min. LC data was recorded on a Shimadzu LC-10AS liquid chromatograph equipped with a Xterra, 7 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 2 min, a hold time of 1 min, and an analysis time of 3 min where solvent A was 10% methanol/90% H$_2$O/10 mM TFA and solvent B was 10% H$_2$O/90% methanol/10 mM TFA. MS data was determined using a Micromass Platform for LC in electrospray mode. m/z 430.8 (MH$^+$).

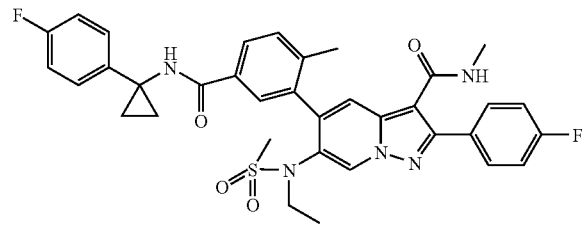

6-(N-ethylmethylsulfonamido)-2-(4-fluorophenyl)-5-(5-(1-(4-fluorophenyl)cyclopropylcarbamoyl)-2-methylphenyl)-N-methylpyrazolo[1,5-a]pyridine-3-carboxamide. 6-(N-ethylmethylsulfonamido)-2-(4-fluorophenyl)-5-(5-(1-(4-fluorophenyl)cyclopropylcarbamoyl)-2-methylphenyl)-N-methylpyrazolo[1,5-a]pyridine-3-carboxamide was prepared from 3-(6-(N-ethylmethylsulfonamido)-2-(4-fluorophenyl)-3-(methylcarbamoyl)pyrazolo[1,5-a]pyridin-5-yl)-4-methylbenzoic acid (0.024 g, 0.046 mmol) and 1-(4-fluorophenyl)cyclopropanamine hydrochloride (0.013 g, 0.069 mmol). The resultant residue was purified using preparative HPLC (Waters-Xbridge, 50×100 mm, 5 micron, C18 column; 0.1M ammonium acetate, 10-100% B (B=5% H$_2$O/CH$_3$CN)/A (A=95% H$_2$O/CH$_3$CN), 15 min. gradient) to afford 6-(N-ethylmethylsulfonamido)-2-(4-fluorophenyl)-5-(5-(1-(4-fluorophenyl)cyclopropylcarbamoyl)-2-methylphenyl)-N-methylpyrazolo[1,5-a]pyridine-3-carboxamide as a white solid. Preparative HPLC retention time: 8.5 min. 1H NMR (400 MHz, CHLOROFORM-d) δ ppm 8.54 (s, 1H), 8.29 (s, 1H), 7.82 (br. s., 2H), 7.65-7.77 (m, 2H), 7.40 (d, J=7.78 Hz, 2H), 7.31-7.38 (m, 3H), 7.22-7.30 (m, 4H), 6.90-7.00 (m, 2H), 5.55 (d, J=4.77 Hz, 1H), 3.42 (br. s., 1H), 3.00-3.12 (m, 2H), 2.78-2.90 (m, 4H), 2.34 (s, 3H), 1.62 (br. s., 2H), 1.25-1.37 (m, 5H), 1.08 (br. s., 3H). LCMS retention time: 1.920 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 5% CH$_3$CN/95% H$_2$O/10 mM ammonium acetate and solvent B was 5% H$_2$O/95% CH$_3$CN/10 mM ammonium acetate. MS data was determined using a Micromass Platform for LC in electrospray mode. m/z 658 (MH$^+$).

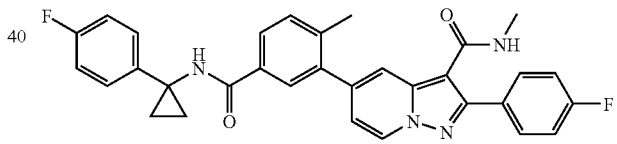

2-(4-fluorophenyl)-5-(5-(1-(4-fluorophenyl)cyclopropylcarbamoyl)-2-methylphenyl)-N-methylpyrazolo[1,5-a]pyridine-3-carboxamide. 2-(4-fluorophenyl)-5-(5-(1-(4-fluorophenyl)cyclopropylcarbamoyl)-2-methylphenyl)-N-methylpyrazolo[1,5-a]pyridine-3-carboxamide was prepared from 3-(2-(4-fluorophenyl)-3-(methylcarbamoyl)pyrazolo[1,5-a]pyridin-5-yl)-4-methylbenzoic acid (0.016 g, 0.040 mmol) and 1-(4-fluorophenyl)cyclopropanamine hydrochloride (0.011 g, 0.059 mmol). The resultant residue was purified using preparative HPLC (Waters-Xbridge, 50×100 mm, 5 micron, C18 column; 0.1M ammonium acetate, 10-100% B (B=5% H$_2$O/CH$_3$CN)/A (A=95% H$_2$O/CH$_3$CN), 15 min. gradient) to afford 2-(4-fluorophenyl)-5-(5-(1-(4-fluorophenyl)cyclopropylcarbamoyl)-2-methylphenyl)-N-methylpyrazolo[1,5-a]pyridine-3-carboxamide as a white solid. Preparative HPLC retention time: 10.5 min. 1H NMR (400 MHz, DMSO-d$_6$) δ ppm 9.24 (s, 1H), 8.84 (d, J=7.03 Hz, 1H), 7.83-7.96 (m, 5H), 7.75 (s, 1H), 7.47 (d, J=8.03 Hz, 1H), 7.26-7.38 (m, 4H), 7.05-7.16 (m, 3H), 2.78 (d, J=4.77 Hz, 3H), 2.37 (s, 3H), 1.26 (d, J=6.27 Hz, 4H). LCMS retention time: 2.533 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 mM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% methanol/90% water/10 mM TFA and solvent B was 10% water/90% methanol/10 mM TFA. MS data was determined using a Micromass Platform for LC in electrospray mode. m/z 537 (MH+).

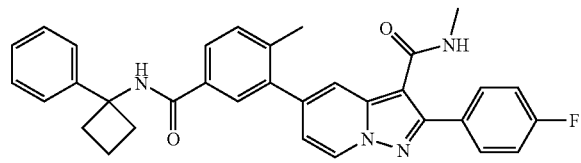

2-(4-fluorophenyl)-N-methyl-5-(2-methyl-5-(1-phenylcyclobutylcarbamoyl)phenyl)pyrazolo[1,5-a]pyridine-3-carboxamide. 2-(4-fluorophenyl)-N-methyl-5-(2-methyl-5-(1-phenylcyclobutylcarbamoyl)phenyl)pyrazolo[1,5-a]pyridine-3-carboxamide was prepared from 3-(2-(4-fluorophenyl)-3-(methylcarbamoyl)pyrazolo[1,5-a]pyridin-5-yl)-4-methylbenzoic acid (0.024 g, 0.059 mmol) and 1-phenylcyclobutanamine hydrochloride (0.016 g, 0.089 mmol). The resultant residue was purified using preparative HPLC (Waters-Xbridge, 50×100 mm, 5 micron, C18 column; 0.1M TFA, 10-100% B (B=5% H₂O/CH₃CN)/A (A=95% H₂O/CH₃CN), 15 min. gradient) to afford 2-(4-fluorophenyl)-N-methyl-5-(2-methyl-5-(1-phenylcyclobutylcarbamoyl)phenyl)pyrazolo[1,5-a]pyridine-3-carboxamide as a white solid. Preparative HPLC retention time: 11 min. 1H NMR (400 MHz, CHLOROFORM-d) δ ppm 8.52 (d, J=7.03 Hz, 1H), 8.29 (s, 1H), 7.67-7.79 (m, 4H), 7.54 (d, J=7.78 Hz, 2H), 7.32-7.43 (m, 3H), 7.20-7.32 (m, 6H), 6.94 (d, J=7.03 Hz, 1H), 6.80 (s, 1H), 5.66 (d, J=4.27 Hz, 1H), 2.88 (d, J=4.77 Hz, 3H), 2.75 (t, J=7.78 Hz, 4H), 2.38 (s, 3H), 2.11-2.24 (m, 1H), 1.95 (dt, J=11.48, 7.94 Hz, 1H). LCMS retention time: 1.870 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 2 min, a hold time of 1 min, and an analysis time of 3 min where solvent A was 10% methanol/90% water/10 mM TFA and solvent B was 10% water/90% methanol/10 mM TFA. MS data was determined using a Micromass Platform for LC in electrospray mode. m/z 533 (MH+).

Example 24

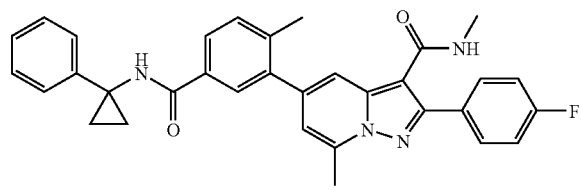

2-(4-fluorophenyl)-N,7-dimethyl-5-(2-methyl-5-(1-phenylcyclopropylcarbamoyl)phenyl)pyrazolo[1,5-a]pyridine-3-carboxamide. Following the procedure for preparing 4-fluoro-2-(4-fluorophenyl)-N-methyl-5-(2-methyl-5-(1-phenylcyclopropylcarbamoyl)phenyl)pyrazolo[1,5-a]pyridine-3-carboxamide (Example 25), 2-(4-fluorophenyl)-N,7-dimethyl-5-(2-methyl-5-(1-phenylcyclopropylcarbamoyl)phenyl)pyrazolo[1,5-a]pyridine-3-carboxamide was prepared from 3-(2-(4-fluorophenyl)-7-methyl-3-(methylcarbamoyl)pyrazolo[1,5-a]pyridin-5-yl)-4-methylbenzoic acid (0.022 g, 0.053 mmol) and 1-phenylcyclopropanamine hydrochloride (0.013 g, 0.079 mmol). The residue thus obtained was purified using preparative HPLC (Waters-Xbridge, 50×100 mm, 5 micron, C18 column; 0.1M TFA, 10-100% B (B=5% H₂O/CH₃CN)/A (A=95% H₂O/CH₃CN), 15 min. gradient) to afford 2-(4-fluorophenyl)-N,7-dimethyl-5-(2-methyl-5-(1-phenylcyclopropyl)carbamoyl)phenyl)pyrazolo[1,5-a]pyridine-3-carboxamide as a white solid. Preparative HPLC retention time: 11.5 mM. 1H NMR (400 MHz, CHLOROFORM-d) δ ppm 8.23 (d, J=1.25 Hz, 1H), 7.69-7.82 (m, 4H), 7.39 (d, J=8.03 Hz, 1H), 7.29-7.36 (m, 4H), 7.23-7.29 (m, 6H), 7.17-7.23 (m, 1H), 7.04 (s, 1H), 6.82 (s, 1H), 5.66 (d, J=4.52 Hz, 1H), 2.87 (d, J=5.02 Hz, 4H), 2.84 (s, 3H), 2.40 (s, 3H), 1.34-1.46 (m, 4H). LCMS retention time: 2.413 min. LC data was recorded on a Shimadzu LC-10AS liquid chromatograph equipped with a Sunfire C18, 5 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 mM, and an analysis time of 4 mM where solvent A was 10% CH₃CN/90% H₂O/10 mM TFA and solvent B was 10% H₂O/90% CH₃CN/10 mM TFA. MS data was determined using a Micromass Platform for LC in electrospray mode. m/z 533 (MH+).

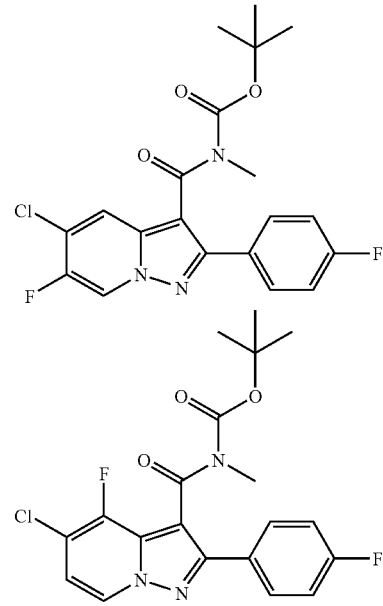

tert-butyl 5-chloro-6-fluoro-2-(4-fluorophenyl)pyrazolo[1,5-a]pyridine-3-carbonyl(methyl)carbamate and tert-butyl 5-chloro-4-fluoro-2-(4-fluorophenyl)pyrazolo[1,5-a]pyridine-3-carbonyl(methyl)carbamate. tert-butyl 5-chloro-6-fluoro-2-(4-fluorophenyl)pyrazolo[1,5-a]pyridine-3-carbonyl(methyl)carbamate and tert-butyl 5-chloro-4-fluoro-2-(4- fluorophenyl)pyrazolo[1,5-a]pyridine-3-carbonyl(methyl) carbamate were prepared as a residue containing a mixture of regioisomers starting from 4-chloro-3-fluoropyridine (2.0 g, 15.2 mmol). Isolation on silica gel (0-80% ethyl acetate/hexanes, 60 mM gradient) afforded tert-butyl 5-chloro-6-fluoro-2-(4-fluorophenyl)pyrazolo[1,5-a]pyridine-3-carbonyl(methyl)carbamate as the first eluting isomer and tert-butyl 5-chloro-4-fluoro-2-(4-fluorophenyl)pyrazolo[1,5-a]pyridine-3-carbonyl(methyl)carbamate as the second eluting isomer which was favored in a 2.2/1 ratio. Each isomer was an off white solid. tert-butyl 5-chloro-6-fluoro-2-(4-fluorophenyl)pyrazolo[1,5-a]pyridine-3-carbonyl (methyl)carbamate: 1H NMR (400 MHz, CHLOROFORM-d) δ ppm 8.48 (d, J=3.76 Hz, 1H), 7.93 (d, J=7.28 Hz, 1H), 7.65 (dd, J=8.66, 5.40 Hz, 2H), 7.15 (t, J=8.66 Hz, 2H), 3.26 (s, 3H), 1.11 (s, 9H). LCMS retention time: 2.681 min. LC data was recorded on a Shimadzu LC-10AS liquid chromatograph equipped with a Sunfire C18, 5 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% CH$_3$CN/90% H$_2$O/10 mM TFA and solvent B was 10% H$_2$O/90% CH$_3$CN/10 mM TFA. MS data was determined using a Micromass Platform for LC in electrospray mode. m/z 422 (MH$^+$). tert-butyl 5-chloro-4-fluoro-2-(4-fluorophenyl)pyrazolo[1,5-a]pyridine-3-carbonyl(methyl) carbamate: 1H NMR (400 MHz, CHLOROFORM-d) δ ppm 8.26 (dd, J=7.28, 1.00 Hz, 1H), 7.71 (dd, J=8.91, 5.40 Hz, 2H), 7.15 (t, J=8.66 Hz, 2H), 6.80-6.89 (m, 1H), 3.34 (s, 3H), 1.15 (s, 9H). LCMS retention time: 2.625 min. LC data was recorded on a Shimadzu LC-10AS liquid chromatograph equipped with a Sunfire C18, 5 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 mM, and an analysis time of 4 mM where solvent A was 10% CH$_3$CN/90% H$_2$O/10 mM TFA and solvent B was 10% H$_2$O/90% CH$_3$CN/10 mM TFA. MS data was determined using a Micromass Platform for LC in electrospray mode. m/z 422 (MH$^+$).

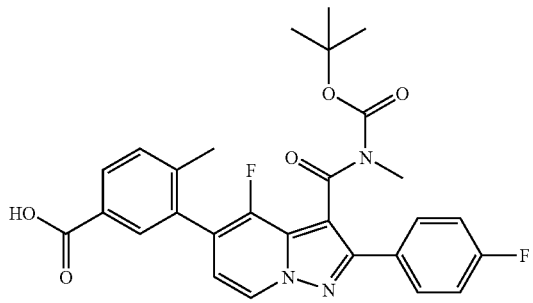

3-(3-(tert-butoxycarbonyl(methyl)carbamoyl)-4-fluoro-2-(4-fluorophenyl)pyrazolo[1,5-a]pyridin-5-yl)-4-methylbenzoic acid. To a degassed solution containing tert-butyl 5-chloro-4-fluoro-2-(4-fluorophenyl)pyrazolo[1,5-a]pyridine-3-carbonyl(methyl)carbamate (0.10 g, 0.24 mmol), 4-methyl-3-(4,4,5,5-tetramethyl-1,3,2-dioxaborolan-2-yl)benzoic acid (0.078 g, 0.30 mmol), sodium carbonate (0.075 g, 0.71 mmol), dioxane (2.0 mL) and water (0.40 mL) was added tetrakis(tiphenylphosphine)palladium(0) (0.008 g, 0.007 mmol). The mixture was stirred at 95° C. for 18 h. The solution was cooled to room temperature, filtered to remove solids and adjusted to below pH 4 with 1 N aqueous hydrochloric acid (2.0 mL). Water was added (10 mL) and the aqueous portion was extracted with ethyl acetate (2×15 mL). The combined organic portions were washed with brine (20 mL) and dried over magnesium sulfate. The mixture was filtered and concentrated to afford 3-(3-(tert-butoxycarbonyl(methyl)carbamoyl)-4-fluoro-2-(4-fluorophenyl)pyrazolo[1,5-a]pyridin-5-yl)-4-methylbenzoic acid as a residue which was used without further purification. LCMS retention time: 2.467 min. LC data was recorded on a Shimadzu LC-10AS liquid chromatograph equipped with a Sunfire C18, 5 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% CH$_3$CN/90% H$_2$O/10 mM TFA and solvent B was 10% H$_2$O/90% CH$_3$CN/10 mM TFA. MS data was determined using a Micromass Platform for LC in electrospray mode. m/z 522 (MH$^+$).

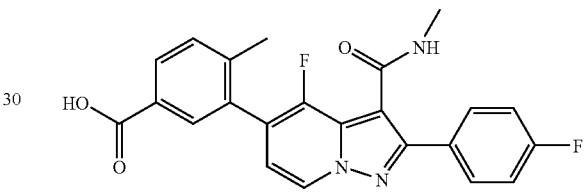

3-(4-fluoro-2-(4-fluorophenyl)-3-(methylcarbamoyl)pyrazolo[1,5-a]pyridin-5-yl)-4-methylbenzoic acid. To a solution containing 3-(3-(tert-butoxycarbonyl(methyl)carbamoyl)-4-fluoro-2-(4-fluorophenyl)pyrazolo[1,5-a]pyridin-5-yl)-4-methylbenzoic acid (0.070 g, 0.13 mmol) and dichloromethane (8.0 mL) was added TFA (0.84 mL, 10.9 mmol) at room temperature. The solution was maintained for 15 min and concentrated to dryness to afford 3-(4-fluoro-2-(4-fluorophenyl)-3-(methylcarbamoyl)pyrazolo[1,5-a]pyridin-5-yl)-4-methylbenzoic acid as an off white solid which was used without further purification. LCMS retention time: 1.825 min. LC data was recorded on a Shimadzu LC-10AS liquid chromatograph equipped with a Sunfire C18, 5 micron, C18, 4.6×50 mm column using a SPD-10AV UV-Vis detector at a detector wave length of 220 nM. The elution conditions employed a flow rate of 4 ml/min, a gradient of 100% solvent A/0% solvent B to 0% solvent A/100% solvent B, a gradient time of 3 min, a hold time of 1 min, and an analysis time of 4 min where solvent A was 10% CH$_3$CN/90% H$_2$O/10 mM TFA and solvent B was 10% H$_2$O/90% CH$_3$CN/10 mM TFA. MS data was determined using a Micromass Platform for LC in electrospray mode. m/z 444 (MNa$^+$).

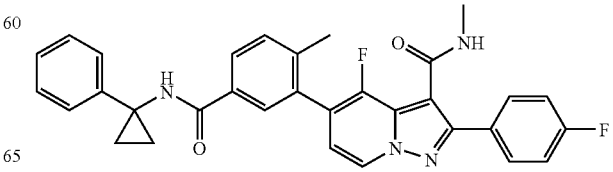

4-fluoro-2-(4-fluorophenyl)-N-methyl-5-(2-methyl-5-(1-phenylcyclopropylcarbamoyl)phenyl)pyrazolo[1,5-a]pyridine-3-carboxamide. To a solution containing 1-phenylcyclopropanamine hydrochloride (0.030 g, 0.18 mmol), diisopropylethylamine (0.16 mL, 0.95 mmol), 3-(4-fluoro-2-(4-fluorophenyl)-3-(methylcarbamoyl)pyrazolo[1,5-a]pyridin-5-yl)-4-methylbenzoic acid (0.050 g, 0.12 mmol) and DMF (0.8 mL) was added HATU (0.09 g, 0.24 mmol) in one portion. The solution was maintained at room temperature for 1 h and concentrated. The resultant residue was purified using preparative HPLC (Waters-Xbridge, 50×100 mm, 5 micron, C18 column; 0.1M ammonium acetate, 10-100% B (B=5% H$_2$O/CH$_3$CN)/A (A=95% H$_2$O/CH$_3$CN), 15 min. gradient) to afford 4-fluoro-2-(4-fluorophenyl)-N-methyl-5-(2-methyl-5-(1-phenylcyclopropylcarbamoyl)phenyl)pyrazolo[1,5-a]pyridine-3-carboxamide as a white solid. Preparative HPLC retention time: 9.0 min. 1H NMR (400 MHz, CHLOROFORM-d) δ ppm 8.35 (d, J=6.78 Hz, 1H), 7.81-7.90 (m, 2H), 7.76 (d, J=7.78 Hz, 1H), 7.72 (s, 1H), 7.40 (d, J=8.03 Hz, 1H), 7.29-7.37 (m, 4H), 7.13-7.24 (m, 3H), 6.90 (s, 1H), 6.73 (t, J=6.65 Hz, 1H), 5.90 (d, J=4.52 Hz, 1H), 2.97 (d, J=4.77 Hz, 3H), 2.32 (s, 3H), 1.39 (br. s., 4H). LCMS retention time: 1.975 min. LC data was recorded on a Shimadzu LC-10AS liquid chromatograph equipped with a Xbridge, 5 micron, C18, 4.6×50 mm column using a SPD-10AV UV-Vis detector at a detector wave length of 220 nM. The elution conditions employed a flow rate of 4 ml/min, a gradient of 100% solvent A/0% solvent B to 0% solvent A/100% solvent B, a gradient time of 3 min, a hold time of 1 min, and an analysis time of 4 min where solvent A was 5% CH$_3$CN/95% H$_2$O/10 mM ammonium acetate and solvent B was 5% H$_2$O/95% CH$_3$CN/10 mM ammonium acetate. MS data was determined using a Micromass Platform for LC in electrospray mode. m/z 537 (MH$^+$).

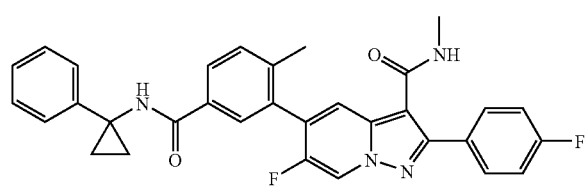

6-fluoro-2-(4-fluorophenyl)-N-methyl-5-(2-methyl-5-(1-phenylcyclopropylcarbamoyl)phenyl)pyrazolo[1,5-a]pyridine-3-carboxamide. 6-fluoro-2-(4-fluorophenyl)-N-methyl-5-(2-methyl-5-(1-phenylcyclopropyl carbamoyl)phenyl)pyrazolo[1,5-a]pyridine-3-carboxamide was prepared from 3-(6-fluoro-2-(4-fluorophenyl)-3-(methylcarbamoyl)pyrazolo[1,5-a]pyridin-5-yl)-4-methylbenzoic acid (0.024 g, 0.059 mmol) and 1-phenylcyclopropanamine hydrochloride (0.015 g, 0.089 mmol). The resultant residue was purified using preparative HPLC (Waters-Xbridge, 50×100 mm, 5 micron, C18 column; 0.1M ammonium acetate, 10-100% B (B=5% H$_2$O/CH$_3$CN)/A (A=95% H$_2$O/CH$_3$CN), 15 min. gradient) to afford 6-fluoro-2-(4-fluorophenyl)-N-methyl-5-(2-methyl-5-(1-phenylcyclopropylcarbamoyl)phenyl)pyrazolo[1,5-a]pyridine-3-carboxamide as a white solid. Preparative HPLC retention time: 10.5 min. 1H NMR (400 MHz, CHLOROFORM-d) δ ppm 8.49 (d, J=4.02 Hz, 1H), 8.31 (d, J=7.53 Hz, 1H), 7.84 (dd, J=8.03, 1.76 Hz, 1H), 7.66-7.74 (m, 3H), 7.40 (d, J=8.03 Hz, 1H), 7.29-7.37 (m, 4H), 7.24-7.27 (m, 1H), 7.20 (t, J=6.02 Hz, 1H), 6.89 (s, 1H), 5.56 (d, J=4.27 Hz, 1H), 2.86 (d, J=4.77 Hz, 3H), 2.32 (s, 3H), 1.40 (d, J=9.03 Hz, 4H). LCMS retention time: 2.535 mM. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% methanol/90% water/10 mM TFA and solvent B was 10% water/90% methanol/10 mM TFA. MS data was determined using a Micromass Platform for LC in electrospray mode. m/z 537 (MH$^+$).

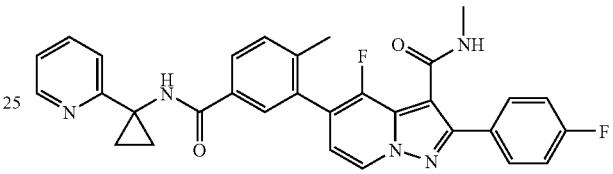

4-fluoro-2-(4-fluorophenyl)-N-methyl-5-(2-methyl-5-(1-(pyridin-2-yl)cyclopropylcarbamoyl)phenyl)pyrazolo[1,5-a]pyridine-3-carboxamide. 4-fluoro-2-(4-fluorophenyl)-N-methyl-5-(2-methyl-5-(1-(pyridin-2-yl)cyclopropylcarbamoyl)phenyl)pyrazolo[1,5-a]pyridine-3-carboxamide was prepared from 3-(4-fluoro-2-(4-fluorophenyl)-3-(methylcarbamoyl)pyrazolo[1,5-a]pyridin-5-yl)-4-methylbenzoic acid (0.065 g, 0.154 mmol) and 1-(pyridin-2-yl)cyclopropanamine dihydrochloride (0.032 g, 0.154 mmol). The resultant residue was purified using preparative HPLC (Waters-Xbridge, 50×100 mm, 5 micron, C18 column; 0.1M ammonium acetate, 10-100% B (B=5% H$_2$O/CH$_3$CN)/A (A=95% H$_2$O/CH$_3$CN), 20 min. gradient) to afford 4-fluoro-2-(4-fluorophenyl)-N-methyl-5-(2-methyl-5-(1-(pyridin-2-yl)cyclopropylcarbamoyl)phenyl)pyrazolo[1,5-a]pyridine-3-carboxamide as a white solid. Preparative HPLC: retention time: 9.5 mM. 1H NMR (400 MHz, CHLOROFORM-d) δ ppm 8.48 (d, J=4.02 Hz, 1H), 8.37 (d, J=7.03 Hz, 1H), 7.78-7.90 (m, 4H), 7.60 (td, J=7.78, 1.76 Hz, 1H), 7.44 (d, J=8.03 Hz, 1H), 7.38 (d, J=7.78 Hz, 1H), 7.13-7.22 (m, 2H), 7.04-7.13 (m, 2H), 6.76 (t, J=6.78 Hz, 1H), 5.87 (d, J=4.52 Hz, 1H), 2.97 (d, J=5.02 Hz, 3H), 2.35 (s, 3H), 1.69-1.80 (m, 2H), 1.37-1.48 (m, 2H). LCMS retention time: 1.642 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% methanol/90% water/10 mM TFA and solvent B was 10% water/90% methanol/10 mM TFA. MS data was determined using a Micromass Platform for LC in electrospray mode. m/z 538 (MH$^+$).

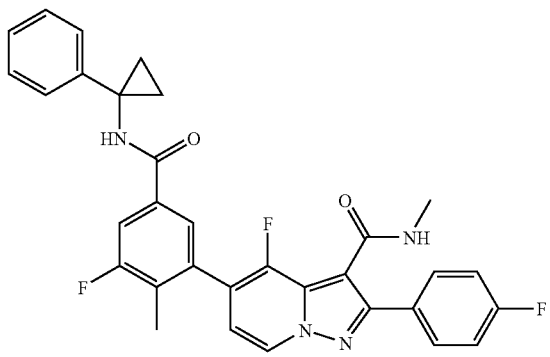

4-fluoro-5-(3-fluoro-2-methyl-5-(1-phenylcyclopropylcarbamoyl)phenyl)-2-(4-fluorophenyl)-N-methylpyrazolo[1,5-a]pyridine-3-carboxamide. To a solution containing 1-phenylcyclopropanamine hydrochloride (0.059 g, 0.027 mmol), diisopropylethylamine (0.04 mL, 0.22 mmol), 3-fluoro-5-(4-fluoro-2-(4-fluorophenyl)-3-(methylcarbamoyl)pyrazolo[1,5-a]pyridin-5-yl)-4-methylbenzoic acid (0.012 g, 0.027 mmol) and DMF (0.19 mL) was added HATU (0.021 g, 0.055 mmol) in one portion. The solution was maintained at room temperature for 1 h and concentrated. The resultant residue was purified using preparative HPLC (Waters-Xbridge, 50×100 mm, 5 micron, C18 column; 0.1M ammonium acetate, 0-100% B (B=5% H$_2$O/CH$_3$CN)/A (A=95% H$_2$O/CH$_3$CN), 20 min. gradient) afforded 4-fluoro-5-(3-fluoro-2-methyl-5-(1-phenylcyclopropylcarbamoyl)phenyl)-2-(4-fluorophenyl)-N-methylpyrazolo[1,5-a]pyridine-3-carboxamide as a white solid. Preparative HPLC retention time: 15.0 min. 1H NMR (400 MHz, CHLOROFORM-d) δ ppm 8.36 (d, J=7.03 Hz, 1H), 7.80-7.89 (m, 2H), 7.56 (d, J=9.79 Hz, 1H), 7.51 (s, 1H), 7.28-7.36 (m, 4H), 7.13-7.25 (m, 3H), 6.91 (s, 1H), 6.72 (t, J=6.78 Hz, 1H), 5.85 (d, J=4.27 Hz, 1H), 2.97 (d, J=4.77 Hz, 3H), 2.23 (s, 3H), 1.38 (s, 4H). LCMS retention time: 2.437 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% CH$_3$OH/90% H$_2$O/10 mM TFA and solvent B was 10% H$_2$O/90% CH$_3$OH/10 mM TFA. MS data was determined using a Micromass Platform for LC in electrospray mode. m/z 555 (MH$^+$).

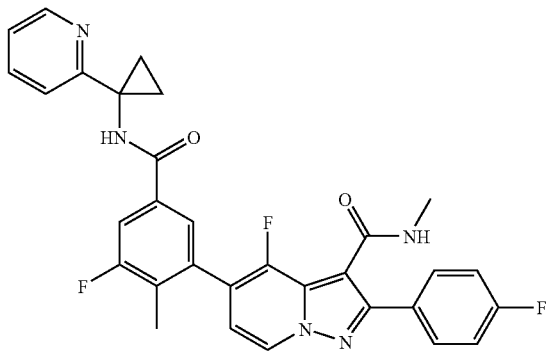

4-fluoro-5-(3-fluoro-2-methyl-5-(1-(pyridin-2-yl)cyclopropylcarbamoyl)phenyl)-2-(4-fluorophenyl)-N-methylpyrazolo[1,5-a]pyridine-3-carboxamide. To a solution containing 1-(pyridin-2-yl)cyclopropanamine dihydrochloride (0.070 g, 0.033 mmol), diisopropylethylamine (0.04 mL, 0.22 mmol), 3-fluoro-5-(4-fluoro-2-(4-fluorophenyl)-3-(methylcarbamoyl)pyrazolo[1,5-a]pyridin-5-yl)-4-methylbenzoic acid (0.012 g, 0.027 mmol) and DMF (0.19 mL) was added HATU (0.021 g, 0.055 mmol) in one portion. The solution was maintained at room temperature for 1 h and concentrated. The resultant residue was purified using preparative HPLC (Waters-Xbridge, 50×100 mm, 5 micron, C18 column; 0.1M ammonium acetate, 0-100% B (B=5% H$_2$O/CH$_3$CN)/A (A=95% H$_2$O/CH$_3$CN), 20 min. gradient) afforded 4-fluoro-5-(3-fluoro-2-methyl-5-(1-(pyridin-2-yl)cyclopropylcarbamoyl)phenyl)-2-(4-fluorophenyl)-N-methylpyrazolo[1,5-a]pyridine-3-carboxamide as a white solid. Preparative HPLC retention time: 11.0 min. 1H NMR (400 MHz, CHLOROFORM-d) δ ppm 8.44-8.53 (m, 1H), 8.38 (d, J=7.03 Hz, 1H), 7.80-7.90 (m, 2H), 7.55-7.67 (m, 3H), 7.36 (d, J=8.03 Hz, 1H), 7.31 (s, 1H), 7.14-7.22 (m, 2H), 7.10 (ddd, J=7.47, 4.96, 1.13 Hz, 1H), 6.74 (t, J=6.78 Hz, 1H), 5.87 (d, J=4.77 Hz, 1H), 2.97 (d, J=4.77 Hz, 3H), 2.25 (s, 3H), 1.66-1.73 (m, 2H), 1.38-1.46 (m, 2H). LCMS retention time: 1.828 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 mM, a hold time of 1 min, and an analysis time of 4 min where solvent A was 10% CH$_3$OH/90% H$_2$O/10 mM TFA and solvent B was 10% H$_2$O/90% CH$_3$OH/10 mM TFA. MS data was determined using a Micromass Platform for LC in electrospray mode. m/z 556 (MH$^+$).

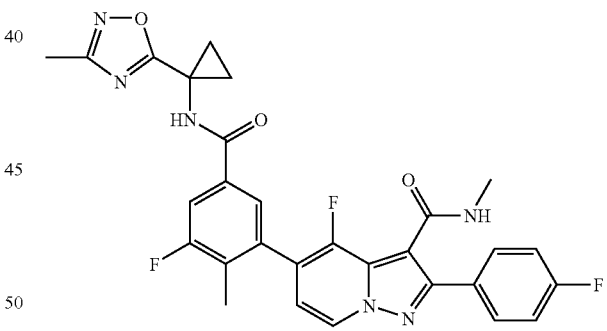

4-fluoro-5-(3-fluoro-2-methyl-5-(1-(3-methyl-1,2,4-oxadiazol-5-yl)cyclopropylcarbamoyl)phenyl)-2-(4-fluorophenyl)-N-methylpyrazolo[1,5-a]pyridine-3-carboxamide. To a solution containing 1-(3-methyl-1,2,4-oxadiazol-5-yl)cyclopropanaminium 2,2,2-trifluoroacetate (0.021 g, 0.083 mmol), diisopropylethylamine (0.08 mL, 0.51 mmol), 3-fluoro-5-(4-fluoro-2-(4-fluorophenyl)-3-(methylcarbamoyl)pyrazolo[1,5-a]pyridin-5-yl)-4-methylbenzoic acid (0.028 g, 0.064 mmol) and DMF (0.43 mL) was added HATU (0.048 g, 0.13 mmol) in one portion. The solution was maintained at room temperature for 1 h and concentrated. The resultant residue was purified using preparative HPLC (Waters-Xbridge, 50×100 mm, 5 micron, C18 column; 0.1M ammonium acetate, 0-100% B (B=5% H$_2$O/CH$_3$CN)/A (A=95% H$_2$O/CH$_3$CN), 15 min. gradient) afforded 4-fluoro-5-(3-fluoro-2- methyl-5-(1-(3-methyl-1,2,4-oxadiazol-5-yl)cyclopropyl-carbamoyl)phenyl)-2-(4-fluorophenyl)-N-methylpyrazolo[1,5-a]pyridine-3-carboxamide as a white solid. Preparative HPLC retention time: 8.5 min. 1H NMR (400 MHz, CHLOROFORM-d) δ ppm 8.35 (d, J=7.03 Hz, 1H), 7.77-7.88 (m, 2H), 7.61 (dd, J=9.54, 1.51 Hz, 1H), 7.54 (s, 1H), 7.27-7.33 (m, 1H), 7.13-7.22 (m, 2H), 6.71 (t, J=6.65 Hz, 1H), 5.92 (d, J=4.52 Hz, 1H), 2.97 (d, J=5.02 Hz, 3H), 2.32 (s, 3H), 2.22 (s, 3H), 1.77-1.87 (m, 2H), 1.55-1.65 (m, 2H). LCMS retention time: 2.137 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% CH₃OH/90% H₂O/10 mM TFA and solvent B was 10% H₂O/90% CH₃OH/10 mM TFA. MS data was determined using a Micromass Platform for LC in electrospray mode. m/z 561 (MH⁺).

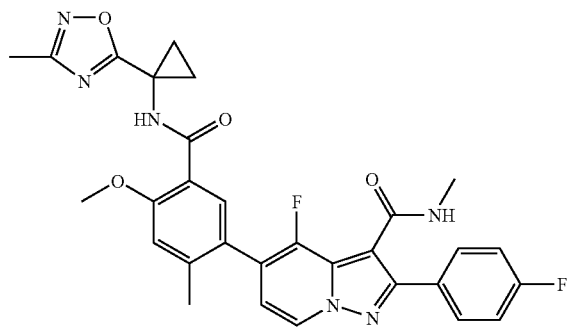

4-fluoro-2-(4-fluorophenyl)-5-(4-methoxy-2-methyl-5-(1-(3-methyl-1,2,4-oxadiazol-5-yl)cyclopropylcarbamoyl)phenyl)-N-methylpyrazolo[1,5-a]pyridine-3-carboxamide. To a solution containing 1-(3-methyl-1,2,4-oxadiazol-5-yl)cyclopropanaminium 2,2,2-trifluoroacetate (0.024 g, 0.095 mmol), diisopropylethylamine (0.10 mL, 0.56 mmol), 5-(4-fluoro-2-(4-fluorophenyl)-3-(methylcarbamoyl)pyrazolo[1,5-a]pyridin-5-yl)-2-methoxy-4-methylbenzoic acid (0.033 g, 0.073 mmol) and DMF (0.49 mL) was added HATU (0.056 g, 0.15 mmol) in one portion. The solution was maintained at room temperature for 1 h and concentrated. The resultant residue was purified using preparative HPLC (Waters-Xbridge, 50×100 mm, 5 micron, C18 column; 0.1M ammonium acetate, 0-100% B (B=5% H₂O/CH₃CN)/A (A=95% H₂O/CH₃CN), 15 min. gradient) afforded 4-fluoro-2-(4-fluorophenyl)-5-(4-methoxy-2-methyl-5-(1-(3-methyl-1,2,4-oxadiazol-5-yl)cyclopropylcarbamoyl)phenyl)-N-methylpyrazolo[1,5-a]pyridine-3-carboxamide as a white solid. Preparative HPLC retention time: 9.0 min. 1H NMR (400 MHz, CHLOROFORM-d) δ ppm 8.57 (s, 1H), 8.34 (d, J=7.03 Hz, 1H), 8.13 (s, 1H), 7.79-7.92 (m, 2H), 7.10-7.21 (m, 2H), 6.97 (s, 1H), 6.73 (t, J=6.78 Hz, 1H), 5.89 (d, J=4.52 Hz, 1H), 4.07 (s, 3H), 2.97 (d, J=5.02 Hz, 3H), 2.34 (s, 6H), 1.77-1.88 (m, 2H), 1.50-1.63 (m, 2H). LCMS retention time: 2.533 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 0.4 min, a hold time of 1 min, and an analysis time of 5 min where solvent A was 10% CH₃OH/90% H₂O/10 mM TFA and solvent B was 10% H₂O/90% CH₃OH/10 mM TFA. MS data was determined using a Micromass Platform for LC in electrospray mode. m/z 573 (MH⁺).

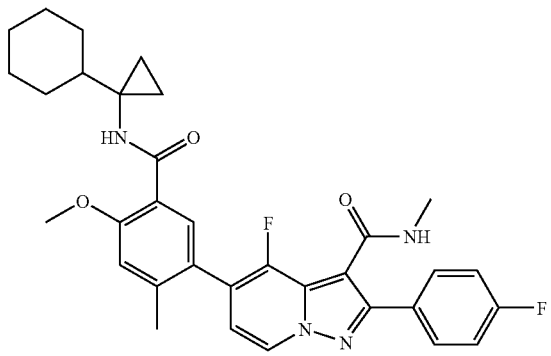

5-(5-(1-cyclohexylcyclopropylcarbamoyl)-4-methoxy-2-methylphenyl)-4-fluoro-2-(4-fluorophenyl)-N-methylpyrazolo[1,5-a]pyridine-3-carboxamide. To a solution containing 1-cyclohexylcyclopropanamine hydrochloride (0.020 g, 0.12 mmol), diisopropylethylamine (0.12 mL, 0.71 mmol), 5-(4-fluoro-2-(4-fluorophenyl)-3-(methylcarbamoyl)pyrazolo[1,5-a]pyridin-5-yl)-2-methoxy-4-methylbenzoic acid (0.040 g, 0.089 mmol) and DMF (0.60 mL) was added HATU (0.067 g, 0.18 mmol) in one portion. The solution was maintained at room temperature for 1 h and concentrated. The resultant residue was purified using preparative HPLC (Waters-Xbridge, 50×100 mm, 5 micron, C18 column; 0.1M TFA, 0-100% B (B=10% H₂O/CH₃OH)/A (A=90% H₂O/CH₃OH), 12 min. gradient, analysis time 20 min.) afforded 5-(5-(1-cyclohexylcyclopropylcarbamoyl)-4-methoxy-2-methylphenyl)-4-fluoro-2-(4-fluorophenyl)-N-methylpyrazolo[1,5-a]pyridine-3-carboxamide as a white solid. Preparative HPLC retention time: 13.0 min. 1H NMR (400 MHz, CHLOROFORM-d) δ ppm 8.35 (d, J=7.03 Hz, 1H), 8.02-8.14 (m, 2H), 7.84 (dd, J=8.53, 5.27 Hz, 2H), 7.17 (t, J=8.66 Hz, 2H), 6.94 (s, 1H), 6.76 (t, J=6.78 Hz, 1H), 5.97 (br. s., 1H), 4.04 (s, 3H), 2.98 (d, J=4.77 Hz, 3H), 2.33 (s, 3H), 2.18 (br. s., 1H), 1.87 (d, J=11.80 Hz, 2H), 1.76 (d, J=12.55 Hz, 2H), 1.20-1.31 (m, 2H), 1.18 (br. s., 1H), 1.10 (d, J=2.76 Hz, 2H), 1.08 (br. s., 1H), 0.77-0.90 (m, 4H). LCMS retention time: 2.726 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% CH₃OH/90% H₂O/10 mM TFA and solvent B was 10% H₂O/90% CH₃OH/10 mM TFA. MS data was determined using a Micromass Platform for LC in electrospray mode. m/z 573 (MH⁺).

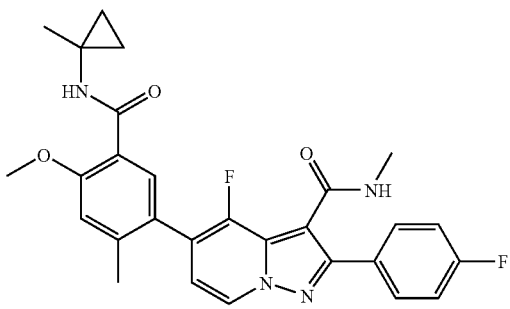

4-fluoro-2-(4-fluorophenyl)-5-(4-methoxy-2-methyl-5-(1-methylcyclopropylcarbamoyl)phenyl)-N-methylpyrazolo[1,5-a]pyridine-3-carboxamide. To a solution containing 1-methylcyclopropanamine hydrochloride (0.012 g, 0.12 mmol), diisopropylethylamine (0.12 mL, 0.71 mmol), 5-(4-fluoro-2-(4-fluorophenyl)-3-(methylcarbamoyl)pyrazolo[1,5-a]pyridin-5-yl)-2-methoxy-4-methylbenzoic acid (0.040 g, 0.089 mmol) and DMF (0.60 mL) was added HATU (0.067 g, 0.18 mmol) in one portion. The solution was maintained at room temperature for 1 h and concentrated. The resultant residue was purified using preparative HPLC (Waters-Xbridge, 50×100 mm, 5 micron, C18 column; 0.1M TFA, 0-100% B (B=10% H$_2$O/CH$_3$OH)/A (A=90% H$_2$O/CH$_3$OH), 12 min. gradient, analysis time 20 min) afforded 4-fluoro-2-(4-fluorophenyl)-5-(4-methoxy-2-methyl-5-(1-methylcyclopropylcarbamoyl)phenyl)-N-methylpyrazolo[1,5-a]pyridine-3-carboxamide as a white solid. Preparative HPLC retention time: 11.7 min. 1H NMR (400 MHz, CHLOROFORM-d) δ ppm 8.35 (d, J=7.03 Hz, 1H), 8.14 (s, 1H), 8.10 (s, 1H), 7.79-7.89 (m, 2H), 7.12-7.21 (m, 2H), 6.92 (s, 1H), 6.75 (t, J=6.78 Hz, 1H), 5.97 (d, J=3.76 Hz, 1H), 4.03 (s, 3H), 2.98 (d, J=5.02 Hz, 3H), 2.32 (s, 3H), 1.50 (s, 3H), 0.82-0.89 (m, 2H), 0.68-0.78 (m, 2H). LCMS retention time: 2.232 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 mM, a hold time of 1 min, and an analysis time of 4 min where solvent A was 10% CH$_3$OH/90% H$_2$O/10 mM TFA and solvent B was 10% H$_2$O/90% CH$_3$OH/10 mM TFA. MS data was determined using a Micromass Platform for LC in electrospray mode. m/z 505 (MH$^+$).

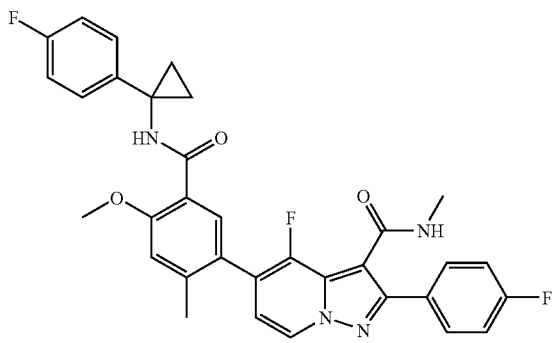

4-fluoro-2-(4-fluorophenyl)-5-(5-(1-(4-fluorophenyl)cyclopropylcarbamoyl)-4-methoxy-2-methylphenyl)-N-methylpyrazolo[1,5-a]pyridine-3-carboxamide. To a solution containing 1-(4-fluorophenyl)cyclopropanamine hydrochloride (0.022 g, 0.12 mmol), diisopropylethylamine (0.12 mL, 0.71 mmol), 5-(4-fluoro-2-(4-fluorophenyl)-3-(methylcarbamoyl)pyrazolo[1,5-a]pyridin-5-yl)-2-methoxy-4-methylbenzoic acid (0.040 g, 0.089 mmol) and DMF (0.60 mL) was added HATU (0.067 g, 0.18 mmol) in one portion. The solution was maintained at room temperature for 1 h and concentrated. The resultant residue was purified using preparative HPLC (Waters-Xbridge, 50×100 mm, 5 micron, C18 column; 0.1M TFA, 0-100% B (B=10% H$_2$O/CH$_3$OH)/A (A=90% H$_2$O/CH$_3$OH), 12 min. gradient, analysis time 20 min.) afforded 4-fluoro-2-(4-fluorophenyl)-5-(5-(1-(4-fluorophenyl)cyclopropylcarbamoyl)-4-methoxy-2-methylphenyl)-N-methylpyrazolo[1,5-a]pyridine-3-carboxamide as a white solid. Preparative HPLC retention time: 12.1 mM. 1H NMR (400 MHz, CHLOROFORM-d) δ ppm 8.46 (s, 1H), 8.34 (d, J=7.03 Hz, 1H), 8.10 (s, 1H), 7.79-7.90 (m, 2H), 7.28-7.37 (m, 2H), 7.11-7.23 (m, 2H), 6.91-7.03 (m, 3H), 6.74 (t, J=6.78 Hz, 1H), 5.93 (d, J=4.52 Hz, 1H), 4.06 (s, 3H), 2.97 (d, J=5.02 Hz, 3H), 2.33 (s, 3H), 1.35 (dd, J=6.15, 1.88 Hz, 4H). LCMS retention time: 2.438 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 mM, and an analysis time of 4 min where solvent A was 10% CH$_3$OH/90% H$_2$O/10 mM TFA and solvent B was 10% H$_2$O/90% CH$_3$OH/10 mM TFA. MS data was determined using a Micromass Platform for LC in electrospray mode. m/z 585 (MH$^+$).

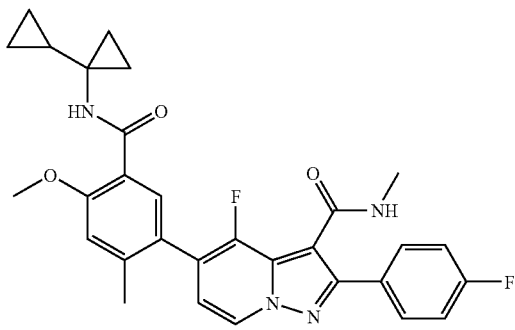

5-(5-(bi(cycloprop)ylcarbamoyl)-4-methoxy-2-methylphenyl)-4-fluoro-2-(4-fluorophenyl)-N-methylpyrazolo[1,5-a]pyridine-3-carboxamide. To a solution containing bi(cyclopropan)-1-amine hydrochloride (0.015 g, 0.12 mmol), diisopropylethylamine (0.12 mL, 0.71 mmol), 5-(4-fluoro-2-(4-fluorophenyl)-3-(methylcarbamoyl)pyrazolo[1,5-a]pyridin-5-yl)-2-methoxy-4-methylbenzoic acid (0.040 g, 0.089 mmol) and DMF (0.60 mL) was added HATU (0.067 g, 0.18 mmol) in one portion. The solution was maintained at room temperature for 1 h and concentrated. The resultant residue was purified using preparative HPLC (Waters-Xbridge, 50×100 mm, 5 micron, C18 column; 0.1M TFA, 0-100% B (B=10% H$_2$O/CH$_3$OH)/A (A=90% H$_2$O/CH$_3$OH), 12 min. gradient, analysis time 20 min.) afforded 5-(5-(bi(cycloprop)ylcarbamoyl)-4-methoxy-2-methylphenyl)-4-fluoro-2-(4-fluorophenyl)-N-methylpyrazolo[1,5-a]pyridine-3-carboxamide as a white solid. Preparative HPLC retention time: 11.7 min. 1H NMR (400 MHz, CHLOROFORM-d) δ ppm 8.35 (d, J=7.03 Hz, 1H), 8.09-8.20 (m, 2H), 7.79-7.89 (m, 2H), 7.12-7.23 (m, 2H), 6.93 (s, 1H), 6.76 (t, J=6.78 Hz, 1H), 5.96 (br. s., 1H), 4.03 (s, 3H), 2.98 (d, J=5.02 Hz, 3H), 2.33 (s, 3H), 1.53 (tt, J=8.28, 5.02 Hz, 1H), 0.78-0.84 (m, 2H), 0.67-0.75 (m, 2H), 0.41-0.50 (m, 2H), 0.18-0.28 (m, 2H). LCMS retention time: 2.405 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% $CH_3OH$/90% $H_2O$/10 mM TFA and solvent B was 10% $H_2O$/90% $CH_3OH$/10 mM TFA. MS data was determined using a Micromass Platform for LC in electrospray mode. m/z 531 ($MH^+$).

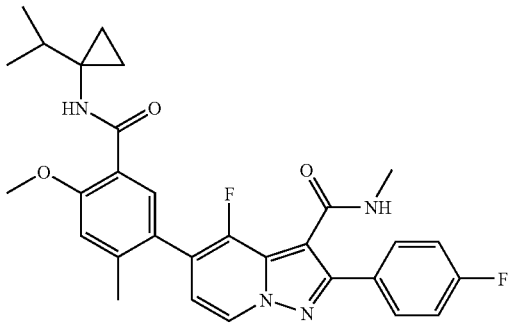

4-fluoro-2-(4-fluorophenyl)-5-(5-(1-isopropylcyclopropylcarbamoyl)-4-methoxy-2-methylphenyl)-N-methylpyrazolo[1,5-a]pyridine-3-carboxamide. To a solution containing 1-isopropylcyclopropanamine hydrochloride (0.016 g, 0.12 mmol), diisopropylethylamine (0.12 mL, 0.71 mmol), 5-(4-fluoro-2-(4-fluorophenyl)-3-(methylcarbamoyl)pyrazolo[1,5-a]pyridin-5-yl)-2-methoxy-4-methylbenzoic acid (0.040 g, 0.089 mmol) and DMF (0.60 mL) was added HATU (0.067 g, 0.18 mmol) in one portion. The solution was maintained at room temperature for 1 h and concentrated. The resultant residue was purified using preparative HPLC (Waters-Xbridge, 50×100 mm, 5 micron, C18 column; 0.1M TFA, 0-100% B (B=10% $H_2O$/$CH_3OH$)/A (A=90% $H_2O$/$CH_3OH$), 12 min. gradient, analysis time 15 min.) afforded 4-fluoro-2-(4-fluorophenyl)-5-(5-(1-isopropylcyclopropylcarbamoyl)-4-methoxy-2-methylphenyl)-N-methylpyrazolo[1,5-a]pyridine-3-carboxamide as a white solid. Preparative HPLC retention time: 12.1 min. 1H NMR (400 MHz, CHLOROFORM-d) δ ppm 8.35 (d, J=7.03 Hz, 1H), 8.06 (s, 2 Fr), 7.81-7.93 (m, 2H), 7.13-7.23 (m, 2H), 6.94 (s, 1H), 6.76 (t, J=6.78 Hz, 1H), 5.95 (d, J=4.52 Hz, 1H), 4.04 (s, 3H), 2.98 (d, J=5.02 Hz, 3H), 2.33 (s, 3H), 1.61-1.72 (m, 1H), 1.02 (d, J=6.78 Hz, 6H), 0.84-0.96 (m, 2H), 0.73-0.84 (m, 2H). LCMS retention time: 2.502 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 mM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% $CH_3OH$/90% $H_2O$/10 mM TFA and solvent B was 10% $H_2O$/90% $CH_3OH$/10 mM TFA. MS data was determined using a Micromass Platform for LC in electrospray mode. m/z 533 ($MH^+$).

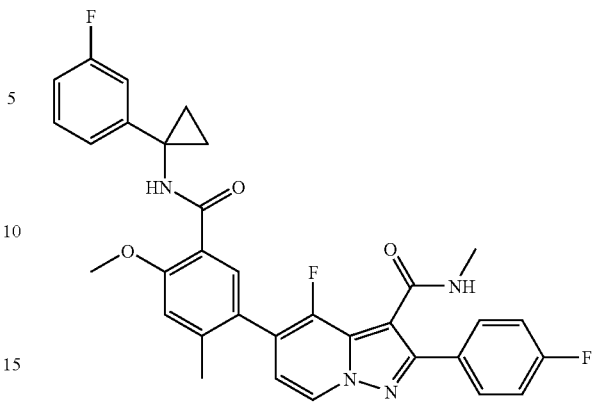

4-fluoro-2-(4-fluorophenyl)-5-(5-(1-(3-fluorophenyl)cyclopropylcarbamoyl)-4-methoxy-2-methylphenyl)-N-methylpyrazolo[1,5-a]pyridine-3-carboxamide. To a solution containing 1-(3-fluorophenyl)cyclopropanamine hydrochloride (0.022 g, 0.12 mmol), diisopropylethylamine (0.12 mL, 0.71 mmol), 5-(4-fluoro-2-(4-fluorophenyl)-3-(methylcarbamoyl)pyrazolo[1,5-a]pyridin-5-yl)-2-methoxy-4-methylbenzoic acid (0.040 g, 0.089 mmol) and DMF (0.60 mL) was added HATU (0.067 g, 0.18 mmol) in one portion. The solution was maintained at room temperature for 1 h and concentrated. The resultant residue was purified using preparative HPLC (Waters-Xbridge, 50×100 mm, 5 micron, C18 column; 0.1M TFA, 0-100% B (B=10% $H_2O$/$CH_3OH$)/A (A=90% $H_2O$/$CH_3OH$), 12 min. gradient, analysis time 15 min.) afforded 4-fluoro-2-(4-fluorophenyl)-5-(5-(1-(3-fluorophenyl)cyclopropylcarbamoyl)-4-methoxy-2-methylphenyl)-N-methylpyrazolo[1,5-a]pyridine-3-carboxamide as a white solid. Preparative HPLC retention time: 12.0 min. 1H NMR (400 MHz, CHLOROFORM-d) δ ppm 8.46 (s, 1H), 8.34 (d, J=7.03 Hz, 1H), 8.11 (s, 1H), 7.80-7.89 (m, 2H), 7.22-7.27 (m, 1H), 7.13-7.21 (m, 2H), 6.96-7.06 (m, 3H), 6.84-6.92 (m, 1H), 6.75 (t, J=6.78 Hz, 1H), 5.92 (d, J=4.02 Hz, 1H), 4.08 (s, 3H), 2.97 (d, J=5.02 Hz, 3H), 2.34 (s, 3H), 1.36-1.45 (m, 4H). LCMS retention time: 2.480 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 mM where solvent A was 10% $CH_3OH$/90% $H_2O$/10 mM TFA and solvent B was 10% $H_2O$/90% $CH_3OH$/10 mM TFA. MS data was determined using a Micromass Platform for LC in electrospray mode. m/z 585 ($MH^+$).

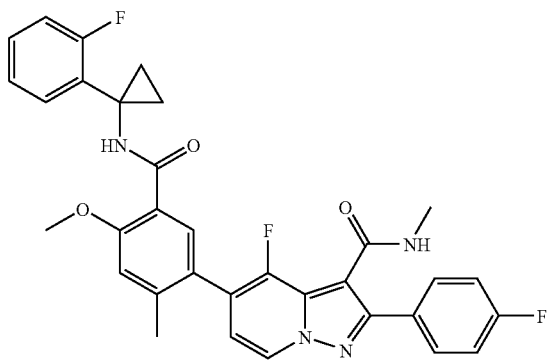

4-fluoro-2-(4-fluorophenyl)-5-(5-(1-(2-fluorophenyl)cyclopropylcarbamoyl)-4-methoxy-2-methylphenyl)-N-methylpyrazolo[1,5-a]pyridine-3-carboxamide. To a solution containing 1-(2-fluorophenyl)cyclopropanamine hydrochloride (0.022 g, 0.12 mmol), diisopropylethylamine (0.12 mL, 0.71 mmol), 5-(4-fluoro-2-(4-fluorophenyl)-3-(methylcarbamoyl)pyrazolo[1,5-a]pyridin-5-yl)-2-methoxy-4-methylbenzoic acid (0.040 g, 0.089 mmol) and DMF (0.60 mL) was added HATU (0.067 g, 0.18 mmol) in one portion. The solution was maintained at room temperature for 1 h and concentrated. The resultant residue was purified using preparative HPLC (Waters-Xbridge, 50×100 mm, 5 micron, C18 column; 0.1M TFA, 0-100% B (B=10% H$_2$O/CH$_3$OH)/A (A=90% H$_2$O/CH$_3$OH), 12 min. gradient, analysis time 15 min.) afforded 4-fluoro-2-(4-fluorophenyl)-5-(5-(1-(2-fluorophenyl)cyclopropylcarbamoyl)-4-methoxy-2-methylphenyl)-N-methylpyrazolo[1,5-a]pyridine-3-carboxamide as a white solid. Preparative HPLC retention time: 12.3 min. 1H NMR (400 MHz, CHLOROFORM-d) δ ppm 8.63 (s, 1H), 8.32 (d, J=7.03 Hz, 1H), 8.05 (s, 1H), 7.79-7.89 (m, 2H), 7.67 (td, J=7.65, 1.76 Hz, 1H), 7.13-7.25 (m, 3H), 7.10 (td, J=7.53, 1.25 Hz, 1H), 7.02 (ddd, J=10.67, 8.16, 1.00 Hz, 1H), 6.91 (s, 1H), 6.70 (t, 0.7=6.78 Hz, 1H), 5.87 (br. s., 1H), 4.05 (s, 3H), 2.96 (d, J=5.02 Hz, 3H), 2.30 (s, 3H), 1.29 (s, 4H). LCMS retention time: 2.553 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% CH$_3$OH/90% H$_2$O/10 mM TFA and solvent B was 10% H$_2$O/90% CH$_3$OH/10 mM TFA. MS data was determined using a Micromass Platform for LC in electrospray mode. m/z 585 (MH$^+$).

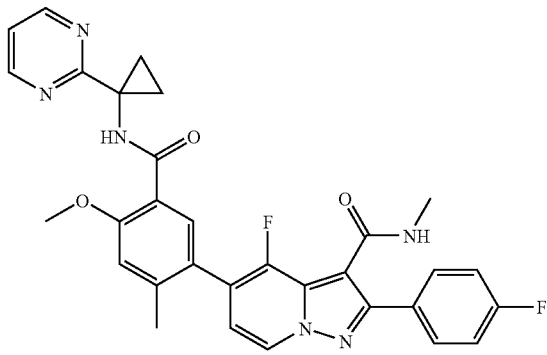

4-fluoro-2-(4-fluorophenyl)-5-(4-methoxy-2-methyl-5-(1-(pyrimidin-2-yl)cyclopropylcarbamoyl)phenyl)-N-methylpyrazolo[1,5-a]pyridine-3-carboxamide. To a solution containing 1-(pyrimidin-2-yl)cyclopropanamine (0.021 g, 0.089 mmol), diisopropylethylamine (0.12 mL, 0.71 mmol), 5-(4-fluoro-2-(4-fluorophenyl)-3-(methylcarbamoyl)pyrazolo[1,5-a]pyridin-5-yl)-2-methoxy-4-methylbenzoic acid (0.040 g, 0.089 mmol) and DMF (0.60 mL) was added HATU (0.067 g, 0.18 mmol) in one portion. The solution was maintained at room temperature for 1 h and concentrated. The resultant residue was purified using preparative HPLC (Waters-Xbridge, 50×100 mm, 5 micron, C18 column; 0.1M TFA, 0-100% B (B=10% H$_2$O/CH$_3$OH)/A (A=90% H$_2$O/CH$_3$OH), 12 min. gradient, analysis time 15 min.) afforded 4-fluoro-2-(4-fluorophenyl)-5-(4-methoxy-2-methyl-5-(1-(pyrimidin-2-yl)cyclopropylcarbamoyl)phenyl)-N-methylpyrazolo[1,5-a]pyridine-3-Carboxamide as a white solid. Preparative HPLC retention time: 10.3 mM. 1H NMR (500 MHz, MeOD) δ ppm 8.70 (d, J=4.88 Hz, 2H), 8.54 (d, J=7.02 Hz, 1H), 7.96 (s, 1H), 7.86-7.94 (m, 2H), 7.21-7.31 (m, 4H), 6.92 (t, J=6.87 Hz, 1H), 4.85-4.95 (m, 14H), 4.10 (s, 3H), 3.28-3.38 (m, 21H), 2.91 (s, 3H), 2.38 (s, 3H), 1.78-1.88 (m, 2H), 1.50-1.59 (m, 2H). LCMS retention time: 2.138 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% CH$_3$OH/90% H$_2$O/10 mM TFA and solvent B was 10% H$_2$O/90% CH$_3$OH/10 mM TFA. MS data was determined using a Micromass Platform for LC in electrospray mode. m/z 569 (MH$^+$).

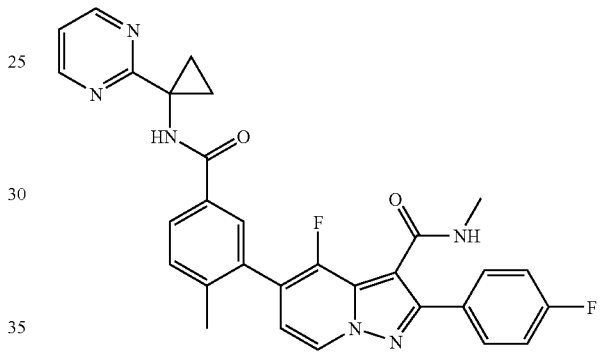

4-fluoro-2-(4-fluorophenyl)-N-methyl-5-(2-methyl-5-(1-(pyrimidin-2-yl)cyclopropylcarbamoyl)phenyl)pyrazolo[1,5-a]pyridine-3-carboxamide. To a solution containing 1-(pyrimidin-2-yl)cyclopropanamine (0.030 g, 0.18 mmol), diisopropylethylamine (0.16 mL, 0.95 mmol), 3-(4-fluoro-2-(4-fluorophenyl)-3-(methylcarbamoyl)pyrazolo[1,5-a]pyridin-5-yl)-4-methylbenzoic acid (0.050 g, 0.12 mmol) and DMF (0.8 mL) was added HATU (0.09 g, 0.24 mmol) in one portion. The solution was maintained at room temperature for 1 h and concentrated. The resultant residue was purified using preparative HPLC (Waters-Xbridge, 50×100 mm, 5 micron, C18 column; 0.1M TFA, 10-100% B (B=10% H$_2$O/CH$_3$OH)/A (A=90% H$_2$O/CH$_3$OH), 12 min. gradient) to afford 4-fluoro-2-(4-fluorophenyl)-N-methyl-5-(2-methyl-5-(1-(pyrimidin-2-yl)cyclopropylcarbamoyl)phenyl)pyrazolo[1,5-a]pyridine-3-carboxamide as a white solid. Preparative HPLC retention time: 10.1 min. 1H NMR (400 MHz, CHLOROFORM-d) δ ppm 8.77 (d, J=5.02 Hz, 2H), 8.40 (d, J=7.03 Hz, 1H), 7.76-7.87 (m, 3H), 7.73 (s, 1H), 7.43 (d, J=7.78 Hz, 1H), 7.29-7.36 (m, 2H), 7.12-7.23 (m, 2H), 6.79 (t, J=6.78 Hz, 1H), 5.97 (br. s., 1H), 2.99 (d, J=5.02 Hz, 3H), 2.34 (s, 3H), 1.92-2.00 (m, 2H), 1.60-1.70 (m, 2H). LCMS retention time: 2.000 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% CH$_3$OH/90% H$_2$O/10 mM TFA and solvent B was 10% H$_2$O/90% CH$_3$OH/10 mM TFA. MS data was determined using a Micromass Platform for LC in electrospray mode. m/z 539 (MH$^+$).

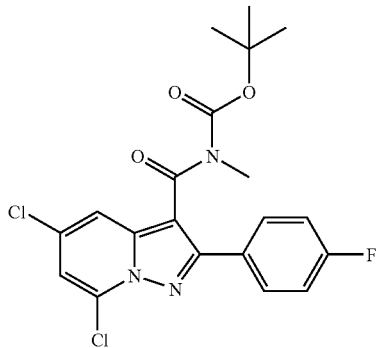

tert-butyl 5,7-dichloro-2-(4-fluorophenyl)pyrazolo[1,5-a]pyridine-3-carbonyl(methyl)carbamate. To a cooled solution (0° C., ice bath) containing 2,4-dichloropyridine (4.0 g, 27.0 mmol) and dichloromethane (60 mL) was added O-(mesitylsulfonyl)hydroxylamine (10.2 g, 27.0 mmol) in dichloromethane (75 mL) quickly, dropwise. The solution was maintained at 0° C. for 15 min, removed from the cooling bath and maintained at ambient temperature for 20 h. The solution was concentrated to afford 1-amino-2,4-dichloropyridinium 2,4,6-trimethylbenzenesulfonate as a light yellow foam (165 MH$^+$). The product thus obtained was combined with tert-butyl 3-(4-fluorophenyl)propioloyl(methyl)carbamate (6.6 g, 24.0 mmol) and THF (100 mL). The resultant solution was cooled to −78° C. (dry ice, acetone bath) and DBU (7.2 mL, 48.0 mmol) was added dropwise over 10 min with rapid stirring. The mixture was kept in the cooling bath with stirring and allowed to proceed for 15 h at ambient temperature. The mixture was then filtered and concentrated. Purification on silica gel (0-80% ethyl acetate/hexanes, 60 min gradient) afforded an off white residue. The residue thus obtained was further purified using preparative HPLC (Phenomonex-Luna, 50×100 mm, 5 micron, C18 column; 0.1M TFA, 0-100% B (B=10% H$_2$O/CH$_3$OH)/A (A=90% H$_2$O/CH$_3$OH), 15 min. gradient) to afford tert-butyl 5,7-dichloro-2-(4-fluorophenyl)pyrazolo[1,5-a]pyridine-3-carbonyl(methyl)carbamate as a white solid. Preparative HPLC retention time: 14.0 min. 1H NMR (400 MHz, CHLOROFORM-d) δ ppm 7.81 (d, J=2.26 Hz, 1H), 7.71 (dd, J=8.91, 5.40 Hz, 2H), 7.16 (t, J=8.66 Hz, 2H), 7.03 (d, J=2.26 Hz, 1H), 3.26 (s, 3H), 1.12 (s, 9H). LCMS retention time: 2.810 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 mM where solvent A was 10% CH$_3$OH/90% H$_2$O/10 mM TFA and solvent B was 10% H$_2$O/90% CH$_3$OH/10 mM TFA. MS data was determined using a Micromass Platform for LC in electrospray mode. m/z 460 (MNa$^+$).

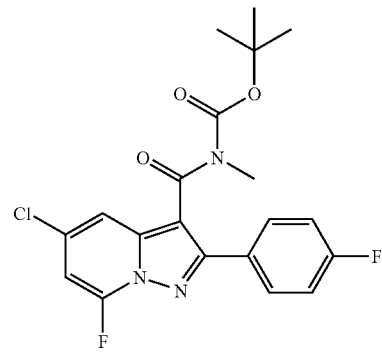

Tert-butyl 5-chloro-7-fluoro-2-(4-fluorophenyl)pyrazolo[1,5-a]pyridine-3-carbonyl(methyl)carbamate. To a solution containing tetrabutylammoniumcyanide and THF (0.912 mL, 1.0 M) was added a solution containing hexafluorobenzene and THF (0.760 mL, 0.2 M) at −35° C. (caution, exothermic). The solution was removed from cooling and maintained at ambient temperature for 150 min. The solution thus obtained was cooled to 0° C. (ice bath) and added dropwise with stirring to a pre-cooled solution (−50° C., dry ice, acetone) containing tert-butyl 5,7-dichloro-2-(4-fluorophenyl)pyrazolo[1,5-a]pyridine-3-carbonyl(methyl) carbamate and THF (0.608 mL, 0.38 M). The solution thus obtained was removed from cooling and allowed to proceed for 18 h. The solution was poured into water (25 mL). The aqueous portion was then extracted with ethyl acetate (2×25 mL). The organic portions were combined, then washed with water (3×20 mL), then washed with brine (25 mL), then dried over MgSO$_4$, filtered and concentrated. The residue thus obtained was purified on silica gel (0-20% ethyl acetate/hexanes, 25 min gradient) to afford tert-butyl 5-chloro-7-fluoro-2-(4-fluorophenyl)pyrazolo[1,5-a]pyridine-3-carbonyl(methyl)carbamate as a white solid. 1H NMR (400 MHz, CHLOROFORM-d) δ ppm 7.65-7.76 (m, 3H), 7.11-7.20 (m, 2H), 6.64 (dd, J=4.77, 2.01 Hz, 1H), 3.27 (s, 3H), 1.12 (s, 9H). LCMS retention time: 2.743 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% CH$_3$OH/90% H$_2$O/10 mM TFA and solvent B was 10% H$_2$O/90% CH$_3$OH/10 mM TFA. MS data was determined using a Micromass Platform for LC in electrospray mode. m/z 422 (MH$^+$).

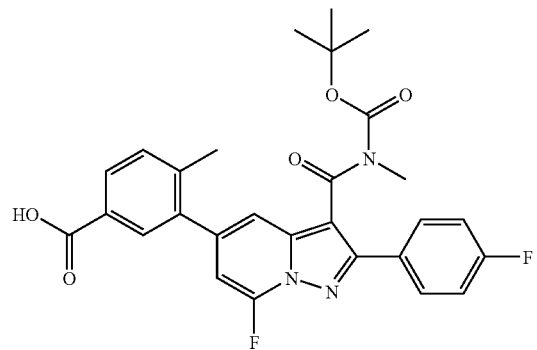

3-(3-(tert-butoxycarbonyl(methyl)carbamoyl)-7-fluoro-2-(4-fluorophenyl)pyrazolo[1,5-a]pyridin-5-yl)-4-methylbenzoic acid. To a degassed mixture containing tert-butyl 5-chloro-7-fluoro-2-(4-fluorophenyl)pyrazolo[1,5-a]pyridine-3-carbonyl(methyl)carbamate (0.060 g, 0.14 mmol), 4-methyl-3-(4,4,5,5-tetramethyl-1,3,2-dioxaborolan-2-yl)benzoic acid (0.047 g, 0.18 mmol), sodium carbonate (0.043 g, 0.43 mmol), dioxane (1.2 mL) and water (0.24 mL) was added tetrakis(tiphenylphosphine)palladium(0) (0.005 g, 0.004 mmol). The mixture was stirred at 95° C. for 18 h. The mixture was cooled to room temperature, filtered to remove solids and adjusted to below pH 4 with 1 N aqueous hydrochloric acid (2.0 mL). Water was added (10 mL) and the aqueous portion was extracted with ethyl acetate (2×15 mL). The combined organic portions were washed with brine (20 mL) and dried over magnesium sulfate. The mixture was filtered and concentrated to afford 3-(3-(tert-butoxycarbonyl(methyl)carbamoyl)-7-fluoro-2-(4-fluorophenyl)pyrazolo[1,5-a]pyridin-5-yl)-4-methylbenzoic acid as a residue which was used without further purification. LCMS retention time: 2.725 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% $CH_3OH$/90% $H_2O$/10 mM TFA and solvent B was 10% $H_2O$/90% $CH_3OH$/10 mM TFA. MS data was determined using a Micromass Platform for LC in electrospray mode. m/z 522 (MH$^+$).

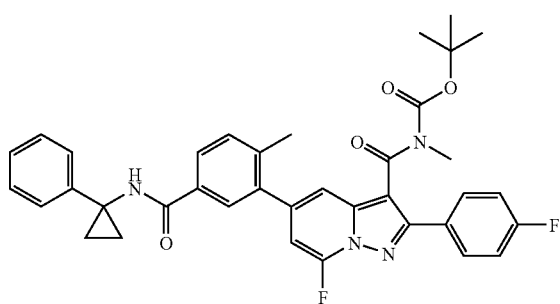

Tert-butyl 7-fluoro-2-(4-fluorophenyl)-5-(2-methyl-5-(1-phenylcyclopropyl carbamoyl)phenyl)pyrazolo[1,5-a]pyridine-3-carbonyl(methyl)carbamate. To a solution containing 1-phenylcyclopropanamine hydrochloride (0.010 g, 0.061 mmol), diisopropylethylamine (0.086 mL, 0.49 mmol), 3-(3-(tert-butoxycarbonyl(methyl)carbamoyl)-7-fluoro-2-(4-fluorophenyl)pyrazolo[1,5-a]pyridin-5-yl)-4-methylbenzoic acid (0.032 g, 0.061 mmol) and DMF (0.41 mL) was added HATU (0.047 g, 0.12 mmol) in one portion. The solution was maintained at room temperature for 1 h and concentrated. The resultant residue was purified on silica gel (30-100% ethyl acetate/hexanes, 45 min. gradient) to afford tert-butyl 7-fluoro-2-(4-fluorophenyl)-5-(2-methyl-5-(1-phenylcyclopropylcarbamoyl)phenyl)pyrazolo[1,5-a]pyridine-3-carbonyl(methyl)carbamate as a residue. LCMS retention time: 2.938 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% $CH_3OH$/90% $H_2O$/10 mM TFA and solvent B was 10% $H_2O$/90% $CH_3OH$/10 mM TFA. MS data was determined using a Micromass Platform for LC in electrospray mode. m/z 637 (MH$^+$).

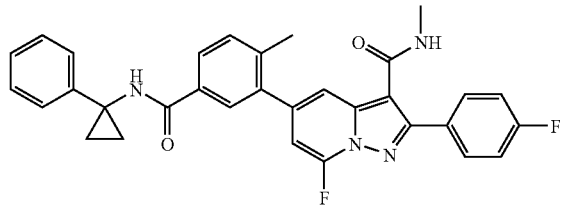

7-fluoro-2-(4-fluorophenyl)-N-methyl-5-(2-methyl-5-(1-phenylcyclopropylcarbamoyl)phenyl)pyrazolo[1,5-a]pyridine-3-carboxamide. To a solution containing tert-butyl 7-fluoro-2-(4-fluorophenyl)-5-(2-methyl-5-(1-phenylcyclopropyl carbamoyl)phenyl)pyrazolo[1,5-a]pyridine-3-carbonyl(methyl) carbamate (0.035 g, 0.053 mmol) and dichloromethane (4.0 mL) was added TFA (0.33 mL, 4.3 mmol) at room temperature. The solution was maintained for 15 min at room temperature and concentrated to dryness. The residue thus obtained was purified using preparative HPLC (Waters-Xbridge, 50×100 mm, 5 micron, C18 column; 0.1M ammonium acetate, 10-100% B (B=5% $H_2O$/$CH_3CN$)/A (A=95% $H_2O$/$CH_3CN$), 15 min. gradient) to afford 7-fluoro-2-(4-fluorophenyl)-N-methyl-5-(2-methyl-5-(1-phenylcyclopropylcarbamoyl)phenyl)pyrazolo[1,5-a]pyridine-3-carboxamide as a white solid. Preparative HPLC retention time: 11.0 mM. 1H NMR (400 MHz, CHLOROFORM-d) δ ppm 8.15 (d, J=1.51 Hz, 1H), 7.70-7.83 (m, 4H), 7.39 (d, J=8.03 Hz, 1H), 7.23-7.36 (m, 7H), 6.91 (s, 1H), 6.66 (dd, J=5.52, 1.51 Hz, 1H), 5.57 (d, J=4.27 Hz, 1H), 2.87 (d, J=5.02 Hz, 3H), 2.40 (s, 3H), 1.35-1.47 (m, 4H). LCMS retention time: 2.510 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 mM where solvent A was 10% $CH_3OH$/90% $H_2O$/10 mM TFA and solvent B was 10% $H_2O$/90% $CH_3OH$/10 mM TFA. MS data was determined using a Micromass Platform for LC in electrospray mode. m/z 537 (MH$^+$).

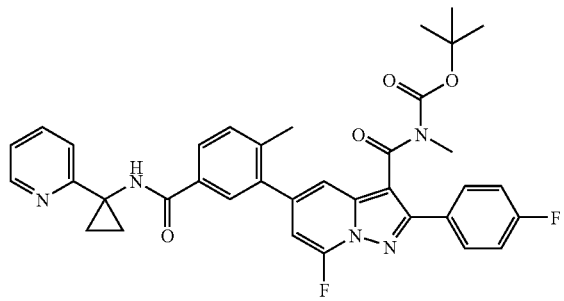

tert-butyl 7-fluoro-2-(4-fluorophenyl)-5-(2-methyl-5-(1-(pyridin-2-yl)cyclopropylcarbamoyl)phenyl)pyrazolo[1,5-a]pyridine-3-carbonyl(methyl)carbamate. To a solution containing 1-(pyridin-2-yl)cyclopropanamine dihydrochloride (0.011 g, 0.054 mmol), diisopropylethylamine (0.075 mL, 0.43 mmol), 3-(3-(tert-butoxycarbonyl(methyl)carbamoyl)-7-fluoro-2-(4-fluorophenyl)pyrazolo[1,5-a]pyridin-5-yl)-4-methylbenzoic acid (0.028 g, 0.054 mmol) and DMF (0.36 mL) was added HATU (0.041 g, 0.11 mmol) in one portion. The solution was maintained at room temperature for 1 h and concentrated. The resultant residue was purified on silica gel (30-100% ethyl acetate/hexanes, 45 min. gradient) to afford tert-butyl 7-fluoro-2-(4-fluorophenyl)-5-(2-methyl-5-(1-(pyridin-2-yl)cyclopropylcarbamoyl)phenyl)pyrazolo[1,5-a]pyridine-3-carbonyl(methyl)carbamate as a residue. LCMS retention time: 2.428 mM. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% $CH_3OH$/90% $H_2O$/10 mM TFA and solvent B was 10% $H_2O$/90% $CH_3OH$/10 mM TFA. MS data was determined using a Micromass Platform for LC in electrospray mode. m/z 638 (MH$^+$).

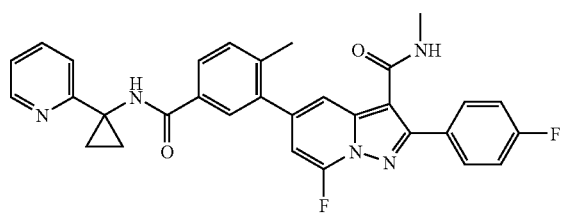

7-fluoro-2-(4-fluorophenyl)-N-methyl-5-(2-methyl-5-(1-(pyridin-2-yl)cyclopropylcarbamoyl)phenyl)pyrazolo[1,5-a]pyridine-3-carboxamide. To a solution containing tert-butyl 7-fluoro-2-(4-fluorophenyl)-5-(2-methyl-5-(1-(pyridin-2-yl)cyclopropylcarbamoyl)phenyl)pyrazolo[1,5-a]pyridine-3-carbonyl(methyl)carbamate (0.022 g, 0.035 mmol) and dichloromethane (3.0 mL) was added TFA (0.22 mL, 2.8 mmol) at room temperature. The solution was maintained for 15 min at room temperature and concentrated to dryness. The residue thus obtained was purified using preparative HPLC (Waters-Xbridge, 50×100 mm, 5 micron, C18 column; 0.1M ammonium acetate, 10-100% B (B=5% $H_2O$/$CH_3CN$)/A (A=95% $H_2O$/$CH_3CN$), 15 min. gradient) to afford 7-fluoro-2-(4-fluorophenyl)-N-methyl-5-(2-methyl-5-(1-(pyridin-2-yl)cyclopropylcarbamoyl)phenyl)pyrazolo[1,5-a]pyridine-3-carboxamide as a white solid. Preparative HPLC retention time: 9.0 min. 1H NMR (400 MHz, CHLOROFORM-d) δ ppm 8.44-8.54 (m, 1H), 8.18 (d, J=1.51 Hz, 1H), 7.79-7.85 (m, 2H), 7.72-7.78 (m, 2H), 7.61 (td, J=7.78, 1.76 Hz, 1H), 7.41 (dd, J=8.03, 3.26 Hz, 2H), 7.22-7.32 (m, 2H), 7.20 (s, 1H), 7.08 (ddd, J=7.40, 4.89, 1.25 Hz, 1H), 6.69 (dd, J=5.65, 1.63 Hz, 1H), 5.58 (d, J=4.52 Hz, 1H), 2.87 (d, J=5.02 Hz, 3H), 2.42 (s, 3H), 1.67-1.78 (m, 2H), 1.39-1.48 (m, 2H). LCMS retention time: 1.873 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% $CH_3OH$/90% $H_2O$/10 mM TFA and solvent B was 10% $H_2O$/90% $CH_3OH$/10 mM TFA. MS data was determined using a Micromass Platform for LC in electrospray mode. m/z 538 (MH$^+$).

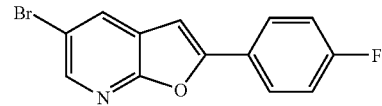

5-bromo-2-(4-fluorophenyl)furo[2,3-b]pyridine. 5-bromo-3-iodopyridin-2-ol (6.7 g, 22 mmol) (Heterocycles. 57, 1, pp 55), 1-ethynyl-4-fluorobenzene (4.03 g, 33.5 mmol), copper(I) iodide (0.255 g, 1.34 mmol), trans-dichlorobis (triphenylphosphine)palladium (II) (0.784 g, 1.12 mmol) were combined and evacuated/backfilled with N2 (3×) then diluted with triethylamine (223 mL) and heated to 90° C. for 2 hours. The solvent was evaporated and the reaction was dissolved in EtOAc. The organic phase was washed with water (50 mL), brine, dried over Na2SO4, filtered, and concentrated. Trituration with Et2O afforded the expected product 5-bromo-2-(4-fluorophenyl)furo[2,3-b]pyridine (4.2 g, 14.4 mmol, 64% yield). 1H NMR (400 MHz, DMSO-d$_6$) δ ppm 8.35-8.42 (2H, m), 8.03 (2H, dd, J=8.78, 5.27 Hz), 7.46 (1H, s), 7.39 (2H, t, J=8.91 Hz). LC-MS retention time: 2.36 min; m/z (MH+): 292, 294. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

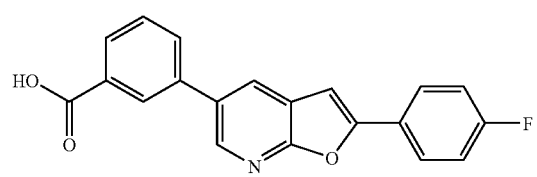

3-(2-(4-fluorophenyl)furo[2,3-b]pyridin-5-yl)benzoic acid. 3-Carboxyphenylboronic acid (700 mg, 4.22 mmol), 5-bromo-2-(4-fluorophenyl)furo[2,3-b]pyridine (750 mg, 2.57 mmol), Pd(Ph3P)4 (30 mg, 0.026 mmol), and Cs2CO3 (1.25 g, 3.84 mmol) were combined in dioxane (20 mL) and water (4 mL). The mixture was evacuated/backfilled with nitrogen (3×). The reaction was heated to 95° C. under N2 (g) overnight. The mixture was partitioned between EtOAc and 1 N HCl. The organic phase was washed with water and brine, dried over MgSO4, filtered, and concentrated to give a brown solid which was triturated with Et2O to give the expected product 3-(2-(4-fluorophenyl)furo[2,3-b]pyridin-5-yl)benzoic acid (255 mg, 30% yield) consistent by LCMS. LC-MS retention time: 1.83 min; m/z (MH+): 334. LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode.

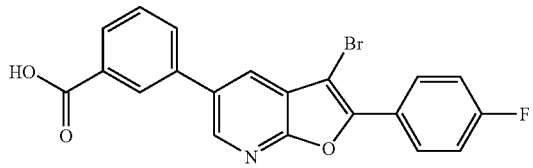

3-(3-bromo-2-(4-fluorophenyl)furo[2,3-b]pyridin-5-yl)benzoic acid. NBS (125 mg, 0.702 mmol) was added to a stirred suspension of 3-(2-(4-fluorophenyl)furo[2,3-b]pyridin-5-yl)benzoic acid (215 mg, 0.645 mmol) in THF (5 mL)/DMF (1 mL). The solids dissolved and the reaction was stirred at room temperature for 30 min, then quenched with 10% Na2S2O3, and acidified with 1 N HCl. The solvent was evaporated and the material was diluted with water, filtered and dried to afford a mixture of starting material and product. The material was resubjected to the reaction conditions (80 mg of NBS in 3 mL THF/0.5 mL DMF). After 3 h, the reaction was quenched by the addition of 10% Na2S2O3, and the solution was acidified with 0.1 N HCl. The volatiles were removed and the resulting off-white precipitate was collected by filtration, rinsed with water and Et2O, and air-dried to afford the expected product 3-(3-bromo-2-(4-fluorophenyl)furo[2,3-b]pyridin-5-yl)benzoic acid (140 mg, 53% yield) as an off-white powder consistent by LCMS and NMR. 1H NMR (400 MHz, DMSO-$d_6$) δ ppm 8.73 (1H, d, J=2.26 Hz), 8.27-8.33 (2H, m), 8.19-8.26 (2H, m), 8.05-8.12 (1H, m), 8.03 (1H, d, J=7.78 Hz), 7.68 (1H, t, J=7.78 Hz), 7.45-7.55 (2H, m). LC-MS retention time: 1.20 min; m/z (MH+): 412, 414. LC data was recorded on a Shimadzu LC-10AS liquid chromatograph equipped with a Waters XBridge 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

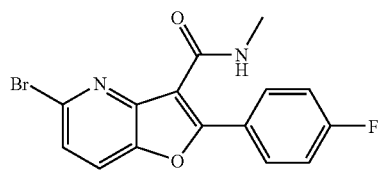

5-bromo-2-(4-fluorophenyl)-N-methylfuro[3,2-b]pyridine-3-carboxamide. Step 1: Preparation of 6-bromo-2-iodopyridin-3-ol: N-iodosuccinimide (6.47 g, 28.7 mmol) was added to a stirring solution of 6-bromopyridin-3-ol (5 g, 28.7 mmol) in MeOH (144 mL) at 45° C. It was allowed to stir for 3 hours. The mixture was concentrated and triturated with Et2O. The precipitate was discarded and the filtrate was concentrated and triturated with dichloromethane to give the expected product, 1 6-bromo-2-iodopyridin-3-ol (3150 mg, 10.50 mmol, 37% yield) by LCMS and NMR. 1H NMR (400 MHz, DMSO-d6) δ ppm 11.12 (1H, s), 7.42 (1H, d, J=8.28 Hz), 7.1.0 (1H, d, J=8.28 Hz). LC-MS retention time: 1.27 min; m/z (MH+): 300, 302. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A 100% solvent B, a gradient time of 3 min, a hold time of 1 min, and an analysis time of 4 mM where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 2: Preparation of 6-bromo-2-iodopyridin-3-yl acetate. 6-bromo-2-iodopyridin-3-ol (150 mg, 0.500 mmol) was added to acetic anhydride (2.4 mL, 25 mmol) at 130° C. It was allowed to stir for 30 min then concentrated and chased with toluene to give the expected product 6-bromo-2-iodopyridin-3-yl acetate (171 mg, 0.500 mmol, 100% yield) by NMR. 1H NMR (400 MHz, DMSO-d6) δ ppm. 7.74 (1H, d, J=8.28 Hz), 7.62 (1H, d, J=8.28 Hz), 2.36 (3H, s). LC-MS retention time: 1.66 min; m/z (MH+): 342, 344. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 3: Preparation of 6-bromo-2-((4-fluorophenyl)ethynyl)pyridin-3-yl acetate. 6-bromo-2-iodopyridin-3-yl acetate (3.50 g, 10.24 mmol), 1-ethynyl-4-fluorobenzene (1.11 g, 9.21 mmol), copper (I) iodide (117 mg, 0.614 mmol), trans-dichlorobis(triphenylphosphine)palladium (II) (359 mg, 0.512 mmol) were combined and evacuated/backfilled with N2 (3×) then diluted with triethylamine (100 ml) and heated to 85° C. for 2 hours. The solvent was evaporated and the reaction was dissolved in EtOAc. The organic phase was washed with water (50 mL) and brine, dried over Na2SO4, filtered, and concentrated and was purified on silica gel (Biotage, EtOAc/hexanes gradient, fraction collection at λ=254 nm) to give the expected product 6-bromo-2-((4-fluorophenyl)ethynyl)pyridin-3-yl acetate (2.26 g, 6.76 mmol, 66.1% yield) consistent by NMR. 1H NMR (400 MHz, DMSO-d6) δ ppm 7.77 (2H, s), 7.70 (2H, dd, J=8.78, 5.52 Hz), 7.34 (2H, t, J=8.91 Hz), 2.41 (3H, s). LC-MS retention time: 2.18 min; m/z: parent ion not observed, —Ac: 292, 294. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 4: Preparation of methyl 5-bromo-2-(4-fluorophenyl)furo[3,2-b]pyridine-3-carboxylate. Sodium acetate (15 mg, 0.18 mmol), K2CO3 (25 mg, 0.18 mmol), copper(II) chloride dihydrate (46 mg, 0.27 mmol), palladium(II) chloride (2.0 mg, 0.012 mmol) was added to a stirring solution of 6-bromo-2-(4-fluorophenyl)ethynyl)pyridin-3-yl acetate (30 mg, 0.090 mmol) in MeOH (2 mL) at room temperature in a Parr Bomb. The vessel was charged with 300 PSI of CO (g) and allowed to stir at room temperature overnight. The mixture was diluted with EtOAc and washed with sat NaHCO3, and sat NaCl. The organic phase was dried over Na2SO4, filtered and concentrated and purified on silica gel (Biotage, EtOAc/hexanes gradient, fraction collection at $\lambda$=254 nm) to give the expected product methyl 5-bromo-2-(4-fluorophenyl)furo[3,2-b]pyridine-3-carboxylate (25 mg, 0.071 mmol, 80% yield) consistent by LCMS and NMR. 1H NMR (400 MHz, DMSO-d6) $\delta$ ppm 8.16 (1H, d, J=8.78 Hz), 8.04 (2H, dd, J=8.91, 5.40 Hz), 7.67 (1H, d, J=8.78 Hz), 7.44 (2H, t, J=8.78 Hz), 3.89 (3H, s). LC-MS retention time: 2.05 min; m/z (MH+): 350. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 5: Preparation of 5-bromo-2-(4-fluorophenyl)-N-methylfuro[3,2-b]pyridine-3-carboxamide. NaOH (5 mL, 5.00 mmol, 1M aq) was added to a stirring solution of methyl 5-bromo-2-(4-fluorophenyl)furo[3,2-b]pyridine-3-carboxylate (350 mg, 1.00 mmol) in THF (5 mL) and MeOH (5 mL) at 60° C. It was allowed to stir for 1 hr. The mixture was diluted with EtOAc and washed with 1M HCl, and sat NaCl. The organic phase was dried over Na2SO4, filtered and concentrated to give 5-bromo-2-(4-fluorophenyl)furo[3,2-b]pyridine-3-carboxylic. The crude residue was diluted with DMF (10 mL) and treated with HATU (456 mg, 1.20 mmol), methanamine (2.5 mL, 5.00 mmol, 2.0 M in THF), followed by DIEA (524 μL, 3.00 mmol). It was allowed to stir for 1 hr. The mixture was diluted with EtOAc and washed with sat NaHCO3, and sat NaCl. The organic phase was dried over Na2SO4, filtered and concentrated to give the expected product (250 mg, 68% yield) consistent by LCMS and NMR. 1H NMR (400 MHz, DMSO-d6) $\delta$ ppm 8.57 (1H, br. s.), 8.10-8.18 (3H, m), 7.67 (1H, d, J=8.53 Hz), 7.42 (2H, t, J=8.78 Hz), 2.90 (3H, d, J=4.52 Hz). LC-MS retention time: 2.03 min; m/z (MH+): 349, 351. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90%1.120/0.1% trifluoroacetic acid and solvent B was 10% H$_2$O/90% acetonitrile/0.1% trifluoroacetic acid. MS data was determined using a Micromass Platform for LC in electrospray mode.

2-(4-fluorophenyl)-3-(methylcarbamoyl)furo[2,3-c]pyridin-5-yl trifluoromethanesulfonate. Step 1: Preparation of 2-(benzyloxy)-5-(methoxymethoxy)pyridine. NaH (1.2 g, 29.8 mmol) was added to a stirring solution of 6-(benzyloxy)pyridin-3-ol (5.0 g, 24.85 mmol) in DMF (100 mL) at 0° C. Then it was allowed to warm to room temperature and stir for 25 min then was treated with MOM-Cl (2.55 mL, 28.6 mmol) and the reaction was allowed to stir for 2 hrs. The mixture was quenched with H2O then concentrated about 80% then diluted with EtOAc and washed with H2O, and sat NaCl. The organic phase was dried over Na2SO4, filtered and concentrated was purified on silica gel (Biotage, EtOAc/hexanes gradient, fraction collection at $\lambda$=254 nm) to give the expected product 2-(benzyloxy)-5-(methoxymethoxy)pyridine (5.41 g, 22.1 mmol, 89% yield) consistent by LCMS and NMR. 1H NMR (400 MHz, CHLOROFORM-d) $\delta$ ppm 7.97 (1H, d, J=3.01 Hz), 7.42-7.49 (2H, m), 7.29-7.41 (4H, m), 6.76 (1H, d, J=9.03 Hz), 5.34 (2H, s), 5.12 (2H, s), 3.50 (3H, s). LC-MS retention time: 1.88 min; m/z (MH+): 246. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 2: Preparation of 2-(benzyloxy)-4-iodo-5-(methoxymethoxy)pyridine. tBuLi (27 mL, 46.2 mmol) was added drop wise to a stirring solution of 2-(benzyloxy)-5-(methoxymethoxy)pyridine (5.4 g, 22.06 mmol) in THF (110 mL) at –78° C. The light yellow solution was allowed to stir for 30 min then treated with a solution of iodine (8.4 g, 33.1 mmol) in THF (55 mL) dropwise (the purple color per drop dissipated until after 1.05 equiv was added, then it turned progressively purple). It was allowed to stir for 1 hour and then quenched with H2O and diluted with EtOAc washed with sodium thiosulfate sat. soln and sat NaCl. The organic phase was dried over Na2SO4, filtered and concentrated and was purified on silica gel (Biotage, EtOAc/hexanes gradient, fraction collection at $\lambda$=254 nm) to give the expected product 2-(benzyloxy)-4-iodo-5-(methoxymethoxy)pyridine (3.90 g, 10.5 mmol, 48% yield) by LCMS and NMR. 1H NMR (400 MHz, DMSO-d6) $\delta$ ppm 7.87 (1H, s), 7.28-7.44 (6H, m), 5.28 (2H, s), 5.21 (2H, s), 3.43 (3H, s). LC-MS retention time: 2.36 min; m/z (MH+): 372. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 3: Preparation of 2-(benzyloxy)-4-((4-fluorophenyl)ethynyl)-5-(methoxymethoxy)pyridine. 2-(benzyloxy)-4-iodo-5-(methoxymethoxy)pyridine (3.0 g, 8.08 mmol), copper (I) iodide (92 mg, 0.485 mmol), PdCl2(PPh3)2 (284 mg, 0.404 mmol), 1-ethynyl-4-fluorobenzene (1.07 g, 8.89 mmol) were combined in dioxane (40 mL) and TEA (40 mL), degassed and stirred at 80° C. for 1.5 hrs. The mixture was diluted with EtOAc and washed with sat NaCl and H2O. The organic phase was dried over Na2SO4, filtered and concentrated and was purified on silica gel (Biotage, EtOAc/hexanes gradient, fraction collection at $\lambda$=254 nm) to give the expected product 2-(benzyloxy)-4-((4-fluorophenyl)ethynyl)-5-(methoxymethoxy)pyridine (2.52 g, 6.93 mmol, 86% yield) consistent by LCMS. LC-MS retention time: 2.71 min;

m/z (MH+): 364. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 4: Preparation of 6-(benzyloxy)-4-((4-fluorophenyl)ethynyl)pyridin-3-ol. Trifluoroacetic acid (0.95 mL, 12.4 mmol) was added to a stirring solution of 2-(benzyloxy)-4-((4-fluorophenyl)ethynyl)-5-(methoxymethoxy)pyridine (450 mg, 1.24 mmol) in dichloroethane (5 mL) at room temperature. It was allowed to stir for 5 hours and then concentrated to dryness to give 6-(benzyloxy)-4-((4-fluorophenyl)ethynyl)pyridin-3-ol (395 mg, 1.24 mmol, 100% yield) consistent by LCMS. LC-MS retention time: 2.49 min; m/z (MH+): 320. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 5: Preparation of methyl 5-(benzyloxy)-2-(4-fluorophenyl)furo[2,3-c]pyridine-3-carboxylate. Sodium acetate (1.14 g, 13.9 mmol), K2CO3 (1.92 g, 13.9 mmol), copper (II) chloride dihydrate (3.56 g, 20.9 mmol), palladium (II) chloride (0.205 g, 1.15 mmol) was added to a stirring solution of 6-(benzyloxy)-4-((4-fluorophenyl)ethynyl)pyridin-3-ol (2.22 g, 6.95 mmol) in MeOH (150 mL) at room temperature in a Parr Bomb. The vessel was charged with 300 PSI of CO (g) and allowed to stir at room temperature overnight. The mixture was concentrated then diluted with EtOAc and washed with H2O, and sat NaCl. The organic phase was dried over Na2SO4, filtered and concentrated to give the expected product methyl 5-(benzyloxy)-2-(4-fluorophenyl)furo[2,3-c]pyridine-3-carboxylate (2.62 g, 6.95 mmol, 100% yield) by LCMS. LC-MS retention time: 2.66 min; m/z (MH+): 378. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 6: Preparation of 5-(benzyloxy)-2-(4-fluorophenyl)furo[2,3-c]pyridine-3-carboxylic acid. NaOH (27.8 mL, 27.8 mmol, 1M aq.) was added to a stirring solution of methyl 5-(benzyloxy)-2-(4-fluorophenyl)furo[2,3-c]pyridine-3-carboxylate (2.62 g, 6.94 mmol) in THF (174 mL) and MeOH (174 mL) at 60° C. for 2 hours. The mixture was diluted with ethyl acetate and washed with 1M HCl, and sat NaCl. The organic phase was dried over Na2SO4, filtered and concentrated to give the expected product 5-(benzyloxy)-2-(4-fluorophenyl)furo[2,3-c]pyridine-3-carboxylic acid (2.52 g, 6.94 mmol, 100% yield) consistent by LCMS. LC-MS retention time: 2.19 min; m/z (MH+): 364. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 7: Preparation of 5-(benzyloxy)-2-(4-fluorophenyl)-N-methylfuro[2,3-c]pyridine-3-carboxamide. Methanamine (3.1 mL, 6.2 mmol, 2M in THF) was added to a stirring solution of DIEA (646 µL, 3.70 mmol), HATU (563 mg, 1.48 mmol), 5-(benzyloxy)-2-(4-fluorophenyl)furo[2,3-c]pyridine-3-carboxylic acid (448 mg, 1.23 mmol) in DMF (12 mL) at room temperature. The mixture concentrated then diluted with EtOAc and washed with sat NaCl. The organic phase was dried over Na2SO4, filtered and concentrated and was purified on silica gel (Biotage, EtOAc/hexanes gradient, fraction collection at λ=254 nm) to give 5-(benzyloxy)-2-(4-fluorophenyl)-N-methylfuro[2,3-c]pyridine-3-carboxamide (180 mg, 39% yield) consistent by LCMS and NMR. 1H NMR (400 MHz, DMSO-d6) δ ppm 8.62 (1H, s), 8.37-8.45 (1H, m), 7.98-8.08 (2H, m), 7.29-7.50 (7H, m), 7.06 (1H, s), 5.42 (2H, s), 2.83 (3H, d, J=4.52 Hz). LC-MS retention time: 2.00 min; m/z (MH+): 377. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 8: Preparation of 2-(4-fluorophenyl)-5-hydroxy-N-methylfuro[2,3-c]pyridine-3-carboxamide. Pd/C (178 mg, 0.084 mmol) (10%; 50% wet) was added to a stirring solution of 5-(benzyloxy)-2-(4-fluorophenyl)-N-methylfuro[2,3-c]pyridine-3-carboxamide (630 mg, 1.674 mmol) in THF (83 ml) at room temperature. It was placed under an atmosphere of H2 and allowed to stir for 20 minutes after which a precipitate had formed. The reaction was purged with N2 and diluted with MeOH until all solids had dissolved. The mixture was filtered through a pad of celite washing with MeOH and the filtrate was concentrated to give the expected product 2-(4-fluorophenyl)-5-hydroxy-N-methylfuro[2,3-c]pyridine-3-carboxamide (460 mg, 1.53 mmol, 91% yield) consistent by LCMS and NMR. 1H NMR (400 MHz, DMSO-d6) δ ppm 8.30-8.40 (2H, m), 7.98 (2H, dd, J=8.78, 5.77 Hz), 7.35-7.45 (3H, m), 6.61 (1H, s), 2.81 (3H, d, J=4.52 Hz). LC-MS retention time: 0.847 min; m/z (MH+): 287. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 9: 2-(4-fluorophenyl)-3-(methylcarbamoyl)furo[2,3-c]pyridin-5-yl trifluoromethanesulfonate. Triflic anhydride (Tf2O, 319 µL, 1.89 mmol) was added to a stirring solution of 2-(4-fluorophenyl)-5-hydroxy-N-methylfuro[2,3-c]pyridine-3-carboxamide (270 mg, 0.943 mmol) in pyridine (13 mL) at 0° C. and the mixture was allowed to warm to room temperature. It was allowed to stir for 1 hour then concentrated and diluted with EtOAc and washed with sat NaHCO3, and sat NaCl. The organic phase was dried over Na2SO4, filtered and concentrated and was purified on silica gel (Biotage, EtOAc/hexanes gradient, fraction collection at λ=254 nm) to give the expected product 2-(4-fluorophenyl)-3-(methylcarbamoyl)furo[2,3-c]pyridin-5-yl trifluoromethanesulfonate (188 mg, 0.449 mmol, 34.8% yield) consistent by LCMS and NMR. 1H NMR (400 MHz, DMSO-d6) δ ppm 8.91 (1H, s), 8.53-8.61 (1H, m), 8.01-8.11 (2H, m), 7.87 (1H, s), 7.46 (2H, t, J=8.91 Hz), 2.85 (3H, d, J=4.52 Hz). LC-MS retention time: 2.06 min; m/z (MH+): 419. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

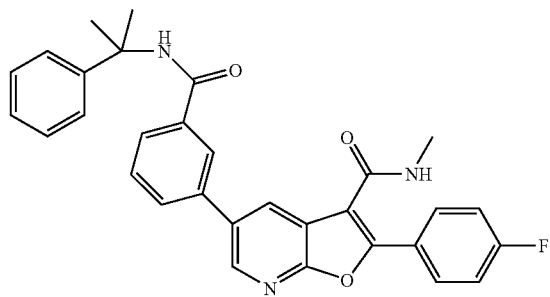

2-(4-fluorophenyl)-N-methyl-5-(3-(2-phenylpropan-2-ylcarbamoyl)phenyl)furo[2,3-b]pyridine-3-carboxamide. Step 1: Preparation of 3-(3-bromo-2-(4-fluorophenyl)furo[2,3-b]pyridin-5-yl)-N-(2-phenylpropan-2-yl)benzamide. DIEA (210 µL, 1.20 mmol) was added to a stirring solution of HATU (228 mg, 0.600 mmol), 2-phenylpropan-2-amine (69.1 µL, 0.480 mmol), 3-(3-bromo-2-(4-fluorophenyl)furo[2,3-b]pyridin-5-yl)benzoic acid (165 mg, 0.400 mmol) in DMF (4 mL) at room temperature. It was allowed to stir for 1 hour. The mixture was diluted with EtOAc and washed with 1M HCl, and sat NaCl. The organic phase was dried over Na2SO4, filtered and concentrated and triturated with Et2O to give the expected product 3-(3-bromo-2-(4-fluorophenyl)furo[2,3-b]pyridin-5-yl)-N-(2-phenylpropan-2-yl)benzamide (180 mg, 0.340 mmol, 85% yield) consistent by LCMS and NMR. 1H NMR (500 MHz, DMSO-d$_6$) δ ppm 8.78-8.86 (1H, m), 8.60 (1H, s), 8.34-8.38 (1H, m), 8.27 (1H, s), 8.19-8.26 (2H, m), 7.99 (1H, d, J=7.93 Hz), 7.89 (1H, d, J=7.93 Hz), 7.61 (1H, t, J=7.63 Hz), 7.46-7.55 (2H, m), 7.42 (2H, d, J=7.32 Hz), 7.30 (2H, t, J=7.78 Hz), 7.18 (1H, t, J=7.17 Hz), 1.72 (6H, s). LC-MS retention time: 1.97 min; m/z (MH+): 529, 531. LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

Step 2: Preparation of 3-(2-(4-fluorophenyl)-3-methylfuro[2,3-b]pyridin-5-yl)-N-(2-phenylpropan-2-yl)benzamide. Pd(Ph3P)4 (4.4 mg, 3.8 µmol) was added to a stirring solution of 3-(3-bromo-2-(4-fluorophenyl)furo[2,3-b]pyridin-5-yl)-N-(2-phenylpropan-2-yl)benzamide (20 mg, 0.038 mmol), trimethylboroxine (11 µL, 0.076 mmol), and Na2CO3 (12.0 mg, 0.11 mmol) in DMF (1.4 mL) and Water (0.14 mL) at room temperature. It was subjected to microwave irradiation: 180° C. for 30 min. The mixture was diluted with EtOAc and washed with sat NaHCO3, and sat NaCl. The organic phase was dried over Na2SO4, filtered and concentrated was purified on silica gel (Biotage, EtOAc/hexanes gradient, fraction collection at λ=254 nm) to give the expected product 3-(2-(4-fluorophenyl)-3-methylfuro[2,3-b]pyridin-5-yl)-N-(2-phenylpropan-2-yl)benzamide (15 mg, 0.032 mmol, 85% yield) by LCMS. LC-MS retention time: 1.87 min; m/z (MH+): 465. LC data was recorded on a Shimadzu LC-10AS liquid chromatograph equipped with a Waters XBridge 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

Step 3: Preparation of 3-(2-(4-fluorophenyl)-3-formylfuro[2,3-b]pyridin-5-yl)-N-(2-phenylpropan-2-yl)benzamide. AIBN (1.0 mg, 6.1 µmol) was added to a stirring solution of NBS (4.6 mg, 0.026 mmol) and 3-(2-(4-fluorophenyl)-3-methylfuro[2,3-b]pyridin-5-yl)-N-(2-phenylpropan-2-yl)benzamide (11 mg, 0.024 mmol) in CCl4 (1 mL). The mixture was heated to 76° C. and allowed to stir for 2 hours. The reaction was concentrated and diluted with DMSO (1 mL) and treated with NMO (3.4 mg, 0.028 mmol) and subjected to microwave irradiation (150° C.) for 5 min. The reaction was purified by preparative reverse phase HPLC on a C18 column using a suitably buffered H2O/CH3CN gradient, and concentrated to give to give the expected product 3-(2-(4-fluorophenyl)-3-formylfuro[2,3-b]pyridin-5-yl)-N-(2-phenylpropan-2-yl)benzamide (7.5 mg, 0.016 mmol, 66% yield) consistent by LCMS and NMR. 1H NMR (500 MHz, DMSO-d$_6$) δ ppm 10.31 (1H, s), 8.84 (1H, s), 8.79 (1H, s), 8.65 (1H, s), 8.19-8.26 (3H, m), 7.89-7.97 (2H, m), 7.59-7.67 (1H, m), 7.54 (2H, t, J=8.55 Hz), 7.42 (2H, d, J=7.93 Hz), 7.30 (2H, t, J=7.63 Hz), 7.13-7.23 (1H, m), 1.71 (6H, s). LC-MS retention time: 1.75 min; m/z (MH+): 479. LC data was recorded on a Shimadzu LC-10AS liquid chromatograph equipped with a Waters XBridge 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

Step 4: Preparation of 2-(4-fluorophenyl)-5-(3-(2-phenylpropan-2-ylcarbamoyl)phenyl)furo[2,3-b]pyridine-3-carboxylic acid. Oxone (28 mg, 0.046 mmol) was added to a stirring solution of 3-(2-(4-fluorophenyl)-3-formylfuro[2,3-b]pyridin-5-yl)-N-(2-phenylpropan-2-yl)benzamide (20 mg, 0.042 mmol) in DMF (0.5 mL) at room temperature. It was allowed to stir for 3 days. An additional amount of Oxone (28 mg, 0.046 mmol) was added and the reaction was allowed to stir overnight. The mixture was diluted with EtOAc and washed with 1M HCl, and sat NaCl. The organic phase was dried over Na2SO4, filtered and concentrated was purified on silica gel (Biotage, EtOAc/hexanes gradient, fraction collection at λ=254 nm) to give the expected product 2-(4-fluorophenyl)-5-(3-(2-phenylpropan-2-ylcarbamoyl)phenyl) furo[2,3-b]pyridine-3-carboxylic acid (7 mg, 0.014 mmol, 34% yield) consistent by LCMS and NMR. 1H NMR (500 MHz, MeOD) δ ppm 7.42 (1H, d, J=2.14 Hz), 7.31-7.39 (2H, m), 6.93-7.02 (2H, m), 6.87 (1H, s), 6.59 (2H, t, J=8.70 Hz), 6.34 (1H, t, J=7.63 Hz), 6.20 (2H, d, J=7.63 Hz), 5.97-6.07 (4H, m), 5.92 (1H, t, J=7.32 Hz), 0.52 (6H, s). LC-MS retention time: 1.15 min; m/z (MH+): 495. LC data was recorded on a Shimadzu LC-10AS liquid chromatograph equipped with a Waters XBridge 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 mM, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

Step 5: Preparation of the title compound, 2-(4-fluorophenyl)-N-methyl-5-(3-(2-phenylpropan-2-ylcarbamoyl)phenyl)furo[2,3-b]pyridine-3-carboxamide. Methanamine (253 µL, 0.506 mmol, 2M in THF) was added to a stirring solution of 2-(4-fluorophenyl)-5-(3-(2-phenylpropan-2-ylcarbamoyl) phenyl)furo[2,3-b]pyridine-3-carboxylic acid (50 mg, 0.10 mmol), DIEA (53 µL, 0.30 mmol), DMAP (1.2 mg, 10 µmol), HATU (58 mg, 0.15 mmol) in DMF (1 mL) at room temperature. It was allowed to stir for 1 hour and then was purified by preparative reverse phase HPLC on a C18 column using a suitably buffered H2O/CH3CN gradient, and concentrated to give the expected product 2-(4-fluorophenyl)-N-methyl-5-(3-(2-phenylpropan-2-ylcarbamoyl)phenyl)furo[2,3-b]pyridine-3-carboxamide (7 mg, 0.013 mmol, 13% yield) consistent by LCMS and NMR. 1H NMR (500 MHz, MeOD) δ ppm 8.65 (1H, d, J=2.14 Hz), 8.41 (1H, d, J=2.14 Hz), 8.12-8.17 (1H, m), 8.00-8.06 (2H, m), 7.84-7.92 (2H, m), 7.62 (1H, t, J=7.63 Hz), 7.43-7.50 (2H, m), 7.26-7.35 (4H, m), 7.19 (1H, t, J=7.32 Hz), 2.98 (3H, s), 1.78 (6H, s). LC-MS retention time: 1.77 min; m/z (MH+): 508. LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% CH3CN/95% H2O/0.1% TFA, Solvent B=95% CH3CN/5% H2O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, $R_t$=12.82 min, purity=95%; Column: Waters Xbridge Phenyl column 4.6×150 mm, 3.5 mm, $R_t$=11.20 min, purity=94%. Additional HPLC method: Solvent A=5% MeOH/95% H2O/10 mM ammonium bicarbonate, Solvent B=95% MeOH/5% H2O/10 mM ammonium bicarbonate, Start % B=10, Final % B=100, Gradient time=15 min, Stop time=18 min, Flow Rate=1 ml/min. Column: Phenomenex Gemini C1 C-18, 4.6×150 mm, 3 mm, $R_t$=14.10 min, purity=95%; Column: Waters Xbridge Phenyl column 4.6×150 mm, 3.5 mm, $R_t$=13.85 min, purity=95%.

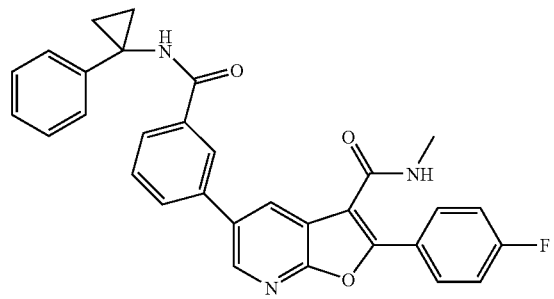

2-(4-fluorophenyl)-N-methyl-5-(3-(1-phenylcyclopropylcarbamoyl)phenyl)furo[2,3b]pyridine-3-carboxamide. Step 1 Preparation of 3-(3-bromo-2-(4-fluorophenyl)furo[2,3-b] pyridin-5-yl)-N-(1-phenylcyclopropyl)benzamide. DIEA (286 µL, 1.64 mmol) was added to a stirring solution of HATU (311 mg, 0.819 mmol), 1-phenylcyclopropanamine hydrochloride (111 mg, 0.655 mmol), and 3-(3-bromo-2-(4-fluorophenyl)furo[2,3-b]pyridin-5-yl)benzoic acid (225 mg, 0.546 mmol) in DMF (6 mL) at room temperature. It was allowed to stir for 1 hour. The mixture was diluted with EtOAc and washed with 1M HCl, and sat NaCl. The organic phase was dried over Na2SO4, filtered and concentrated to give the expected product 3-(3-bromo-2-(4-fluorophenyl) furo[2,3-b]pyridin-5-yl)-N-(1-phenylcyclopropyl)benzamide (180 mg, 0.341 mmol, 63% yield) consistent by LCMS. LC-MS retention time: 1.89 min; m/z (MH+): 529. LC data was recorded on a Shimadzu LC-10AS liquid chromatograph equipped with a Waters XBridge 5u C18 4.6×50 min column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

Step 2: Preparation of 3-(2-(4-fluorophenyl)-3-methylfuro [2,3-b]pyridin-5-yl)-N-(1-phenylcyclopropyl)benzamide. Pd(Ph3P)4 (16 mg, 0.014 mmol) was added to a stirring solution of 3-(3-bromo-2-(4-fluorophenyl)furo[2,3-b]pyridin-5-yl)-N-(1-phenylcyclopropyl)benzamide (75 mg, 0.14 mmol), trimethylboroxine (40 µL, 0.28 mmol), and Na2CO3 (45 mg, 0.43 mmol) in DMF (1.3 mL) and Water (0.13 mL) at room temperature. It was subjected to microwave irradiation: 180° C. for 30 min. The mixture was diluted with EtOAc and washed with sat NaHCO3, and sat NaCl. The organic phase was dried over Na2SO4, filtered and concentrated was purified on silica gel (Biotage, EtOAc/hexanes gradient, fraction collection at λ=254 nm) to give the expected product 3-(2-(4-fluorophenyl)-3-methylfuro[2,3-b]pyridin-5-yl)-N-(1-phenylcyclopropyl)benzamide (61 mg, 0.132 mmol, 93% yield) consistent by LCMS. LC-MS retention time: 1.81 min; m/z (MH+): 463. LC data was recorded on a Shimadzu LC-10AS liquid chromatograph equipped with a Waters XBridge 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

Step 3: Preparation of 3-(2-(4-fluorophenyl)-3-formylfuro[2,3-b]pyridin-5-yl)-N-(1-phenylcyclopropyl)benzamide. AIBN (6.5 mg, 0.040 mmol) was added to a stirring solution of NBS (26 mg, 0.15 mmol) and 3-(2-(4-fluorophenyl)-3-methylfuro[2,3-b]pyridin-5-yl)-N-(1-phenylcyclopropyl)benzamide (61 mg, 0.13 mmol) in CCl4 (20 ml). The mixture was heated to 76° C. and allowed to stir for 2 hours. The reaction was concentrated and diluted with DMSO (1 mL) and treated with NMO (18.5 mg, 0.158 mmol) and subjected to MW irradiation (150° C.) for 10 min. The mixture was diluted with EtOAc and washed with 10% NaHSO4 2× followed by H2O and Brine. The organic phase was dried over Na2SO4, filtered and concentrated and was purified on silica gel (Biotage, EtOAc/hexanes gradient, fraction collection at λ=254 nm) to give the expected product 3-(2-(4-fluorophenyl)-3-formylfuro[2,3-b]pyridin-5-yl)-N-(1-phenylcyclopropyl)benzamide (34 mg, 0.071 mmol, 54% yield) consistent by LCMS. LC-MS retention time: 1.64 min; m/z (MH+): 477. LC data was recorded on a Shimadzu LC-10AS liquid chromatograph equipped with a Waters XBridge 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 mM, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

Step 4: Preparation of the title compound, 2-(4-fluorophenyl)-N-methyl-5-(3-(1-phenylcyclopropylcarbamoyl)phenyl)furo[2,3-b]pyridine-3-carboxamide. AIBN (3.6 mg, 0.022 mmol) and NBS (17 mg, 0.095 mmol) was added to a stirring solution of 3-(2-(4-fluorophenyl)-3-formylfuro[2,3-b]pyridin-5-yl)-N-(1-phenylcyclopropyl)benzamide (35 mg, 0.073 mmol) in CCl4 (10 mL) at 95° C. It was allowed to stir for 30 mM. The reaction was removed from the heat and allowed to stir for 2 min and treated with methanamine (0.184 mL, 0.367 mmol, 2M in THF). The reaction was allowed to stir for 1 hour and concentrated. The residue was diluted with EtOAc and washed with 10% sodium bisulfate, and sat NaCl. The organic phase was dried over Na2SO4, filtered and concentrated and was purified on silica gel (Biotage, EtOAc/hexanes gradient, fraction collection at λ=254 nm) to give to give the expected product 2-(4-fluorophenyl)-N-methyl-5-(3-(1-phenylcyclopropylcarbamoyl)phenyl)furo[2,3-b]pyridine-3-carboxamide (4 mg, 7.91 μmol, 11% yield) consistent by LCMS and NMR. 1H NMR (500 MHz, DMSO-d$_6$) δ ppm 9.36 (1H, s), 8.77 (1H, d, J=2.14 Hz), 8.54-8.62 (1H, m), 8.41 (1H, d, J=2.14 Hz), 8.31 (1H, s), 8.04-8.09 (2H, m), 7.99 (1H, d), 7.95 (1H, d, J=7.63 Hz), 7.64 (1H, t, J=7.63 Hz), 7.43 (2H, t, J=8.85 Hz), 7.26-7.31 (2H, m), 7.21-7.26 (2H, m), 7.16 (1H, t), 2.87 (3H, d, J=4.88 Hz), 1.31 (4H, d, J=7.93 Hz). LC-MS retention time: 1.98 min; m/z (MH+): 506. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent 13, a gradient time of 3 min, a hold time of 1 min, and an analysis time of 4 mM where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode. Additional HPLC method: Solvent A=5% MeOH/95% H$_2$O/10 mM ammonium bicarbonate, Solvent B=95% MeOH/5% H$_2$O/10 mM ammonium bicarbonate, Start % B=10, Final % B=100, Gradient time=15 min, Stop time=18 min, Flow Rate=1 ml/min. Column: Phenomenex Gemini C1 C-18, 4.6×150 mm, 3 mm, R$_t$=14.12 mM, purity=95%; Column: Waters Xbridge Phenyl column 4.6×150 mm, 3.5 mm, R$_t$=14.45 min, purity=96%.

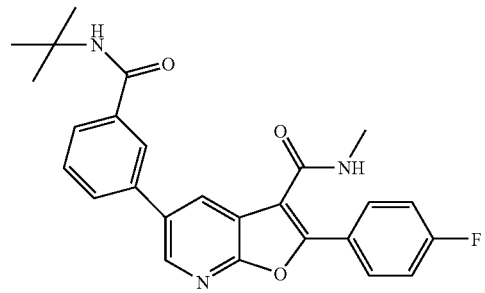

5-(3-(tert-butylcarbamoyl)phenyl)-2-(4-fluorophenyl)-N-methylfuro[2,3-b]pyridine-3-carboxamide. Step 1: Preparation of methyl 3-(3-bromo-2-(4-fluorophenyl)furo[2,3-b]pyridin-5-yl)benzoate. (Diazomethyl)trimethylsilane (467 μL, 0.934 mmol) was added to a stirring solution of 3-(3-bromo-2-(4-fluorophenyl)furo[2,3-b]pyridin-5-yl)benzoic acid (350 mg, 0.849 mmol) in MeOH (5.7 mL) and Ether (2.8 mL) at room temperature. It was allowed to stir overnight. The mixture was concentrated and resubjected to the reaction conditions using DCM as the solvent. This was repeated again using THF as the solvent. The reaction was concentrated to give the expected product methyl 3-(3-bromo-2-(4-fluorophenyl)furo[2,3-b]pyridin-5-yl)benzoate (350 mg, 0.821 mmol, 97% yield) consistent by LCMS. LC-MS retention time: 2.01 min; m/z (MH+): 426, 428. LC data was recorded on a Shimadzu LC-10AS liquid chromatograph equipped with a Waters XBridge 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

Step 2: Preparation of methyl 3-(2-(4-fluorophenyl)-3-methylfuro[2,3-b]pyridin-5-yl)benzoate. 2,4,6-trimethyl-1,3,5,2,4,6-trioxatriborinane (0.236 mL, 1.69 mmol) was added to a stirring solution of methyl 3-(3-bromo-2-(4-fluorophenyl)furo[2,3-b]pyridin-5-yl)benzoate (360 mg, 0.845 mmol), sodium carbonate (269 mg, 2.53 mmol), Pd(Ph3P)4 (98 mg, 0.084 mmol) in DMF (10 mL) and Water (1.0 mL). It was subjected to MW irradiation (180° C.) for 30 mM. The mixture was diluted with EtOAc and washed with sat NaHCO3, and sat NaCl. The organic phase was dried over Na2SO4, filtered and concentrated. The crude residue was diluted with MeOH and treated with (Diazomethyl)trimethylsilane (467 µL, 0.934 mmol) to re-esterfy the acid which had formed. It was allowed to stir for 1 hour and then concentrated and purified on silica gel (Biotage, EtOAc/hexanes gradient, fraction collection at λ=254 nm) to give the expected product methyl 3-(2-(4-fluorophenyl)-3-methylfuro[2,3-b]pyridin-5-yl)benzoate (163 mg, 0.451 mmol, 53% yield) consistent by LCMS. LC-MS retention time: 1.79 min; m/z (MH+): 362. LC data was recorded on a Shimadzu LC-10AS liquid chromatograph equipped with a Waters XBridge 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

Step 3: Preparation of methyl 3-(2-(4-fluorophenyl)-3-formylfuro[2,3-b]pyridin-5-yl)benzoate. AIBN (22.2 mg, 0.135 mmol) was added to a stirring solution of NBS (88 mg, 0.49 mmol) and methyl 3-(2-(4-fluorophenyl)-3-methylfuro[2,3-b]pyridin-5-yl)benzoate (163 mg, 0.451 mmol) in CCl4 (40 mL) and was heated to 76° C. The mixture was allowed to stir for 2 hours. The reaction was concentrated and diluted with DMSO (1 mL) and treated with NMO (63 mg, 0.54 mmol) and subjected to MW irradiation (150° C.) for 10 min. The mixture was diluted with EtOAc and washed with 10% NaHSO4 2× followed by H2O and Brine. The organic phase was dried over Na2SO4, filtered and concentrated and was purified on silica gel (Biotage, EtOAc/hexanes gradient, fraction collection at λ=254 nm) to give the expected product methyl 3-(2-(4-fluorophenyl)-3-formylfuro[2,3-b]pyridin-5-yl)benzoate (34 mg, 0.091 mmol, 20% yield) consistent by LCMS and NMR. 1H NMR (500 MHz, DMSO-d$_6$) δ ppm 10.31 (1H, s), 8.79 (1H, d, J=2.44 Hz), 8.74 (1H, d, J=2.44 Hz), 8.28 (1H, s), 8.16-8.25 (2H, m), 8.00-8.13 (2H, m), 7.72 (1H, t, J=7.78 Hz), 7.49-7.57 (2H, m), 3.92 (3H, s). LC-MS retention time: 1.72 min., m/z (MH+): 376. LC data was recorded on a Shimadzu LC-10AS liquid chromatograph equipped with a Waters XBridge 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

Step 4: Preparation of methyl 3-(2-(4-fluorophenyl)-3-(methylcarbamoyl)furo[2,3-b]pyridin-5-yl)benzoate. AIBN (4.6 mg, 0.028 mmol) and NBS (21.6 mg, 0.121 mmol) was added to a stirring solution of methyl 3-(2-(4-fluorophenyl)-3-formylfuro[2,3-b]pyridin-5-yl)benzoate (35 mg, 0.093 mmol) in CCl4 (5 mL) at 95° C. It was allowed to stir for 30 min and then allowed to cool and was then treated with methanamine (0.466 mL, 0.932 mmol, 2M in THF) and the reaction was allowed to stir for 10 min then diluted with MeOH. A ppt formed which was filtered away and the filtrate was concentrated and was purified on silica gel (Biotage, EtOAc/hexanes gradient, fraction collection at λ=320 nm) to give to give the expected product methyl 3-(2-(4-fluorophenyl)-3-(methylcarbamoyl)furo[2,3-b]pyridin-5-yl)benzoate (24 mg, 0.059 mmol, 64% yield) consistent by LCMS and NMR. 1H NMR (500 MHz, CHLOROFORM-d) δ ppm 8.60 (1H, d, J=2.14 Hz), 8.44 (1H, d, J=2.44 Hz), 8.32 (1H, s), 8.10 (1H, d, J=7.93 Hz), 7.95-8.00 (2H, m), 7.84 (1H, d, J=7.63 Hz), 7.59 (1H, t, J=7.78 Hz), 7.22-7.26 (2H, m), 5.91 (1H, br. s.), 3.98 (3H, s), 3.03 (3H, d, J=4.88 Hz). LC-MS retention time: 1.46 mM; m/z (MH+): 405. LC data was recorded on a Shimadzu LC-10AS liquid chromatograph equipped with a Waters XBridge 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 mM, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

Step 5: Preparation of 3-(2-(4-fluorophenyl)-3-(methylcarbamoyl)furo[2,3-b]pyridin-5-yl)benzoic acid. NaOH (0.297 mL, 0.297 mmol, 1M aq.) was added to a stirring solution of methyl 3-(2-(4-fluorophenyl)-3-(methylcarbamoyl)furo[2,3-b]pyridin-5-yl)benzoate (24 mg, 0.059 mmol) in MeOH (2 mL) at room temperature. It was allowed to stir overnight. The mixture was diluted with EtOAc and washed with 1M HCl, and sat NaCl. The organic phase was dried over Na2SO4, filtered and concentrated to give the expected product 3-(2-(4-fluorophenyl)-3-(methylcarbamoyl)furo[2,3-b]pyridin-5-yl)benzoic acid (22 mg, 0.056 mmol, 95% yield) consistent by LCMS. LC-MS retention time: 0.90 min; m/z (MH+): 391. LC data was recorded on a Shimadzu LC-10AS liquid chromatograph equipped with a Waters XBridge 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

Step 6: Preparation of the title compound, 5-(3-(tert-butylcarbamoyl)phenyl)-2-(4-fluorophenyl)-N-methylfuro[2,3-b]pyridine-3-carboxamide. DIEA (31 µL, 0.18 mmol) was added to a stirring solution of 3-(2-(4-fluorophenyl)-3-(methylcarbamoyl)furo[2,3-b]pyridin-5-yl)benzoic acid (23 mg, 0.059 mmol), 2-methylpropan-2-amine (20 µL, 0.059 mmol), and HATU (27 mg, 0.071 mmol) in DMF (0.6 mL) at room temperature. It was allowed to stir for 2 hours. The mixture was diluted with EtOAc and washed with 1M HCl, and sat NaCl. The organic phase was dried over Na2SO4, filtered and concentrated to give the expected product 5-(3-(tert-butylcarbamoyl)phenyl)-2-(4-fluorophenyl)-N-methylfuro[2,3-b]pyridine-3-carboxamide (8 mg, 0.017 mmol, 29% yield) consistent by LCMS and NMR. 1H NMR (500 MHz, DMSO-d$_6$) δ ppm 8.74 (1H, d, J=2.14 Hz), 8.55-8.61 (1H, m), 8.39 (1H, d, J=2.44 Hz), 8.16 (1H, s), 8.07 (2H, dd, J=8.85, 5.19 Hz), 7.94 (1H, s), 7.92 (1H, d, J=7.63 Hz), 7.86 (1H, d, J=7.93 Hz), 7.59 (1H, t, J=7.63 Hz), 7.43 (2H, t, J=8.85 Hz), 2.87 (3H, d, J=4.58 Hz), 1.42 (9H, s). LC-MS retention time: 1.68 min; m/z (MH+): 446. LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 mM, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% MeOH/95% H2O/10 mM ammonium bicarbonate, Solvent B=95% MeOH/5% H2O/10 mM ammonium bicarbonate, Start % B=10, Final % B=100, Gradient time=15 min, Stop time=18 min, Flow Rate=1 ml/min. Column: Phenomenex Gemini C1 C-18, 4.6×150 mm, 3 mm, R$_f$=13.66 min, purity=98%; Column: Waters Xbridge Phenyl column 4.6×150 mm, 3.5 mm, R$_f$=13.69 min, purity=98%.

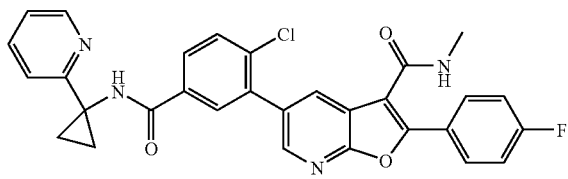

5-(2-chloro-5-(1-(pyridin-2-yl)cyclopropyl carbamoyl)phenyl)-2-(4-fluorophenyl)-N-methylfuro[2,3-b]pyridine-3-carboxamide. Step 1: Preparation of 4-chloro-3-(2-(4-fluorophenyl)furo[2,3-b]pyridin-5-yl)benzoic acid. Cesium carbonate (167 mg, 0.514 mmol) was added to Pd(Ph3P)4 (40 mg, 0.034 mmol), 5-bromo-2-(4-fluorophenyl)furo[2,3-b]pyridine (100 mg, 0.342 mmol), 3-borono-4-chlorobenzoic acid (103 mg, 0.514 mmol) in DMF (3 mL) and Water (0.3 mL) at room temperature. The mixture was degassed 3× and the reaction was heated to 180° C. in the microwave for 10 min. The mixture was diluted with EtOAc and washed with 1M HCl, and sat NaCl. The organic phase was dried over Na2SO4, filtered and concentrated. The crude product was triturated with MeOH to give the expected product 4-chloro-3-(2-(4-fluorophenyl)furo[2,3-b]pyridin-5-yl)benzoic acid (59 mg, 0.160 mmol, 47% yield) consistent by LCMS and NMR. 1H NMR (400 MHz, DMSO-d6) δ ppm 13.22 (1H, br. s.), 8.36 (1H, d, J=2.26 Hz), 8.25 (1H, d, J=2.26 Hz), 8.03-8.11 (2H, m), 7.97-8.02 (2H, m), 7.77 (1H, J=7.78 Hz), 7.55 (1H, s), 7.41 (2H, t, J=8.78 Hz). LC-MS retention time: 1.15 min; m/z (MH+): 368. LC data was recorded on a Shimadzu LC-10AS liquid chromatograph equipped with a Waters XBridge 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

Step 2: Preparation of 3-(3-bromo-2-(4-fluorophenyl)furo[2,3-b]pyridin-5-yl)-4-chlorobenzoic acid. NBS (29.0 mg, 0.163 mmol) was added to a stirring solution of 4-chloro-3-(2-(4-fluorophenyl)furo[2,3b]pyridin-5-yl)benzoic acid (50 mg, 0.136 mmol) in THF (4.5 mL) at room temperature. It was allowed to stir for 1 hour. An additional portion of NBS (29 mg, 0.16 mmol) was added it was allowed to stir for 1 hour after which another portion of NBS (29 mg, 0.16 mmol) was added and the reaction was allowed to stir overnight. The mixture was diluted with EtOAc and washed with 10% NaHSO3, and sat NaCl. The organic phase was dried over Na2SO4, filtered and concentrated and triturated with DCM to give the expected product 3-(3-bromo-2-(4-fluorophenyl)furo[2,3-b]pyridin-5-yl)-4-chlorobenzoic acid (57 mg, 0.128 mmol, 94% yield) consistent by LCMS and NMR. 1H NMR (500 MHz, DMSO-d6) δ ppm 8.48 (1H, d, J=2.14 Hz), 8.19-8.24 (2H, m), 8.17 (1H, d, J=2.14 Hz), 7.99-8.05 (2H, m), 7.79 (1H, d, J=8.24 Hz), 7.46-7.52 (2H, m). LC-MS retention time: 1.29 mM; m/z (MH+): 447. LC data was recorded on a Shimadzu LC-10AS liquid chromatograph equipped with a Waters XBridge 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

Step 3: Preparation of 4-chloro-3-(2-(4-fluorophenyl)-3-(methoxycarbonyl)furo[2,3-b]pyridin-5-yl)benzoic acid. 1,3-bis(diphenylphosphino)propane (28 mg, 0.067 mmol) was added to a stirring solution of palladium(II) acetate (7.5 mg, 0.034 mmol) and 3-(3-bromo-2-(4-fluorophenyl)furo[2,3-b]pyridin-5-yl)-4-chlorobenzoic acid (75 mg, 0.17 mmol) in MeOH (0.6 mL) and DMSO (1.1 mL) at 80° C. in a Parr bomb which was charged with 150 psi CO (g) and allowed to stir overnight. The mixture was diluted with ethyl acetate and washed with 1M HCl, and sat NaCl. The organic phase was dried over Na2SO4, filtered and concentrated to give the expected product 4-chloro-3-(2-(4-fluorophenyl)-3-(methoxycarbonyl)furo[2,3-b]pyridin-5-yl)benzoic acid (75 mg, 0.113 mmol, 67% yield) by LCMS. LC-MS retention time: 2.28 min; m/z (MH+): 427. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 4: 5-(2-chloro-5-(1-(pyridin-2-yl)cyclopropylcarbamoyl)phenyl)-2-(4-fluorophenyl)-N-methylfuro[2,3-b]pyridine-3-carboxamide. DIEA (142 μL, 0.810 mmol) was added to a stirring solution of 1-(pyridin-2-yl)cyclopropanamine dihydrochloride (84 mg, 0.405 mmol), 4-chloro-3-(2-(4-fluorophenyl)-3-(methoxycarbonyl)furo[2,3-b]pyridin-5-yl)benzoic acid (115 mg, 0.270 mmol) and HATU (154 mg, 0.405 mmol) in DMF (2.7 mL) at room temperature. It was allowed to stir for 1 hour. The mixture was diluted with ethyl acetate and washed with sat NaHCO3, and sat NaCl. The organic phase was dried over Na2SO4, filtered and concentrated to give crude methyl 5-(2-chloro-5-(1-(pyridin-2-yl)cyclopropylcarbamoyl)phenyl)-2-(4-fluorophenyl)furo[2,3-b]pyridine-3-carboxylate. The crude residue was diluted with MeOH (4 mL) and treated with NaOH (810 μL, 0.810 mmol) in H2O; the reaction was heated to 60° C. and allowed to stir for 1 hr. The mixture was diluted with EtOAc and washed with 1M HCl, and sat NaCl. The organic phase was dried over Na2SO4, filtered and concentrated to give crude 5-(2-chloro-5-(1-(pyridin-2-yl)cyclopropylcarbamoyl)phenyl)-2-(4-fluorophenyl)furo[2,3-b]pyridine-3-carboxylic acid. The crude residue was diluted with DMF (2 mL) and treated with HATU (154 mg, 0.405 mmol), methanamine (675 μL, 1.35 mmol, 2 M in THF) in THF, followed by DIEA (142 μL, 0.810 mmol). The reaction was allowed to stir at room temperature for 1 hour. The mixture was concentrated and purified on silica gel (Biotage, EtOAc/hexanes gradient, fraction collection at λ=254 nm) to give the expected product consistent by LCMS and NMR. 1H NMR (400 MHz, DMSO-d6) δ ppm 9.40 (1H, s), 8.52 (1H, d, J=4.77 Hz), 8.50 (1H, d, J=2.01 Hz), 8.44 (1H, d, J=4.77 Hz), 8.23 (1H, d, J=2.01 Hz), 8.12 (1H, d, J=2.01 Hz), 7.97-8.09 (3H, m), 7.78 (1H, d, J=8.28 Hz), 7.67 (1H, td, J=7.72, 1.88 Hz), 7.39-7.47 (2H, m), 7.36 (1H, d, J=8.03 Hz), 7.15 (1H, dd, J=7.40, 4.89 Hz), 2.83 (3H, d, J=4.52 Hz), 1.50-1.60 (2H, m), 1.22-1.32 (2H, m). LC-MS retention time: 1.31 min; m/z (MH+): 541. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode. Additional HPLC method: Solvent A=5% MeOH/95% H2O/10 mM ammonium bicarbonate, Solvent B=95% MeOH/5% H2O/10 mM ammonium bicarbonate, Start % B=10, Final % B=100, Gradient time=15 min, Stop time=18 min, Flow Rate=1 ml/min. Column: Phenomenex Gemini C1 C-18, 4.6×150 mm, 3 mm, $R_t$=9.66 mM, purity=98%; Column: Waters Xbridge Phenyl column 4.6×150 mm, 3.5 mm, $R_t$=9.69 min, purity=98%.

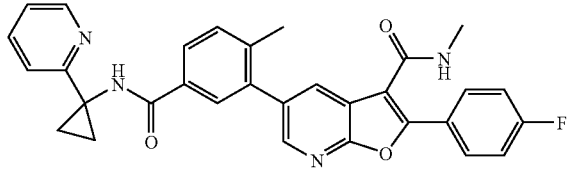

2-(4-fluorophenyl)-N-methyl-5-(2-methyl-5-(1-(pyridin-2-yl)cyclopropylcarbamoyl)phenyl)furo[2,3-b]pyridine-3-carboxamide. Step 1: Preparation of methyl 3-(2-(4-fluorophenyl)furo[2,3-b]pyridin-5-yl)-4-methylbenzoate. Cs2CO3 (379 mg, 1.164 mmol) was added to a stirring solution of 5-bromo-2-(4-fluorophenyl)furo[2,3-b]pyridine (200 mg, 0.685 mmol), 4-methyl-3-(4,4,5,5-tetramethyl-1,3,2-dioxaborolan-2-yl)benzoic acid (269 mg, 1.027 mmol), Pd(Ph3P)4 (158 mg, 0.137 mmol) in 1,4-dioxane (5.7 mL) and Water (1.1 mL). It was heated to 90° C. overnight. The mixture was diluted with EtOAc and washed with 1M HCl, and sat NaCl. The organic phase was dried over Na2SO4, filtered and concentrated and diluted with MeOH/DCM and treated with TMS-diazomethane (685 μL, 1.369 mmol, 2M in ether). The mixture was allowed to stir for 1 hour. The reaction was concentrated and was purified on silica gel (Biotage, EtOAc/hexanes gradient, fraction collection at λ=254 nm) to give the expected product methyl 3-(2-(4-fluorophenyl)furo[2,3-b]pyridin-5-yl)-4-methylbenzoate (250 mg, 0.692 mmol, 100% yield) by LCMS and NMR. 1H NMR (400 MHz, DMSO-d6) δ ppm 8.28 (1H, d, J=2.26 Hz), 8.16 (1H, d, J=2.01 Hz), 8.01-8.10 (2H, m), 7.93 (1H, dd, J=7.91, 1.88 Hz), 7.85 (1H, d, J=1.76 Hz), 7.49-7.57 (2H, m), 7.36-7.44 (2H, m), 3.86 (3H, s), 2.34 (3H, s). LC-MS retention time: 2.55 min; m/z (MH+): 362. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 2: Preparation of methyl 3-(3-bromo-2-(4-fluorophenyl)furo[2,3-b]pyridin-5-yl)-4-methylbenzoate. The reaction flask was wrapped in aluminum foil. NBS (175 mg, 0.983 mmol) was added to a stirring solution of methyl 3-(2-(4-fluorophenyl)furo[2,3-b]pyridin-5-yl)-4-methylbenzoate (289 mg, 0.800 mmol) in DCE (8 mL) at room temperature. It was allowed to stir overnight. The mixture was diluted with EtOAc and quenched with 10% sodium metabisulfate and washed with sat NaCl. The organic phase was dried over Na2SO4, filtered and concentrated was purified on silica gel (Biotage, EtOAc/hexanes gradient, fraction collection at λ=254 nm) the expected product consistent by LCMS and NMR. 1H NMR (400 MHz, DMSO-d6) δ ppm 8.41 (1H, d, J=2.01 Hz), 8.16-8.26 (2H, m), 8.06 (1H, d, J=2.26 Hz), 7.95 (1H, dd, J=8.03, 1.76 Hz), 7.87 (1H, d), 7.45-7.57 (3H, m), 3.86 (3H, s), 2.34 (3H, s). LC-MS retention time: 2.85 min; m/z (MH+): 440, 442. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 3: Preparation of 3-(3-bromo-2-(4-fluorophenyl)furo[2,3-b]pyridin-5-yl)-4-methylbenzoic acid. NaOH (3.3 mL, 3.3 mmol, 1M aq) was added to a stirring solution of methyl 3-(3-bromo-2-(4-fluorophenyl)furo[2,3-b]pyridin-5-yl)-4-methylbenzoate (294 mg, 0.668 mmol) in MeOH (7 mL) and THF (7 mL) at 60° C. It was allowed to stir for 1 hr. The mixture was diluted with EtOAc and washed with 1M HCl, and sat NaCl. The organic phase was dried over Na2SO4, filtered and concentrated to give the expected product 3-(3-bromo-2-(4-fluorophenyl)furo[2,3b]pyridin-5-yl)-4-methylbenzoic acid (275 ing, 0.645 mmol, 97% yield) consistent by LCMS and NMR. 1H NMR (400 MHz, DMSO-d6) δ ppm 12.90 (1H, br. s.), 8.40 (1H, d, J=2.26 Hz), 8.18-8.25 (2H, m), 8.05 (1H, d, J=2.26 Hz), 7.92 (1H, dd, J=7.78, 1.76 Hz), 7.85 (1H, d, J=1.76 Hz), 7.43-7.54 (3H, m), 2.35 (3H, s). LC-MS retention time: 2.42 min; m/z (MH+): 426, 428. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 4: Preparation of 3-(2-(4-fluorophenyl)-3-(methoxycarbonyl)furo[2,3-b]pyridin-5-yl)-4-methylbenzoic acid. 1,3-bis(diphenylphosphino)propane (160 mg, 0.387 mmol) was added to a stirring solution of palladium(II) acetate (44 mg, 0.19 mmol) and 3-(3-bromo-2-(4-fluorophenyl)furo[2,3-b]pyridin-5-yl)-4-methylbenzoic acid (275 mg, 0.645 mmol) in MeOH (2.1 mL) and DMSO (4.3 mL) at 80° C. in a Parr bomb which was charged with 150 psi CO (g) and allowed to stir overnight. The mixture was diluted with EtOAc and washed with sat NaHCO3, and sat NaCl. The organic phase was dried over Na2SO4, filtered and concentrated and triturated with DCM to give the expected product 3-(2-(4-fluorophenyl)-3-(methoxycarbonyl)furo[2,3-b]pyridin-5-yl)-4-methylbenzoic acid (176 mg, 0.434 mmol, 67% yield) consistent by LCMS and NMR. 1H NMR (400 MHz, DMSO-d6) δ ppm 12.95 (1H, br. s.), 8.42 (1H, d, J=2.01 Hz), 8.34 (1H, d, J=2.01 Hz), 8.14-8.21 (2H, m), 7.93 (1H, dd, J=8.03, 1.76 Hz), 7.84 (1H, d, J=1.76 Hz), 7.45-7.53 (3H, m), 3.89 (3H, s), 2.32 (3H, s). LC-MS retention time: 2.16 min; m/z (MH+): 406. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 5: Preparation of the titled compound; 2-(4-fluorophenyl)-N-methyl-5-(2-methyl-5-(1-(pyridin-2-yl)cyclopropylcarbamoyl)phenyl)furo[2,3-b]pyridine-3-carboxamide. Hunig's Base (65 μL, 0.37 mmol) was added to a stirring solution of HATU (56 mg, 0.15 mmol), 3-(2-(4-fluorophenyl)-3-(methoxycarbonyl)furo[2,3-b]pyridin-5-yl)-4-methylbenzoic acid (50 mg, 0.12 mmol), 1-(pyridin-2-yl)cyclopropanamine dihydrochloride (31 mg, 0.15 mmol) in DMF (1.2 mL) at room temperature. It was allowed to stir for 30 min. The mixture was diluted with ethyl acetate and washed with sat NaHCO3, 1M NaOH, and sat NaCl. The organic phase was dried over Na2SO4, filtered and concentrated to give methyl 2-(4-fluorophenyl)-5-(2-methyl-5-(1-(pyridin-2-yl)cyclopropylcarbamoyl)phenyl)furo[2,3-b]pyridine-3-carboxylate. The crude residue was diluted with MeoH (2 mL) and treated with NaOH (0.617 μL, 0.617 mmol, 1M aq). The mixture was allowed to stir at 60° C. for 1 hour. The mixture was diluted with EtOAc and washed with 1M HCl, and sat NaCl. The organic phase was dried over Na2SO4, filtered and concentrated to give 2-(4-fluorophenyl)-5-(2-methyl-5-(1-(pyridin-2-yl)cyclopropylcarbamoyl)phenyl)furo[2,3-b]pyridine-3-carboxylic acid. The residue was diluted with DMF (1.2 mL) and treated with HATU (56 mg, 0.15 mmol), methanamine (308 μL, 0.617 mmol, 2M in THF), followed by Hunig's Base (65 μL, 0.37 mmol). The reaction was allowed to stir for 1 hour. The mixture was diluted with EtOAc and washed with sat NaHCO3, and sat NaCl. The organic phase was dried over Na2SO4, filtered and concentrated and was purified on silica gel (Biotage, EtOAc/hexanes gradient, fraction collection at λ=254 nm) to give 2-(4-fluorophenyl)-N-methyl-5-(2-methyl-5-(1-(pyridin-2-yl)cyclopropylcarbamoyl)phenyl)furo[2,3-b]pyridine-3-carboxamide (19 mg, 0.035 mmol, 29% yield) consistent by LCMS and NMR. 1H NMR (400 MHz, DMSO-d6) δ ppm 9.27 (1H, s), 8.48-8.54 (1H, m), 8.46 (1H, d, J=4.02 Hz), 8.42 (1H, d, J=2.01 Hz), 8.13 (1H, d, J=2.26 Hz), 8.05-8.11 (2H, m), 7.90-7.95 (2H, m), 7.68 (1H, td, J=7.78, 1.76 Hz), 7.51 (1H, d, J=8.78 Hz), 7.41-7.47 (2H, m), 7.36 (1H, d, J=8.03 Hz), 7.16 (1H, dd, J=7.03, 5.27 Hz), 2.85 (3H, d, J=4.52 Hz), 2.35 (3H, s), 1.53-1.59 (2H, 1.25-1.30 (2H, m). LC-MS retention time: 1.34 min; m/z (MH+): 521. LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode. Additional HPLC method: Solvent A=5% MeOH/95% H2O/10 mM ammonium bicarbonate, Solvent B=95% MeOH/5% H2O/10 mM ammonium bicarbonate, Start % B=10, Final % B=100, Gradient time=15 min, Stop time=18 min, Flow Rate=1 ml/min. Column: Phenomenex Gemini C1 C-18, 4.6×150 mm, 3 mm, $R_t$=13.32 min, purity=97%; Column: Waters Xbridge Phenyl column 4.6×150 mm, 3.5 mm, $R_t$=13.90 min, purity=97%.

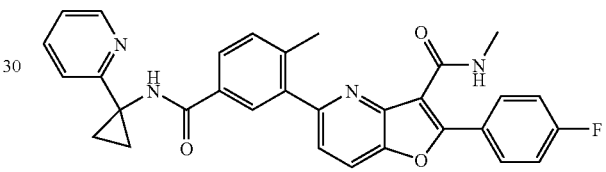

2-(4-fluorophenyl)-N-methyl-5-(2-methyl-5-(1-(pyridin-2-yl)cyclopropylcarbamoyl)phenyl)furo[3,2-b]pyridine-3-carboxamide. Sodium 2'-(dicyclohexylphosphino)-2,6-dimethoxybiphenyl-3-sulfonate (18 mg, 0.034 mmol), PdOAc2 (3.9 mg, 0.017 mmol), Cs2CO3 (168 mg, 0.516 mmol), 4-methyl-3-(4,4,5,5-tetramethyl-1,3,2-dioxaborolan-2-yl)benzoic acid (68 mg, 0.26 mmol) was added to a stirring solution of 5-bromo-2-(4-fluorophenyl)-N-methylfuro[3,2-b]pyridine-3-carboxamide (60 mg, 0.17 mmol) in DMF (3.1 mL) and Water (310 μL). It was degassed and heated to 60° C. and allowed to stir for 1 hour. The mixture was diluted with ethyl acetate and washed with 1M HCl, and sat NaCl. The organic phase was dried over Na2SO4, filtered and concentrated to give 3-(2-(4-fluorophenyl)-3-(methylcarbamoyl)furo[3,2-b]pyridin-5-yl)-4-methylbenzoic acid crude. The residue was diluted with DMF (3.1 mL) and treated with HATU (98 mg, 0.26 mmol), 1-(pyridin-2-yl)cyclopropanamine dihydrochloride (54 mg, 0.260 mmol), followed by DIEA (150 μL, 0.859 mmol) at room temperature. The reaction was allowed to stir for 1 hr. The mixture was diluted with EtOAc and washed with 1M NaOH, and sat NaCl. The organic phase was dried over Na2SO4, filtered, concentrated and was purified on silica gel (Biotage, EtOAc/hexanes gradient, fraction collection at λ=254 nm) to give 2-(4-fluorophenyl)-N-methyl-5-(2-methyl-5-(1-(pyridin-2-yl)cyclopropylcarbamoyl)phenyl)furo[3,2-b]pyridine-3-carboxamide (27 mg, 0.049 mmol, 29% yield) consistent by LCMS and NMR. 1H NMR (400 MHz, DMSO-d6) δ ppm 9.29 (1H, s), 8.98-9.07 (1H, m), 8.45 (1H, d, J=4.02 Hz), 8.25-8.34 (3H, m), 8.10 (1H, d, J=1.76 Hz), 7.94 (1H, dd, J=8.03, 1.76 Hz), 7.73 (1H, d, J=8.53 Hz), 7.67 (1H, td, J=7.65, 1.76 Hz), 7.50 (1H, d, J=7.78 Hz), 7.39-7.46 (2H, m), 7.35 (1H, d, J=8.03 Hz), 7.14 (1H, dd, J=6.53, 4.77 Hz), 2.91 (3H, d, J=4.77 Hz), 2.45 (3H, s), 1.52-1.59 (2H, m), 1.23-1.31 (2H, m). LC-MS retention time: 1.46 min; m/z (MH+): 521. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode. Additional HPLC method: Solvent A=5% MeOH/95% H2O/10 mM ammonium bicarbonate, Solvent B=95% MeOH/5% H2O/10 mM ammonium bicarbonate, Start % B=10, Final % B=100, Gradient time=15 min, Stop time=18 min, Flow Rate=1 ml/min. Column: Phenomenex Gemini C1 C-18, 4.6× 150 mm, 3 mm, $R_t$=13.35 min, purity=98%; Column: Waters Xbridge Phenyl column 4.6×150 mm, 3.5 mm, $R_t$=12.68 min, purity=98%.

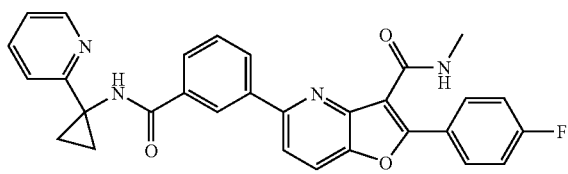

2-(4-fluorophenyl)-N-methyl-5-(3-(1-(pyridin-2-yl)cyclopropylcarbamoyl)phenyl)furo[3,2-b]pyridine-3-carboxamide. Sodium 2'-(dicyclohexylphosphino)-2,6-dimethoxybiphenyl-3-sulfonate (8.8 mg, 0.017 mmol), PdOAc2 (1.9 mg, 8.6 μmol), Cs2CO3 (84 mg, 0.26 mmol), 3-boronobenzoic acid (21 mg, 0.13 mmol) was added to a stirring solution of 5-bromo-2-(4-fluorophenyl)-N-methylfuro[3,2-b]pyridine-3-carboxamide (30 mg, 0.086 mmol) in DMF (1.6 mL) and Water (160 μL). It was degassed and heated to 60° C. and allowed to stir for 1 hour. The mixture was diluted with ethyl acetate and washed with 1M HCl, and sat NaCl. The organic phase was dried over Na2SO4, filtered and concentrated to give 3-(2-(4-fluorophenyl)-3-(methylcarbamoyl)furo[3,2-b]pyridin-5-yl)benzoic acid. The residue was diluted with DMF (1.6 mL) and treated with HATU (49 mg, 0.13 mmol), 1-(pyridin-2-yl)cyclopropanamine dihydrochloride (27 mg, 0.13 mmol), followed by DIEA (75 μL, 0.43 mmol) at room temperature. The reaction was allowed to stir for 1 hr. The mixture was diluted with EtOAc and washed with 1M NaOH, and sat NaCl. The organic phase was dried over Na2SO4, filtered and concentrated and was purified by preparative reverse phase HPLC on a C18 column using a suitably buffered H2O/CH3CN gradient, and concentrated to give the expected product 2-(4-fluorophenyl)-N-methyl-5-(3-(1-(pyridin-2-yl)cyclopropylcarbamoyl)phenyl)furo[3,2-b]pyridine-3-carboxamide (12 mg, 0.023 mmol, 27% yield) consistent by LCMS and NMR. 1H NMR (400 MHz, DMSO-$d_6$) δ ppm 9.44 (1H, s), 9.09-9.18 (1H, m), 8.73 (1H, s), 8.46 (1H, d), 8.39 (1H, d), 8.27-8.35 (3H, m), 8.19 (1H, d, J=8.78 Hz), 8.01 (1H, d), 7.65-7.74 (2H, m), 7.39-7.46 (3H, m), 7.13-7.20 (1H, m), 2.98 (3H, d, J=4.77 Hz). LC-MS retention time: 1.50 min; m/z (MH+): 507. LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 mM where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. Additional HPLC method: Solvent A=5% MeOH/95% H2O/10 mM ammonium bicarbonate, Solvent B=95% MeOH/5% H2O/10 mM ammonium bicarbonate, Start % B=10, Final % B=100, Gradient time=15 min, Stop time=18 min, Flow Rate=1 ml/min. Column: Phenomenex Gemini C1 C-18, 4.6×150 mm, 3 mm, $R_t$=25.18 min, purity=99%; Column: Waters) (bridge Phenyl column 4.6× 150 mm, 3.5 mm, $R_t$=25.85 mM, purity=99%.

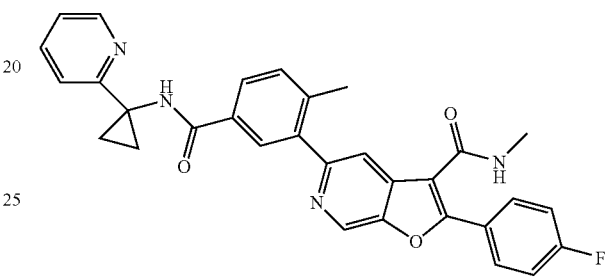

2-(4-fluorophenyl)-N-methyl-5-(2-methyl-5-(1-(pyridin-2-yl)cyclopropylcarbamoyl)phenyl)furo[2,3-c]pyridine-3-carboxamide. Sodium 2'-(dicyclohexylphosphino)-2,6-dimethoxybiphenyl-3-sulfonate (9.8 mg, 0.019 mmol), PdOAc2 (2.2 mg, 9.6 μmol), Cs2CO3 (93 mg, 0.29 mmol), 4-methyl-3-(4,4,5,5-tetramethyl-1,3,2-dioxaborolan-2-yl)benzoic acid (38 mg, 0.14 mmol) was added to a stirring solution of 2-(4-fluorophenyl)-3-(methylcarbamoyl)furo[2,3-c]pyridin-5-yl trifluoromethanesulfonate (40 mg, 0.096 mmol) in DMF (1.7 mL) and Water (170 μl). It was degassed and heated to 60° C. and allowed to stir for 1 hour. The mixture was diluted with ethyl acetate and washed with 1M HCl, and sat NaCl. The organic phase was dried over Na2SO4, filtered and concentrated to give 3-(2-(4-fluorophenyl)-3-(methylcarbamoyl)furo[2,3-c]pyridin-5-yl)-4-methylbenzoic acid. The residue was diluted with DMF (1.7 mL) and treated with HAM (55 mg, 0.15 mmol), 1-(pyridin-2-yl)cyclopropanamine dihydrochloride (30 mg, 0.15 mmol), followed by DIEA (84 μL, 0.48 mmol) at room temperature. The reaction was allowed to stir for 1 hr. The mixture was diluted with EtOAc and washed with 1M NaOH, and sat NaCl. The organic phase was dried over Na2SO4, filtered, concentrated and was purified on silica gel (Biotage, EtOAc/hexanes gradient, fraction collection at λ=254 nm) to give 2-(4-fluorophenyl)-N-methyl-5-(2-methyl-5-(1-(pyridin-2-yl)cyclopropylcarbamoyl)phenyl)furo[2,3-c]pyridine-3-carboxamide (5.4 mg, 9.85 μmol, 10% yield) consistent by LCMS and NMR. $^1$H NMR (500 MHz, MeOD) δ ppm 7.68-7.73 (1H, m), 7.10-7.18 (1H, m), 6.75-6.82 (2H, m), 6.68-6.72 (1H, m), 6.61-6.66 (1H, m), 6.54-6.59 (1H, m), 6.38-6.46 (1H, m), 6.15-6.24 (2H, m), 6.02-6.09 (2H, m), 5.85-5.92 (1H, m), 1.69 (3H, s), 1.12 (3H, s), 0.38-0.43 (2H, m), 0.07-0.13 (2H, m). LC-MS retention time: 0.913 min; m/z (MID): 521. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode. Additional HPLC method: Solvent A=5% CH3CN/95% H2O/0.1% TFA, Solvent B=95% CH3CN/5% H2O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, $R_t$=5.61 min, purity=95%; Column: Waters Xbridge Phenyl column 4.6×150 mm, 3.5 mm, $R_t$=6.00 min, purity=96%. Additional HPLC method: Solvent A=5% MeOH/95% H2O/10 mM ammonium bicarbonate, Solvent B=95% MeOH/5% H2O/10 mM ammonium bicarbonate, Start % B=10, Final % B=100, Gradient time=15 min, Stop time=18 min, Flow Rate=1 ml/min. Column: Phenomenex Gemini C1 C-18, 4.6×150 mm, 3 mm, $R_t$=9.41 min, purity=97%; Column: Waters Xbridge Phenyl column 4.6×150 mm, 3.5 mm, $R_t$=9.38 min, purity=100%.

Hz), 1.58-1.69 (2H, m), 1.36-1.45 (2H, m). LC-MS retention time: 1.26 min; m/z (MH+): 507. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode. Additional HPLC method: Solvent A=5% CH3CN/95% H2O/0.1% TFA, Solvent B=95% CH3CN/5% H2O/0.1% TFA, Start % B=10, Final % B=100, Gradient time=15 min, Stop time=18 min, Flow Rate=1 ml/min. Column: Waters Sunfire C-18, 4.6×150 mm, 3.5 mm, $R_t$=13.20 min, purity=100%; Column: Waters Xbridge Phenyl column 4.6×150 mm, 3.5 mm, $R_t$=12.12 min, purity=100%.

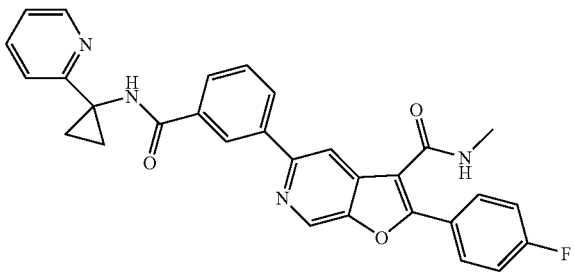

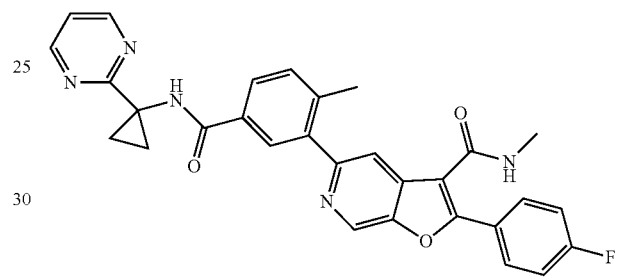

2-(4-fluorophenyl)-N-methyl-5-(3-(1-(pyridin-2-yl)cyclopropylcarbamoyl)phenyl)furo[2,3-c]pyridine-3-carboxamide. Sodium 2'-(dicyclohexylphosphino)-2,6-dimethoxybiphenyl-3-sulfonate (9.8 mg, 0.019 mmol), PdOAc2 (2.2 mg, 9.6 μmol), Cs2CO3 (93 mg, 0.29 mmol), 3-boronobenzoic acid (24 mg, 0.14 mmol) was added to a stirring solution of 2-(4-fluorophenyl)-3-(methylcarbamoyl)furo[2,3-c]pyridin-5-yl trifluoromethanesulfonate (40 mg, 0.096 mmol) in DMF (1.7 mL) and Water (170 μL). It was degassed and heated to 60° C. and allowed to stir for 1 hour. The mixture was diluted with ethyl acetate and washed with 1M HCl, and sat NaCl. The organic phase was dried over Na2SO4, filtered and concentrated to give 3-(2-(4-fluorophenyl)-3-(methylcarbamoyl)furo[2,3-c]pyridin-5-yl)benzoic acid. The residue was diluted with DMF (1.7 mL) and treated with HATU (55 mg, 0.15 mmol), 1-(pyridin-2-yl)cyclopropanamine dihydrochloride (24 mg, 0.12 mmol), followed by DIEA (84 μL, 0.48 mmol) at room temperature. The reaction was allowed to stir for 1 hr. The mixture was diluted with EtOAc and washed with 1M NaOH, and sat NaCl. The organic phase was dried over Na2SO4, filtered and concentrated and was purified by preparative reverse phase HPLC on a C18 column using a suitably buffered H2O/MeOH gradient, and concentrated to give 2-(4-fluorophenyl)-N-methyl-5-(3-(1-(pyridin-2-yl)cyclopropylcarbamoyl)phenyl)furo[2,3-c]pyridine-3-carboxamide (14 mg, 0.028 mmol, 29% yield) consistent by LCMS and NMR. 1H NMR (400 MHz, DMSO-d6) δ ppm 9.45 (1H, s), 9.14 (1H, s), 8.67 (1H, s), 8.55-8.61 (1H, m), 8.51 (1H, d, J=5.02 Hz), 8.34 (1H, d, J=7.78 Hz), 8.27 (1H, s), 8.07 (2H, dd, J=8.78, 5.52 Hz), 7.99 (1H, d, J=7.78 Hz), 7.80-7.91 (1H, m), 7.64 (1H, t, J=7.78 Hz), 7.49 (1H, d, J=8.03 Hz), 7.45 (2H, t, J=8.91 Hz), 7.25-7.34 (1H, m), 2.89 (3H, d, J=4.52

2-(4-fluorophenyl)-N-methyl-5-(2-methyl-5-(1-(pyrimidin-2-yl)cyclopropylcarbamoyl)phenyl)furo[2,3-b]pyridine-3-carboxamide. Step 1: Preparation of 5-bromo-2-(4-fluorophenyl)furo[2,3-b]pyridine. 5-bromo-3-iodopyridin-2-ol (6.7 g, 22 mmol) (Heterocycles. 57, 1, pp 55), 1-ethynyl-4-fluorobenzene (4.03 g, 33.5 mmol), copper(I) iodide (0.255 g, 1.34 mmol), trans-dichlorobis(triphenylphosphine)palladium (II) (0.784 g, 1.12 mmol) were combined and evacuated/backfilled with N2 (3×) then diluted with triethylamine (223 mL) and heated to 90° C. for 2 hours. The solvent was evaporated and the residue was dissolved in EtOAc. The organic phase was washed with water (50 mL), brine, dried over Na2SO4, filtered, and concentrated. Trituration with Et2O afforded the expected product 5-bromo-2-(4-fluorophenyl)furo[2,3-b]pyridine (4.2 g, 14.4 mmol, 64% yield). 1H NMR (400 MHz, DMSO-d6) δ ppm 8.35-8.42 (2H, m), 8.03 (2H, dd, J=8.78, 5.27 Hz), 7.46 (1H, s), 7.39 (2H, t, J=8.91 Hz). LC-MS retention time: 2.36 min; m/z (MH+): 292, 294. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 2: Preparation of methyl 3-(2-(4-fluorophenyl)furo[2,3-b]pyridin-5-yl)-4-methylbenzoate. Cesium carbonate (379 mg, 1.164 mmol) was added to a stirring solution of 5-bromo-2-(4-fluorophenyl)furo[2,3-b]pyridine (200 mg, 0.685 mmol), 4-methyl-3-(4,4,5,5-tetramethyl-1,3,2-dioxaborolan-2-yl)benzoic acid (269 mg, 1.027 mmol), Pd(Ph3P)4 (158 mg, 0.137 mmol) in 1,4-dioxane (5.7 mL) and Water (1.1 mL). It was heated to 90° C. overnight. The mixture was diluted with EtOAc and washed with 1M HCl, and sat NaCl. The organic phase was dried over Na2SO4, filtered and concentrated and diluted with MeOH/DCM and treated with TMS-diazomethane (685 µL, 1.37 mmol, 2M in ether). The mixture was allowed to stir for 1 hour. The reaction was concentrated and was purified on silica gel (Biotage, EtOAc/hexanes gradient, fraction collection at $\lambda$=254 nm) to give the expected product methyl 3-(2-(4-fluorophenyl)furo[2,3-b]pyridin-5-yl)-4-methylbenzoate (247 mg, 0.685 mmol, quant) by LCMS and NMR. 1H NMR (400 MHz, DMSO-d6) $\delta$ ppm 8.28 (1H, d, J=2.26 Hz), 8.16 (1H, d, J=2.01 Hz), 8.01-8.10 (2H, m), 7.93 (1H, dd, J=7.91, 1.88 Hz), 7.85 (1H, d, J=1.76 Hz), 7.49-7.57 (2H, m), 736-7.44 (2H, m), 3.86 (3H, s), 2.34 (3H, s). LC-MS retention time: 2.55 min; m/z (MH+): 362. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 3: Preparation of methyl 3-(3-bromo-2-(4-fluorophenyl)furo[2,3-b]pyridin-5-yl)-4-methylbenzoate. The reaction flask was wrapped in aluminum foil. NBS (175 mg, 0.983 mmol) was added to a stirring solution of methyl 3-(2-(4-fluorophenyl)furo[2,3-b]pyridin-5-yl)-4-methylbenzoate (289 mg, 0.800 mmol) in dichloroethane (8 mL) at room temperature. It was allowed to stir overnight. The mixture was diluted with EtOAc and quenched with 10% sodium metabisulfate and washed with sat NaCl. The organic phase was dried over Na2SO4, filtered and concentrated was purified on silica gel (Biotage, EtOAc/hexanes gradient, fraction collection at $\lambda$=254 nm) the expected product consistent by LCMS and NMR. $^1$H NMR (400 MHz, DMSO-d6) $\delta$ ppm 8.41 (1H, d, J=2.01 Hz), 8.16-8.26 (2H, m), 8.06 (1H, d, J=2.26 Hz), 7.95 (1H, dd, J=8.03, 1.76 Hz), 7.87 (1H, d), 7.45-7.57 (3H, m), 3.86 (3H, s), 2.34 (3H, s). LC-MS retention time: 2.85 min; m/z (MH+): 440, 442. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 4: Preparation of 3-(3-bromo-2-(4-fluorophenyl)furo[2,3-b]pyridin-5-yl)-4-methylbenzoic acid. NaOH (3.3 mL, 3.3 mmol, 1M aq) was added to a stirring solution of methyl 3-(3-bromo-2-(4-fluorophenyl)furo[2,3-b]pyridin-5-yl)-4-methylbenzoate (294 mg, 0.668 mmol) in MeOH (7 mL) and THF (7 mL) at 60° C. It was allowed to stir for 1 hr. The mixture was diluted with EtOAc and washed with 1M HCl, and sat NaCl. The organic phase was dried over Na2SO4, filtered and concentrated to give the expected product 3-(3-bromo-2-(4-fluorophenyl)furo[2,3-b]pyridin-5-yl)-4-methylbenzoic acid (275 mg, 0.645 mmol, 97% yield) consistent by LCMS and NMR. 1H NMR (400 MHz, DMSO-d6) $\delta$ ppm 12.90 (1H, br. s.), 8.40 (1H, d, J=2.26 Hz), 8.18-8.25 (2H, m), 8.05 (1H, d, J=2.26 Hz), 7.92 (1H, dd, J=7.78, 1.76 Hz), 7.85 (1H, d, J=1.76 Hz), 7.43-7.54 (3H, m), 2.35 (3H, s). LC-MS retention time: 2.42 min; m/z (MH+): 426, 428. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 5: Preparation of tert-butyl 3-(3-bromo-2-(4-fluorophenyl)furo[2,3-b]pyridin-5-yl)-4-methylbenzoate. N,N-Dimethylformamide di-tert-butyl acetal (653 µL, 2.72 mmol) was added to a stirring solution of 3-(3-bromo-2-(4-fluorophenyl)furo[2,3-b]pyridin-5-yl)-4-methylbenzoic acid (290 mg, 0.680 mmol) in toluene (6.8 mL) at 80° C. The reaction was allowed to stir for 1 hour. The mixture was concentrated to dryness and was purified on silica gel (Biotage, EtOAc/hexanes gradient, fraction collection at $\lambda$=254 nm) to give the expected product, tert-butyl 3-(3-bromo-2-(4-fluorophenyl)furo[2,3-b]pyridin-5-yl)-4-methylbenzoate (231 mg, 0.479 mmol, 70% yield) consistent by LCMS. LC-MS retention time: 2.34 mM; m/z (MH+): 482. LC data was recorded on a Shimadzu LC-10AS liquid chromatograph equipped with a Waters XBridge 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

Step 6: Preparation of methyl 5-(5-(tert-butoxycarbonyl)-2-methylphenyl)-2-(4-fluorophenyl)furo[2,3-b]pyridine-3-carboxylate. 1,3-bis(diphenylphosphino)propane (119 mg, 0.287 mmol) was added to a stirring solution of palladium(II) acetate (32 mg, 0.144 mmol) and tert-butyl 3-(3-bromo-2-(4-fluorophenyl)furo[2,3-b]pyridin-5-yl)-4-methylbenzoate (231 mg, 0.479 mmol) in MeOH (1.6 mL) and DMSO (3 mL) at 80° C. in a PARR bomb which was then charged with 300 psi CO (g) and allowed to stir overnight. The mixture was diluted with EtOAc and filtered through a pad of celite. The filtrate was washed with sat. aq. NaHCO3, and brine. The organic phase was dried over Na2SO4, filtered and concentrated to give the expected product methyl 5-(5-(tert-butoxycarbonyl)-2-methylphenyl)-2-(4-fluorophenyl)furo[2,3-b]pyridine-3-carboxylate (211 mg, 0.457 mmol, 95% yield) crude by LCMS which was used directly in the next step. LC-MS retention time: 2.32 min; m/z (MH+): 462. LC data was recorded on a Shimadzu LC-10AS liquid chromatograph equipped with a Waters XBridge 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 mM, a hold time of 1 mM, and an analysis time of 4 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode.

Step 7: Preparation of 5-(5-(tert-butoxycarbonyl)-2-methylphenyl)-2-(4-fluorophenyl)furo[2,3-b]pyridine-3-carboxylic acid. NaOH (1.4 mL, 1.37 mmol) was added to a stirring solution of methyl 5-(5-(tert-butoxycarbonyl)-2-methylphenyl)-2-(4-fluorophenyl)furo[2,3-b]pyridine-3-carboxylate (211 mg, 0.457 mmol) in MeOH (2.3 mL) and THF (2.3 mL) at 60° C. It was allowed to stir for 4 hours. The mixture was diluted with EtOAc and washed with 1M HCl, and sat NaCl. The organic phase was dried over Na2SO4, filtered and concentrated to give the expected product 5-(5-(tert-butoxycarbonyl)-2-methylphenyl)-2-(4-fluorophenyl)furo[2,3-b]pyridine-3-carboxylic acid (205 mg, 0.457 mmol, quant.) consistent by LCMS crude which was used directly in the next step. LC-MS retention time: 1.88 min; m/z (MH+): 448. LC data was recorded on a Shimadzu LC-10AS liquid chromatograph equipped with a Waters XBridge 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode.

Step 8: Preparation of tert-butyl 3-(2-(4-fluorophenyl)-3-(methylcarbamoyl)furo[2,3-b]pyridin-5-yl)-4-methylbenzoate. HATU (209 mg, 0.550 mmol) was added to a stirring solution of methanamine (1.2 mL, 2.4 mmol, 2M in THF), DIEA (240 µL, 1.37 mmol) and 5-(5-(tert-butoxycarbonyl)-2-methylphenyl)-2-(4-fluorophenyl)furo[2,3-b]pyridine-3-carboxylic acid (205 mg, 0.458 mmol) in DMF (4.5 mL) at rt. It was allowed to stir for 1 hour. The mixture was diluted with EtOAc and washed with sat NaCl. The organic phase was dried over Na2SO4, filtered and concentrated and was purified on silica gel (Biotage, EtOAc/hexanes gradient, fraction collection at λ=254 nm) to give the expected product tert-butyl 3-(2-(4-fluorophenyl)-3-(methylcarbamoyl)furo[2,3-b]pyridin-5-yl)-4-methylbenzoate (190 mg, 0.413 mmol, 90% yield) consistent by LCMS and NMR. 1H NMR (400 MHz, MeOD) δ ppm 8.28 (1H, d, J=2.26 Hz), 8.08 (1H, d, J=2.01 Hz), 7.99-8.06 (2H, m), 7.92 (1H, dd, J=8.03, 1.76 Hz), 7.86 (1H, d, J=1.51 Hz), 7.45 (1H, d, J=8.03 Hz), 7.30 (2H, t, J=8.78 Hz), 2.95 (3H, s), 2.34 (3H, s), 1.60 (9H, s). LC-MS retention time: 2.70 min; m/z (MH+): 461. LC data was recorded on a Shimadzu LC-10AS liquid chromatograph equipped with a Waters SunFire 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 8: Preparation of the titled compound: 2-(4-fluorophenyl)-N-methyl-5-(2-methyl-5-(1-(pyrimidin-2-yl)cyclopropylcarbamoyl)phenyl)furo[2,3-b]pyridine-3-carboxamide. TFA (544 µL, 7.06 mmol) was added to a stirring solution of tert-butyl 3-(2-(4-fluorophenyl)-3-(methylcarbamoyl)furo[2,3-b]pyridin-5-yl)-4-methylbenzoate (65 mg, 0.141 mmol) in DCE (1.4 mL) at rt. It was allowed to stir for 2 hours then concentrated. The white solid was taken up in DMF (1.5 mL) and treated with DIEA (123 µL, 0.706 mmol), 1-(pyrimidin-2-yl)cyclopropanamine hydrochloride (29.1 mg, 0.169 mmol) followed by HATU (81 mg, 0.212 mmol) at rt. The reaction was allowed to stir for 1 hour and then was purified by preparative reverse phase HPLC on a C18 column using a TFA buffered H2O/MeOH gradient, and concentrated to give the expected product 2-(4-fluorophenyl)-N-methyl-5-(2-methyl-5-(1-(pyrimidin-2-yl)cyclopropylcarbamoyl)phenyl)furo[2,3-b]pyridine-3-carboxamide (45 mg, 0.086 mmol, 61.1% yield) consistent by LCMS and NMR. 1H NMR (300 MHz, DMSO-d6) δ ppm 9.19 (1H, s), 8.66 (2H, d, J=4.76 Hz), 8.45-8.57 (1H, m), 8.40 (1H, d, J=1.83 Hz), 8.10 (1H, d, J=1.83 Hz), 8.00-8.08 (2H, m), 7.85-7.94 (2H, m), 7.35-7.50 (3H, m), 7.26 (1H, t, J=4.76 Hz), 2.83 (3H, d, J=4.39 Hz), 2.31 (3H, s), 1.55-1.67 (2H, m), 1.27-1.39 (2H, m). LC-MS retention time: 1.75 min; m/z (MH+): 522. LC data was recorded on a Shimadzu LC-10AS liquid chromatograph equipped with a Waters XBridge 5u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% MeOH/95% H2O/10 mM ammonium acetate and solvent B was 5% H2O/95% MeOH/10 mM ammonium acetate. MS data was determined using a Micromass Platform for LC in electrospray mode.

6-(N-ethylmethylsulfonamido)-2-(4-fluorophenyl)-N-methyl-5-(2-methyl-5-(1-(pyridin-2-yl)cyclopropylcarbamoyl)phenyl)pyrazolo[1,5-a]pyridine-3-carboxamide. 6-(N-ethylmethylsulfonamido)-2-(4-fluorophenyl)-3-(methylcarbamoyl)pyrazolo[1,5-a]pyridin-5-yl trifluoromethanesulfonate (0.07 g, 0.13 mmol, 1 eq), 4-methyl-N-(1-(pyridin-2-yl)cyclopropyl)-3-(4,4,5,5-tetramethyl-1,3,2-dioxaborolan-2-yl)benzamide (0.054 g, 0.14 mmol, 1.1 eq), tetrakistriphenylphosphine palladium (0.0045 g, 0.0039 mmol, 0.03 eq) and cesium carbonate (0.12 g, 0.39 mmol, 3 eq) were dissolved in 1,4-dioxane (10 ml) and water (2 ml). Nitrogen gas was passed through the solution and the reaction was heated at 90° C. for 14 h. The solution was filtered through celite. Water was added to the filtrate which was then extracted with ethyl acetate. The organic layer was concentrated and the residue obtained purified by Preparative HPLC.

Yield: 22 mg (26%). 1HNMR (400 MHz, CD3OD): δ 1.12 (broad s, 3H), 1.35 (s, 2H), 1.66 (s, 2H), 2.34 (s, 3H), 2.85 (s, 3H), 3.00-3.32 (br, 3H), 3.51 (br, 2H), 7.13 (m, 1H), 7.24 (m, 2H), 7.46 (m, 2H), 7.68 (m, 1H), 7.97 (m, 4H), 8.0 (s, 1H), 8.41-8.42 (d, J=4 Hz, 1H), 8.92 (s, 1H). LCMS: (ES+) m/z=641.2 (M+H) Method: Column-Ascentis Express C18 (5×2.1 mm-2.7 µm); Mphase A: 2% MeCN-98% H2O-10 mM NH4COOH; Mphase B: 98% MeCN—2% H2O-10 mM NH4COOH Flow: 1 mL/Min; RT min: 1.796; Wavelength: 220 nm. HPLC Method: SUNFIRE C18 (4.6×150) mm, 3.5 micron; Buffer: 0.05% TFA in water pH 2.5; Mobile Phase A: Buffer:MeCN (95:5); Mobile Phase B: MeCN:Buffer (95:5); FLOW: 1 ml/min; Wavelength: 254 nm, RT min: 8.675; Purity: 96.6%.

6-(N-ethylmethylsulfonamido)-2-(4-fluorophenyl)-N-methyl-5-(3-(1-(pyridin-2-yl)cyclopropylcarbamoyl)phenyl)pyrazolo[1,5-a]pyridine-3-carboxamide. 6-(N-ethylmethylsulfonamido)-2-(4-fluorophenyl)-3-(methylcarbamoyl)pyrazolo[1,5-a]pyridin-5-yl trifluoromethanesulfonate (0.1 g, 0.17 mmol, 1 eq), N-(1-(pyridin-2-yl)cyclopropyl)-3-(4,4,5,5-tetramethyl-1,3,2-dioxaborolan-2-yl)benzamide (0.0.65 g, 0.18 mmol, 1.1 eq), tetrakistriphenylphosphine palladium (0.0058 g, 0.0051 mmol, 0.03 eq) and cesium carbonate (0.165 g, 0.51 mmol, 3 eq) were dissolved in 1,4-dioxane (10 ml) and water (2 ml) and the reaction was heated at 90° C. for 14 hours. The solution was filtered through ciliate. Water was added to the filtrate which was then extracted with ethyl acetate. The organic layer was concentrated and the residue obtained purified by Preparative HPLC. Yield: 22 mg (26%) $^1$HNMR (400 MHz, CD$_3$OD): δ 1.05 (t, J=8 Hz, 3H), 1.65-1.66 (m, 2H), 1.78-1.82 (m, 2H), 2.89 (s, 3H), 3.20 (s, 3H), 3.62 (br s, 2H), 7.28-7.30 (t, J=7.76 Hz, 2H), 7.57 (br s, 1H), 7.67 (t, J=7.72 Hz, 1H), 7.75 (d, J=8.20 Hz, 1H), 7.86-7.88 (m, 3H), 7.96 (s, 1H), 8.02 (d, J=2.09 Hz, 1H), 8.18 (br, 1H), 8.23 (s, 1H), 8.55 (d, J=5.32 Hz, 1H), 8.98 (s, 1H). LCMS: (ES+) m/z=627.2 (M+H); Method: Column-Ascentis Express C18 (5×2.1 mm-2.7 μm); Mphase A: 2% MeCN-98% H$_2$O-10 mM NH$_4$COOH; Mphase B: 98% MeCN—2% H$_2$O-10 mM NH$_4$COOH; Flow: 1 mL/Min; RT min: 1.768;

3-iodo-4-methylbenzoic acid. Methyl-3-Iodo-4-methylbenzoate (3 g, 109 mmol, 1 eq) dissolved in MeOH (30 ml) was added sodium hydroxide (1.3 g, 327 mmol, 3 eq) followed by the addition of water (15 ml). The above solution was stirred at room temperature for 14 h. The solution was concentrated under vacuum, and then added water. The pH of the reaction was bought to 3 using Conc. HCl. The solid obtained was filtered and dried under vacuum. Yield: 2.7 g (96%). $^1$HNMR (400 MHz, DMSO-d6): δ 2.44 (s, 3H), 7.45 (d, J=8.00 Hz, 1H), 7.85 (d, J=3.18 Hz, 1H), 8.31 (s, 1H).

3-iodo-4-methyl-N-(1-(pyridin-2-yl)cyclopropyl)benzamide. 3-Iodo-4-methylbenzoic acid (2.5 g, 9.5 mmol, 1 eq), 1-(pyridin-2-yl)cyclopropanamine (1.41 g, 10.4 mmol, 1.1 eq), EDCI.HCl (2.1 g, 11.4 mmol, 1.2 eq), HOBT (1.5 g, 11.4 mmol, 1.2 eq) and DIPEA (4.9 ml, 28.62 mmol, 3 eq) were dissolved in DCM and the above solution was stirred at room temperature for 18 h. Water was added and product was extracted with DCM. The organic layer was concentrated and the crude product crystallized using dichloromethane and hexane. Yield: 2.3 g (55%). $^1$HNMR (400 MHz, DMSO-d$_6$): δ 1.26 (m, 2H), 1.53 (m, 2H), 2.43 (s, 3H), 7.13 (m, 1H), 7.29 (d, J=8.00 Hz, 1H), 7.44 (d, 1H), 7.67 (t, J=3.46 Hz, 1H), 7.87 (d, J=3.24 Hz, 1H), 8.38 (s, 1H), 8.44 (d, J=1.10 Hz, 1H), 9.29 (s, 1H).

4-methyl-N-(1-(pyridin-2-yl)cyclopropyl)-3-(4,4,5,5-tetramethyl-1,3,2-dioxaborolan-2-yl)benzamide. 3-Iodo-4-methyl-N-(1-(pyridin-2-yl)cyclopropyl)benzamide (2.2 g, 5.8 mmol, 1 eq), Bispinnacolatodiboron (2.21 g, 8.7 mmol, 1.5 eq), Pd(dppf)Cl$_2$ (0.18 g, 0.23 mmol, 0.04 eq) and Potassium acetate (1.7 g, 17.4 mmol, 3 eq) were dissolved in DMF and nitrogen was purged for 15 minutes. The above solution was stirred at 90° C. for 15 h. The solution was filtered through celiete, and water was added to the filtrate which was extracted with ethylacetate. The crude product was purified by combiflash chromatography to obtain an off white solid. Yield: 1.5 g (68%). $^1$HNMR (400 MHz, DMSO-d$_6$): δ 1.25 (s, 2H), 1.32 (s, 12H), 1.54 (s, 2H), 2.53 (s, 3H), 7.13 (m, 1H), 7.29 (m, 2H), 7.69 (t, J=7.48 Hz, 1H), 7.92 (m, 1H), 8.18 (s, 1H), 8.45 (d, 1H), 9.29 (s, 1H). LCMS: (ES+) m/z=379 (M+H). Method: Column-Chromolith SpeedROD C18 (4.6× 30); Mphase A: 10% MeOH-90% H$_2$O-0.1% TFA; Mphase B: 90% MeOH-10% H$_2$O-0.1% TFA; Flow: 5 mL/Min; RT min: 1.658; Wavelength: 220 nm.

3-iodo-N-(1-(pyridin-2-yl)cyclopropyl)benzamide. 3-Iodobenzoic acid (2.7 g, 11.1 mmol, 1 eq), 1-(pyridin-2-yl) cyclopropanamine (1.5 g, 11.1 mmol, 1 eq), EDCI.HCl (3.2 g, 16.7 mmol, 1.5 eq), HOBT (2.2 g, 16.7 mmol, 1.5 eq) and DIPEA (6 ml, 33.5 mmol, 3 eq) were dissolved in DCM and the resulting mixture was stirred at room temperature for 18 hours. Water was added to the mixture and the product was extracted with DCM. The organic layer was concentrated and the product crystallized using dichloromethane and hexane. Yield: 2.3 g (57%). $^1$HNMR (400 MHz, DMSO-d$_6$): δ 1.26 (m, 2H), 1.54 (m, 2H), 7.13 (t, J=4.04 Hz, 1H), 7.29 (m, 2H), 7.69 (t, J=8.06 Hz, 1H), 7.92 (d, J=3.05 Hz, 2H), 8.29 (s, 1H), 8.45 (d, J=4.56 Hz, 1H), 9.33 (s, 1H).

N-(1-(pyridin-2-yl)cyclopropyl)-3-(4,4,5,5-tetramethyl-1,3,2-dioxaborolan-2-yl)benzamide. 3-Iodo-N-(1-(pyridin-2-yl)cyclopropyl)benzamide (1 g, 2.7 mmol, 1 eq), Bispinnacolatodiboron (1.04 g, 4.1 mmol, 1.5 eq), Pd(dppf)Cl$_2$ (0.044 g, 0.054 mmol, 0.02 eq) and Potassium acetate (1.04 g, 13.5 mmol, 3 eq) were dissolved in DMF and nitrogen was purged for 15 minutes, and the above mixture was stirred at 90° C. for 15 h. The solution was filtered through celiete, and water was added to the filtrate which was then extracted with ethylacetate. The crude product was purified by combiflash chromatography to get of off white solid. Yield: 0.7 g (70%). $^1$HNMR (400 MHz, DMSO-d$_6$): δ 1.27 (m, 2H), 1.32 (s, 12H), 1.54 (m, 2H), 7.12 (s, 1H), 7.30 (d, J=8.00 Hz, 1H), 7.49 (t, J=7.56 Hz, 1H), 7.65 (t, J=3.44 Hz, 1H), 7.80 (d, J=7.32 Hz, 1H), 8.03 (m, 1H), 8.24 (s, 1H), 8.44 (m, 1H), 9.35 (s, 1H).

4-(benzyloxy)pyridine-3-amine. 4-(benzyloxy)-3-nitropyridine (15 g, 65 mmol, 1 eq) was dissolved in THF, then Raney Nickel (2.25 g, 10% w/w) (washed with THF) was added under nitrogen atmosphere and the reaction was stirred at room temperature with 2 kg hydrogen pressure for 6 h. The reaction solution was filtered through celite and the filtrate was concentrated under vacuum to get brown oil. The product was taken to the next step without purification. Yield: 12.3 g (94%). $^1$HNMR (400 MHz, DMSO-d$_6$): δ 4.86 (s, 2H), 5.18 (s, 2H), 6.88 (d, 1H, J=5.32 Hz), 7.31 (t, 1H, J=3.90 Hz), 7.4 (s, 2H, J=5.08 Hz), 7.5 (t, 2H, J=8.08 Hz), 7.71 (d, J=2.05 Hz, 1H), 7.89 (s, 1H).

N-(4-(benzyloxy)pyridin-3-yl)-N-(methylsulfonyl)methane sulfonamide. 4-(Benzyloxy)-3-nitropyridine (14 g, 69.8 mmol, 1 eq) was dissolved in dichloromethane and cooled to 0° C. Then added TEA (29.2 ml, 209.6 mmol, 3 eq), followed by the addition of potassium carbonate (9.96 g, 69.8 mmol, 1 eq) at 0° C. and stirred for 15 minutes. Methane sulfonyl chloride (20 g, 174 mmol, 2.5 eq) was added slowly at 0° C. to the above mixture and stirred for 14 h. After the completion of reaction, monitored by TLC, the reaction mixture was diluted with water and organic layer was separated. Water layer was extracted twice with 200 ml of dichloromethane, and the combined dichloromethane mixture was washed with water (500 ml) and brine (500 ml). The organic solution was concentrated under vacuum to yield the pure product. Yield: 19.5 g (78%). $^1$HNMR (400 MHz, DMSO-d$_6$): δ 3.47 (S, 6H), 5.35 (s, 2H), 7.32 (d, J=5.76 Hz, 1H), 7.40-7.49 (m, 3H), 7.51 (t, J=4.12 Hz, 2H), 8.52 (d, J=5.68 Hz, 1H), 8.57 (s, 1H).

N-(4-(benzyloxy)pyridin-3-yl)methane sulfonamide. Tetrabutylammonium fluoride 1 M in THF (12.2 ml, 42 mmol, 2.5 eq) was added to a solution of N-(4-(benzyloxy)pyridin-3-yl)-N-(methylsulfonyl)methane sulfonamide (6 g, 16.8 mmol, 1 eq) in THF at room temperature. The reaction mixture was refluxed at 60° C. for 10 h. The solution was concentrated completely and diluted with water (5 mL) and was allowed to stir for 15 minutes, The solid precipitated was filtered, washed with water and dried under vacuum yielding the expected product as a pale brown solid. $^1$HNMR (400 MHz, DMSO-d$_6$): δ 335 (s, 3H), 5.27 (s, 2H), 7.21 (d, J=5.64 Hz, 1H), 7.36-7.54 (m, 3H), 7.54 d, J=7.28 Hz, 2H), 8.30 (s, 1H), 8.33 (d, J=5.64 Hz, 1H), 9.34 (s, 1H).

tert-butyl 4-(benzyloxy)pyridin-3-yl(methylsulfonyl) carbamate. N-(4-(benzyloxy)pyridin-3-yl)methane sulfonamide (3 g, 10 mmol, 1 eq) was dissolved in THF and cooled to 0° C. Then TEA (4.4 ml, 32.1 mmol, 3 eq) and DMAP (0.13 g, 1.07 mmol, 0.1 eq) were added and stirred for 15 minutes. Boc-anhydride (2.3 g, 10 mmol, 1 eq) was added slowly at 0° C. and the mixture was stirred at room temperature for 14 h. The solution was concentrated and diluted with water and the product was extracted twice with dichloromethane (125 ml) and purified by combiflash chromatography using 12 g column and 50% ethyl acetate/hexane as the eluent. Yield: 3.1 g (77%). $^1$HNMR (400 MHz, DMSO-$d_6$): δ 1.33 (s, 9H), 3.41 (s, 3H), 5.32 (d, J=10.4 Hz, 2H), 7.28 (d, J=5.76 Hz, 1H), 7.30-7.46 (m, 5H), 8.47 (s, 1H), 8.47 (d, J=5.68 Hz, 1H).

N-Amino tert-butyl 4-(benzyloxy)pyridin-3-yl(methylsulfonyl)carbamate. To a cooled solution of tert-butyl 4-(benzyloxy)pyridin-3-yl(methylsulfonyl) carbamate (1 g, 1 eq) in dichloromethane was added O-(mesitylsulfonyl)hydroxylamine) (0.85 g, 1.5 eq) in dichloromethane, the solution was stirred at 0° C. for 20 minutes. The ice bath was removed and was stirred at room temperature for 7 h. The reaction mixture was concentrated at room temperature and re-dissolved in a mixture of dichloromethane and methanol (10/1), and then re-concentrated. The solid was placed under high vacuum yielding white foam which was taken to the next step without purification. Yield: 1.3 g. LCMS: (ES+) m/z observed 394.0.

Ethyl 5-(benzyloxy)-6-(N-(tert-butoxycarbonyl) methylsulfonamido)-2-(4-fluorophenyl)pyrazolo[1,5-a]pyridine-3-carboxylate. Ethyl-3(4-fluorophenylpropiolate) (0.87 g, 2.8 mmol, 1.3 eq) was dissolved in DMF and cooled to 0° C. To the above solution Potassium carbonate (1.68 g, 8.8 mmol, 4 eq) was added, and the reaction mixture stirred for 15 minutes. Subsequently, N-amino tert-butyl 4-(benzyloxy)pyridin-3-yl(methylsulfonyl)carbamate (1.2 g, 2.2 mmol 1 eq) dissolved in DMF, was added to the above mixture, which was then stirred at room temperature for 24 h. The solution was filtered through celite and purified by combiflash chromatography using 35% ethyl acetate/hexane as eluent. Yield: 0.37 g (22%). $^1$HNMR (400 MHz, DMSO-$d_6$): δ 1.21-1.25 (t, J=7.08 Hz, 3H), 1.33 (s, 9H), 3.49 (s, 3H), 4.20-4.25 (m, 2H), 5.37-5.45 (m, 2H), 7.33 (t, J=8.9 Hz, 2H), 7.42 (m, 3H), 7.50 (d, J=6.8 Hz, 2H), 7.57 (s, 1H), 7.78 (m, 2H), 9.28 (s, 1H). LCMS: (ES+) m/z=584.0 (M+H).

Ethyl 5-(benzyloxy)-2-(4-fluorophenyl)-6-(methylsulfonamido)pyrazolo[1,5-a]pyridine-3-carboxylate. Ethyl 5-(benzyloxy)-6-(N-(tert-butoxycarbonyl)methylsulfonamido)-2-(4-fluorophenyl)pyrazolo[1,5-a]pyridine-3-carboxylate (0.32 g, 0.54 mmol, 1 eq) was dissolved in dichloromethane and cooled to 0° C. Then added trifluoroacetic acid (3.2 ml). The above mixture was stirred at room temperature for 12 h. The solution was concentrated and the pH was brought to 8 and extracted with dichloromethane. The organic layer was concentrated yielding the desired product and was taken to the next step without further purification. Yield: 0.23 g (88%). $^1$HNMR (400 MHz, DMSO-$d_6$): δ 1.21-1.24 (t, 3H), 3.33 (s, 3H), 4.1-4.23 (q, 2H), 5.39 (s, 2H), 7.27 (t, J=5 Hz, 2H), 7.38 (d, J=2 Hz, 1H), 7.43 (m, 2H), 7.53 (s, 1H), 7.61 (d, J=2 Hz, 2H), 7.78 (t, J=6 Hz, 2H), 8.73 (s, 1H), 9.58 (s, 1H). LCMS: (ES+) m/z=484.0 (M+H).

Ethyl 5-(benzyloxy)-6-(N-ethylmethylsulfonamido)-2-(4-fluorophenyl)pyrazolo[1,5-a]pyridine-3-carboxylate. Ethyl 5-(benzyloxy)-2-(4-fluorophenyl)-6-(methylsulfonamido) pyrazolo[1,5-a]pyridine-3-carboxylate (0.2 g, 0.41 mmol, 1 eq) was dissolved in DMF and cooled to 0° C. Potassium carbonate (0.171 g, 1.6 mmol, 3 eq) was then added and the reaction mixture stirred for 15 minutes. Ethyl iodide (0.037 ml, 0.45 mmol, 1.1 eq) was added slowly dropwise and the resulting mixture was stirred at room temperature for 4 h. The solution was concentrated completely and diluted with water and the product was extracted with dichloromethane twice. The combined organic extracts were washed with water and concentrated yielding the desired product. Yield: 0.16 g (76 N. $^1$HNMR (400 MHz, DMSO-$d_6$): δ 1.07-1.10 (t, J=7.16 Hz, 3H), 1.21-1.24 (t, 3H), 3.04 (s, 3H), 3.64 (m, 2H), 4.19-4.24 (q, J=7.04 Hz, 2H), 5.38 (s, 2H), 7.28 (t, J=8.8 Hz, 2H), 7.42-7.54 (m, 3H), 7.57-7.65 (m, 3H), 7.77-7.95 (m, 2H), 9.02 (s, 1H). LCMS: (ES+) m/z=512.0 (M+H).

5-(benzyloxy)-6-(N-ethylmethylsulfonamido)-2-(4-fluorophenyl)pyrazolo[1,5-a]pyridine-3-carboxylic acid. Ethyl 5-(benzyloxy)-6-(N-ethylmethylsulfonamido)-2-(4-fluorophenyl)pyrazolo[1,5-a]pyridine-3-carboxylate (0.15 g, 0.29 mmol, 1 eq) was dissolved in ethanol. Then sodium hydroxide (0.035 g, 1.17 mmol, 3 eq) was added, followed by the addition of water (1 ml). The reaction was warmed to 45° C. for 14 h. The solution was concentrated and diluted with water and the pH of the reaction was brought to 3 using Conc.HCl. The solid precipitated was filtered and dried under vacuum. Yield: 0.12 g (86%). $^1$HNMR (400 MHz, DMSO-$d_6$): δ 1.06-1.10 (t, J=7.14 Hz, 3H), 3.01 (s, 3H), 3.62 (m, 2H), 534 (s, 2H), 7.27 (t, J=8.9 Hz, 2H), 7.32-7.46 (m, 4H), 7.56 (d, J=7.0 Hz, 2H), 7.63 (s, 1H), 7.80 (t, J=4.77 Hz, 2H), 8.98 (s, 1H). LCMS: (ES+) m/z=484.0 (M+H).

5-(benzyloxy)-6-(N-ethylmethylsulfonamido)-2-(4-fluorophenyl)-N-methylpyrazolo[1,5-a]pyridine-3-carboxamide. 5-(Benzyloxy)-6-(N-ethyl methylsulfonamido)-2-(4-fluorophenyl)pyrazolo[1,5-a]pyridine-3-carboxylic acid (0.11 g, 0.22 mmol, 1 eq), EDCI.HCl (0.048 g, 0.25 mmol, 1.1 eq), HOBT (0.036 g, 0.27 mmol, 1.2 eq), DIPEA (0.12 ml, 0.68 mmol, 3 eq) were dissolved in dichloromethane and the reaction was stirred at room temperature for 10 minutes. Then Methylamine (1 M in THF, 0.6 ml, 5 eq) was added to the above solution and the reaction was stirred at room temperature for 14 h. Finally, the mixture was diluted with water and the product was extracted with dichloromethane. The organic layer was washed with water, dried and concentrated. Yield: 0.1 g (90%). $^1$HNMR (400 MHz, DMSO-$d_6$): δ 1.06 (t, J=7.12 Hz, 3H), 2.77 (s, 3H), 3.00 (s, 3H), 3.62 (br m, 2H), 5.30 (s, 2H), 7307.32 (m, 3H), 7.33 (d, J=5.8 Hz, 1H), 7.40-7.43 (m, 21-1), 7.53-7.55 (m, 2H), 7.81 (t, J=3.52 Hz, 1H), 7.95 (s, 2H), 8.88 (s, 1H). LCMS: (ES+) m/z=497.0 (M+H).

6-(N-ethylmethylsulfonamido)-2-(4-fluorophenyl)-5-hydroxy-N-methylpyrazolo[1,5-a]pyridine-3-carboxamide. 5-(Benzyloxy)-6-(N-ethylmethylsulfonamido)-2-(4-fluorophenyl)-N-methylpyrazolo[1,5-a]pyridine-3-carboxamide (2.5 g, 5 mmol, 1 eq) was dissolved in dichloromethane and cooled to −78° C. Tetrabutylammonium iodide (0.19 g, 0.5 mmol, 0.1 eq) was added to the above mixture followed by slow dropwise addition of $BCl_3$ (25 ml) at −78° C. The above solution was stirred at room temperature for 14 h. The solution was quenched with 10% sodium bicarbonate solution and the product was extracted with dichloromethane. The dichloromethane solution was evaporated to get off-brown solid. Yield: 1.6 g (79%). $^1$HNMR (400 MHz, DMSO-$d_6$): δ 1.08 (t, J=7.14 Hz, 3H), 2.71 (d, J=4.52 Hz, 3H), 3.11 (s, 3H), 3.62 (q, J=6.92 Hz, 2H), 7.14 (s, 1H), 7.30 (t, J=8.86 Hz, 2H), 7.57 (d, J=4.56 Hz, 1H), 7.81-7.82 (m, 2H), 8.72 (s, 1H), 11.32 (br s, 1H). LCMS: (ES+) m/z=407.0 (M+H).

6-(N-ethylmethylsulfonamido)-2-(4-fluorophenyl)-3-(methylcarbamoyl)pyrazolo[1,5-a]pyridin-5-yl trifluoromethanesulfonate. 6-(N-ethylmethylsulfonamido)-2-(4-fluorophenyl)-5-hydroxy-N-methylpyrazolo[1,5-a]pyridine-3-carboxamide (0.2 g, 0.49 mmol, 1 eq) was dissolved in dichloromethane and cooled to 0° C. Then triethylamine (0.2 ml, 1.47 mmol, 3 eq) was added, followed by the portion-wise addition of N-Phenylbis(Trifluoromethanesulphonamide) (0.21 g, 0.58 mmol, 1.2 eq). Then the reaction was stirred at room temperature for 2 h. Water was added to the above mixture which was then extracted with dichloromethane. The crude product was purified by combiflash chromatography using 20% ethyl acetate/hexane as the eluent. Yield: 0.07 g (70%). LCMS: (ES+) m/z=539.0 (M+H).

O-(mesitylsulfonyl)hydroxylamine. Ethyl N-hydroxyacetimidate (10.3 g, 47 mmol, 1.1 eq) and triethylamine (25.5 ml, 94 mmol, 2 eq) were dissolved in DMF (40 ml, 2 vol) and the mixture cooled to 0° C. O-mesitylene chloride (20 g, 47 mmol, 1 eq) was then added portionwise and the mixture stirred at 0° C. for 45 minutes. The above solution was poured into ice water, and solid obtained was filtered and washed with water. Yield: 23 g (92%). $^1$HNMR (400 MHz, DMSO-d6): δ 1.16 (t, 3H), 2.03 (s, 3H), 2.31 (s, 3H), 2.64 (s, 6H), 3.89 (q, 2H), 6.96 (s, 2H).

Ethyl N-mesitylsulfonyloxyacetimidate (20 g, 65.7 mmol, 1 eq) was dissolved in 1,4-dioxane (6 ml) and the solution was cooled to 0° C. To the mixture was added dropwise Perchloric acid (10 in), and the reaction mixture was then stirred at 0° C. for 45 minutes. The solution was poured into ice water, and the solid precipitated was filtered and washed with water and dried for 15 minutes in vacuum. The sample was stored in plastic container at −20° C. $^1$HNMR (400 MHz, DMSO-d6): δ 2.32 (s, 3H), 2.64 (s, 6H), 4.98 (br peak, 2H), 6.99 (s, 2H).

Ethyl 3-(4-fluorophenyl)propiolate. 4-Fluorophenylacetylene (1 g, 8.3 mmol, 1 eq) was dissolved in diethylether and cooled to −78° C. The mixture was added n-butyl lithium (6.9 ml, 2 eq) dropwise slowly at −78° C. and allowed to stirr at −78° C. for 2 hours. Later Ethyl chloroformate (3.06 ml, 33.3 mmol, 4 eq) cooled to −78° C. was added to the above solution as fast as possibly, and the mixture was allowed to stir for 1 h at −78° C. The solution was quenched with saturated ammonium chloride solution, and the product was extracted with ethylacetate and purified by silica column (60-120) using 5% ethylacetate/hexane as eluent to obtain an off pale brown solid. Yield: 1.3 g (81%). $^1$HNMR (400 MHz, DMSO-d6): δ 1.35 (t, J=7.14 Hz, 3H), 4.30 (q, J=7.14 Hz, 2H), 7.07 (t, J=4.33 Hz, 2H), 7.59 (m, 2H).

All the Prep HPLC purifications were run at following conditions until noted otherwise except for the other conditions that are mentioned in individual procedures. Solvent A: 10% MeOH-90% H$_2$O-0.1% TFA; Solvent B: 90% MeOH-10% H$_2$O-0.1% TFA; Column: Phenomenex-LUNA AXIA 5 u 21×100 mm S5. LCMS methods: All LCMS analysis conditions used method 1 except mentioned in individual procedure. Method 1: Start % B: 0; Final % B: 100; Gradient time: 4 min; Stop time: 5 min; Flow rate: 5 ml/min; Wavelength: 220; Solvent A: 10% MeOH/90% H$_2$O/0.1% Trifluoroacetic Acid; Solvent B: 10% H$_2$O/90% MeOH/0.1% Trifluoroacetic Acid; Column: Phenomenex-luna 3.0×50 mm S10.

2-(4-fluorophenyl)-6-(2-methoxy-5-(2-phenylpropan-2-ylcarbamoyl)phenyl)-N-methylimidazo[1,2-a]pyridine-3-carboxamide

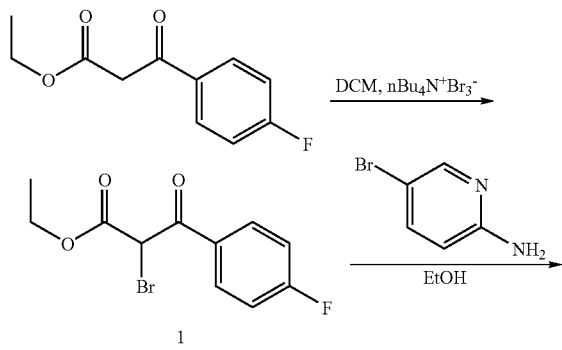

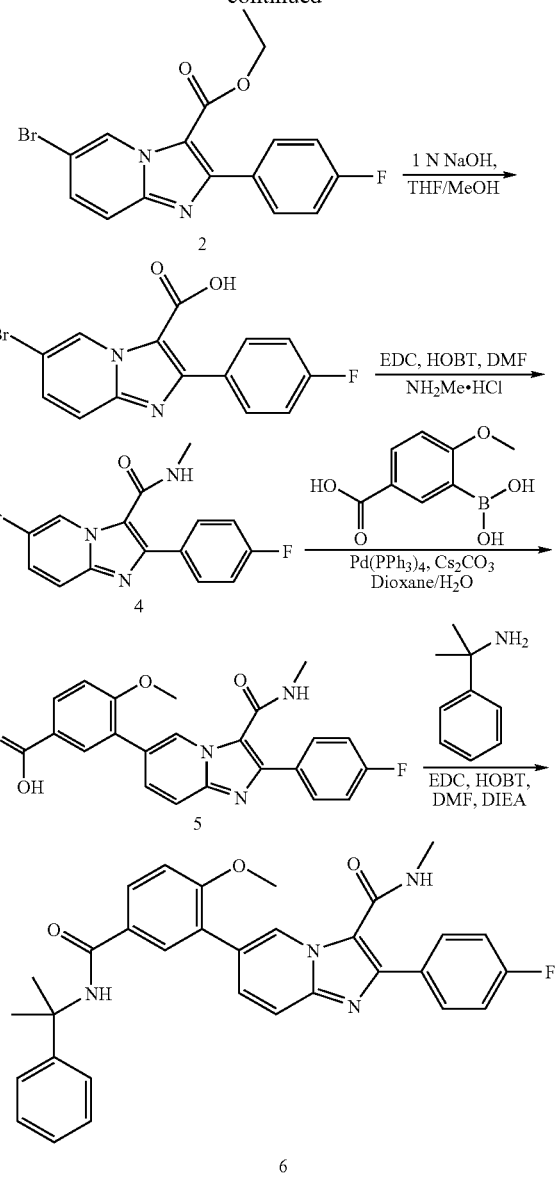

Step 1: Preparation of compound 1. To a solution of ethyl 3-(4-fluorophenyl)-3-oxopropanoate (0.42 g, 2.01 mmol) in DCM (8.0 mL) cooled at 0° C. was added tetra-n-butylammonium tribromide (0.97 g, 2.01 mmol). The reaction mixture was stirred at 0° C. for 2 hrs and then at rt for 16 hrs. The reaction mixture was charged to a 80 g silica gel cartridge which was eluted with a 20 min gradient of 0-80% EtOAc in hexane. The fractions containing the desired product were concentrated to yield compound 1 (0.50 g, 1.73 mmol, 86% yield) as a clear oil. LC/MS m/z 288 (M+H)$^+$ 289.04, RT=2.44 min; 1H NMR (400 MHz, CHLOROFORM-d) ppm 7.94-8.00 (2H, m), 7.06-7.13 (2H, m), 5.61 (1H, s), 4.20 (2H, q, J=7.30 Hz), 1.10-1.21 (3H, m).

Step 2: Preparation of compound 2. To a solution of compound 1 (1.5 g, 5.2 mmol) in Ethanol (30 mL) was added 5-bromopyridin-2-amine (3.1 g, 18.0 mmol). The reaction was stirred at 70° C. under nitrogen for 16 hrs. The solvent was removed through vacuum. The reaction residue was dissolved in EtOAc, washed with sat NaHCO$_3$ and water, dried over anhydrous Na$_2$SO$_4$, filtered and concentrated to yield a yellow solid. The solid was dissolved with DCM and charged to a 80 g silica gel cartridge which was eluted with a 20 min gradient of 0-60% EtOAc in hexane. The fractions containing the desired product were concentrated to yield compound 2 (0.7 g, 1.9 mmol, 36% yield) as a pale yellow solid. LC/MS m/z 363 (M+H)+ 363.2, RT=2.90 min [Phenomenex Luna C18 4.6×50 mm-4 min gradient from 0-100% (A: 95/5/10 mm H₂O/ACN/10 mM ammonium acetate; B: 95/5/10 mm ACN/H₂O/10 mM ammonium acetate)]; 1HNMR (500 MHz, DMSO-D6) ppm 9.45 (1H, d, J=1.83 Hz), 7.81-7.85 (2H, m), 7.80 (1H, s), 7.74-7.77 (1H, m), 7.28-7.33 (2H, m), 4.29 (2H, q, J=7.22 Hz), 1.20 (3H, t, J=7.17 Hz).

Step 3: Preparation of compound 3. To a solution of compound 2 (0.42 g, 1.16 mmol) in THF (5 mL) and MeOH (1 mL) was added 1.0 N NaOH. (2.3 mL, 2.3 mmol). The reaction mixture was stirred at rt for 16 hrs. The solvent was removed through vacuum. The residue was diluted with EtOAc, washed with 1 N HCl, sat. NaCl, dried over anhydrous Na₂SO₄, filtered and concentrated to yield compound 3 (0.39 g, 1.16 mmol, 100% yield) as a white solid. LC/MS m/z 334 (M+H)+ 335.15, RT=1.48 min [Phenomenex Luna C18 3.0×50 min—2 min gradient from 0-100% B. (A: 90/10/ 0.1H₂O/MeOH/TFA; B: 90/10/0.1 MeOH/H₂O/TFA)].

Step 4: Preparation of compound 4. To a solution of compound 3 (0.39 g, 1.16 mmol) in DMF (5 mL) was added EDC (0.34 g, 1.75 mmol), HOBT (0.27 g, 1.75 mmol), methylamine hydrochloride (0.16 g, 2.33 mmol) and DIEA (0.61 mL, 3.49 mmol). The reaction mixture was stirred at 50° C. for 2 hrs. The reaction mixture was diluted with EtOAc, washed with sat. NaHCO₃, sat. NaCl. The white solid was filtered and washed with EtOAc, then dried to yield compound 4 (0.20 g, 0.57 mmol, 49% yield) as a yellow solid. LC/MS m/z 347 (M+H)+ 348, RT=1.24 min [Phenomenex Luna C18 3.0×50 mm-2 min gradient from 0-100% B. (A: 90/10/0.1H₂O/MeOH/TFA; B: 90/10/0.1 MeOH/H₂O/TFA)]

Step 5: Preparation of compound 5. To a solution of compound 4 (0.058 g, 0.17 mmol) in dioxane (1 mL) and Water (0.2 mL) was added 3-borono-4-methoxybenzoic acid (0.049 g, 0.25 mmol), CS₂CO₃ (0.081 g, 0.25 mmol). The reaction mixture was stirred and degassed for 5 min, then tetrakis (3.9 mg, 3.3 mmol) was added. The reaction was heated at 85° C. for 16 hrs. The reaction mixture was cooled to rt, diluted with EtOAc, washed with 1 N HCl, the solid was filtered off. The filtrate two phases were separated and the organic phase was washed with sat. NaCl, dried over anhydrous Na₂SO₄, filtered and concentrated to yield compound 5 (0.056 g, 0.13 mmol, 76% yield) as a yellow solid. Compound 5 was used without further purification. LC/MS m/z 419 (M+H)+ 420.21, RT=1.478 min [Phenomenex Luna C18 3.0×50 mm—2 min gradient from 0-100% B. (A: 90/10/0.1H₂O/MeOH/TFA; B: 90/10/0.1 MeOH/H₂O/TFA)].

Step 6: Preparation of compound 6. To a solution of compound 5 (0.055 g, 0.13 mmol) in DMF (1 mL) was added EDC (0.038 g, 0.20 mmol), HOBT (0.030 g, 0.20 mmol), 2-phenylpropan-2-amine (0.018 g, 0.13 mmol) and DIEA (0.07 mL, 0.39 mmol). The reaction mixture was stirred at 50° C. for 16 hrs. The reaction mixture was diluted in MeOH, filtered and purified by purified by reverse phase prep-HPLC. Fractions from main peak were evaporated in the SpeedVac to yield compound 6 in mono TFA salt form (0.022 g, 0.033 mmol, 25.01% yield) as a yellow solid. LC/MS m/z 536 (M+H)+ 537.40, RT=2.86 min; 1H NMR (400 MHz, CHLOROFORM-D) ppm 9.46 (1H, s), 8.04 (1H, d, J=9.32 Hz), 7.93 (1H, dd, J=9.32, 1.51 Hz), 7.81 (1H, dd, J=8.56, 2.27 Hz), 7.77 (1H, d, J=2.27 Hz), 7.68-7.73 (2H, m), 7.41-7.45 (2H, m), 7.29-7.34 (2H, m), 7.19-7.26 (3H, m) 7.01 (1H, d, J=8.56 Hz), 6.63 (1H, s), 6.42 (1H, d, J=4.78 Hz), 3.87 (3H, s), 2.89 (3H, d, J=4.78 Hz), 1.78-1.82 (6H, m).

2-(4-fluorophenyl)-N-methyl-6-(2-methyl-5-(1-(pyridin-2-yl)cyclopropylcarbamoyl)phenyl)imidazo[1, 2-a]pyridine-3-carboxamide (8)

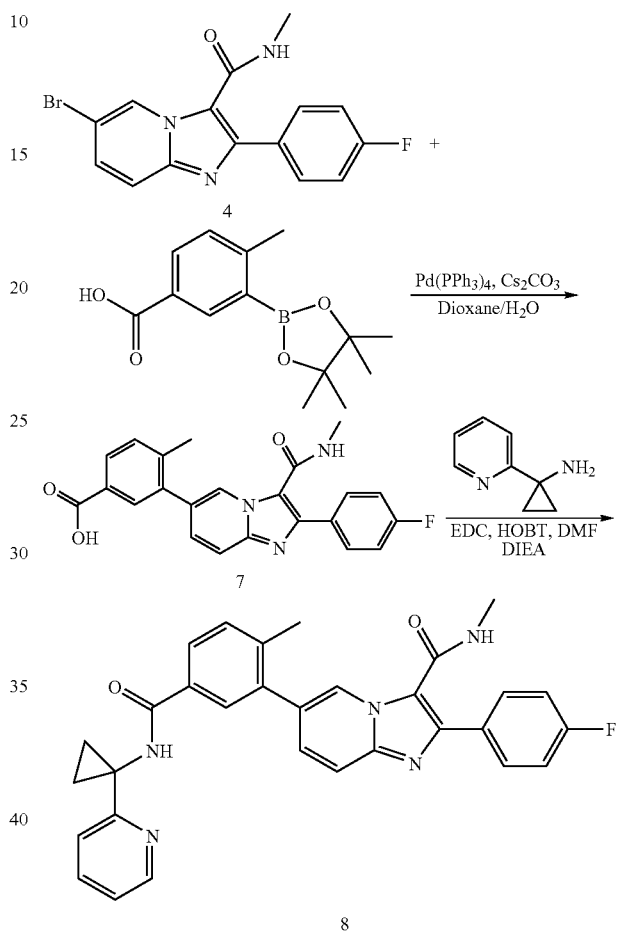

Step 1: Preparation of compound 7. To a solution of compound 4 (0.12 g, 0.33 mmol) in dioxane (1 mL) and water (0.2 mL) was added 4-methyl-3-(4,4,5,5-tetramethyl-1,3,2-dioxaborolan-2-yl)benzoic acid (0.13 g, 0.50 mmol), CS₂CO₃ (0.16 g, 0.50 mmol). The reaction mixture was stirred and degassed for 5 min, then tetrakis (7.7 mg, 6.7 μmol) was added. The reaction mixture was heated at 85° C. for 3 hrs. The reaction mixture was cooled to rt, diluted with EtOAc, washed with 1 N HCl, the solid was filtered off. The filtrate two phases were separated and the organic phase was washed with sat. NaCl, dried over anhydrous Na₂SO₄, filtered and concentrated to yield compound 7 (0.050 g, 0.12 mmol, 36% yield) as a yellow solid. The crude product was used without further purification. LC/MS m/z 403 (M+H)+ 404.2, RT=– 1.54 min [Phenomenex Luna C18 3.0×50 mm—2 min gradient from 0-100% B. (A: 90/10/0.1H₂O/MeOH/TFA; B: 90/10/0.1 MeOH/H₂O/TFA)].

Step 2: Preparation of compound 8. To a solution of compound 7 (0.050 g, 0.12 mmol) in DMF (1 mL) was added EDC (0.036 g, 0.19 mmol), HOBT (0.028 g, 0.19 mmol), 1-(pyridin-2-yl)cyclopropanamine (0.020 g, 0.15 mmol) and DIEA (0.087 mL, 0.50 mmol). The reaction mixture was stirred at 50° C. for 16 hrs. The reaction mixture was diluted in MeOH, filtered and purified by purified by reverse phase prep-HPLC. Fractions from main peak were evaporated in SpeedVac to yield compound 8 mono TFA salt (0.022 g, 0.029 mmol, 24% yield) as a white solid. LC/MS m/z 519 (M+H)+ 520.34, RT=1.99 min; 1H NMR (400 MHz, CHLOROFORM-D) ppm 9.96 (1H, s), 9.40 (1H, s), 8.64 (1H, d, J=5.54 Hz), 8.27-8.35 (1H, m), 8.12 (1H, d, J=9.32 Hz), 7.99 (1H, d, J=8.06 Hz), 7.87 (1H, dd, J=8.06, 1.76 Hz), 7.82 (1H, s), 7.68-7.79 (4H, m), 7.37 (1H, d, J=8.06 Hz), 7.25-7.30 (2H, m), 6.01 (1H, d, J=4.53 Hz), 2.87 (3H, d, J=5.04 Hz), 2.32 (3H, s), 1.59-1.66 (2H, m), 1.49-1.56 (2H, m).

6-(2-chloro-5-(2-phenylpropan-2-ylcarbamoyl)phenyl)-2-(4-fluorophenyl)-N-methylimidazo[1,2-a]pyridine-3-carboxamide (10)

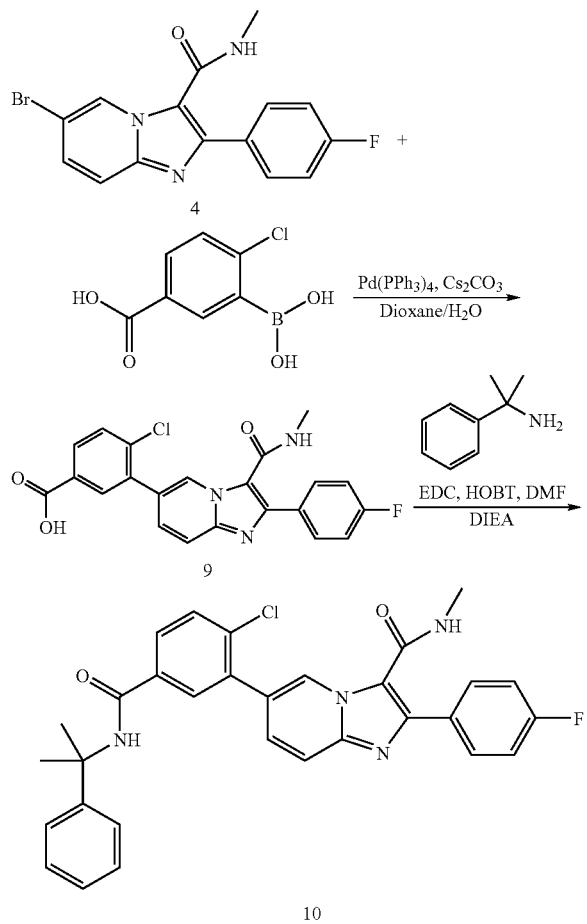

Step 1: Preparation of compound 9. To a solution of compound 4 (0.058 g, 0.17 mmol) in dioxane (1 mL) and water (0.200 mL) was added 3-borono-4-chlorobenzoic acid (0.050 g, 0.25 mmol), Cs$_2$CO$_3$ (0.081 g, 0.25 mmol). The reaction mixture was stirred and degassed for 5 min, then tetrakis (4 mg, 3 μmol) was added. The reaction mixture was heated at 85° C. for 3 hrs. The reaction mixture was cooled to rt, diluted with EtOAc, washed with 1 N HCl, the solid was filtered off. The filtrate two phases were separated and the organic phase was washed with sat. NaCl, dried over anhydrous Na$_2$SO$_4$, filtered and concentrated to yield compound 9 (0.074 g, 0.175 mmol) as a yellow solid. The crude product was used without further purification. LC/MS m/z 423 (M+H)+ 424.22, RT=1.65 min [Phenomenex Luna C18 3.0×50 mm—2 min gradient from 0-100% B. (A: 90/10/0.1H$_2$O/MeOH/TFA; B: 90/10/0.1 MeOH/H$_2$O/TFA)].

Step 2: Preparation of compound 10. To a solution of compound 9 (0.074 g, 0.17 mmol) in DMF (1 mL) was added EDC (0.050 g, 0.26 mmol), HOBT (0.040 g, 0.26 mmol), 2-phenylpropan-2-amine (0.024 g, 0.18 mmol) and DIEA (0.091 mL, 0.52 mmol). The reaction mixture was stirred at 50° C. for 16 hrs. The reaction mixture was diluted in MeOH, filtered and purified by purified by reverse phase prep-HPLC. Fractions from main peak were evaporated to yield a clear oil. The oil was dissolved in methylene chloride and charged to a 4 g silica gel cartridge which was eluted with a 15 min gradient of 0-100% EtOAc in hexane. The fractions containing the desired product were concentrated to yield compound 10 (0.022 g, 0.040 mmol, 22% yield) as a white solid. LC/MS m/z 540 (M+H)+ 541.27, RT=1.91 min [Phenomenex Luna C18 3.0×50 mm—2 min gradient from 0-100% B. (A: 90/10/0.1H$_2$O/MeOH/TFA; B: 90/10/0.1 MeOH/H$_2$O/TFA)]; 1H NMR (500 MHz, CHLOROFORM-D) ppm 9.50 (1H, s), 7.80 (1H, d, J=2.14 Hz), 7.73 (1H, dd, J=8.39, 2.29 Hz), 7.66-7.70 (3H, m), 7.53 (1H, d, J=8.24 Hz), 7.42-7.46 (3H, m), 7.33 (2H, t, J=7.63 Hz), 7.17-7.26 (3H, m), 6.59 (1H, s), 5.77 (1H, d, J=4.58 Hz), 2.84 (3H, d, J=4.58 Hz), 1.81 (6H, s).

2-(4-fluorophenyl)-N-methyl-6-(2-methyl-5-(2-phenylpropan-2-ylcarbamoyl)phenyl)imidazo[1,2-a]pyridine-3-carboxamide (11)

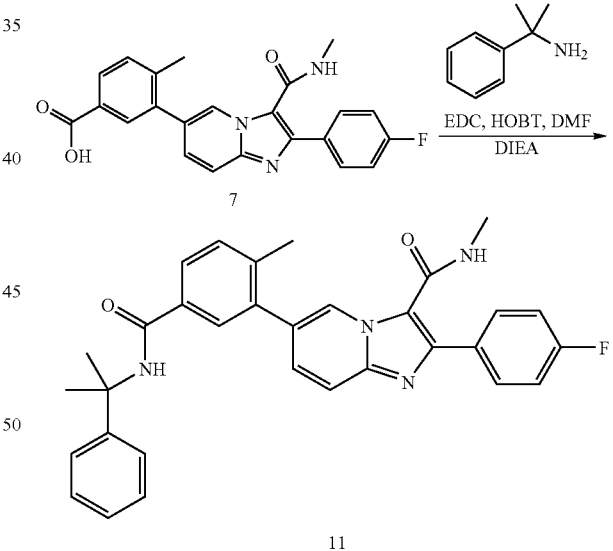

Step 1: Preparation of compound 11. To a solution of compound 7 (0.050 g, 0.12 mmol) in DMF (1 mL) was added EDC (0.036 g, 0.19 mmol), HOBT (0.028 g, 0.19 mmol), 2-phenylpropan-2-amine (0.017 g, 0.12 mmol) and DIEA (0.065 mL, 0.37 mmol). The reaction mixture was stirred at 50° C. for 16 hrs. The reaction mixture was diluted in MeOH, filtered and purified by reverse phase prep-HPLC. Fractions from main peak were evaporated to yield a clear oil. The oil was dissolved in methylene chloride and charged to a 4 g silica gel cartridge which was eluted with a 15 min gradient of 0-100% EtOAc in hexane. The fractions containing the desire product were combined and concentrated to yield compound 11 (0.015 g, 0.029 mmol, 23% yield) as a white solid. LC/MS m/z 520 (M+H)+ 521.38, RT=2.91 min; 1H NMR (500 MHz, CHLOROFORM-D) ppm 9.42 (1H, s), 7.66-7.73 (5H, m), 7.45 (2H, d, J=7.32 Hz), 7.31-7.37 (4H, m), 7.19-7.24 (3H, m), 6.46 (1H, s), 5.74 (1H, d, J=4.58 Hz), 2.85 (3H, d, J=4.88 Hz), 2.34 (3H, s), 1.82 (6H, s).

Trans-2-(4-fluorophenyl)-N-methyl-6-((1S,2R)-2-(1-(pyridin-2-yl)cyclopropylcarbamoyl)cyclopropyl)imidazo[1,2-a]pyridine-3-carboxamide and cis-2-(4-fluorophenyl)-N-methyl-6-((1S,2R)-2-(1-(pyridin-2-yl)cyclopropylcarbamoyl)cyclopropyl)imidazo[1,2-a]pyridine-3-carboxamide

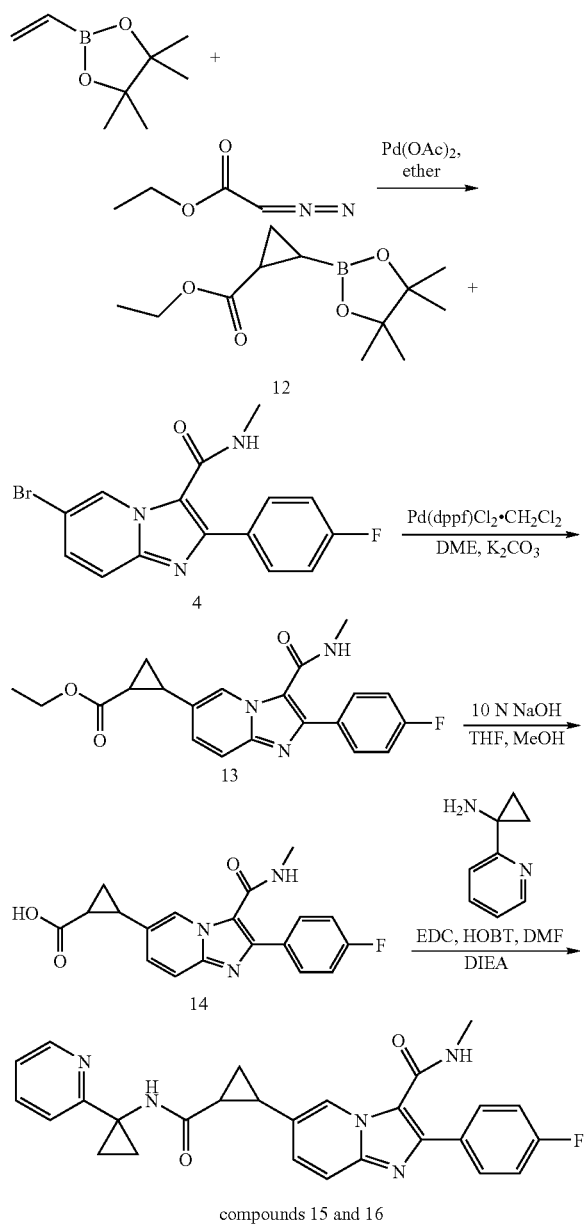

compounds 15 and 16

Step 1: Preparation of compound 12. To a solution of 4,4,5,5-tetramethyl-2-vinyl-1,3,2-dioxaborolane (0.31 g, 2.0 mmol) and PdOAc2 (4.5 mg, 0.02 mmol) in anhydrous Ether (3 mL) was added a solution of ethyl 2-diazoacetate (0.57 g, 5.0 mmol) in ether (2 mL) dropwise under $N_2$. During the halfway of the addition, additional $PdOAc_2$ (4.49 mg, 0.02 mmol) was added. When N2 evolution had ceased, the reaction mixture was filtered through activated neutral aluminum oxide and washed with ether. The filtrate was concentrated to yield compound 12 (0.50 g, 2.0 mmol) as a yellow oil. The crude product was used without further purification.

Step 2: Preparation of compound 13. To a stirring degassed solution of compound 4 (0.060 g, 0.17 mmol), compound 12 (0.083 g, 0.35 mmol) and potassium carbonate (0.119 g, 0.862 mmol) in DME (2 mL) under Ar was added $PdCl_2$ (dppf)-$CH_2Cl_2$ Adduct (4 mg, 5 μmol) and water (0.2 mL). The reaction mixture was heated to 85° C. for 4 hrs. The reaction mixture was cooled to rt, diluted with EtOAc, washed with sat. $NaHCO_3$, sat. NaCl, filtered and concentrated to yield a yellow solid. The solid was dissolved in methylene chloride and charged to a 12 g silica gel cartridge which was eluted with a 20 min gradient of 0-100% EtOAc in hexane. The fractions containing the desired product were concentrated to yield diastereomer mixture of compound 13 (0.036 g, 0.094 mmol, 55% yield) as a yellow solid. LC/MS m/z 381 (M+H)+ . 382.3, RT=1.91 min; LC/MS m/z 381 (M+H)+ 382.3, RT=2.14 min.

Step 3: Preparation of compound 14. A solution of compound 13 (0.036 g, 0.094 mmol) in THF (1 mL) and MeOH (0.250 mL) was added 10 N NaOH (0.028 mL, 0.28 mmol). The reaction mixture was stirred at rt for 2 hrs. The reaction mixture was concentrated. The residue was diluted with EtOAc, washed with 5% citric acid, sat. NaCl, dried over anhydrous $Na_2SO_4$, filtered and concentrated to yield diastereomer mixtures of compound 14 (0.033 g, 0.093 mmol) as a yellow solid. The crude product was used without further purification. LC/MS m/z 353 (M+H)+354.26, RT=1.497 min; LC/MS m/z 353 (M+H)+ 354.26, RT=1.663 min.

Step 4: Preparation of compound 15 and 16. To a solution of compound 14 (0.033 g, 0.093 mmol) in DMF (2 mL) was added EDC (0.036 g, 0.19 mmol), HOBT (0.029 g, 0.19 mmol), DIEA (0.13 mL, 0.75 mmol) and 1-pyridin-2-yl-cyclopropylamine 3HCl salt (0.025 g, 0.19 mmol). The reaction mixture was stirred at rt for 16 hrs. The reaction mixture was dissolved in MeOH, filtered and purified by reverse phase prep-HPLC. The diastereomer mixtures were separated on prep HPLC. Fractions from main peak were evaporated in SpeedVac to yield compound 15 2TFA salt (0.008 g, 0.011 mmol, 12% yield) as a white solid. LC/MS m/z 469 (M+H)4 470.28, RT=1.44 min; 1H NMR (400 MHz, MeOD) ppm 8.82 (1H, s), 8.23 (1H, d, J=5.04 Hz), 7.68-7.74 (2H, m), 7.46-7.55 (2H, m), 7.19-7.29 (3H, m), 6.96 (1H, dd, J=7.43, 4.91 Hz), 6.91 (1H, d, J=8.06 Hz), 2.81-2.85 (3H, m), 2.64 (1H, q, J=8.23 Hz), 2.25 (1H, td, J=8.37, 5.67 Hz), 1.70-1.79 (1H, m), 1.26-1.48 (3H, m), 1.06-1.15 (1H, m), 0.85-0.95 (1H, m); and compound 16 in bis-TFA salt form (0.008 g, 0.011 mmol, 12% yield) as a white solid. LC/MS m/z 469 (M+H)+ 470.28, RT=1.61 min; 1H NMR (400 MHz, MeOD) ppm 8.97 (1H, s), 8.58 (1H, dd, 1.51 Hz), 8.34 (1H, td, J=7.93, 1.76 Hz), 7.79-7.85 (1H, m), 7.71-7.78 (5H, m), 7.32-7.38 (2H, m), 2.86-2.90 (3H, m), 2.59-2.67 (1H, m), 2.13-2.20 (1H, m), 1.68-1.76 (2H, m), 1.60-1.66 (1H, m), 1.54-1.59 (2H, m), 1.47 (1H, ddd, J=8.56, 6.30, 4.78 Hz).

2-(4-fluorophenyl)-6-(3-(isobutylcarbamoyl)-4-(pyridin-3-yl)phenyl)-N-methylimidazo[1,2-a]pyridine-3-carboxamide (19)

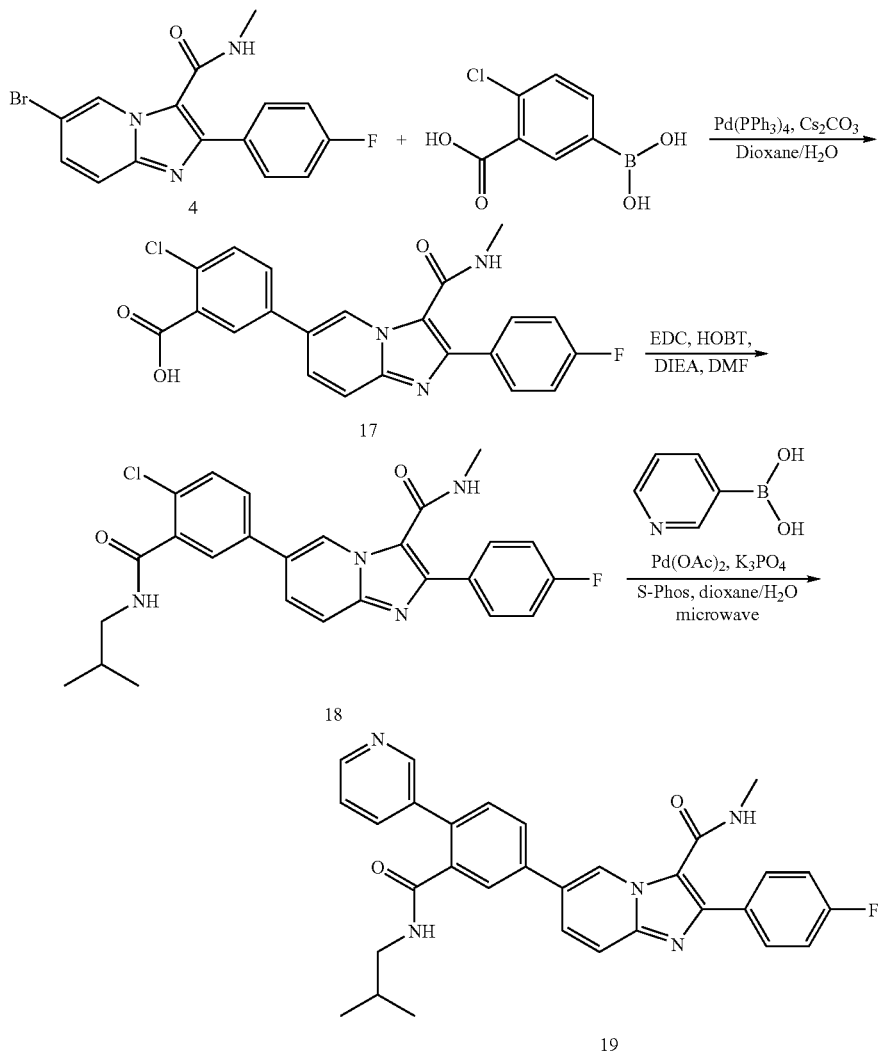

Step 1: Preparation of compound 17. To a solution of compound 4 (0.10 g, 0.29 mmol) in dioxane (1 mL) and water (0.2 mL) was added 5-borono-2-chlorobenzoic acid (0.087 g, 0.44 mmol), $Cs_2CO_3$ (0.14 g, 0.44 mmol). The reaction mixture was stirred and degassed for 5 min, then tetrakis (7 mg, 6 µmol) was added. The reaction mixture was heated at 85° C. for 3 hrs. The reaction mixture was cooled to rt, diluted with EtOAc. The organic phase was washed with 1 N HCl, sat. NaCl, dried over anhydrous $Na_2SO_4$, filtered and concentrated to yield compound 17 as a pale yellow solid. The crude product was used without further purification. LC/MS m/z 423 (M+H)$^+$ 424.10, RT=2.40 min.

Step 2: Preparation of compound 18. To a solution of compound 17 (0.12 g, 0.28 mmol) in DMF (2 mL) was added EDC (0.081 g, 0.43 mmol), HOBT (0.065 g, 0.43 mmol), DIEA (0.15 mL, 0.85 mmol) and isobutylamine (0.042 mL, 0.43 mmol). The reaction mixture was stirred at 50° C. for 2 hrs. The reaction mixture was diluted with EtOAc, washed with sat. $NaHCO_3$, sat. NaCl, dried over anhydrous $Na_2SO_4$, filtered and concentrated to yield a pale yellow solid. The solid was suspended in methylene chloride and charged to a 40 g silica gel cartridge which was eluted with a 20 min gradient of 0-15% MeOH in $CH_2Cl_2$. The fraction containing the desired product was concentrated to yield compound 18 (0.050 g, 0.10 mmol, 37% yield) as a pale yellow solid. LC/MS m/z 478 (M+H)$^+$ 479.26, RT=2.66 min.

Step 3: Preparation of compound 19. To a microwave vial was added compound 18 (0.050 g, 0.104 mmol), pyridin-3-ylboronic acid (0.038 g, 0.313 mmol), Pd(OAc)$_2$ (4.69 mg, 0.021 mmol), 2-dicyclohexylphosphino-2',6'-dimethoxybiphenyl (8.57 mg, 0.021 mmol), potassium phosphate, tribasic (0.089 g, 0.418 mmol), dioxane (1 mL) and Water (0.100 mL). The reaction mixture was degassed and filled with N2. The reaction mixture was heated at 130° C. in microwave reactor for 15 min. The reaction mixture was diluted with EtOAc, washed with sat. $NaHCO_3$, sat. NaCl, dried over anhydrous $Na_2SO_4$, filtered and concentrated to yield a yellow residue. The residue was dissolved in MeOH and DMF, filtered and purified by reverse phase prep HPLC. Fractions from main peak were evaporated to yield a white solid. The solid was dissolved in methylene chloride and CHCl₃ and charged to a 4 g silica gel cartridge which was eluted with a 20 min gradient of 0-15% MeOH in CH₂Cl₂. The fraction containing the desired product was concentrated to yield compound 19 (0.004 g, 7 μmol, 6% yield) as a white solid. LC/MS m/z 521.58 (M+H)⁺ 522.25, RT=2.05 min; 1H NMR (400 MHz, CHLOROFORM-d) ppm 9.77 (1H, s), 8.72 (1H, br. s.), 8.62 (1H, br. s.), 7.88 (1H, d, J=2.01 Hz), 7.86 (1H, d, J=8.06 Hz), 7.74-7.81 (2H, m), 7.65-7.73 (3H, m), 7.47 (1H, d, J=8.06 Hz), 7.39 (1H, dd, J=7.55, 5.04 Hz), 7.19-7.24 (2H, m), 5.78 (1H, br. s.), 5.61 (1H, t, J=5.79 Hz), 3.07 (2H, t, J=6.42 Hz), 2.88 (3H, d, J=4.78 Hz), 1.60 (1H, dt, J=13.41, 6.77 Hz), 0.68-0.76 (6H, m).

2-(4-fluorophenyl)-6-(2-(isobutylcarbamoyl)biphenyl-4-yl)-N-methylimidazo[1,2-a]pyridine-3-carboxamide(20)

2-dicyclohexylphosphino-2',6'-dimethoxybiphenyl (5 mg, 0.01 mmol), potassium phosphate, tribasic (0.053 g, 0.25 mmol), dioxane (1 mL) and water (0.1 mL). The reaction mixture was degassed and filled with N₂. The reaction mixture was heated at 130° C. in microwave reactor for 15 min. The reaction mixture was diluted with EtOAc, washed with sat. NaHCO₃, sat. NaCl, dried over anhydrous Na₂SO₄, filtered and concentrated to yield a yellow solid. The solid was dissolved in MeOH and DMF, filtered and purified by reverse phase prep HPLC. Fractions from main peak were evaporated via SpeedVac to yield compound 20 mono TFA salt (0.024 g, 0.036 mmol, 58% yield) as a white solid. LC/MS m/z 520 (M+H)⁺ 521.12, RT=2.88 min; 1H NMR (400 MHz, MeOD) ppm 9.39 (1H, s), 8.31 (1H, dd, J=9.32, 1.51 Hz), 7.98 (1H, d, J=9.32 Hz), 7.88 (1H, dd, J=8.06, 2.01 Hz), 7.76-7.85 (3H, m), 7.60 (1H, d, J=8.06 Hz), 7.45-7.51 (2H, m), 7.32-7.45 (5H, m), 2.96-3.00 (2H, m), 2.89 (3H, s), 1.63 (1H, dt, J=13.53, 6.70 Hz), 0.71 (6H, d, J=6.80 Hz).

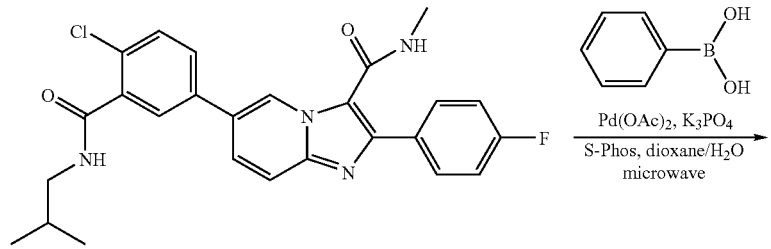

18

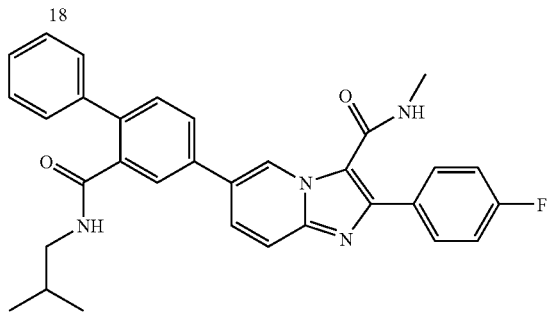

20

Step 1: Preparation of compound 20. To a microwave vial was added compound 18 (0.030 g, 0.063 mmol), phenylboronic acid (0.023 g, 0.19 mmol), PdOAc2 (3 mg, 0.01 mmol), 6-(2'-chloro-2-(isobutylcarbamoyl)biphenyl-4-yl)-2-(4-fluorophenyl)-N-methylimidazo[1,2-a]pyridine-3-carboxamide (21)

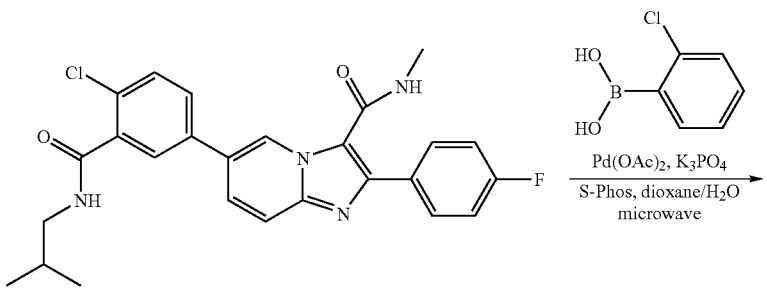

18

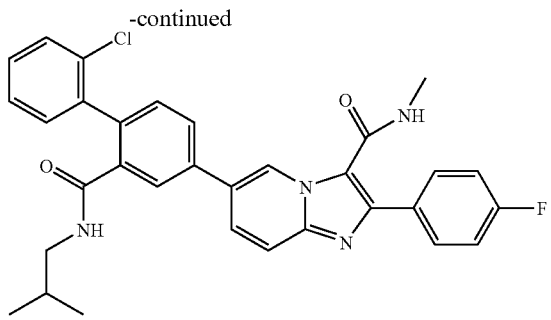

21

Step 1: Preparation of compound 21

To a microwave vial was added compound 18 (0.030 g, 0.063 mmol), 2-chlorophenylboronic acid (0.029 g, 0.19 mmol), PdOAc2 (2.8 mg, 0.01 mmol), 2-dcyclohexylphosphino-2',6'-dimethoxybiphenyl (5 mg, 0.01 mmol), potassium phosphate, tribasic (0.053 g, 0.25 mmol), doxane (1 mL) and water (0.1 mL). The reaction mixture was degassed and filled with N2. The reaction mixture was heated at 130° C. in microwave reactor for 15 min. The reaction mixture was diluted with EtOAc, washed with sat. NaHCO₃, sat. NaCl, dried over anhydrous Na₂SO₄, filtered and concentrated to yield a yellow solid. The solid was dissolved in MeOH and DMF, filtered and purified by reverse phase prep HPLC. Fractions from main peak were evaporated via SpeedVac to yield a yellow residue. The residue was dissolved in methylene chloride and charged to a 4 g silica gel cartridge which was eluted with a 15 min gradient of 0-100% EtOAc in hexane. The fraction containing the desired product was concentrated to yield compound 21 (0.003 g, 4 μmol, 6% yield) as a white solid. LC/MS m/z 554 (M+H)⁺ 555.15, RT=3.16 min; 1H NMR (400 MHz, MeOD) ppm 9.27 (1H, s) 7.84-7.92 (3H, m) 7.73-7.80 (3H, m) 7.38-7.48 (3H, m) 7.32-7.37 (2H, m) 7.21-7.29 (2H, m) 3.00 (2H, d, J=6.80 Hz) 2.87 (3H, s) 1.61-1.66 (1H, m) 0.77 (7H, d, J=6.80 Hz).

6-(2-chloro-4-methoxy-5-(1-(pyridin-2-yl)cyclopropylcarbamoyl)phenyl)-2-(4-fluorophenyl)-N-methylimidazo[1,2-a]pyridine-3-carboxamide (23)

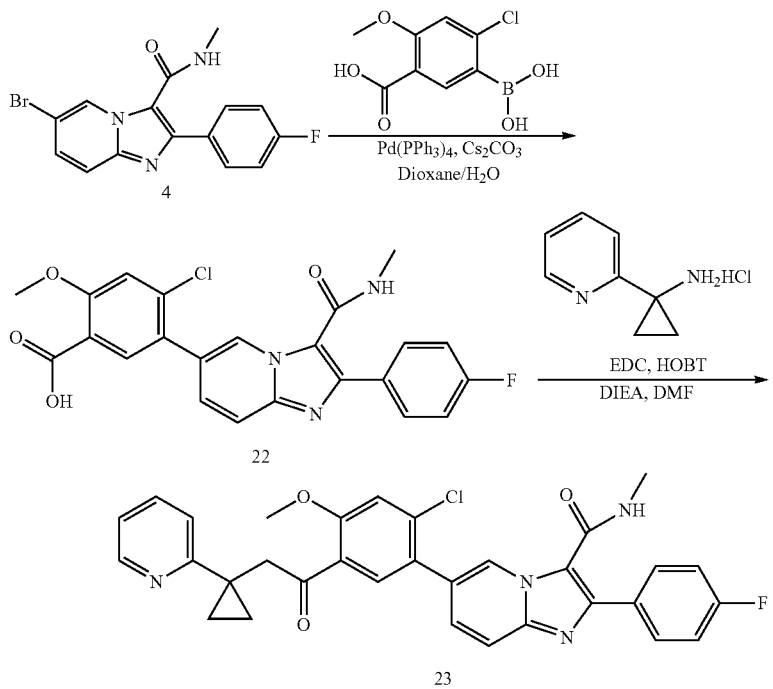

Step 1: Preparation of compound 22. To a solution of compound 4 (0.040 g, 0.12 mmol) in dioxane (2 mL) and water (0.4 mL) was added 5-borono-4-chloro-2-methoxybenzoic acid (0.040 g, 0.17 mmol), CS₂CO₃ (0.056 g, 0.1.7 mmol). The reaction mixture was stirred and degassed for 5 min, then tetrakis (3 mg, 3 μmol) was added. The reaction mixture was heated at 85° C. for 3 hrs. The reaction mixture was cooled to rt, diluted with EtOAc and the organic phase was washed with 5% citric acid, sat. NaCl, dried over anhydrous Na₂SO₄, filtered and concentrated to yield compound 22 (0.052 g, 0.12 mmol) as a pale yellow solid. The crude product was used without further purification. LC/MS m/z 453 (M+H)⁺ 454.10, RT=2.37 min.

Step 2: Preparation of compound 23. To a solution of compound 22 (0.052 g, 0.12 mmol) in DMF (1 mL) was added 1-(pyridin-2-yl)cyclopropanamine 2 hydrochloride (0.020 g, 0.12 mmol), EDC (0.022 g, 0.12 mmol), HOBT (0.018 g, 0.12 mmol) and DIEA (0.080 mL, 0.46 mmol). The reaction mixture was stirred at rt. The reaction mixture was dissolved in MeOH, filtered and purified by reverse phase prep HPLC. Fractions from main peak were evaporated in SpeedVac to yield clear oil. The oil was dissolved in methylene chloride and charged to a 4 g silica gel cartridge which was eluted with a 20 min gradient of 0-15% MeOH in CH$_2$Cl$_2$. The fraction containing the desired product was concentrated to yield compound 23 (0.006 g, 10 μmol, 9% yield) as a white solid. LC/MS m/z 569 (M+H)$^+$ 570.01, RT=2.206 min; 1H NMR (400 MHz, MeOD) d ppm 9.00 (1H, s), 8.40 (1H, d, J=4.03 Hz), 7.90 (1H, s), 7.73-7.78 (2H, m), 7.66-7.73 (2H, m), 7.52-7.60 (2H, m), 7.41 (1H, s), 7.21-7.27 (2H, m), 7.15 (1H, ddd, J=7.43, 4.91, 1.26 Hz), 4.06 (3H, s), 2.82 (3H, s), 1.63-1.68 (2H, m), 1.34-1.38 (2H, m).

2-(4-fluorophenyl)-N,7-dimethyl-6-(2-methyl-5-(2-phenylpropan-2-ylcarbamoyl)phenyl)imidazo[1,2-a]pyridine-3-carboxamide (28)

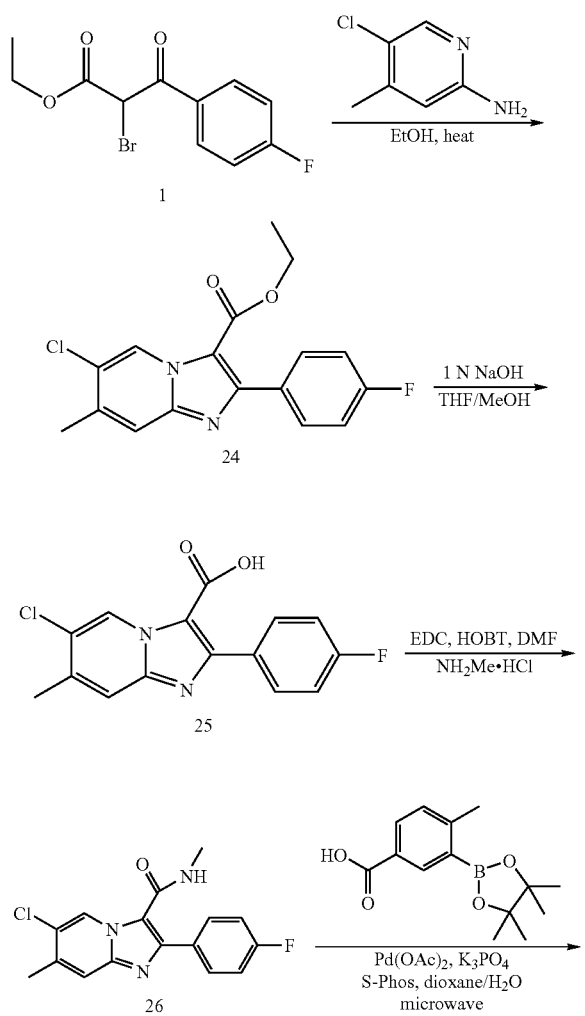

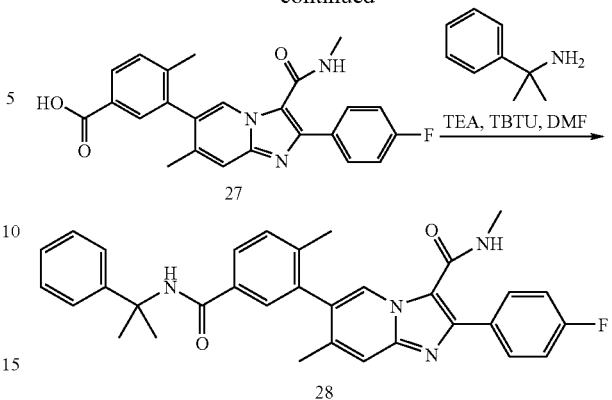

Step 1: Preparation of compound 24. To a solution of compound 1 (3 g, 12.8 mmol) in ethanol (16 mL) was added 5-chloro-4-methylpyridin-2-amine (2 g, 14.0 mmol), the reaction mixture was stirred at 70° C. under N2 for 16 hrs. The reaction mixture was diluted in EtOAc, washed with sat. NaHCO$_3$, water and sat. NaCl, dried over anhydrous Na$_2$SO$_4$, filtered and concentrated to yield yellow oil. The oil was dissolved in DCM and charged to a 80 g silica gel cartridge which was eluted with a 20 min gradient of 0-80% EtOAc in hexane. The fractions containing the desired product were concentrated to yield compound 24 (1.2 g, 3.5 mmol, 27% yield) as a white solid. LC/MS m/z 332 (M+H)$^+$ 333, RT=1.96 min [Phenomenex Luna C18 3.0×50 mm—2 min gradient from 0-100% B. (A: 90/10/0.1H$_2$O/MeOH/TFA; B: 90/10/0.1 MeOH/H$_2$O/TFA)]

Step 2: Preparation of compound 25. To a solution of compound 24 (0.8 g, 2.4 mmol) in THF (8 mL) and MeOH (2 mL) was added 1 N NaOH (6 mL, 6 mmol). The reaction mixture was stirred at 45° C. for 2 hrs. The reaction mixture was cooled to it and concentrated to remove most solvent. The reaction residue was acidified with 1 N HCl, the white solid precipitated. The solid was filtered and dried to yield compound 25 (0.58 g, 1.9 mmol, 79% yield) as a white solid. LC/MS m/z 304 (M+H)$^+$ 305.1, RT=1.58 min [Phenomenex Luna C18 3.0×50 mm—2 min gradient from 0-100% B. (A: 90/10/0.1H$_2$O/MeOH/TEA; B: 90/10/0.1 MeOH/H$_2$O/TFA)].

Step 3: Preparation of compound 26. To a solution of compound 25 (0.58 g, 1.9 mmol) in DMF (5 mL) was added EDC (0.55 g, 2.9 mmol), HOBT (0.44 g, 2.9 mmol), methylamine hydrochloride (0.26 g, 3.8 mmol) and DIEA (1.0 mL, 5.7 mmol). The reaction mixture was stirred at 50° C. for 2 hrs. The reaction mixture was diluted with EtOAc, washed with sat. NaHCO$_3$, sat. NaCl, dried over anhydrous Na$_2$SO$_4$, filtered and concentrated to yield compound 26 (0.60 g, 1.9 mmol) as a yellow solid. The crude product was used without further purification. LC/MS m/z 317 (M+H)$^+$ 318.11, RT=1.257 min [Phenomenex Luna C18 3.0×50 mm—2 min gradient from 0-100% B. (A: 90/10/0.1H$_2$O/MeOH/TFA; B: 90/10/0.1 MeOH/H$_2$O/TFA)].

Step 4: Preparation of compound 27. To a microwave vial was added compound 26 (0.030 g, 0.09 mmol), 4-methyl-3-(4,4,5,5-tetramethyl-1,3,2-dioxaborolan-2-yl)benzoic acid (0.025 g, 0.09 mmol), PdOAc$_2$ (4 mg, 0.02 mmol), 2-dicyclohexylphosphino-2',6'-dimethoxybiphenyl (8 mg, 0.02 mmol), potassium phosphate, tribasic (0.060 g, 0.3 mmol), dioxane (1 mL) and water (0.1 mL). The reaction mixture was degassed and filled with N2. The reaction mixture was heated at 130° C. in microwave reactor for 15 min. The reaction residue was dissolved in MeOH and DMF, filtered and purified by reverse phase prep HPLC. Fractions from main peak were evaporated via SpeedVac to yield compound 27 (0.040 g, 0.09 mmol, 100% yield) as a white solid. LC/MS m/z 417 (M+H)+ 418.35, RT=2.35 min.

Step 5: Preparation of compound 28. To a solution of compound 27 (0.040 g, 0.09 mmol) in DMF (8 mL) was added o-benzotriazol-1-yl-N,N,N',N'-tetramethyluronium tetrafluoroborate (0.058 g, 0.18 mmol) and TEA (0.033 mL, 0.24 mmol) and 2-phenylpropan-2-amine (0.016 g, 0.12 mmol). The reaction mixture was stirred at rt for 16 hrs. The reaction mixture was diluted in MeOH, filtered and purified by reverse phase prep HPLC. Fractions from main peak were evaporated overnight in SpeedVac to yield compound 28 mono TFA salt (0.012 g, 0.018 mmol, 15% yield) as a white solid. LC/MS m/z 534 (M+H)+ 535.19, RT=2.79 min; 1H NMR (400 MHz, MeOD) ppm 8.90 (1H, s), 7.87 (1H, dd, J=8.06, 1.76 Hz), 7.83 (1H, s), 7.76-7.81 (2H, m), 7.64 (1H, d, J=2.01 Hz), 7.49 (1H, d, J=8.06 Hz), 7.33-7.44 (4H, m), 7.23-7.30 (2H, m), 7.11-7.18 (1H, m), 2.79-2.85 (3H, m), 2.28 (3H, s), 2.19 (3H, s), 1.73 (6H, s).

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula I or II

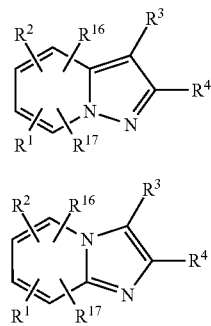

where:
R$^1$ is phenyl where said phenyl is substituted with 1-2 substituents selected from the group consisting of alkyl, alkoxy, hydroxyalkyl, alkoxyalkyl, carboxy, and CONR$^7$R$^8$, and where said phenyl is also substituted with 0-2 halo, alkyl, alkoxy, pyridinyl, phenyl or halophenyl substituents;
R$^2$ is hydrogen, halo, alkyl, cycloalkyl, alkoxy, or R$^5$R$^6$N;
R$^3$ is cyano, alkoxycarbonyl, (cycloalkyl)oxycarbonyl, (alkylsulfonyl)aminocarbonyl, CONR$^{11}$R$^{12}$, (R$^{13}$)(R$^{14}$)NCONH, triazolyl, thiazolyl, or tetrazolyl;
R$^4$ is phenyl substituted with 0-2 halo;
R$^5$ is hydrogen, alkyl, cycloalkyl, (cycloalkyl)alkyl, benzyl, alkylcarbonyl, haloalkylcarbonyl, phenylcarbonyl, (alkoxyphenyl)carbonyl, alkylsulfonyl, phenylsulfonyl, (alkoxyphenyl)sulfonyl or (haloalkoxyphenyl)sulfonyl;
R$^6$ is hydrogen, alkyl, hydroxyalkyl, or alkoxyalkyl;
or R$^5$ and R$^6$ taken together with the nitrogen to which they are attached is oxazolidinonyl or dioxothiazinyl;
R$^7$ is hydrogen, alkyl,

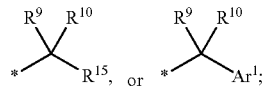

R$^8$ is hydrogen or alkyl;
R$^9$ is hydrogen or alkyl;
R$^{10}$ is hydrogen or alkyl;
or R$^9$ and R$^{10}$ taken together is ethylene, propylene, butylene, or pentylene;
R$^{11}$ is hydrogen or alkyl;
R$^{12}$ is hydrogen or alkyl;
or R$^{11}$ and R$^{12}$ taken together with the nitrogen to which they are attached is azetidinyl, pyrrolidinyl, piperidinyl, piperazinyl, or morpholinyl;
R$^{13}$ is hydrogen or alkyl;
R$^{14}$ is hydrogen or alkyl;
or R$^{13}$ and R$^{14}$ taken together with the nitrogen to which they are attached is azetidinyl, pyrrolidinyl, piperidinyl, piperazinyl, or morpholinyl;
R$^{15}$ is alkyl or cycloalkyl;
R$^{16}$ is hydrogen, halo, alkyl, or alkoxy;
R$^{17}$ is hydrogen, halo, alkyl, or alkoxy; and
Ar$^1$ is isoxazolyl, oxadiazolyl, pyridinyl, pyrimidinyl, or phenyl, and is substituted with 0-1 halo, alkyl, or phenyl substituents;
or a pharmaceutically acceptable salt thereof.

2. A compound of claim 1 where
R$^1$ is phenyl where said phenyl is substituted with 1-2 substituents selected from the group consisting of alkyl, alkoxy, hydroxyalkyl, alkoxyalkyl, and CONR$^7$R$^8$, and where said phenyl is substituted with 0-1 alkyl substituents;
R$^2$ is hydrogen, halo, alkoxy, or R$^5$R$^6$N;
R$^3$ is cyano, alkoxycarbonyl, (cycloalkyl)oxycarbonyl, (alkylsulfonyl)aminocarbonyl, CONR$^{11}$R$^{12}$, (R$^{13}$)(R$^{14}$)NCONH, triazolyl, thiazolyl, or tetrazolyl;
R$^4$ is phenyl substituted with 0-2 halo;
R$^5$ is alkylsulfonyl;
R$^6$ is hydrogen, alkyl, hydroxyalkyl, or alkoxyalkyl;
R$^7$ is hydrogen, alkyl, or

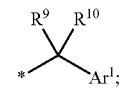

R$^8$ is hydrogen or alkyl;
R$^9$ is hydrogen or alkyl;
R$^{10}$ is hydrogen or alkyl;
or R$^9$ and R$^{10}$ taken together is ethylene, propylene, butylene, or pentylene;
R$^{11}$ is hydrogen or alkyl;
R$^{12}$ is hydrogen or alkyl;
R$^{13}$ is hydrogen or alkyl;
R$^{14}$ is hydrogen or alkyl;
or R$^{13}$ and R$^{14}$ taken together with the nitrogen to which they are attached is azetidinyl, pyrrolidinyl, piperidinyl, piperazinyl, or morpholinyl;
R$^{16}$ is hydrogen;
R$^{17}$ is hydrogen; and
Ar$^1$ is phenyl or pyridinyl;
or a pharmaceutically acceptable salt thereof.

3. A compound of claim 1 where
R¹ is phenyl where said phenyl is substituted with 1-2 substituents selected from the group consisting of alkyl, alkoxy, hydroxyalkyl, and CONR⁷R³, and where said phenyl is also substituted with 0-2 alkyl substituents;
R² is hydrogen, halo or R⁵R⁶N;
R³ is CONR¹³R¹⁴;
R⁴ is phenyl substituted with 0-2 halo;
R⁵ is alkylsulfonyl;
R⁶ is hydrogen or hydroxyalkyl;
R⁷ is hydrogen, alkyl, or

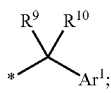

R⁸ is hydrogen;
R⁹ is alkyl;
R¹⁰ is alkyl;
or R⁹ and R¹⁰ taken together is ethylene or propylene;
R¹¹ is hydrogen or alkyl;
R¹² is hydrogen or alkyl;
R¹³ is hydrogen or alkyl;
R¹⁴ is hydrogen or alkyl;
or R¹³ and R¹⁴ taken together with the nitrogen to which they are attached is azetidinyl, pyrrolidinyl, piperidinyl, piperazinyl, or morpholinyl;
R¹⁶ is hydrogen;
R¹⁷ is hydrogen; and
Ar¹ is pyridinyl or phenyl, and is substituted with 0-1 alkyl or phenyl substituents;
or a pharmaceutically acceptable salt thereof.

4. A compound of claim 1 where
R¹ is phenyl where said phenyl is substituted with 1-2 substituents selected from the group consisting of alkyl, alkoxy, hydroxyalkyl, carboxy, and CONR⁷R⁸, and where said phenyl is also substituted with 0-2 halo, alkyl, alkoxy, pyridinyl, phenyl or halophenyl substituents;
R² is hydrogen, halo, cycloalkyl, or R⁵R⁶N;
R³ is CONR¹¹R¹²;
R⁴ is phenyl substituted with 0-2 halo;
R⁵ is hydrogen, (cycloalkyl)alkyl, benzyl, haloalkylcarbonyl, (alkoxyphenyl)carbonyl, alkylsulfonyl, (alkoxyphenyl)sulfonyl or (haloalkoxyphenyl)sulfonyl;
R⁶ is hydrogen or hydroxyalkyl;
R⁷ is hydrogen, alkyl,

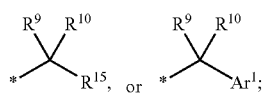

R⁸ is hydrogen;
R⁹ is alkyl;
R¹⁰ is alkyl;
or R⁹ and R¹⁰ taken together is ethylene or propylene;
R¹¹ is alkyl;
R¹² is hydrogen;
R¹⁵ is alkyl or cycloalkyl;
R¹⁶ is hydrogen;
R¹⁷ is hydrogen; and
Ar¹ is isoxazolyl, oxadiazolyl, pyridinyl, pyrimidinyl, or phenyl, and is substituted with 0-1 alkyl or phenyl substituents;
or a pharmaceutically acceptable salt thereof.

5. A compound of claim 1 where R¹ is phenyl substituted with 1 CONR⁷R⁸ substituent and 0-2 halo, alkyl, or alkoxy substituents; R² is hydrogen, halo, alkyl, or R⁵R⁶N; R³ is CONR¹¹R¹²; R⁴ is monofluorophenyl; R⁵ is alkylsulfonyl; R⁶ is alkyl; R⁷ is

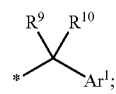

R⁸ is hydrogen; R⁹ is methyl; R¹⁰ is methyl; or R⁹ and R¹⁰ taken together is ethylene; R¹¹ is alkyl; R¹² is hydrogen or alkyl; R¹⁶ is hydrogen; R¹⁷ is hydrogen; and Ar¹ is oxadiazolyl, pyridinyl, pyrimidinyl, or phenyl, and is substituted with 0-1 halo or alkyl substituents; or a pharmaceutically acceptable salt thereof.

6. A compound of claim 1 where R¹ is phenyl substituted with 1-2 substituents selected from the group consisting of alkyl, alkoxy, hydroxyalkyl, alkoxyalkyl, carboxy, and CONR⁷R⁸, and where said phenyl is also substituted with 0-2 halo, alkyl, alkoxy, pyridinyl, phenyl or halophenyl substituents.

7. A compound of claim 1 where R¹ is phenyl is substituted with 1-2 substituents selected from the group consisting of alkyl, alkoxy, hydroxyalkyl, alkoxyalkyl, and CONR⁷R⁸, and where said phenyl is substituted with 0-1 halo, alkyl, or alkoxy substituents.

8. A compound of claim 1 selected from the group consisting of
4-fluoro-2-(4-fluorophenyl)-5-(4-methoxy-2-methyl-5-(1-phenylcyclopropylcarbamoyl)phenyl)-N-methylpyrazolo[1,5-a]pyridine-3-carboxamide;
4-fluoro-2-(4-fluorophenyl)-5-(4-methoxy-2-methyl-5-(1-(pyridin-2-yl)cyclopropylcarbamoyl)phenyl)-N-methylpyrazolo[1,5-a]pyridine-3-carboxamide;
2-(4-fluorophenyl)-N-methyl-5-(2-methyl-5-(1-(pyridin-2-yl)cyclopropylcarbamoyl)phenyl)pyrazolo[1,5-a]pyridine-3-carboxamide;
6-(N-ethylmethylsulfonamido)-2-(4-fluorophenyl)-N-methyl-5-(3-(2-phenylpropan-2-ylcarbamoyl)phenyl)pyrazolo[1,5-a]pyridine-3-carboxamide;
6-(N-ethylmethylsulfonamido)-2-(4-fluorophenyl)-N-methyl-5-(3-(1-(pyridin-2-yl)cyclopropylcarbamoyl)phenyl)pyrazolo[1,5-a]pyridine-3-carboxamide;
4-fluoro-2-(4-fluorophenyl)-N-methyl-5-(2-methyl-5-(1-phenylcyclopropylcarbamoyl)phenyl)pyrazolo[1,5-a]pyridine-3-carboxamide;
4-fluoro-2-(4-fluorophenyl)-5-(4-methoxy-2-methyl-5-(1-(3-methyl-1,2,4-oxadiazol-5-yl)cyclopropylcarbamoyl)phenyl)-N-methylpyrazolo[1,5-c]pyridine-3-carboxamide;
4-fluoro-2-(4-fluorophenyl)-5-(4-methoxy-2-methyl-5-(1-(pyrimidin-2-yl)cyclopropylcarbamoyl)phenyl)-N-methylpyrazolo[1,5-a]pyridine-3-carboxamide; and
4-fluoro-2-(4-fluorophenyl)-5-(5-(1-(3-fluorophenyl)cyclopropylcarbamoyl)-4-methoxy-2-methylphenyl)-N-methylpyrazolo[1,5-a]pyridine-3-carboxamide;
or a pharmaceutically acceptable salt thereof.

9. A composition comprising a compound of claim 1, or a pharmaceutically acceptable salt thereof, and a pharmaceutically acceptable carrier.

10. A method of treating hepatitis C infection comprising administering a therapeutically effective amount of a compound of claim 1 to a patient.

* * * * *

UNITED STATES PATENT AND TRADEMARK OFFICE
CERTIFICATE OF CORRECTION

PATENT NO. : 8,198,449 B2
APPLICATION NO. : 12/549983
DATED : June 12, 2012
INVENTOR(S) : Richard Pracitto et al.

It is certified that error appears in the above-identified patent and that said Letters Patent is hereby corrected as shown below:

On the Title Page:

Item (56), References Cited, under OTHER PUBLICATIONS:

Column 2, Trappani et al. reference, change "Trappani" to -- Trapani --.

The reference should read:

-- Trapani et. al. "Synthesis and Binding Affinity of 2-Phenylimidazo[1,2-a]pyridine Derivatives for both Central and Peripheral Benzodiazepine Receptors. A New Series of High-Affinity and Selective Ligands for the Peripheral Type" J. Med. Chem. 1997, 40, 3109-3118.* --.

Column 2, Kakehi et al. reference, change "thiacliazine" to -- thiadiazine --.

The reference should read:

-- Kakehi, A. et al., "Preparation of New Nitrogen-Bridged Heterocycles. XIV. Further Investigation of the Desulfurization and the Rearrangement of Pyrido[1,2-*d*]-1,3,4-thiadiazine Intermediates", Chem. Pharm. Bull., vol. 35, No. 1, pp. 156-169 (1987). --.

In the Claims:

Claim 3:
   Column 197, line 4, change "$CONR^7R^3$," to -- $CONR^7R^8$, --.

Claim 8:
   Column 198, line 49, change "[1,5-c]" to -- [1,5-a] --.

Signed and Sealed this
Eleventh Day of March, 2014

Michelle K. Lee
*Deputy Director of the United States Patent and Trademark Office*